United States Patent
Buechler et al.

(10) Patent No.: US 9,822,353 B2
(45) Date of Patent: Nov. 21, 2017

(54) PEGYLATED ASPARTYL-TRNA SYNTHETASE POLYPEPTIDES

(71) Applicant: aTyr Pharma, Inc., San Diego, CA (US)

(72) Inventors: Ying Ji Buechler, Carlsbad, CA (US); Chi-Fang Wu, San Diego, CA (US); Jeffrey Greve, Berkeley, CA (US); John D. Mendlein, Encinitas, CA (US)

(73) Assignee: aTyr Pharma, Inc., San Diego, CA (US)

( * ) Notice: Subject to any disclaimer, the term of this patent is extended or adjusted under 35 U.S.C. 154(b) by 257 days.

(21) Appl. No.: 14/360,573

(22) PCT Filed: Dec. 6, 2012

(86) PCT No.: PCT/US2012/068296
§ 371 (c)(1),
(2) Date: May 23, 2014

(87) PCT Pub. No.: WO2013/086228
PCT Pub. Date: Jun. 13, 2013

(65) Prior Publication Data
US 2015/0159148 A1 Jun. 11, 2015

Related U.S. Application Data

(60) Provisional application No. 61/567,602, filed on Dec. 6, 2011.

(51) Int. Cl.
| | |
|---|---|
| *C12N 9/96* | (2006.01) |
| *A61K 38/43* | (2006.01) |
| *C12N 9/00* | (2006.01) |
| *A61K 47/48* | (2006.01) |
| *A61K 38/00* | (2006.01) |
| *A61K 38/53* | (2006.01) |

(52) U.S. Cl.
CPC .......... *C12N 9/93* (2013.01); *A61K 47/48215* (2013.01); *C12N 9/96* (2013.01); *C12Y 601/01023* (2013.01); *A61K 38/00* (2013.01); *A61K 38/53* (2013.01); *C12Y 601/01012* (2013.01)

(58) Field of Classification Search
CPC ...... C12N 9/96; A61K 38/43; C07K 2319/30; C12Y 601/01012; C12Y 601/01023
See application file for complete search history.

(56) References Cited

U.S. PATENT DOCUMENTS

| | | | |
|---|---|---|---|
| 5,370,995 A | 12/1994 | Hennecke et al. |
| 5,484,703 A | 1/1996 | Raben et al. |
| 5,663,066 A | 9/1997 | Raben et al. |
| 5,747,315 A | 5/1998 | Lawlor |
| 5,750,387 A | 5/1998 | Hodgson et al. |
| 5,753,480 A | 5/1998 | Lawlor |
| 5,756,327 A | 5/1998 | Sassanfar et al. |
| 5,759,833 A | 6/1998 | Shiba et al. |
| 5,776,749 A | 7/1998 | Hodgson et al. |
| 5,795,757 A | 8/1998 | Hodgson et al. |
| 5,798,240 A | 8/1998 | Martinis et al. |
| 5,801,013 A | 9/1998 | Tao et al. |
| 5,866,390 A | 2/1999 | Lawlor |
| 5,885,815 A | 3/1999 | Sassanfar et al. |
| 5,928,920 A | 7/1999 | Hodgson et al. |
| 5,939,298 A | 8/1999 | Brown et al. |
| 6,225,060 B1 | 5/2001 | Clark et al. |
| 6,255,090 B1 | 7/2001 | Famodu et al. |
| 6,265,188 B1 | 7/2001 | Brown et al. |
| 6,428,960 B1 | 8/2002 | Clark et al. |
| 6,548,060 B1 | 4/2003 | Kim |
| 6,696,619 B1 | 2/2004 | Famodu et al. |
| 6,852,512 B2 | 2/2005 | Choi et al. |
| 6,903,189 B2 | 6/2005 | Schimmel et al. |
| 7,037,505 B2 | 5/2006 | Kim et al. |
| 7,067,126 B2 | 6/2006 | Schimmel et al. |
| 7,144,984 B2 | 12/2006 | Schimmel et al. |
| 7,196,068 B2 | 3/2007 | Kim et al. |
| 7,273,844 B2 | 9/2007 | Schimmel et al. |
| 7,282,208 B2 | 10/2007 | Kim |
| 7,413,885 B2 | 8/2008 | Schimmel et al. |
| 7,459,529 B2 | 12/2008 | Kim |
| 7,476,651 B2 | 1/2009 | Schimmel et al. |
| 7,521,215 B2 | 4/2009 | Schimmel et al. |
| 7,528,106 B2 | 5/2009 | Friedlander et al. |

(Continued)

FOREIGN PATENT DOCUMENTS

| | | |
|---|---|---|
| CA | 2531146 | 3/2005 |
| CN | 1341725 | 3/2002 |

(Continued)

OTHER PUBLICATIONS

International Preliminary Report on Patentability for International Application No. PCT/US2009/048915, dated Jan. 5, 2011.
International Search Report and Written Opinion for International Application No. PCT/US2009/048915, dated Nov. 2, 2009.
Office Action for U.S. Appl. No. 12/482,151, dated Oct. 11, 2011, 43 pages.
Office Action for U.S. Appl. No. 12/482,151, dated Mar. 18, 2011, 11 pages.
International Preliminary Report on Patentability for International Application No. PCT/US2009/046910, dated Dec. 13, 2010.

(Continued)

*Primary Examiner* — Kagnew H Gebreyesus
(74) *Attorney, Agent, or Firm* — Cooley LLP

(57) ABSTRACT

The present invention provides PEGylated aspartyl-tRNA synthetase (DRS) polypeptides, compositions comprising the same, and methods of using such polypeptides and compositions for treating or diagnosing a variety of conditions. The PEGylated DRS polypeptides of the invention have improved controlled release properties, stability, half-life, and other pharmacokinetic properties compared to non-PEGylated DRS polypeptides.

9 Claims, 12 Drawing Sheets

(56) References Cited

U.S. PATENT DOCUMENTS

| | | |
|---|---|---|
| 7,572,452 B2 | 8/2009 | Kim |
| 7,745,391 B2 | 6/2010 | Mintz et al. |
| 7,842,467 B1 | 11/2010 | Heidbrink et al. |
| 7,901,917 B2 | 3/2011 | Schimmel et al. |
| 7,902,165 B2 | 3/2011 | Kim |
| 7,981,426 B2 | 7/2011 | Kim |
| 8,003,780 B2 | 8/2011 | Kim et al. |
| 8,017,593 B2 | 9/2011 | Schimmel et al. |
| 8,026,088 B2 | 9/2011 | Yang |
| 8,101,566 B2 | 1/2012 | Schimmel et al. |
| 8,148,125 B2 | 4/2012 | Schimmel et al. |
| 8,404,242 B2 | 3/2013 | Zhou et al. |
| 8,404,471 B2 | 3/2013 | Greene et al. |
| 8,481,296 B2 | 7/2013 | Yang |
| 8,747,840 B2 | 6/2014 | Greene et al. |
| 8,753,638 B2 | 6/2014 | Zhou et al. |
| 8,828,395 B2 | 9/2014 | Watkins et al. |
| 8,835,387 B2 | 9/2014 | Chiang et al. |
| 8,945,541 B2 | 2/2015 | Greene et al. |
| 8,946,157 B2 | 2/2015 | Greene et al. |
| 8,961,960 B2 | 2/2015 | Chiang et al. |
| 8,961,961 B2 | 2/2015 | Greene et al. |
| 8,962,560 B2 | 2/2015 | Greene et al. |
| 8,969,301 B2 | 3/2015 | Greene et al. |
| 8,980,253 B2 | 3/2015 | Greene et al. |
| 8,981,045 B2 | 3/2015 | Greene et al. |
| 8,986,680 B2 | 3/2015 | Greene et al. |
| 8,986,681 B2 | 3/2015 | Greene et al. |
| 8,993,723 B2 | 3/2015 | Greene et al. |
| 8,999,321 B2 | 4/2015 | Greene et al. |
| 9,029,506 B2 | 5/2015 | Greene et al. |
| 9,034,320 B2 | 5/2015 | Greene et al. |
| 9,034,321 B2 | 5/2015 | Greene et al. |
| 9,034,598 B2 | 5/2015 | Greene et al. |
| 9,062,301 B2 | 6/2015 | Greene et al. |
| 9,062,302 B2 | 6/2015 | Greene et al. |
| 9,068,177 B2 | 6/2015 | Greene et al. |
| 9,127,268 B2 | 9/2015 | Watkins et al. |
| 9,273,302 B2 | 3/2016 | Chiang et al. |
| 9,315,794 B2 | 4/2016 | Greene et al. |
| 2002/0182666 A1 | 12/2002 | Schimmel et al. |
| 2003/0004309 A1 | 1/2003 | Kim et al. |
| 2003/0017564 A1 | 1/2003 | Schimmel et al. |
| 2003/0018985 A1 | 1/2003 | Falco et al. |
| 2003/0082575 A1 | 5/2003 | Schultz et al. |
| 2003/0158400 A1 | 8/2003 | Tang et al. |
| 2003/0165921 A1 | 9/2003 | Tang et al. |
| 2003/0166241 A1 | 9/2003 | Famodu et al. |
| 2003/0215827 A1 | 11/2003 | Yue et al. |
| 2004/0009163 A1 | 1/2004 | Schimmel et al. |
| 2004/0018505 A1 | 1/2004 | Lee et al. |
| 2004/0048290 A1 | 3/2004 | Lee et al. |
| 2004/0101879 A1 | 5/2004 | Seidel-Dugan et al. |
| 2004/0152079 A1 | 8/2004 | Schimmel et al. |
| 2004/0203094 A1 | 10/2004 | Martinis et al. |
| 2004/0214216 A1 | 10/2004 | Famodu et al. |
| 2004/0224981 A1 | 11/2004 | Janjic et al. |
| 2005/0136513 A1 | 6/2005 | Zhang |
| 2005/0196754 A1 | 9/2005 | Drmanac et al. |
| 2005/0208536 A1 | 9/2005 | Schultz et al. |
| 2006/0024288 A1 | 2/2006 | Glidden |
| 2006/0035232 A1 | 2/2006 | McGregor et al. |
| 2006/0046250 A1 | 3/2006 | Kim |
| 2006/0078553 A1 | 4/2006 | Glidden |
| 2006/0160175 A1 | 7/2006 | Anderson et al. |
| 2006/0248617 A1 | 11/2006 | Imanaka et al. |
| 2007/0048322 A1 | 3/2007 | Schimmel et al. |
| 2007/0061916 A1 | 3/2007 | Kovalic et al. |
| 2007/0111238 A1 | 5/2007 | Jamieson et al. |
| 2007/0224201 A1 | 9/2007 | Wu et al. |
| 2008/0044854 A1 | 2/2008 | Wang et al. |
| 2008/0113914 A1 | 5/2008 | Hays et al. |
| 2008/0153745 A1 | 6/2008 | Tian |
| 2009/0123971 A1 | 5/2009 | Paulsel et al. |
| 2009/0221794 A1 | 9/2009 | Kim et al. |
| 2009/0226966 A1 | 9/2009 | Yokoyama et al. |
| 2009/0227002 A1 | 9/2009 | Schultz et al. |
| 2009/0227662 A1 | 9/2009 | Schimmel et al. |
| 2009/0285792 A1 | 11/2009 | Friedlander et al. |
| 2009/0305973 A1 | 12/2009 | Kim et al. |
| 2010/0003230 A1 | 1/2010 | Glidden |
| 2010/0028352 A1 | 2/2010 | Greene et al. |
| 2010/0048413 A1 | 2/2010 | Arcus et al. |
| 2010/0092434 A1 | 4/2010 | Belani et al. |
| 2010/0093082 A1 | 4/2010 | Tian et al. |
| 2010/0138941 A1 | 6/2010 | Kim et al. |
| 2010/0167997 A1 | 7/2010 | Kim |
| 2010/0297149 A1 | 11/2010 | Zhou et al. |
| 2010/0310576 A1 | 12/2010 | Adams et al. |
| 2011/0104139 A1 | 5/2011 | Faber |
| 2011/0110917 A1 | 5/2011 | Schimmel et al. |
| 2011/0117572 A1 | 5/2011 | Kim et al. |
| 2011/0124582 A1 | 5/2011 | Kim et al. |
| 2011/0136119 A1 | 6/2011 | Kim et al. |
| 2011/0150885 A1 | 6/2011 | Watkins et al. |
| 2011/0189195 A1 | 8/2011 | Kim et al. |
| 2011/0250701 A1 | 10/2011 | Kim et al. |
| 2011/0256119 A1 | 10/2011 | Kim et al. |
| 2012/0004185 A1 | 1/2012 | Greene |
| 2012/0010141 A1 | 1/2012 | Kim |
| 2012/0015383 A1 | 1/2012 | Park et al. |
| 2012/0058133 A1 | 3/2012 | Whitman et al. |
| 2012/0064082 A1 | 3/2012 | Watkins et al. |
| 2013/0052177 A1 | 2/2013 | Schimmel et al. |
| 2013/0108630 A1 | 5/2013 | Watkins et al. |
| 2013/0129703 A1 | 5/2013 | Chiang et al. |
| 2013/0129704 A1 | 5/2013 | Greene et al. |
| 2013/0129705 A1 | 5/2013 | Greene et al. |
| 2013/0142774 A1 | 6/2013 | Greene et al. |
| 2013/0195832 A1 | 8/2013 | Greene et al. |
| 2013/0202574 A1 | 8/2013 | Greene et al. |
| 2013/0202575 A1 | 8/2013 | Greene et al. |
| 2013/0202576 A1 | 8/2013 | Greene et al. |
| 2013/0209434 A1 | 8/2013 | Greene et al. |
| 2013/0209472 A1 | 8/2013 | Greene et al. |
| 2013/0224173 A1 | 8/2013 | Greene et al. |
| 2013/0224174 A1 | 8/2013 | Greene et al. |
| 2013/0230505 A1 | 9/2013 | Greene et al. |
| 2013/0230507 A1 | 9/2013 | Greene et al. |
| 2013/0230508 A1 | 9/2013 | Greene et al. |
| 2013/0236440 A1 | 9/2013 | Greene et al. |
| 2013/0236455 A1 | 9/2013 | Greene et al. |
| 2013/0243745 A1 | 9/2013 | Greene et al. |
| 2013/0243766 A1 | 9/2013 | Zhou et al. |
| 2013/0273045 A1 | 10/2013 | Watkins et al. |
| 2013/0280230 A1 | 10/2013 | Greene et al. |
| 2013/0287755 A1 | 10/2013 | Greene et al. |
| 2013/0315887 A1 | 11/2013 | Greene et al. |
| 2013/0330312 A1 | 12/2013 | Greene et al. |
| 2013/0344096 A1 | 12/2013 | Chiang et al. |
| 2014/0066321 A1 | 3/2014 | Xu et al. |
| 2014/0255375 A1 | 9/2014 | Belani et al. |
| 2014/0255378 A1 | 9/2014 | Watkins et al. |
| 2014/0302075 A1 | 10/2014 | Buechler et al. |
| 2014/0335087 A1 | 11/2014 | Buechler et al. |
| 2014/0349369 A1 | 11/2014 | Buechler et al. |
| 2014/0363415 A1 | 12/2014 | Greene et al. |
| 2014/0371294 A1 | 12/2014 | Zhou et al. |
| 2015/0064188 A1 | 3/2015 | Greene |
| 2015/0093799 A1 | 4/2015 | Chiang et al. |
| 2015/0140072 A1 | 5/2015 | Watkins et al. |
| 2015/0231214 A1 | 8/2015 | Greene et al. |
| 2015/0240227 A1 | 8/2015 | Greene et al. |
| 2015/0240228 A1 | 8/2015 | Greene et al. |
| 2015/0252347 A1 | 9/2015 | Greene et al. |
| 2015/0252348 A1 | 9/2015 | Greene et al. |
| 2015/0252349 A1 | 9/2015 | Greene et al. |
| 2015/0284704 A1 | 10/2015 | Greene et al. |
| 2015/0284705 A1 | 10/2015 | Greene et al. |
| 2015/0284706 A1 | 10/2015 | Greene et al. |
| 2015/0290304 A1 | 10/2015 | Greene et al. |
| 2015/0290305 A1 | 10/2015 | Greene et al. |
| 2015/0344866 A1 | 12/2015 | Greene et al. |
| 2015/0353914 A1 | 12/2015 | Greene et al. |

(56) References Cited

U.S. PATENT DOCUMENTS

| | | |
|---|---|---|
| 2015/0361411 A1 | 12/2015 | Greene et al. |
| 2015/0361412 A1 | 12/2015 | Greene et al. |
| 2015/0361413 A1 | 12/2015 | Greene et al. |
| 2016/0010075 A1 | 1/2016 | Greene et al. |
| 2016/0017311 A1 | 1/2016 | Greene |

FOREIGN PATENT DOCUMENTS

| | | |
|---|---|---|
| CN | 1341727 | 3/2002 |
| CN | 1352242 | 6/2002 |
| CN | 1352252 | 6/2002 |
| EP | 0785265 | 7/1997 |
| EP | 0893494 | 1/1999 |
| EP | 0893496 | 1/1999 |
| EP | 0897004 | 2/1999 |
| EP | 1275720 | 1/2003 |
| EP | 1300468 | 4/2003 |
| EP | 1377305 | 1/2009 |
| EP | 1776138 | 10/2009 |
| EP | 2177610 | 4/2010 |
| EP | 1274834 | 7/2010 |
| EP | 2084190 | 3/2011 |
| JP | 2008-508349 | 3/2008 |
| WO | WO 97/25426 | 7/1997 |
| WO | WO 97/26351 | 7/1997 |
| WO | WO 97/39017 | 10/1997 |
| WO | WO 98/14591 | 4/1998 |
| WO | WO 98/50554 | 11/1998 |
| WO | WO 99/45130 | 9/1999 |
| WO | WO 01/07628 | 2/2001 |
| WO | WO 01/19999 | 3/2001 |
| WO | WO 01/64892 | 9/2001 |
| WO | WO 01/74841 | 10/2001 |
| WO | WO 01/75067 | 10/2001 |
| WO | WO 01/75078 | 10/2001 |
| WO | WO 01/88188 | 11/2001 |
| WO | WO 01/90330 | 11/2001 |
| WO | WO 01/94568 | 12/2001 |
| WO | WO 02/44349 | 6/2002 |
| WO | WO 02/055663 | 7/2002 |
| WO | WO 02/059323 | 8/2002 |
| WO | WO 02/067970 | 9/2002 |
| WO | WO 03/009813 | 2/2003 |
| WO | WO 03/080648 | 10/2003 |
| WO | WO 03/094862 | 11/2003 |
| WO | WO 2004/030615 | 4/2004 |
| WO | WO 2004/087875 | 10/2004 |
| WO | WO 2005/019258 | 3/2005 |
| WO | WO 2005/019415 | 3/2005 |
| WO | WO 2005/102395 | 11/2005 |
| WO | WO 2005/117954 | 12/2005 |
| WO | WO 2006/016217 | 2/2006 |
| WO | WO 2006/057500 | 6/2006 |
| WO | WO 2007/064941 | 6/2007 |
| WO | WO 2007/139397 | 12/2007 |
| WO | WO 2008/007818 | 1/2008 |
| WO | WO 2008/016356 | 2/2008 |
| WO | WO 2008/021290 | 2/2008 |
| WO | WO 2008/133359 | 11/2008 |
| WO | WO 2009/059056 | 5/2009 |
| WO | WO 2009/114623 | 9/2009 |
| WO | WO 2009/152247 | 12/2009 |
| WO | WO 2009/158649 | 12/2009 |
| WO | WO 2010/021415 | 2/2010 |
| WO | WO 2010/041892 | 4/2010 |
| WO | WO 2010/041913 | 4/2010 |
| WO | WO 2010/090471 | 8/2010 |
| WO | WO 2010/096170 | 8/2010 |
| WO | WO 2010/099477 | 9/2010 |
| WO | WO 2010/107825 | 9/2010 |
| WO | WO 2010/120509 | 10/2010 |
| WO | WO 2011/072265 | 6/2011 |
| WO | WO 2011/072266 | 6/2011 |
| WO | WO 2011/097031 | 8/2011 |
| WO | WO 2011/139714 | 11/2011 |
| WO | WO 2011/139799 | 11/2011 |
| WO | WO 2011/139801 | 11/2011 |
| WO | WO 2011/139853 | 11/2011 |
| WO | WO 2011/139854 | 11/2011 |
| WO | WO 2011/139907 | 11/2011 |
| WO | WO 2011/139986 | 11/2011 |
| WO | WO 2011/139988 | 11/2011 |
| WO | WO 2011/140132 | 11/2011 |
| WO | WO 2011/140135 | 11/2011 |
| WO | WO 2011/140266 | 11/2011 |
| WO | WO 2011/140267 | 11/2011 |
| WO | WO 2011/143482 | 11/2011 |
| WO | WO 2011/146410 | 11/2011 |
| WO | WO 2011/150279 | 12/2011 |
| WO | WO 2011/153277 | 12/2011 |
| WO | WO 2012/009289 | 1/2012 |
| WO | WO 2012/021247 | 2/2012 |
| WO | WO 2012/021249 | 2/2012 |
| WO | WO 2012/027611 | 3/2012 |
| WO | WO 2012/048125 | 4/2012 |
| WO | WO 2012/158945 | 11/2012 |
| WO | WO 2013/022982 | 2/2013 |
| WO | WO 2013/086216 | 6/2013 |
| WO | WO 2013/086228 | 6/2013 |
| WO | WO 2013/115926 | 8/2013 |
| WO | WO 2013/123432 | 8/2013 |

OTHER PUBLICATIONS

International Search Report and Written Opinion for International Application No. PCT/US2009/046910, dated Mar. 4, 2010.
Supplementary European Search Report for European Application No. 06838844.6, dated Apr. 9, 2009, 10 pages.
Office Action for European Patent Application No. 06838844.6, dated Apr. 9, 2009.
Office Action for U.S. Appl. No. 12/085,884, dated Jan. 20, 2011.
International Preliminary Report on Patentability for International Application No. PCT/US2006/046106, dated Jun. 4, 2008.
International Search Report and Written Opinion for International Application No. PCT/US2006/046106, dated Aug. 9, 2007.
Supplementary European Search Report for European Application No. 10746935.5, dated Oct. 26, 2012.
Office Action for U.S. Appl. No. 13/203,831, dated Oct. 7, 2013, 20 pages.
International Preliminary Report on Patentability for International Application No. PCT/US2010/025642, dated Aug. 30, 2011.
International Search Report and Written Opinion for International Application No. PCT/US2010/025642, dated Oct. 29, 2010.
Supplementary European Search Report for European Application No. 10764856.0, dated Sep. 5, 2012.
Office Action for U.S. Appl. No. 12/751,358, dated Dec. 2, 2014.
Office Action for U.S. Appl. No. 12/751,358, dated Jun. 11, 2014.
Office Action for U.S. Appl. No. 12/751,358, dated Oct. 3, 2011.
Office Action for U.S. Appl. No. 12/751,358, dated Mar. 3, 2011.
International Preliminary Report on Patentability for International Application No. PCT/US2010/029377, dated Oct. 4, 2011.
International Search Report and Written Opinion for International Application No. PCT/US2010/029377, dated Jan. 26, 2011.
Office Action for U.S. Appl. No. 12/725,272, dated Jul. 13, 2012, 9 pages.
Restriction Requirement for U.S. Appl. No. 12/725,272, dated Apr. 27, 2012.
International Preliminary Report on Patentability for International Application No. PCT/US2010/027525, dated Sep. 20, 2011.
International Search Report and Written Opinion for International Application No. PCT/US2010/027525, dated Jan. 10, 2011.
International Search Report and Written Opinion for International Application No. PCT/US2010/059964, dated Aug. 25, 2011.
International Preliminary Report on Patentability for International Application No. PCT/US2010/059964, dated Jun. 12, 2012.
International Preliminary Report on Patentability for International Application No. PCT/US2010/059963, dated Jun. 12, 2012, 18 pages.

(56) References Cited

OTHER PUBLICATIONS

International Search Report and Written Opinion for International Application No. PCT/US2010/059963, dated May 12, 2011.
International Search Report and Written Opinion for International Application No. PCT/US2011/000210, dated Aug. 12, 2011.
International Preliminary Report on Patentabiltity for International Application No. PCT/US2011/000210, dated Aug. 7, 2012.
Supplementary European Search Report for European Application No. 11778025.4, dated Nov. 6, 2013.
International Search Report and Written Opinion for International Application No. PCT/US2011/034387, dated Mar. 23, 2012.
International Preliminary Report on Patentability for International Application No. PCT/US2011/034387, dated Oct. 30, 2012.
Supplementary European Search Report for European Application No. 11778026.2, dated Oct. 22, 2013.
International Search Report and Written Opinion for International Application No. PCT/US2011/034388, dated Mar. 23, 2012.
International Preliminary Report on Patentability for International Application No. PCT/US2011/034388, dated Oct. 30, 2012.
Supplementary European Search Report for European Application No. 11807357.6, dated Dec. 22, 2014.
Notice of Allowance for U.S. Appl. No. 13/809,750, dated Oct. 17, 2014, 10 pages.
International Search Report and Written Opinion for International Application No. PCT/US2011/043596, dated Feb. 29, 2012.
International Preliminary Report on Patentability for International Application No. PCT/US2011/043596, dated Jan. 15, 2013.
Supplementary European Search Report for European Application No. 11778118.7, dated Aug. 19, 2013.
International Search Report and Written Opinion for International Application No. PCT/US2011/034838, dated Jan. 9, 2012.
International Preliminary Report on Patentability for International Application No. PCT/US2011/034838, dated Nov. 6, 2012.
International Search Report and Written Opinion for International Application No. PCT/US2011/033988, dated Feb. 9, 2012.
International Preliminary Report on Patentability for International Application No. PCT/US2011/033988, dated Oct. 30, 2012.
International Search Report and Written Opinion for International Application No. PCT/US2011/038240, dated Feb. 9, 2012.
International Preliminary Report on Patentability for International Application No. PCT/US2011/038240, dated Nov. 27, 2012.
Supplementary European Search Report for European Application No. 11778296.1, dated Nov. 12, 2013.
International Search Report and Written Opinion for International Application No. PCT/US2011/035250, dated Jan. 19, 2012.
International Preliminary Report on Patentability for International Application No. PCT/2011/035250, dated Nov. 6, 2012.
International Search Report and Written Opinion for International Application No. PCT/US2011/043756, dated Mar. 2, 2012.
International Preliminary Report on Patentability for International Application No. PCT/US2011/043756, dated Jan. 15, 2013.
International Search Report and Written Opinion for International Application No. PCT/US2011/043758, dated Mar. 2, 2012.
International Preliminary Report on Patentability for International Application No. PCT/US2011/043758, dated Jan. 15, 2013.
International Search Report and Written Opinion for International Application No. PCT/US2011/034205, dated Feb. 8, 2012.
International Preliminary Report on Patentability for International Application No. PCT/US2011/034205, dated Oct. 30, 2012.
International Search Report and Written Opinion for International Application No. PCT/US2011/036684, dated Feb. 9, 2012.
International Preliminary Report on Patentability for International Application No. PCT/US2011/036684, dated Nov. 20, 2012.
International Search Report and Written Opinion for International Application No. PCT/US2011/038813, dated Mar. 28, 2012.
International Preliminary Report on Patentability for International Application No. PCT/US2011/038813, dated Dec. 4, 2012.
International Search Report and Written Opinion for International Application No. PCT/US2011/035056, dated Mar. 23, 2012.
International Preliminary Report on Patentability for International Application No. PCT/US2011/035056, dated Nov. 6, 2012.
International Search Report and Written Opinion for International Application No. PCT/US2011/035053, dated Mar. 23, 2012.
International Preliminary Report on Patentability for International Application No. PCT/US2011/035053, dated Nov. 6, 2012.
Supplementary European Search Report for European Application No. 11778120.3, dated Nov. 15, 2013.
International Search Report and Written Opinion for International Application No. PCT/US2011/034840, dated Feb. 10, 2012.
International Preliminary Report on Patentability for International Application No. PCT/US2011/034840, dated Nov. 6, 2012.
Supplementary European Search Report for European Application No. 11777984.3, dated Oct. 18, 2013.
International Search Report and Written Opinion for International Application No. PCT/US2011/034207, dated Feb. 8, 2012.
International Preliminary Report on Patentability for International Application No. PCT/US2011/034207, dated Oct. 30, 2012.
International Search Report and Written Opinion for International Application No. PCT/US2011/055130, dated May 14, 2012.
International Preliminary Report on Patentability for International Application No. PCT/US2011/055130, dated Apr. 9, 2013.
International Search Report and Written Opinion for International Application No. PCT/US2011/049223, dated Mar. 27, 2012.
International Preliminary Report on Patentability for International Application No. PCT/US2011/049223, dated Feb. 26, 2013.
International Search Report and Written Opinion for International Application No. PCT/US2011/034626, dated Jan. 19, 2012.
International Preliminary Report on Patentability for International Application No. PCT/US2011/034626, dated Oct. 30, 2012.
Supplementary European Search Report for European Application No. 11781304.8, dated Oct. 23, 2013.
International Search Report and Written Opinion for International Application No. PCT/US2011/036326, dated Feb. 9, 2012.
International Preliminary Report on Patentability for International Application No. PCT/US2011/036326, dated Nov. 20, 2012.
International Search Report and Written Opinion for International Application No. PCT/US2011/035251, dated Feb. 8, 2012.
International Preliminary Report on Patentability for International Application No. PCT/US2011/035251, dated Nov. 6, 2012.
International Search Report and Written Opinion for International Application No. PCT/US2012/068282, dated Apr. 1, 2013.
International Search Report and Written Opinion for International Application No. PCT/US2012/068296, dated Apr. 19, 2013.
Supplementary Partial European Search Report for European Application No. 12867497.5, dated Apr. 29, 2015.
International Preliminary Report on Patentability for International Application No. PCT/US2012/071762, dated Jul. 1, 2014.
Adams, M. D. et al., "The genome sequence of drosophila melanogaster," Science, 287(5961):2185-2195 (2000).
Aderem, A. et al., "Toll-like receptors in the induction of the innate immune response," Nature, 406:782-787 (2000).
Amaar, Y. G. et al., "Cloning and characterization of the C.elegans histidyl-tRNA synthetase gene," Nucleic Acids Research, 21(18):4344-4347 (1993).
Antonellis, A. et al., "The Role of Aminoacyl-tRNA Synthetases in Genetic Diseases," Annual Review of Genomics and Human Genetics, 9(1):87-107 (2008).
Ascherman, D. P. et al., "Critical Requirement for Professional APCs in Eliciting T Cell Responses to Novel Fragments of Histidyl-tRNA Synthetase (Jo-1) in Jo-1 Antibody-Positive Polymyositis," J. Immunol., 169:7127-7134 (2002).
Ascherman, D. P., "The Role of Jo-1 in the Immunopathogenesis of Polymyositis: Current Hypotheses," Current Rheumatology Reports, 5:425-430 (2003).
Barbasso, S. et al., "Sera From Anti-Jo-1-Positive Patients with Polymyositis and Interstitial Lung Disease Induce Expression of Intercellular Adhesion Molecule 1 in Human Lung Endothelial Cells," Arthritis & Rheumatism, 60(8):2524-2530 (2009).
Bernstein, R. M. et al., "Anti-Jo-1 antibody: a marker for myositis with interstitial lung disease," British Medical Journal, 289:151-152 (1984).

(56) References Cited

OTHER PUBLICATIONS

Blechynden, L.M. et al., "Sequence and polymorphism analysis of the murine gene encoding histidyl-tRNA synthetase," Gene, 178:151-156 (1996).
Blechynden, L.M. et al., "Myositis Induced by Naked DNA Immunization with the Gene for Histidyl-tRNA Synthetase," Human Gene Therapy, 8:1469-1480 (Aug. 10, 1997).
Blum, D. et al., "Extracellular toxicity of 6-hydroxydopamine on PC12 cells," Neuroscience Letters, 283(3):193-196 (2000).
Branden et al., "Introduction to Protein Structure," Garland Publishing Inc., New York, p. 247 (1991).
Brightbill, H. D. et al., "Toll-like receptors: molecular mechanisms of the mammalian immune response," Immunology, 101:1-10 (2000).
Broun, P. et al., "Catalytic plasticity of fatty acid modification enzymes underlying chemical diversity of plant lipids," Science, 282:1315-1317 (1998).
Brown, M. V. et al., "Mammalian aminoacyl-tRNA synthetases: Cell signaling functions of the protein translation machinery," Vascular Pharmacology, 52(1-2):21-26 (2010).
Car, B. D. et al., "Interferon y Receptor Deficient Mice Are Resistant to Endotoxic Shock," J. Exp. Med., 179:1437-1444, 1994.
Casciola-Rosen, L. et al., "Cleavage by Granzyme B Is Strongly Predictive of Autoantigen Status: Implications for Initiation of Autoimmunity," J. Exp. Med., 190(6):815-825 (1999).
Casciola-Rosen, L., "Histidyl-Transfer RNA Synthetase: A Key Participant in Idiopathic Inflammatory Myopathies," Arthritis and Rheumatism, 63(2):331-333 (2011).
Cheong et al., "Structure of the N-terminal extension of human aspartyl-tRNA synthetase: implications for its biological function," The International Journal of Biochemistry & Cell Biology, 35:1548-1557, 2003.
Chica, R. A. et al., "Semi-rational approaches to engineering enzyme activity: combining the benefits of directed evolution and rational design," Curr. Opin. Biotechnol., 16:378-384 (2005).
Choi, W. S. et al., "Two Distinct Mechanisms Are Involved in 6-Hydroxydopamine-and MPP+-Induced Dopaminergic Neuronal Cell Death: Role of Caspases, ROS, and JNK," Journal of Neuroscience Research, 57(1):86-94 (1999).
Datson, N. A. et al., "Development of the first marmoset-specific DNA microarray (EUMAMA): a new genetic tool for large-scale expression profiling in a non-human primate," BMC Genomics, 8(190):1-9 (2007).
Deiters, A. et al., "Site-specific PEGylation of proteins containing unnatural amino acids," Bioorg Med Chem Lett, 14(23):5743-5745 (2004).
Delgado, C. et al., "The uses and properties of PEG-linked proteins," Critical Reviews in Therapeutic Drug Carrier Systems, 9(3,4):249-304 (1992).
Devos, D. et al., "Practical limits of function prediction," Proteins: Structure, Function, and Genetics, 41:98-107 (2000).
Dumont, J. A. et al., "Monomeric Fc Fusions: Impact on pharmacokinetic and biological activity of protein therapeutics," Biodrugs: Clinical Immunotherapeutics, Biopharmaceuticals and Gene Therapy, 20(3):151-160 (2006).
Eriani, G. et al., "Cytoplasmic aspartyl-tRNA synthetase from *Saccharomyces cerevisiae*. Study of its functional organisation by deletion analysis," European Journal of Biochemistry, 200(2):337-343 (1991).
Escalante, C., et al., "Expression of human aspartyl-tRNA synthetase in COS cells," Molecular and Cellular Biochemistry, 140(1):55-63 (1994).
Escalante, C. et al., "Expression of Human Aspartyl-tRNA Synthetase in *Escherichia coli*: Functional Analysis of the N-Terminal Putative Amphiphilic Helix," The Journal of Biological Chemistry, 268(8):6014-6023 (1993).
Ewalt, K. L. et al., "Activation of Angiogenic Signaling Pathways by Two Human tRNA Synthetases," Biochemistry, 41(45):13344-13349 (2002).

Fontanesi, L. et al., "Identification and association analysis of several hundred single nucleotide polymorphisms within candidate genes for back fat thickness in Italian large white pigs using a selective genotyping approach," J Anim Sci, 90(8):2450-2464 (2012).
Frommhold, D. et al., "Sialyltransferase ST3Gal-IV controls CXCR2-mediated firm leukocyte arrest during inflammation," Journal of Experimental Medicine, 205(6):1435-1446 (2008).
GenBank Accession No. AA131122, Nov. 27, 1996.
GenBank Accession No. AA281081, Apr. 2, 1997.
GenBank Accession No. AA355758, Apr. 21, 1997.
GenBank Accession No. AA984229, published May 27, 1998.
GenBank Accession No. AAP36306.1, published May 13, 2003.
GenBank Accession No. BT007638.1, published May 13, 2003.
GenBank Accession No. AI985978, Aug. 31, 1999.
GenBank Accession No. AK055917, published Jan. 19, 2008.
GenBank Accession No. AK124831, published Jul. 3, 2008.
GenBank Accession No. AK225776, published Jul. 22, 2006.
GenBank Accession No. AK293154, published Jul. 24, 2008.
GenBank Accession No. AK295219, published Jul. 24, 2008.
GenBank Accession No. AK302295, published Jul. 24, 2008.
GenBank Accession No. AK303778, published Jul. 24, 2008.
GenBank Accession No. AU129836, published Feb. 18, 2011.
GenBank Accession No. AV685924, Sep. 25, 2000.
GenBank Accession No. AW070887, Oct. 13, 1999.
GenBank Accession No. BE561651, Aug. 10, 2000.
GenBank Accession No. BE695954, Sep. 11, 2000.
GenBank Accession No. BE872272, published Jan. 13, 2011.
GenBank Accession No. BF437672, Nov. 29, 2000.
GenBank Accession No. BF526055, Dec. 4, 2000.
GenBank Accession No. BF791754, published Jan. 13, 2011.
GenBank Accession No. BG108830, published Jun. 1, 2001.
GenBank Accession No. BG700836, May 7, 2001.
GenBank Accession No. BI559642, Sep. 4, 2001.
GenBank Accession No. BI599431, Sep. 5, 2001.
GenBank Accession No. BM827507, Mar. 6, 2002.
GenBank Accession No. BP268250, published Feb. 10, 2011.
GenBank Accession No. BQ002750, Mar. 26, 2002.
GenBank Accession No. BU599828, Sep. 19, 2002.
GenBank Accession No. CA865450, Dec. 20, 2002.
GenBank Accession No. CA865692, Dec. 20, 2002.
GenBank Accession No. CD694017, Jun. 25, 2003.
GenBank Accession No. CR749809, Oct. 7, 2008.
GenBank Accession No. DA083923, published Feb. 17, 2011.
GenBank Accession No. DB146646, published Feb. 16, 2011.
GenBank Accession No. J05032, published Apr. 27, 1993.
GenBank Accession No. Q7QD89, Anopheles gambiae Sequence Committee, submitted Apr. 2002, [Retrieved from the Internet Apr. 24, 2007], <URL: http://www.ncbi.nlm.nih.gov/entrez/viewer.fcgi?db=protein&val=74803944>.
GenBank Accession No. Q9VV60, published May 1, 2000.
GenBank Accession No. Z11518, published Oct. 7, 2008.
Goldgur, Y. et al., "The crystal structure of phenylalanyl-tRNA synthetase from Thermus thermophilus complexed with cognate tRNA," Structure, 5(1):59-68 (1997).
Greenberg, Y. et al., "The novel fragment of tyrosyl tRNA synthetase, mini-TyrRS, is secreted to induce an angiogenic response in endothelial cells," FASEB Journal, 22(5):1597-1605 (2008).
Guijarro, J. I. et al., "Structure and Dynamics of the Anticodon Arm Binding Domain of Bacillus stearothermophilus Tyrosyl-tRNA Synthetase," Structure, 10(3):311-317 (2002).
Guo, R-T. et al., "Crystal structures and biochemical analyses suggest a unique mechanism and role for human glycyl-tRNA synthetase in Ap4A homeostasis," Journal of Biological Chemistry, 284(42):28968-28976 (2009).
Guo, M. et al., "Functional expansion of human tRNA synthetases achieved by structural inventions," FEBS Letters, 584(2):434-442 (2010).
Guo, M. et al., "New functions of aminoacyl-tRNA synthetases beyond translation," Nature Reviews Molecular Cell Biology, 11:668-674 (2010).

(56) References Cited

OTHER PUBLICATIONS

Hanrott, K. et al., "6-Hydroxydopamine-induced Apoptosis Is Mediated via Extracellular Auto-oxidation and Caspase 3-dependent Activation of Protein Kinase C8," The Journal of Biological Chemistry, 281(9):5373-5382 (2006).
Hausmann, C. D. et al., "Aminoacyl-tRNA synthetase complexes: molecular multitasking revealed," FEMS Microbiol. Rev., 32(4):705-721 (2008).
Hengstman, G. J. D. et al., "Anti-Jo-1 positive inclusion body myositis with a marked and sustained clinical improvement after oral prednisone," J. Neurol. Neurosurg. Psychiatry, 70(5):706 (2001).
Hou, Y-M. et al., "Sequence determination and modeling of structural motifs for the smallest monomeric aminoacyl-tRNA synthetase," Proc. Nat. Acad. Sci., 88(3):976-980 (1991).
Howard, O. M. Z. et al., "Histidyl-tRNA Synthetase and Asparaginyl-tRNA Synthetase, Autoantigens in Myositis, Activate Chemokine Receptors on T Lymphocytes and Immature Dendritic Cells," The Journal of Experimental Medicine, 196(6):781-791 (2002).
Howard, O. M. Z. et al., "Autoantigens signal through cheokine receptors: uveitis antigens induce CXCR3- and CRCR5-expressing lymphocytes and immature dendritic cells to migrate", Blood, 105(11) 4207-4214 (2005).
Ivakhno, S. S. et al., "Cytokine-Like Activities of Some Aminoacyl-tRNA Synthetases and Auxiliary p43 Cofactor of Aminoacylation Reaction and Their Role in Oncogenesis," Exp. Oncol., 26(4):250-255 (2004).
Ivanov, K. A. et al., "Non-canonical Functions of Aminoacyl-tRNA Synthetases," Biochemistry (Moscow), 65(8):888-897 (2000).
Izumi, Y. et al., "p-Quinone Mediates 6-Hydroxydopamine-Induced Dopaminergic Neuronal Death and Ferrous Iron Accelerates the conversion of p-Quinone Into Melanin Extracellularly," Journal of Neuroscience Research, 79(6):849-860 (2005).
Jacobo-Molina, A. et al., "cDNA Sequence, Predicted Primary Structure, and Evolving Amphiphilic Helix of Human Aspartyl-tRNA Synthetase," Journal of Biological Chemistry, 264(28):16608-16612 (1989).
Jura, M. et al., "Comprehensive Insight into human aminoacyl-tRNA synthetases as autoantigens in idiopathic inflammatory myopathies," Critical Reviews in Immunology, 27(6):559-572 (2007).
Kapoor, M. et al., "Mutational separation of aminoacylation and cytokine activities of human tyrosyl-tRNA synthetase," Chemistry & Biology, 16(5):531-539 (2009).
Katsumata, Y. et al., "Species-specific immune responses generated by histidyl-tRNA synthetase immunization are associated with muscle and lung inflammation," Journal of Autoimmunity, 29(2-3):174-186 (2007).
Katsumata, Y. et al., "Animal models in myositis," Current Opinion in Rheumatology, 20:681-685 (2008).
Kimchi-Sarfaty, C. et al., "A 'Silent' polymorphism in the MDR1 gene changes substrate specificty," Science, 315:525-528 (2007).
Kise, Y. et al., "A short peptide insertion crucial for angiostatic activity of human tryptophanyl-tRNA synthetase," Nature Structural & Molecular Biology, 11(2):149-156 (2004).
Kochendoerfer, G. G., "Site-specific polymer modification of therapeutic proteins," Current Opinion in Chemical Biology, 9:555-560 (2005).
Kovaleski, B. J. et al.,"In vitro characterization of the interaction between HIV-1 Gag and human lysyl-tRNA synthetase," J. Bio. Chem., 281(28):19449-19456 (2006).
Levine, S. M. et al., "Anti-aminoacyl tRNA synthetase immune responses: insights into the pathogenesis of the idiopathic inflammatory myopathies," Current Opinion in Rheumatology, 15(6):708-713 (2003).
Levine, S. M., et al., "Novel Conformation of Histidyl-Transfer RNA Synthetase in the Lung", Arthritis & Rheumatism, 56(8): 2729-2739 (2007).
Link, A. J. et al., "Discovery of aminoacyl-tRNA synthetase activity through cell-surface display of noncanonical amino acids, " Proc. Nat. Acad. Sci., 103(27):10180-10185 (2006).
Lorber, B. et al., "Properties of N-terminal truncated yeast aspartyl-tRNA synthetase and structural characteristics of the cleaved domain," Eur. J. Biochem. 174, pp. 155-161 (1988).
Ma, P. T. S. et al., "Mevinolin, an inhibitor of cholesterol synthesis, induces mRNA for low density lipoprotein receptor in livers of hamsters and rabbits," Proc. Natl. Acad. Sci. USA, 83:8370-8374 (1986).
Martin, A. et al., "Epitope studies indicate that histidyl-tRNA synthetase is a stimulating antigen in idiopathic myositis," The FASEB Journal, 9:1226-1233 (1995).
Merritt, E. A. et al., "Crystal structure of the aspartyl-tRNA synthetase from Engamoeba histolytica," Mol. Biochem. Parasitol, 169(2):95-100 (2009).
Miller, F. W., et al., "Origin and Regulation of a Disease-specific Autoantibody Response, Antigenic Epitopes, Spectrotype Stability, and Isotype Restriction of Anti-Jo-1 Autoantibodies," J. Clin. Invest., 85:468-475 (1990).
Mirande, M. et al., "Engineering mammalian aspartyl-tRNA synthetase to probe structural features mediating its association with the multisynthetase complex," Eur. J. Biochem., 203(3):459-466 (1992).
Molecular Modeling Database (Mmdb), "Solution Structures of the Whep-trs domain of human histidyl-trna synthetase," MMDB ID No. 35920, available for www.ncbi.nlm.nih.gov/Structure/mmdb, accessed Aug. 24, 2012.
Mukhopadhyay, R. et al., "The GAIT System: a gatekeeper of inflammatory gene expression," Trends in Biochemical Sciences, 34(7):324-331 (2009).
Nackley, A. G. et al., "Human Caechol-O-Methytransferase haplotypes modulate protein expression by altering mRNA secondary structure," Science, 314:1930-1933 (2006).
NCBI Accession No. NP001340, Feb. 27, 2011.
Ngo, J. T. et al., "Computational complexity, protein structure prediction, and the Levinthal paradox," In The Protein Folding Problem and Tertiary Structure Prediction, Merz et al. (ed.), Birkhauser, Boston, MA, pp. 433 and 492-495 (1994).
Nichols, R. C. et al., "Human isoleucyl-tRNA synthetase: sequence of the cDNA, alternative mRNA splicing, and the characteristics of an unusually long C-terminal extension," Gene, 155(2):299-304 (1995).
Nishikai, M. et al., "Heterogeneity of Precipitating Antibodies in Polymyositis and Dermatomyositis," Arthritis and Rheumatism, 23(8):881-888 (1980).
O'Hanlon, T. P. et al., "Genomic organization, transcriptional mapping, and evolutionary implications of the human bi-directional histidyl-tRNA synthetase locus (HARS/HARSL)," Biochemical and Biophysical Research Communications, 294:609-614 (2002).
Oppenheim, J. J. et al., "Autoantigens act as tissue-specific chemoattractants," Journal of Leukocyte Biology, 77:854-861 (2005).
Park, S. G., et al., "Aminoacyl tRNA synthetases and their connections to disease," PNAS, 105(32):11043-11049 (2008).
Park, S. G. et al., "Dose-dependent biphasic activity of tRNA synthetase-associating factor, p43, in angiogenesis," The Journal of Biological Chemistry, 277(47):45243-45248 (2002).
Park, S. G. et al., "Human lysyl-tRNA syntetase is secreted to trigger proinflammatory response," PNAS, 102(18):6356-6361 (2005).
Park, S. G. et al., "Is there an answer? Do aminoacyl-tRNA synthetases have biological functions other than in protein biosynthesis?" IUBMB Life, 58(9):556-558 (2006).
Parker, L. C. et al., "Toll-Like Receptor (TLR)2 and TLR4 Agonists Regulate CCR Expression in Human Monocytic Cells," The Journal of Immunology, 172:4977-4986 (2004).
Pierce, S. B. et al., "Mutations in mitochondrial histidyl tRNA synthetase HARS2 cause ovarian dysgenesis and sensorineural hearing loss of Perrault syndrome," PNAS, 108(16):6543-6548 (2011).

(56) References Cited

OTHER PUBLICATIONS

Quesniaux, V. F.J. et al., "Hematopoiesis, including lymphocyte developmet and maturation," Principles of Immunopharmacology, pp. 3-17 (2005).

Raben, N. et al., "A Motif in Human Histidyl-tRNA Synthetase Which Is Shared among Several Aminoacyl-tRNA Synthetases Is a Coiled-coil That is Essential for Enzymatic Activity and Contains the Major Autoantigenic Epitope," The Journal of Biological Chemistry, 269(39):24277-24283 (1994).

Reed, V. S. et al., "Characterization of a Novel N-terminal Peptide in Human Aspartyl-tRNA Synthetase," Journal of Biological Chemistry, 269(52):32937-32941 (1994).

Rho, S. B. et al., "Genetic dissection of protein-protein interactions in multi-tRNA synthetase complex," Proc. Natl. Acad. Sci. USA, 96:4488-4493 (1999).

Richardson, R. M. et al., "Role of the cytoplasmic tails of CXCR1 and CXCR2 in mediating leukocyte migration, activation, and regulation," Journal of Immunology, 170(6):2904-2911 (2003).

Rudinger-Thirion et al., "Misfolded human tRNA isodecoder binds and neutralizes a 3' UTR-embedded Alu element," Proc. Natl. Acad. Sci. USA, 108(40):E794-E802 (2011).

Sato et al., "Synergy and Cross-Tolerance Between Toll-Like Receptor (TLR) 2- and TLR4-Mediated Signaling Pathways," The Journal of Immunology, 165:7096-7101 (2000).

Sauna, Z. E. et al., "Silent polymorhisms speak: How they affect pharmacogenomics and the treatment of cancer," Cancer Res., 67(20):9609-9612 (2007).

Seburn, K. L. et al., "An active dominant mutation of glycyl-tRNA synthetase causes neuropathy in a Charcot-Marie-Tooth 2D mouse model," Neuron, 51(6):715-726 (2006).

Sen, S. et al., "Developments in directed evolution for improving enzyme functions," Appl. Biochem. Biotechnol., 143:212-223 (2007).

Smith, D. F. et al., "Leukocyte phosphoinositide-3 kinase γ is required for chemokine-induced, sustained adhesion under flow in vivo," Journal of Leukocyte Biology, 80(6):1491-1499 (2006).

Soejima, M. et al., "Role of Innate Immunity in a Murine Model of Histidyl-Transfer RNA Snythetase (Jo-1)-Mediated Myositis," Arthritis and Rheumatism, 63(2):479-487 (2011).

Sultan, S. M. et al., "Re-classifiyng myositis," Rheumatology, 49:831-833 (2010).

Tarabishy, A. B. et al., "Retinal Vasculitis Associated with the Anti-Synthetase Syndrome," Ocular Immunology & Inflamation, 18(1):16-18 (2010).

Targoff, I. N., "Update on myositis-specific and myositis-associated autoantibodies," Current Opinion in Rheumatology, 12:475-481 (2000).

Traves, S. L. et al., "Specific CXC but not CC chemokines cause elevated monocyte migration in COPD: a role for $CXCR_2$," Journal of Leukocyte Biology, 76(2):441-450 (2004).

Tsui, H. W. et al., "Transcriptional analyses of the gene region that encodes human histidyl-tRNA sysnthetase: identification of a novel bidirectional regulatory element," Gene, 131:201-208 (1993).

Tzioufas, A. G. et al., "Antisynthetase syndrome," Orphanet Encyclopedia, http://www.orpha.net/data/patho/GB/uk-antisynthetase.pdf.pp. 1-5 Nov. 2001.

Veronese, F. M. et al., "Preface: Introduction and overview of peptide and protein pegylation," Advanced Drug Delivery Reviews, 54:453-456 (2002).

Wakasugi, K. et al., "Two distinct cytokines released from a human aminoacyl-tRNA synthetase," Science, 284:147-151 (1999).

Wakasugi, K. et al., "A human aminoacyl-tRNA synthetase as a regulator of angiogenesis," PNAS USA, 99(1):173-177 (2002).

Wakasugi, K. et al., "Induction of angiogenesis by a frament of human tyrosyl-tRNA synthetase," The Journal of Biological Chemistry, 277(23):20124-20126 (2002).

Wallace, E. A. et al., "Diagnosis and management of inflammatory muscle disease," The Journal of Musculoskeletal Medicine, 27(12):1-7 (2010).

Wan et al., "Epitope Map for a Growth Hormone Receptor Agonist Monoclonal Antibody, MAb 263," Molecular Endocrinology, 17(11):2240-2250 (2003).

Whisstock, J. C. et al., "Prediction of protein function from protein sequence," Q. Rev. Biophysics., 36(3):307-340 (2003).

Wishart, M. J. et al., "A single mutation converts a novel phosphotyrosine binding domain into a dual-specificity phosphatase," J. Biol. Chem., 270(45):26782-26785 (1995).

Witkowski, A. et al., "Conversion of β-ketoacyl synthase to a Malonyl Decarboxylase by replacement of the active cysteine with glutamine," Biochemistry, 38:11643-11650 (1999).

WPI Database Accession No. 2002-090149 (2013).
WPI Database Accession No. 2002-501208 (2013).
WPI Database Accession No. 2002-501210 (2013).
WPI Database Accession No. 2002-692409 (2013).
WPI Database Accession No. 2002-714440 (2013).

Xie, W. et al., "Long-range structural effects of a Charcot-Marie-Tooth disease-causing mutation in human glycyl-tRNA synthetase," PNAS, 104(24):9976-9981 (2007).

Yang, X-L et al., "Crystal structure of a human aminoacyl-tRNA synthetase cytokine," PNAS, 99(24):15369-15374 (2002).

Yang, X-L et al., "Relationship of two human tRNA synthetases used in cell signaling," Trends in Biochemical Sciences, 29(5):250-256 (2004).

Yang, X-L et al., "Gain-of-Function Mutational Activation of Human tRNA Synthetase Procytokine," Chemistry & Biology, 14(12):1323-1333 (2007).

Yokoyama, M. et al., "Effects of lipoprotein lipase and statins on cholesterol uptake into heart and skeletal muscle," J. Lipid Res., 48:646-655 (2007).

Yousem, S. A. et al., "The pulmonary histopathologic manifestations of the anti-Jo-1 tRNA synthetase syndrome," Modern Pathology, 23:874-880 (2010).

Yu, Y. et al., "Crystal structure of human tryptophanyl-tRNA synthetase catalytic fragment," The Journal of Biological Chemistry, 279(9):8378-8388 (2004).

Zalipsky, S. et al., "Use of functionalized poly(ethylene glycol)s for modification of polypeptides," Chapter 21 In: Poly(Ethylene Glycol) Chemistry: Biotechnical and Biomedical Applications, Harris, J. M. (ed.), pp. 347-370, Plenum Press, New York (1992).

Zhou, Q. et al., "Orthogonal use of a human tRNA synthetase active site to achieve multifunctionality," Nature Structural & Molecular Biology, 17(1):57-62 (2010).

Zwijnenburg, P. J. G. et al., B-1426, "Tyrosyl tRNA synthetase is a chemotactic factor in cerebrospinal fluid from patients with bacterial meningitis," Abstracts of the 42nd Interscience Conference on Antimicrobial Agents and Chemotherapy, San Diego, California, Sep. 27-30, 2002, Session 156(B), p. 55.

Chappel, M. S. et al., "Identification of the Fcγ Receptor Class I Binding Site in Human IgG Through the Use of Recombinant IgG1/IgG2 Hybrid and Point-Mutated Antibodies," PNAS USA, 88(20):9036-9040 (1991).

Guo, H. H., "Protein tolerance to random amino acid change," PNAS, 101(25):9205-9210 (Jun. 22, 2004).

Kern, D. et al., "The three cysteine residues of cytoplasmic aspartyl-tRNA synthetase from *Saccharomyces cerecisiae* are not essential for its activity," Eur. J. Biochem., 193(1):97-103 (1990).

Matthews, B. W., "Structural and genetic analysis of protein stability," Annu. Rev. Biochem., 62:139-160 (1993).

SEQUENCE LISTING

```
<160> NUMBER OF SEQ ID NOS: 198

<210> SEQ ID NO 1
<211> LENGTH: 501
<212> TYPE: PRT
<213> ORGANISM: Homo sapiens

<400> SEQUENCE: 1

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
```

```
               35                  40                  45
Arg Asp Leu Thr Ile Gln Lys Ala Asp Glu Val Val Trp Val Arg Ala
 50                  55                  60

Arg Val His Thr Ser Arg Ala Lys Gly Lys Gln Cys Phe Leu Val Leu
 65                  70                  75                  80

Arg Gln Gln Gln Phe Asn Val Gln Ala Leu Val Ala Val Gly Asp His
                     85                  90                  95

Ala Ser Lys Gln Met Val Lys Phe Ala Ala Asn Ile Asn Lys Glu Ser
                100                 105                 110

Ile Val Asp Val Glu Gly Val Arg Lys Val Asn Gln Lys Ile Gly
                115                 120                 125

Ser Cys Thr Gln Gln Asp Val Glu Leu His Val Gln Lys Ile Tyr Val
                130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val Ile Asp Leu Arg Thr Ser Thr Ser
                180                 185                 190

Gln Ala Val Phe Arg Leu Gln Ser Gly Ile Cys His Leu Phe Arg Glu
                195                 200                 205

Thr Leu Ile Asn Lys Gly Phe Val Glu Ile Gln Thr Pro Lys Ile Ile
210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Cys Ala Asp Phe Glu Lys Val Phe Ser Ile Gly Pro Val Phe
                260                 265                 270

Arg Ala Glu Asp Ser Asn Thr His Arg His Leu Thr Glu Phe Val Gly
                275                 280                 285

Leu Asp Ile Glu Met Ala Phe Asn Tyr His Tyr His Glu Val Met Glu
                290                 295                 300

Glu Ile Ala Asp Thr Met Val Gln Ile Phe Lys Gly Leu Gln Glu Arg
305                 310                 315                 320

Phe Gln Thr Glu Ile Gln Thr Val Asn Lys Gln Phe Pro Cys Glu Pro
                325                 330                 335

Phe Lys Phe Leu Glu Pro Thr Leu Arg Leu Glu Tyr Cys Glu Ala Leu
                340                 345                 350

Ala Met Leu Arg Glu Ala Gly Val Glu Met Gly Asp Glu Asp Asp Leu
                355                 360                 365

Ser Thr Pro Asn Glu Lys Leu Leu Gly His Leu Val Lys Glu Lys Tyr
                370                 375                 380

Asp Thr Asp Phe Tyr Ile Leu Asp Lys Tyr Pro Leu Ala Val Arg Pro
385                 390                 395                 400

Phe Tyr Thr Met Pro Asp Pro Arg Asn Pro Lys Gln Ser Asn Ser Tyr
                405                 410                 415

Asp Met Phe Met Arg Gly Glu Glu Ile Leu Ser Gly Ala Gln Arg Ile
                420                 425                 430

His Asp Pro Gln Leu Leu Thr Glu Arg Ala Leu His His Gly Ile Asp
                435                 440                 445

Leu Glu Lys Ile Lys Ala Tyr Ile Asp Ser Phe Arg Phe Gly Ala Pro
                450                 455                 460
```

```
Pro His Ala Gly Gly Gly Ile Gly Leu Glu Arg Val Thr Met Leu Phe
465                 470                 475                 480

Leu Gly Leu His Asn Val Arg Gln Thr Ser Met Phe Pro Arg Asp Pro
            485                 490                 495

Lys Arg Leu Thr Pro
            500

<210> SEQ ID NO 2
<211> LENGTH: 1506
<212> TYPE: DNA
<213> ORGANISM: Homo sapiens

<400> SEQUENCE: 2
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgcttc cttagtccta     240
cgtcagcagc agtttaatgt ccaggctctt gtggcggtgg agaccatgca agcaagcag      300 atggttaaat ttgctgccaa catcaacaaa gagagcattg tggatgtaga aggtgttgtg     360
agaaaagtga atcagaaaat tggaagctgt acacagcaag acgttgagtt acatgttcag     420
aagatttatg tgatcagttt ggctgaaccc cgtctgcccc tgcagctgga tgatgctgtt     480
cggcctgagg cagaaggaga agaggaagga agagctactg ttaaccagga tacaagatta     540
gacaacagag tcattgatct taggacatca actagtcagg cagtcttccg tctccagtct     600
ggcatctgcc atctcttccg agaaacttta attaacaaag ttttgtggaa atccaaact      660 cctaaaatta tttcagctgc cagtgaagga ggagccaatg tttttactgt gtcatatttt     720
aaaaataatg catacctggc tcagtcccca cagctatata agcaaatgtg catttgtgct     780
gattttgaga aggttttctc tattggacca gtattcagag cggaagactc taatacccat     840
agacatctaa ctgagtttgt tggtttggac attgaaatgg ctttaattac ccattaccac     900
gaagttatgg aagaaattgc tgacaccatg gtacaaatat caaaggact tcaagaaagg     960 tttcagactg aaattcaaac agtgaataaa cagttcccat gtgagccatt caaatttttg    1020
gagccaactc taagactaga atattgtgaa gcattggcta tgcttaggga agctggagtc    1080
gaaatgggag atgaagacga tctgagcaca ccaaatgaaa agctgttggg tcatttggta    1140
aaggaaaagt atgatacaga tttttatatt cttgataaat atccattggc tgtaagacct    1200
ttctatacca tgcctgaccc aagaaatccc aaacagtcca actcttacga tatgttcatg    1260
agaggagaag aaatattgtc aggagctcaa agaatacatg atcctcaact gctaacagag    1320
agagctttac atcatggaat tgatttggag aaaattaagg cttacattga ttccttccgc    1380
tttggagccc ctcctcatgc tggtggaggc attggattgg aacgagttac tatgctgttt    1440
ctgggattgc ataatgttcg tcagacctcc atgttccctc gtgatcccaa acgactcact    1500
ccttag                                                               1506

<210> SEQ ID NO 3
<211> LENGTH: 154
<212> TYPE: PRT
<213> ORGANISM: Homo sapiens

<400> SEQUENCE: 3

Met Pro Ser Ala Ser Ala Ser Arg Lys Ser Gln Glu Lys Pro Arg Glu
```

```
                1               5                  10                 15
        Ile Met Asp Ala Ala Glu Asp Tyr Ala Lys Glu Arg Tyr Gly Ile Ser
                        20                  25                 30

Ser Met Ile Gln Ser Gln Glu Lys Pro Asp Arg Val Leu Val Arg Val
                        35                  40                 45

Arg Asp Leu Thr Ile Gln Lys Ala Asp Glu Val Val Trp Val Arg Ala
                50                  55                  60

Arg Val His Thr Ser Arg Ala Lys Gly Lys Gln Cys Phe Leu Val Leu
        65                      70                  75                 80

Arg Gln Gln Gln Phe Asn Val Gln Ala Leu Val Ala Val Gly Asp His
                            85                  90                  95

Ala Ser Lys Gln Met Val Lys Phe Ala Ala Asn Ile Asn Lys Glu Ser
                        100                 105                110

Ile Val Asp Val Glu Gly Val Val Arg Lys Val Asn Gln Lys Ile Gly
                        115                 120                 125

Ser Cys Thr Gln Gln Asp Val Glu Leu His Val Gln Lys Ile Tyr Val
                    130                 135                 140

Ile Ser Leu Ala Glu Pro Arg Leu Pro Leu
        145                     150
```

<210> SEQ ID NO 4
<211> LENGTH: 171
<212> TYPE: PRT
<213> ORGANISM: Homo sapiens

<400> SEQUENCE: 4

```
        Met Pro Ser Ala Ser Ala Ser Arg Lys Ser Gln Glu Lys Pro Arg Glu
        1               5                   10                 15

Ile Met Asp Ala Ala Glu Asp Tyr Ala Lys Glu Arg Tyr Gly Ile Ser
                        20                  25                 30

Ser Met Ile Gln Ser Gln Glu Lys Pro Asp Arg Val Leu Val Arg Val
                        35                  40                 45

Arg Asp Leu Thr Ile Gln Lys Ala Asp Glu Val Val Trp Val Arg Ala
                50                  55                  60

Arg Val His Thr Ser Arg Ala Lys Gly Lys Gln Cys Phe Leu Val Leu
        65                      70                  75                 80

Arg Gln Gln Gln Phe Asn Val Gln Ala Leu Val Ala Val Gly Asp His
                            85                  90                  95

Ala Ser Lys Gln Met Val Lys Phe Ala Ala Asn Ile Asn Lys Glu Ser
                        100                 105                110

Ile Val Asp Val Glu Gly Val Val Arg Lys Val Asn Gln Lys Ile Gly
                        115                 120                 125

Ser Cys Thr Gln Gln Asp Val Glu Leu His Val Gln Lys Ile Tyr Val
                    130                 135                 140

Ile Ser Leu Ala Glu Pro Arg Leu Pro Leu Gln Leu Asp Asp Ala Val
        145                     150                 155                160

Arg Pro Glu Ala Glu Gly Glu Glu Glu Gly Arg
                        165                 170
```

<210> SEQ ID NO 5
<211> LENGTH: 174
<212> TYPE: PRT
<213> ORGANISM: Homo sapiens

<400> SEQUENCE: 5

Met Pro Ser Ala Ser Ala Ser Arg Lys Ser Gln Glu Lys Pro Arg Glu

```
            1               5                  10                 15
         Ile Met Asp Ala Ala Glu Asp Tyr Ala Lys Glu Arg Tyr Gly Ile Ser
                        20                 25                 30

Ser Met Ile Gln Ser Gln Glu Lys Pro Asp Arg Val Leu Val Arg Val
                        35                 40                 45

Arg Asp Leu Thr Ile Gln Lys Ala Asp Glu Val Val Trp Val Arg Ala
                        50                 55                 60

Arg Val His Thr Ser Arg Ala Lys Gly Lys Gln Cys Phe Leu Val Leu
         65                 70                 75                 80

Arg Gln Gln Gln Phe Asn Val Gln Ala Leu Val Ala Val Gly Asp His
                        85                 90                 95

Ala Ser Lys Gln Met Val Lys Phe Ala Ala Asn Ile Asn Lys Glu Ser
                        100                105                110

Ile Val Asp Val Glu Gly Val Val Arg Lys Val Asn Gln Lys Ile Gly
                        115                120                125

Ser Cys Thr Gln Gln Asp Val Glu Leu His Val Gln Lys Ile Tyr Val
                        130                135                140

Ile Ser Leu Ala Glu Pro Arg Leu Pro Leu Gln Leu Asp Asp Ala Val
         145                150                155                160

Arg Pro Glu Ala Glu Gly Glu Glu Gly Arg Ala Thr Val
                        165                170

<210> SEQ ID NO 6
<211> LENGTH: 182
<212> TYPE: PRT
<213> ORGANISM: Homo sapiens

<400> SEQUENCE: 6

Met Pro Ser Ala Ser Ala Ser Arg Lys Ser Gln Glu Lys Pro Arg Glu
         1               5                  10                 15

Ile Met Asp Ala Ala Glu Asp Tyr Ala Lys Glu Arg Tyr Gly Ile Ser
                        20                 25                 30

Ser Met Ile Gln Ser Gln Glu Lys Pro Asp Arg Val Leu Val Arg Val
                        35                 40                 45

Arg Asp Leu Thr Ile Gln Lys Ala Asp Glu Val Val Trp Val Arg Ala
                        50                 55                 60

Arg Val His Thr Ser Arg Ala Lys Gly Lys Gln Cys Phe Leu Val Leu
         65                 70                 75                 80

Arg Gln Gln Gln Phe Asn Val Gln Ala Leu Val Ala Val Gly Asp His
                        85                 90                 95

Ala Ser Lys Gln Met Val Lys Phe Ala Ala Asn Ile Asn Lys Glu Ser
                        100                105                110

Ile Val Asp Val Glu Gly Val Val Arg Lys Val Asn Gln Lys Ile Gly
                        115                120                125

Ser Cys Thr Gln Gln Asp Val Glu Leu His Val Gln Lys Ile Tyr Val
                        130                135                140

Ile Ser Leu Ala Glu Pro Arg Leu Pro Leu Gln Leu Asp Asp Ala Val
         145                150                155                160

Arg Pro Glu Ala Glu Gly Glu Glu Gly Arg Ala Thr Val Asn Gln
                        165                170                175

Asp Thr Arg Leu Asp Asn
                        180

<210> SEQ ID NO 7
<211> LENGTH: 184
```

```
<212> TYPE: PRT
<213> ORGANISM: Homo sapiens

<400> SEQUENCE: 7

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
        130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val
                180

<210> SEQ ID NO 8
<211> LENGTH: 274
<212> TYPE: PRT
<213> ORGANISM: Homo sapiens

<400> SEQUENCE: 8

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
        130                 135                 140

Ile Ser Leu Ala Glu Pro Arg Leu Pro Leu Gln Leu Asp Asp Ala Val
145                 150                 155                 160
```

-continued

Arg Pro Glu Ala Glu Gly Glu Glu Gly Arg Ala Thr Val Asn Gln
        165                 170                 175

Asp Thr Arg Leu Asp Asn Arg Val Ile Asp Leu Arg Thr Ser Thr Ser
        180                 185                 190

Gln Ala Val Phe Arg Leu Gln Ser Gly Ile Cys His Leu Phe Arg Glu
        195                 200                 205

Thr Leu Ile Asn Lys Gly Phe Val Glu Ile Gln Thr Pro Lys Ile Ile
        210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Cys Ala Asp Phe Glu Lys Val Phe Ser Ile Gly Pro Val Phe
                260                 265                 270

Arg Ala

<210> SEQ ID NO 9
<211> LENGTH: 224
<212> TYPE: PRT
<213> ORGANISM: Homo sapiens

<400> SEQUENCE: 9

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
        130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val Ile Asp Leu Arg Thr Ser Thr Ser
        180                 185                 190

Gln Ala Val Phe Arg Leu Gln Ser Gly Ile Cys His Leu Phe Arg Glu
        195                 200                 205

Thr Leu Ile Asn Lys Gly Phe Val Glu Ile Gln Thr Pro Lys Ile Ile
        210                 215                 220

<210> SEQ ID NO 10
<211> LENGTH: 255
<212> TYPE: PRT
<213> ORGANISM: Homo sapiens

```
<400> SEQUENCE: 10

Gln Glu Lys Pro Asp Arg Val Leu Val Arg Val Arg Asp Leu Thr Ile
1               5                   10                  15

Gln Lys Ala Asp Glu Val Val Trp Val Arg Ala Arg Val His Thr Ser
            20                  25                  30

Arg Ala Lys Gly Lys Gln Cys Phe Leu Val Leu Arg Gln Gln Gln Phe
        35                  40                  45

Asn Val Gln Ala Leu Val Ala Val Gly Asp His Ala Ser Lys Gln Met
    50                  55                  60

Val Lys Phe Ala Ala Asn Ile Asn Lys Glu Ser Ile Val Asp Val Glu
65                  70                  75                  80

Gly Val Val Arg Lys Val Asn Gln Lys Ile Gly Ser Cys Thr Gln Gln
                85                  90                  95

Asp Val Glu Leu His Val Gln Lys Ile Tyr Val Ile Ser Leu Ala Glu
            100                 105                 110

Pro Arg Leu Pro Leu Gln Leu Asp Asp Ala Val Arg Pro Glu Ala Glu
        115                 120                 125

Gly Glu Glu Glu Gly Arg Ala Thr Val Asn Gln Asp Thr Arg Leu Asp
    130                 135                 140

Asn Arg Val Ile Asp Leu Arg Thr Ser Thr Ser Gln Ala Val Phe Arg
145                 150                 155                 160

Leu Gln Ser Gly Ile Cys His Leu Phe Arg Glu Thr Leu Ile Asn Lys
                165                 170                 175

Gly Phe Val Glu Ile Gln Thr Pro Lys Ile Ile Ser Ala Ala Ser Glu
            180                 185                 190

Gly Gly Ala Asn Val Phe Thr Val Ser Tyr Phe Lys Asn Asn Ala Tyr
        195                 200                 205

Leu Ala Gln Ser Pro Gln Leu Tyr Lys Gln Met Cys Ile Cys Ala Asp
    210                 215                 220

Phe Glu Lys Val Phe Ser Ile Gly Pro Val Phe Arg Ala Glu Asp Ser
225                 230                 235                 240

Asn Thr His Arg His Leu Thr Glu Phe Val Gly Leu Asp Ile Glu
                245                 250                 255

<210> SEQ ID NO 11
<211> LENGTH: 132
<212> TYPE: PRT
<213> ORGANISM: Homo sapiens

<400> SEQUENCE: 11

Asp Tyr Ala Lys Glu Arg Tyr Gly Ile Ser Ser Met Ile Gln Ser Gln
1               5                   10                  15

Glu Lys Pro Asp Arg Val Leu Val Arg Val Arg Asp Leu Thr Ile Gln
            20                  25                  30

Lys Ala Asp Glu Val Val Trp Val Arg Ala Arg Val His Thr Ser Arg
        35                  40                  45

Ala Lys Gly Lys Gln Cys Phe Leu Val Leu Arg Gln Gln Gln Phe Asn
    50                  55                  60

Val Gln Ala Leu Val Ala Val Gly Asp His Ala Ser Lys Gln Met Val
65                  70                  75                  80

Lys Phe Ala Ala Asn Ile Asn Lys Glu Ser Ile Val Asp Val Glu Gly
                85                  90                  95

Val Val Arg Lys Val Asn Gln Lys Ile Gly Ser Cys Thr Gln Gln Asp
            100                 105                 110
```

Val Glu Leu His Val Gln Lys Ile Tyr Val Ile Ser Leu Ala Glu Pro
            115                 120                 125

Arg Leu Pro Leu
        130

<210> SEQ ID NO 12
<211> LENGTH: 122
<212> TYPE: PRT
<213> ORGANISM: Homo sapiens

<400> SEQUENCE: 12

Ser Met Ile Gln Ser Gln Glu Lys Pro Asp Arg Val Leu Val Arg Val
1               5                   10                  15

Arg Asp Leu Thr Ile Gln Lys Ala Asp Glu Val Val Trp Val Arg Ala
            20                  25                  30

Arg Val His Thr Ser Arg Ala Lys Gly Lys Gln Cys Phe Leu Val Leu
        35                  40                  45

Arg Gln Gln Gln Phe Asn Val Gln Ala Leu Val Ala Val Gly Asp His
    50                  55                  60

Ala Ser Lys Gln Met Val Lys Phe Ala Ala Asn Ile Asn Lys Glu Ser
65                  70                  75                  80

Ile Val Asp Val Glu Gly Val Val Arg Lys Val Asn Gln Lys Ile Gly
                85                  90                  95

Ser Cys Thr Gln Gln Asp Val Glu Leu His Val Gln Lys Ile Tyr Val
            100                 105                 110

Ile Ser Leu Ala Glu Pro Arg Leu Pro Leu
        115                 120

<210> SEQ ID NO 13
<211> LENGTH: 205
<212> TYPE: PRT
<213> ORGANISM: Homo sapiens

<400> SEQUENCE: 13

Tyr His Tyr His Glu Val Met Glu Glu Ile Ala Asp Thr Met Val Gln
1               5                   10                  15

Ile Phe Lys Gly Leu Gln Glu Arg Phe Gln Thr Glu Ile Gln Thr Val
            20                  25                  30

Asn Lys Gln Phe Pro Cys Glu Pro Phe Lys Phe Leu Glu Pro Thr Leu
        35                  40                  45

Arg Leu Glu Tyr Cys Glu Ala Leu Ala Met Leu Arg Glu Ala Gly Val
    50                  55                  60

Glu Met Gly Asp Glu Asp Leu Ser Thr Pro Asn Glu Lys Leu Leu
65                  70                  75                  80

Gly His Leu Val Lys Glu Lys Tyr Asp Thr Phe Tyr Ile Leu Asp
                85                  90                  95

Lys Tyr Pro Leu Ala Val Arg Pro Phe Tyr Thr Met Pro Asp Pro Arg
            100                 105                 110

Asn Pro Lys Gln Ser Asn Ser Tyr Asp Met Phe Met Arg Gly Glu Glu
        115                 120                 125

Ile Leu Ser Gly Ala Gln Arg Ile His Asp Pro Gln Leu Leu Thr Glu
    130                 135                 140

Arg Ala Leu His His Gly Ile Asp Leu Glu Lys Ile Lys Ala Tyr Ile
145                 150                 155                 160

Asp Ser Phe Arg Phe Gly Ala Pro Pro His Ala Gly Gly Ile Gly
                165                 170                 175

Leu Glu Arg Val Thr Met Leu Phe Leu Gly Leu His Asn Val Arg Gln
            180                 185                 190

Thr Ser Met Phe Pro Arg Asp Pro Lys Arg Leu Thr Pro
        195                 200                 205

<210> SEQ ID NO 14
<211> LENGTH: 401
<212> TYPE: PRT
<213> ORGANISM: Homo sapiens

<400> SEQUENCE: 14

Met Val Lys Phe Ala Ala Asn Ile Asn Lys Glu Ser Ile Val Asp Val
1               5                   10                  15

Glu Gly Val Val Arg Lys Val Asn Gln Lys Ile Gly Ser Cys Thr Gln
            20                  25                  30

Gln Asp Val Glu Leu His Val Gln Lys Ile Tyr Val Ile Ser Leu Ala
        35                  40                  45

Glu Pro Arg Leu Pro Leu Gln Leu Asp Asp Ala Val Arg Pro Glu Ala
    50                  55                  60

Glu Gly Glu Glu Glu Gly Arg Ala Thr Val Asn Gln Asp Thr Arg Leu
65              70                  75                  80

Asp Asn Arg Val Ile Asp Leu Arg Thr Ser Thr Ser Gln Ala Val Phe
                85                  90                  95

Arg Leu Gln Ser Gly Ile Cys His Leu Phe Arg Glu Thr Leu Ile Asn
            100                 105                 110

Lys Gly Phe Val Glu Ile Gln Thr Pro Lys Ile Ile Ser Ala Ala Ser
        115                 120                 125

Glu Gly Gly Ala Asn Val Phe Thr Val Ser Tyr Phe Lys Asn Asn Ala
130             135                 140

Tyr Leu Ala Gln Ser Pro Gln Leu Tyr Lys Gln Met Cys Ile Cys Ala
145                 150                 155                 160

Asp Phe Glu Lys Val Phe Ser Ile Gly Pro Val Phe Arg Ala Glu Asp
                165                 170                 175

Ser Asn Thr His Arg His Leu Thr Glu Phe Val Gly Leu Asp Ile Glu
            180                 185                 190

Met Ala Phe Asn Tyr His Tyr His Glu Val Met Glu Glu Ile Ala Asp
        195                 200                 205

Thr Met Val Gln Ile Phe Lys Gly Leu Gln Glu Arg Phe Gln Thr Glu
    210                 215                 220

Ile Gln Thr Val Asn Lys Gln Phe Pro Cys Glu Pro Phe Lys Phe Leu
225                 230                 235                 240

Glu Pro Thr Leu Arg Leu Glu Tyr Cys Glu Ala Leu Ala Met Leu Arg
                245                 250                 255

Glu Ala Gly Val Glu Met Gly Asp Glu Asp Leu Ser Thr Pro Asn
            260                 265                 270

Glu Lys Leu Leu Gly His Leu Val Lys Glu Lys Tyr Asp Thr Asp Phe
        275                 280                 285

Tyr Ile Leu Asp Lys Tyr Pro Leu Ala Val Arg Pro Phe Tyr Thr Met
    290                 295                 300

Pro Asp Pro Arg Asn Pro Lys Gln Ser Asn Ser Tyr Asp Met Phe Met
305                 310                 315                 320

Arg Gly Glu Glu Ile Leu Ser Gly Ala Gln Arg Ile His Asp Pro Gln
                325                 330                 335

Leu Leu Thr Glu Arg Ala Leu His His Gly Ile Asp Leu Glu Lys Ile
            340                 345                 350

-continued

```
Lys Ala Tyr Ile Asp Ser Phe Arg Phe Gly Ala Pro Pro His Ala Gly
            355                 360                 365

Gly Gly Ile Gly Leu Glu Arg Val Thr Met Leu Phe Leu Gly Leu His
    370                 375                 380

Asn Val Arg Gln Thr Ser Met Phe Pro Arg Asp Pro Lys Arg Leu Thr
385                 390                 395                 400

Pro

<210> SEQ ID NO 15
<211> LENGTH: 470
<212> TYPE: PRT
<213> ORGANISM: Homo sapiens

<400> SEQUENCE: 15

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Gly Lys Gln Cys Phe Leu Val
        35                  40                  45

Leu Arg Gln Gln Gln Phe Asn Val Gln Ala Leu Val Ala Val Gly Asp
    50                  55                  60

His Ala Ser Lys Gln Met Val Lys Phe Ala Ala Asn Ile Asn Lys Glu
65                  70                  75                  80

Ser Ile Val Asp Val Glu Gly Val Val Arg Lys Val Asn Gln Lys Ile
                85                  90                  95

Gly Ser Cys Thr Gln Gln Asp Val Glu Leu His Val Gln Lys Ile Tyr
            100                 105                 110

Val Ile Ser Leu Ala Glu Pro Arg Leu Pro Leu Gln Leu Asp Asp Ala
        115                 120                 125

Val Arg Pro Glu Ala Gly Glu Gly Glu Gly Arg Ala Thr Val Asn
    130                 135                 140

Gln Asp Thr Arg Leu Asp Asn Arg Val Ile Asp Leu Arg Thr Ser Thr
145                 150                 155                 160

Ser Gln Ala Val Phe Arg Leu Gln Ser Gly Ile Cys His Leu Phe Arg
                165                 170                 175

Glu Thr Leu Ile Asn Lys Gly Phe Val Glu Ile Gln Thr Pro Lys Ile
            180                 185                 190

Ile Ser Ala Ala Ser Glu Gly Gly Ala Asn Val Phe Thr Val Ser Tyr
        195                 200                 205

Phe Lys Asn Asn Ala Tyr Leu Ala Gln Ser Pro Gln Leu Tyr Lys Gln
    210                 215                 220

Met Cys Ile Cys Ala Asp Phe Glu Lys Val Phe Ser Ile Gly Pro Val
225                 230                 235                 240

Phe Arg Ala Glu Asp Ser Asn Thr His Arg His Leu Thr Glu Phe Val
                245                 250                 255

Gly Leu Asp Ile Glu Met Ala Phe Asn Tyr His Tyr His Glu Val Met
            260                 265                 270

Glu Glu Ile Ala Asp Thr Met Val Gln Ile Phe Lys Gly Leu Gln Glu
        275                 280                 285

Arg Phe Gln Thr Glu Ile Gln Thr Val Asn Lys Gln Phe Pro Cys Glu
    290                 295                 300

Pro Phe Lys Phe Leu Glu Pro Thr Leu Arg Leu Glu Tyr Cys Glu Ala
305                 310                 315                 320
```

```
Leu Ala Met Leu Arg Glu Ala Gly Val Glu Met Gly Asp Glu Asp Asp
                325                 330                 335

Leu Ser Thr Pro Asn Glu Lys Leu Leu Gly His Leu Val Lys Glu Lys
            340                 345                 350

Tyr Asp Thr Asp Phe Tyr Ile Leu Asp Lys Tyr Pro Leu Ala Val Arg
        355                 360                 365

Pro Phe Tyr Thr Met Pro Asp Pro Arg Asn Pro Lys Gln Ser Asn Ser
370                 375                 380

Tyr Asp Met Phe Met Arg Gly Glu Glu Ile Leu Ser Gly Ala Gln Arg
385                 390                 395                 400

Ile His Asp Pro Gln Leu Leu Thr Glu Arg Ala Leu His Gly Ile
                405                 410                 415

Asp Leu Glu Lys Ile Lys Ala Tyr Ile Asp Ser Phe Arg Phe Gly Ala
                420                 425                 430

Pro Pro His Ala Gly Gly Ile Gly Leu Glu Arg Val Thr Met Leu
            435                 440                 445

Phe Leu Gly Leu His Asn Val Arg Gln Thr Ser Met Phe Pro Arg Asp
450                 455                 460

Pro Lys Arg Leu Thr Pro
465                 470

<210> SEQ ID NO 16
<211> LENGTH: 454
<212> TYPE: PRT
<213> ORGANISM: Homo sapiens

<400> SEQUENCE: 16

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Thr Ser Thr
    130                 135                 140

Ser Gln Ala Val Phe Arg Leu Gln Ser Gly Ile Cys His Leu Phe Arg
145                 150                 155                 160

Glu Thr Leu Ile Asn Lys Gly Phe Val Glu Ile Gln Thr Pro Lys Ile
                165                 170                 175

Ile Ser Ala Ala Ser Glu Gly Gly Ala Asn Val Phe Thr Val Ser Tyr
            180                 185                 190

Phe Lys Asn Asn Ala Tyr Leu Ala Gln Ser Pro Gln Leu Tyr Lys Gln
        195                 200                 205

Met Cys Ile Cys Ala Asp Phe Glu Lys Val Phe Ser Ile Gly Pro Val
```

-continued

```
                     210                 215                 220
Phe Arg Ala Glu Asp Ser Asn Thr His Arg His Leu Thr Glu Phe Val
225                 230                 235                 240

Gly Leu Asp Ile Glu Met Ala Phe Asn Tyr His Tyr His Glu Val Met
                245                 250                 255

Glu Glu Ile Ala Asp Thr Met Val Gln Ile Phe Lys Gly Leu Gln Glu
                260                 265                 270

Arg Phe Gln Thr Glu Ile Gln Thr Val Asn Lys Gln Phe Pro Cys Glu
                275                 280                 285

Pro Phe Lys Phe Leu Glu Pro Thr Leu Arg Leu Glu Tyr Cys Glu Ala
            290                 295                 300

Leu Ala Met Leu Arg Glu Ala Gly Val Glu Met Gly Asp Glu Asp Asp
305                 310                 315                 320

Leu Ser Thr Pro Asn Glu Lys Leu Leu Gly His Leu Val Lys Glu Lys
                325                 330                 335

Tyr Asp Thr Asp Phe Tyr Ile Leu Asp Lys Tyr Pro Leu Ala Val Arg
                340                 345                 350

Pro Phe Tyr Thr Met Pro Asp Pro Arg Asn Pro Lys Gln Ser Asn Ser
            355                 360                 365

Tyr Asp Met Phe Met Arg Gly Glu Glu Ile Leu Ser Gly Ala Gln Arg
370                 375                 380

Ile His Asp Pro Gln Leu Leu Thr Glu Arg Ala Leu His His Gly Ile
385                 390                 395                 400

Asp Leu Glu Lys Ile Lys Ala Tyr Ile Asp Ser Phe Arg Phe Gly Ala
                405                 410                 415

Pro Pro His Ala Gly Gly Ile Gly Leu Glu Arg Val Thr Met Leu
            420                 425                 430

Phe Leu Gly Leu His Asn Val Arg Gln Thr Ser Met Phe Pro Arg Asp
                435                 440                 445

Pro Lys Arg Leu Thr Pro
            450

<210> SEQ ID NO 17
<211> LENGTH: 452
<212> TYPE: PRT
<213> ORGANISM: Homo sapiens

<400> SEQUENCE: 17

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
            115                 120                 125
```

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                    165                 170                 175

Asp Thr Arg Leu Asp Asn Arg Val Ile Asp Leu Arg Thr Ser Thr Ser
            180                 185                 190

Gln Ala Val Phe Arg Leu Gln Ser Gly Ile Cys His Leu Phe Arg Glu
                195                 200                 205

Thr Leu Ile Asn Lys Gly Phe Val Glu Ile Gln Thr Pro Lys Ile Ile
    210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Cys Ala Asp Phe Glu Lys Val Phe Ser Ile Gly Pro Val Phe
                260                 265                 270

Arg Ala Glu Asp Ser Asn Thr His Arg His Leu Thr Glu Phe Val Gly
            275                 280                 285

Leu Asp Ile Glu Met Ala Phe Asn Tyr His Tyr His Glu Val Met Glu
    290                 295                 300

Glu Ile Ala Asp Thr Met Val Gln Ile Phe Lys Gly Leu Gln Glu Ser
305                 310                 315                 320

Thr Pro Asn Glu Lys Leu Leu Gly His Leu Val Lys Glu Lys Tyr Asp
                325                 330                 335

Thr Asp Phe Tyr Ile Leu Asp Lys Tyr Pro Leu Ala Val Arg Pro Phe
            340                 345                 350

Tyr Thr Met Pro Asp Pro Arg Asn Pro Lys Gln Ser Asn Ser Tyr Asp
    355                 360                 365

Met Phe Met Arg Gly Glu Glu Ile Leu Ser Gly Ala Gln Arg Ile His
370                 375                 380

Asp Pro Gln Leu Leu Thr Glu Arg Ala Leu His His Gly Ile Asp Leu
385                 390                 395                 400

Glu Lys Ile Lys Ala Tyr Ile Asp Ser Phe Arg Phe Gly Ala Pro Pro
                405                 410                 415

His Ala Gly Gly Gly Ile Gly Leu Glu Arg Val Thr Met Leu Phe Leu
            420                 425                 430

Gly Leu His Asn Val Arg Gln Thr Ser Met Phe Pro Arg Asp Pro Lys
    435                 440                 445

Arg Leu Thr Pro
    450

<210> SEQ ID NO 18
<211> LENGTH: 85
<212> TYPE: PRT
<213> ORGANISM: Homo sapiens

<400> SEQUENCE: 18

Met Pro Ser Ala Ser Ala Ser Arg Lys Ser Gln Glu Lys Pro Arg Glu
1               5                   10                  15

Ile Met Asp Ala Ala Glu Asp Trp Asn Glu Leu Leu Cys Cys Phe Trp
            20                  25                  30

Asp Cys Ile Met Phe Val Arg Pro Pro Cys Ser Leu Val Ile Pro Asn
        35                  40                  45

-continued

Asp Ser Leu Leu Lys Phe Thr Leu Cys His Leu Thr Pro Val Trp Met
        50                  55                  60

Thr Glu Arg Asp Pro Ala Ser Lys Lys Lys Lys Lys Glu Ser His
 65                  70                  75                  80

Thr Tyr Ser Phe Gln
            85

<210> SEQ ID NO 19
<211> LENGTH: 27
<212> TYPE: PRT
<213> ORGANISM: Homo sapiens

<400> SEQUENCE: 19

Met Pro Ser Ala Ser Ala Ser Arg Lys Ser Gln Glu Lys Pro Arg Glu
 1               5                  10                  15

Ile Met Asp Ala Ala Glu Gly Asn Ser Ala Ser
            20                  25

<210> SEQ ID NO 20
<211> LENGTH: 401
<212> TYPE: PRT
<213> ORGANISM: Homo sapiens

<400> SEQUENCE: 20

Met Val Lys Phe Ala Ala Asn Ile Asn Lys Glu Ser Ile Val Asp Val
 1               5                  10                  15

Glu Gly Val Val Arg Lys Val Asn Gln Lys Ile Gly Ser Cys Thr Gln
            20                  25                  30

Gln Asp Val Glu Leu His Val Gln Lys Ile Tyr Val Ile Ser Leu Ala
        35                  40                  45

Glu Pro Arg Leu Pro Leu Gln Leu Asp Asp Ala Val Arg Pro Glu Ala
    50                  55                  60

Glu Gly Glu Glu Glu Gly Arg Ala Thr Val Asn Gln Asp Thr Arg Leu
 65                  70                  75                  80

Asp Asn Arg Val Ile Asp Leu Arg Thr Ser Thr Ser Gln Ala Val Phe
                85                  90                  95

Arg Leu Gln Ser Gly Ile Cys His Leu Phe Arg Glu Thr Leu Ile Asn
            100                 105                 110

Lys Gly Phe Val Glu Ile Gln Thr Pro Lys Ile Ile Ser Ala Ala Ser
        115                 120                 125

Glu Gly Gly Ala Asn Val Phe Thr Val Ser Tyr Phe Lys Asn Asn Ala
    130                 135                 140

Tyr Leu Ala Gln Ser Pro Gln Leu Tyr Lys Gln Met Cys Ile Cys Ala
145                 150                 155                 160

Asp Phe Glu Lys Val Phe Ser Ile Gly Pro Val Phe Arg Ala Glu Asp
                165                 170                 175

Ser Asn Thr His Arg His Leu Thr Glu Phe Val Gly Leu Asp Ile Glu
            180                 185                 190

Met Ala Phe Asn Tyr His Tyr His Glu Val Met Glu Glu Ile Ala Asp
        195                 200                 205

Thr Met Val Gln Ile Phe Lys Gly Leu Gln Glu Arg Phe Gln Thr Glu
    210                 215                 220

Ile Gln Thr Val Asn Lys Gln Phe Pro Cys Glu Pro Phe Lys Phe Leu
225                 230                 235                 240

Glu Pro Thr Leu Arg Leu Glu Tyr Cys Glu Ala Leu Ala Met Leu Arg
                245                 250                 255

```
Glu Ala Gly Val Glu Met Gly Asp Glu Asp Leu Ser Thr Pro Asn
            260                 265                 270

Glu Lys Leu Leu Gly His Leu Val Lys Glu Lys Tyr Asp Thr Asp Phe
        275                 280                 285

Tyr Ile Leu Asp Lys Tyr Pro Leu Ala Val Arg Pro Phe Tyr Thr Met
    290                 295                 300

Pro Asp Pro Arg Asn Pro Lys Gln Ser Asn Ser Tyr Asp Met Phe Met
305                 310                 315                 320

Arg Gly Glu Glu Ile Leu Ser Gly Ala Gln Arg Ile His Asp Pro Gln
                325                 330                 335

Leu Leu Thr Glu Arg Ala Leu His His Gly Ile Asp Leu Glu Lys Ile
            340                 345                 350

Lys Ala Tyr Ile Asp Ser Phe Arg Phe Gly Ala Pro Pro His Ala Gly
        355                 360                 365

Gly Gly Ile Gly Leu Glu Arg Val Thr Met Leu Phe Leu Gly Leu His
    370                 375                 380

Asn Val Arg Gln Thr Ser Met Phe Pro Arg Asp Pro Lys Arg Leu Thr
385                 390                 395                 400

Pro

<210> SEQ ID NO 21
<211> LENGTH: 24
<212> TYPE: PRT
<213> ORGANISM: Homo sapiens

<400> SEQUENCE: 21

Met Leu Phe Leu Gly Leu His Asn Val Arg Gln Thr Ser Met Phe Pro
1               5                   10                  15

Arg Asp Pro Lys Arg Leu Thr Pro
            20

<210> SEQ ID NO 22
<211> LENGTH: 154
<212> TYPE: PRT
<213> ORGANISM: Artificial Sequence
<220> FEATURE:
<223> OTHER INFORMATION: DRS polypeptide variant with reduced cysteine
      content

<400> SEQUENCE: 22

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Ser Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125
```

```
Ser Cys Thr Gln Gln Asp Val Glu Leu His Val Gln Lys Ile Tyr Val
    130                 135                 140

Ile Ser Leu Ala Glu Pro Arg Leu Pro Leu
145                 150

<210> SEQ ID NO 23
<211> LENGTH: 154
<212> TYPE: PRT
<213> ORGANISM: Artificial Sequence
<220> FEATURE:
<223> OTHER INFORMATION: DRS polypetide variant with reduced cysteine
      content

<400> SEQUENCE: 23

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Ser Thr Gln Gln Asp Val Glu Leu His Val Gln Lys Ile Tyr Val
    130                 135                 140

Ile Ser Leu Ala Glu Pro Arg Leu Pro Leu
145                 150

<210> SEQ ID NO 24
<211> LENGTH: 154
<212> TYPE: PRT
<213> ORGANISM: Artificial Sequence
<220> FEATURE:
<223> OTHER INFORMATION: DRS polypetide variant with reduced cysteine
      content

<400> SEQUENCE: 24

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Ser Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110
```

Ile Val Asp Val Glu Gly Val Val Arg Lys Val Asn Gln Lys Ile Gly
            115                 120                 125

Ser Ser Thr Gln Gln Asp Val Glu Leu His Val Gln Lys Ile Tyr Val
    130                 135                 140

Ile Ser Leu Ala Glu Pro Arg Leu Pro Leu
145                 150

<210> SEQ ID NO 25
<211> LENGTH: 462
<212> TYPE: DNA
<213> ORGANISM: Artificial Sequence
<220> FEATURE:
<223> OTHER INFORMATION: Codon optimizedversion of the wild type
      AspRS1N1 polypeptide

<400> SEQUENCE: 25
atgccgagcg cgagcgccag ccgtaagagc caggaaaaac cacgtgagat tatggatgcc      60
gcagaggact atgcgaaaga acgttacggt atttccagca tgatccaatc tcaggagaaa     120
ccggaccgcg ttctggttcg tgttcgcgat ctgaccattc agaaggcgga cgaggtggtt     180
tgggtgcgtg cgcgcgtgca caccagccgt gcaaaaggca acagtgctt tctggtcctg      240 cgtcagcagc aattcaacgt ccaggcgctg gtggcagtgg gtgaccacgc cagcaaacaa     300
atggtgaagt cgctgctaa catcaataaa gaatccattg ttgatgttga aggcgtcgtt      360
cgcaaggtca atcaaaagat cggctcgtgt acgaacaag atgtcgagct gcatgtgcag      420
aagatttacg tcatcagcct ggcggagccg cgtttgccgc tg                         462

<210> SEQ ID NO 26
<211> LENGTH: 525
<212> TYPE: DNA
<213> ORGANISM: Artificial Sequence
<220> FEATURE:
<223> OTHER INFORMATION: Codon optimized version of the wild type
      AspRS1N1 polypeptide

<400> SEQUENCE: 26
atgccgagcg cgagcgccag ccgtaagagc caggaaaaac cacgtgagat tatggatgcc      60
gcagaggact atgcgaaaga acgttacggt atttccagca tgatccaatc tcaggagaaa     120
ccggaccgcg ttctggttcg tgttcgcgat ctgaccattc agaaggcgga cgaggtggtt     180
tgggtgcgtg cgcgcgtgca caccagccgt gcaaaaggca acagagctt tctggtcctg      240 cgtcagcagc aattcaacgt ccaggcgctg gtggcagtgg gtgaccacgc cagcaaacaa     300
atggtgaagt cgctgctaa catcaataaa gaatccattg ttgatgttga aggcgtcgtt      360
cgcaaggtca atcaaaagat cggctcgtgt acgaacaag atgtcgagct gcatgtgcag      420
aagatttacg tcatcagcct ggcggagccg cgtttgccgc tgggtaagcc gatccctaac    480
ccgctgttgg gtctggacag cacgcatcac catcaccacc actaa                    525

<210> SEQ ID NO 27
<211> LENGTH: 1503
<212> TYPE: DNA
<213> ORGANISM: Artificial Sequence
<220> FEATURE:
<223> OTHER INFORMATION: Codon optimized version of the wild type full
      length DRS polypeptide

<400> SEQUENCE: 27
atgccatcag cctcagcatc tcgtaaaagc caggaaaaac gcgcgaaat catggacgct       60 gccgaagatt atgccaaaga gcgctatggt atcagttcga tgatccagtc acaagagaaa    120

```
ccagatcgtg tgctggtccg tgttcgtgac ctgaccatcc agaaagcgga tgaagttgtt       180
tgggtccgtg ctcgtgttca tacaagccgt gccaaaggca acagtgctt cctggttctg        240 cgtcaacagc agtttaacgt tcaggccctg gtagccgttg gtgatcacgc ctcaaaacaa       300
atggtgaaat cgccgccaa catcaacaaa gagagcatcg tcgacgttga aggtgtcgtc        360
cgtaaagtga atcagaaaat cggctcctgt acacagcaag atgtggagct gcatgtccaa       420
aaaatctatg tcatctcact ggccgaacct cgtctgcctc tgcaactgga tgatgctgta      480
cgccctgaag ctgaaggcga agaagaaggt cgtgctacgg ttaatcagga tactcgcctg      540
gacaaccgtg tcattgatct cgcacctca acctctcaag cggtattccg cctgcaatcc       600
ggcatctgtc acctgttccg tgaaacgctg atcaacaaag gtttgtgga gattcagacc       660 ccgaaaatca ttagtgccgc cagcgaaggt ggagcaaatg tgtttaccgt gtcctatttc      720
aaaaacaatg cctatctggc acagtctcct cagctgtata acaaatgtg tatctgtgct       780 gacttcgaga aagtgttctc aatcgggccg gtattccgtg cagaggatag caacacacac      840
cgccatctga ccgaatttgt aggcctggac atcgaaatgg ccttcaacta tcattatcac      900
gaggtgatga agaaatcgc tgatacaatg gtacagatct ttaaagggct gcaagaacgc      960
tttcaaacag agattcaaac cgtcaataaa cagttcccgt gtgaaccgtt caaatttctg     1020
gaaccgaccc tgcgtctgga atattgtgaa gcactggcta tgctgcgcga agctggtgtc     1080
gaaatgggtg atgaggatga cctgtctacc cctaacgaaa aactgctggg ccacctggta     1140
aaagaaaaat atgacacaga cttctatatc ctggacaaat atccgctggc agttcgtccg     1200
ttttatacga tgcctgatcc tcgtaatccg aaacaaagca actcctatga catgttcatg     1260
cgtggtgaag atcctgtc tggtgctcaa cgtatccatg atccacagct gctgacagaa       1320
cgtgcactgc atcacggtat tgatctggag aaaatcaaag cctatatcga ctccttcgc     1380 tttggtgccc ctccacatgc cggtggtgga attgggctgg agcgtgtaac aatgctgttc     1440
ctgggactgc acaacgtccg tcaaacctca atgtttccac gtgaccctaa acgtctgaca     1500
cct                                                                    1503
```

<210> SEQ ID NO 28
<211> LENGTH: 525
<212> TYPE: DNA
<213> ORGANISM: Artificial Sequence
<220> FEATURE:
<223> OTHER INFORMATION: An E.coli codon optimized nucleic acid sequence
    encoding the DRS polypeptide AspRS1N1

<400> SEQUENCE: 28

```
atgccgagcg cgagcgccag ccgtaagagc caggaaaaac cacgtgagat tatggatgcc         60
gcagaggact atgcgaaaga acgttacggt atttccagca tgatccaatc tcaggagaaa       120
ccggaccgcg ttctggttcg tgttcgcgat ctgaccattc agaaggcgga cgaggtggtt       180
tgggtgcgtg cgcgcgtgca caccagccgt gcaaaaggca acagagcttt ctggtcctg        240 cgtcagcagc aattcaacgt ccaggcgctg gtggcagtgg gtgaccacgc cagcaaacaa       300
atggtgaagt cgctgctaa catcaataaa gaatccattg ttgatgttga aggcgtcgtt        360
cgcaaggtca atcaaaagat cggctcgtgt acgcaacaag atgtcgagct gcatgtgcag      420
aagatttacg tcatcagcct ggcggagccg cgtttgccgc tgggtaagcc gatccctaac      480
ccgctgttgg gtctggacag cacgcatcac catcaccacc actaa                       525
```

<210> SEQ ID NO 29
<211> LENGTH: 174
<212> TYPE: PRT
<213> ORGANISM: Artificial Sequence
<220> FEATURE:
<223> OTHER INFORMATION: Traqnslated protein of the E.coli codon optimized nucleic acid sequence encoding the DRS polypeptide AspRS1N1

<400> SEQUENCE: 29

```
Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
50                  55                  60

Arg Val His Thr Ser Arg Ala Lys Gly Lys Gln Ser Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
130                 135                 140

Ile Ser Leu Ala Glu Pro Arg Leu Pro Leu Gly Lys Pro Ile Pro Asn
145                 150                 155                 160

Pro Leu Leu Gly Leu Asp Ser Thr His His His His His His
                165                 170
```

<210> SEQ ID NO 30
<211> LENGTH: 525
<212> TYPE: DNA
<213> ORGANISM: Artificial Sequence
<220> FEATURE:
<223> OTHER INFORMATION: The nucleic acid sequence of the native AspRS1N1 cloned into the identical expression cassette

<400> SEQUENCE: 30

```
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgctt cttagtccta      240 cgtcagcagc agtttaatgt ccaggctctt gtggcggtgg gagaccatgc aagcaagcag     300
atggttaaat ttgctgccaa catcaacaaa gagagcattg tggatgtaga aggtgttgtg     360
agaaaagtga atcagaaaat tggaagctgt acacagcaag acgttgagtt acatgttcag     420
aagatttatg tgatcagttt ggctgaaccc cgtctgcccc tgggtaagcc tatccctaac     480
cctctcctcg gtctcgattc tacgcaccac caccaccacc actga                     525
```

<210> SEQ ID NO 31
<211> LENGTH: 174
<212> TYPE: PRT
<213> ORGANISM: Artificial Sequence
<220> FEATURE:

<223> OTHER INFORMATION: the non-mutated AspRS1N1 protein with
      C-terminal tag

<400> SEQUENCE: 31

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gly Lys Pro Ile Pro Asn
145                 150                 155                 160

Pro Leu Leu Gly Leu Asp Ser Thr His His His His His His
                165                 170

<210> SEQ ID NO 32
<211> LENGTH: 45
<212> TYPE: DNA
<213> ORGANISM: Homo sapiens
<220> FEATURE:
<221> NAME/KEY: misc_feature
<222> LOCATION: (1)..(45)
<223> OTHER INFORMATION: Primer

<400> SEQUENCE: 32
agtcttgcac ttgtcacgaa ttcgatgccc agcgccagcg ccagc            45

<210> SEQ ID NO 33
<211> LENGTH: 75
<212> TYPE: DNA
<213> ORGANISM: Homo sapiens
<220> FEATURE:
<221> NAME/KEY: misc_feature
<222> LOCATION: (1)..(75)
<223> OTHER INFORMATION: Primer

<400> SEQUENCE: 33
cggtgggcat gtgtgagttt tgtctcactt gtcgtcatcg tctttgtagt ccgtagaatc    60
gagaccgagg agagg                                                    75

<210> SEQ ID NO 34
<211> LENGTH: 45
<212> TYPE: DNA
<213> ORGANISM: Homo sapiens
<220> FEATURE:
<221> NAME/KEY: misc_feature
<222> LOCATION: (1)..(45)
<223> OTHER INFORMATION: Primer

<400> SEQUENCE: 34
gatcaccggc gaaggagggc caccatgccc agcgccagcg ccagc                      45

<210> SEQ ID NO 35
<211> LENGTH: 75
<212> TYPE: DNA
<213> ORGANISM: Homo sapiens
<220> FEATURE:
<221> NAME/KEY: misc_feature
<222> LOCATION: (1)..(75)
<223> OTHER INFORMATION: Primer

<400> SEQUENCE: 35
cggtgggcat gtgtgagttt tgtctcactt gtcgtcatcg tctttgtagt ccgtagaatc      60
gagaccgagg agagg                                                        75

<210> SEQ ID NO 36
<211> LENGTH: 591
<212> TYPE: DNA
<213> ORGANISM: Artificial Sequence
<220> FEATURE:
<223> OTHER INFORMATION: secretory AspRS1N1 sequence

<400> SEQUENCE: 36
atgtacagga tgcaactcct gtcttgcatt gcactaagtc ttgcacttgt cacgaattcg      60
atgcccagcg ccagcgccag ccgcaagagt caggagaagc cgcgggagat catggacgcg     120
gcggaagatt atgctaaaga gagatatgga atatcttcaa tgatacaatc acaagaaaaa     180
ccagatcgag ttttggttcg ggttagagac ttgacaatac aaaaagctga tgaagttgtt     240
tgggtacgtg caagagttca tacaagcaga gctaaaggga acagtgctt cttagtccta      300 cgtcagcagc agtttaatgt ccaggctctt gtggcggtgg agaccatgc aagcaagcag      360 atggttaaat ttgctgccaa catcaacaaa gagagcattg tggatgtaga aggtgttgtg      420
agaaaagtga atcagaaaat tggaagctgt acacagcaag acgttgagtt acatgttcag      480
aagatttatg tgatcagttt ggctgaaccc cgtctgcccc tgggtaagcc tatccctaac     540
cctctcctcg gtctcgattc tacggactac aaagacgatg acgacaagtg a              591

<210> SEQ ID NO 37
<211> LENGTH: 531
<212> TYPE: DNA
<213> ORGANISM: Artificial Sequence
<220> FEATURE:
<223> OTHER INFORMATION: intracellular AspRS1N1 sequence

<400> SEQUENCE: 37
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgctt cttagtccta      240 cgtcagcagc agtttaatgt ccaggctctt gtggcggtgg agaccatgc aagcaagcag      300 atggttaaat ttgctgccaa catcaacaaa gagagcattg tggatgtaga aggtgttgtg      360
agaaaagtga atcagaaaat tggaagctgt acacagcaag acgttgagtt acatgttcag      420
aagatttatg tgatcagttt ggctgaaccc cgtctgcccc tgggtaagcc tatccctaac     480
cctctcctcg gtctcgattc tacggactac aaagacgatg acgacaagtg a              531

<210> SEQ ID NO 38

```
<211> LENGTH: 37
<212> TYPE: DNA
<213> ORGANISM: Homo sapiens
<220> FEATURE:
<221> NAME/KEY: misc_feature
<222> LOCATION: (1)..(37)
<223> OTHER INFORMATION: Human C76X Primer

<400> SEQUENCE: 38
gctaaaggga aacagagctt cttagtccta cgtcagc                               37

<210> SEQ ID NO 39
<211> LENGTH: 37
<212> TYPE: DNA
<213> ORGANISM: Homo sapiens
<220> FEATURE:
<221> NAME/KEY: misc_feature
<222> LOCATION: (1)..(37)
<223> OTHER INFORMATION: Human C130X Primer

<400> SEQUENCE: 39
gtgaatcaga aaattggaag cagcacacag caagacg                               37

<210> SEQ ID NO 40
<211> LENGTH: 40
<212> TYPE: DNA
<213> ORGANISM: Artificial Sequence
<220> FEATURE:
<223> OTHER INFORMATION: E.coli codon optimized C76X Primer

<400> SEQUENCE: 40
cgtgcaaaag gcaaacagag ctttctggtc ctgcgtcagc                            40

<210> SEQ ID NO 41
<211> LENGTH: 41
<212> TYPE: DNA
<213> ORGANISM: Artificial Sequence
<220> FEATURE:
<223> OTHER INFORMATION: E.coli codon optimized C130X Primer

<400> SEQUENCE: 41
caatcaaaag atcggctcga gcacgcaaca agatgtcgag c                          41

<210> SEQ ID NO 42
<211> LENGTH: 4
<212> TYPE: PRT
<213> ORGANISM: Homo sapiens

<400> SEQUENCE: 42

His Ile Gly His
1

<210> SEQ ID NO 43
<211> LENGTH: 5
<212> TYPE: PRT
<213> ORGANISM: Homo sapiens

<400> SEQUENCE: 43

Lys Met Ser Lys Ser
1               5

<210> SEQ ID NO 44
<211> LENGTH: 18
<212> TYPE: DNA
<213> ORGANISM: Homo sapiens

<400> SEQUENCE: 44
```

```
actttttgat ggggttgt                                                 18
```

<210> SEQ ID NO 45
<211> LENGTH: 39
<212> TYPE: DNA
<213> ORGANISM: Homo sapiens

<400> SEQUENCE: 45

```
ccttttcat gggcttgttt ttttcttgta aatttgttt                           39
```

<210> SEQ ID NO 46
<211> LENGTH: 4
<212> TYPE: PRT
<213> ORGANISM: Artificial Sequence
<220> FEATURE:
<223> OTHER INFORMATION: Thrombin-cleavable amino acid linker sequence

<400> SEQUENCE: 46

Gly Arg Gly Asp
1

<210> SEQ ID NO 47
<211> LENGTH: 6
<212> TYPE: PRT
<213> ORGANISM: Artificial Sequence
<220> FEATURE:
<223> OTHER INFORMATION: Thrombin-cleavable amino acid linker sequence

<400> SEQUENCE: 47

Gly Arg Gly Asp Asn Pro
1               5

<210> SEQ ID NO 48
<211> LENGTH: 5
<212> TYPE: PRT
<213> ORGANISM: Artificial Sequence
<220> FEATURE:
<223> OTHER INFORMATION: Thrombin-cleavable amino acid linker sequence

<400> SEQUENCE: 48

Gly Arg Gly Asp Ser
1               5

<210> SEQ ID NO 49
<211> LENGTH: 7
<212> TYPE: PRT
<213> ORGANISM: Artificial Sequence
<220> FEATURE:
<223> OTHER INFORMATION: Thrombin-cleavable amino acid linker sequence

<400> SEQUENCE: 49

Gly Arg Gly Asp Ser Pro Lys
1               5

<210> SEQ ID NO 50
<211> LENGTH: 4
<212> TYPE: PRT
<213> ORGANISM: Artificial Sequence
<220> FEATURE:
<223> OTHER INFORMATION: Elastase-cleavable amino acid linker sequence

<400> SEQUENCE: 50

Ala Ala Pro Val
1

```
<210> SEQ ID NO 51
<211> LENGTH: 4
<212> TYPE: PRT
<213> ORGANISM: Artificial Sequence
<220> FEATURE:
<223> OTHER INFORMATION: Elastase-cleavable amino acid linker sequence

<400> SEQUENCE: 51

Ala Ala Pro Leu
1

<210> SEQ ID NO 52
<211> LENGTH: 4
<212> TYPE: PRT
<213> ORGANISM: Artificial Sequence
<220> FEATURE:
<223> OTHER INFORMATION: Elastase-cleavable amino acid linker sequence

<400> SEQUENCE: 52

Ala Ala Pro Phe
1

<210> SEQ ID NO 53
<211> LENGTH: 4
<212> TYPE: PRT
<213> ORGANISM: Artificial Sequence
<220> FEATURE:
<223> OTHER INFORMATION: Elastase-cleavable amino acid linker sequence

<400> SEQUENCE: 53

Ala Ala Pro Ala
1

<210> SEQ ID NO 54
<211> LENGTH: 4
<212> TYPE: PRT
<213> ORGANISM: Artificial Sequence
<220> FEATURE:
<223> OTHER INFORMATION: Elastase-cleavable amino acid linker sequence

<400> SEQUENCE: 54

Ala Tyr Leu Val
1

<210> SEQ ID NO 55
<211> LENGTH: 6
<212> TYPE: PRT
<213> ORGANISM: Artificial Sequence
<220> FEATURE:
<223> OTHER INFORMATION: Matrix metalloproteinase-cleavable amino acid
      linker sequence
<220> FEATURE:
<221> NAME/KEY: VARIANT
<222> LOCATION: (3)..(3)
<223> OTHER INFORMATION: Xaa = Any amino acid
<220> FEATURE:
<221> NAME/KEY: VARIANT
<222> LOCATION: (6)..(6)
<223> OTHER INFORMATION: Xaa = Any Amino Acid

<400> SEQUENCE: 55

Gly Pro Xaa Gly Pro Xaa
1               5

<210> SEQ ID NO 56
<211> LENGTH: 4
<212> TYPE: PRT
<213> ORGANISM: Artificial Sequence
<220> FEATURE:
```

```
<223> OTHER INFORMATION: Matrix metalloproteinase-cleavable amino acid
      linker sequence
<220> FEATURE:
<221> NAME/KEY: VARIANT
<222> LOCATION: (4)..(4)
<223> OTHER INFORMATION: Xaa = Any Amino Acid

<400> SEQUENCE: 56

Leu Gly Pro Xaa
1

<210> SEQ ID NO 57
<211> LENGTH: 6
<212> TYPE: PRT
<213> ORGANISM: Artificial Sequence
<220> FEATURE:
<223> OTHER INFORMATION: Matrix metalloproteinase-cleavable amino acid
      linker sequence
<220> FEATURE:
<221> NAME/KEY: VARIANT
<222> LOCATION: (6)..(6)
<223> OTHER INFORMATION: Xaa = Any Amino Acid

<400> SEQUENCE: 57

Gly Pro Ile Gly Pro Xaa
1               5

<210> SEQ ID NO 58
<211> LENGTH: 5
<212> TYPE: PRT
<213> ORGANISM: Artificial Sequence
<220> FEATURE:
<223> OTHER INFORMATION: Matrix metalloproteinase-cleavable amino acid
      linker sequence
<220> FEATURE:
<221> NAME/KEY: VARIANT
<222> LOCATION: (5)..(5)
<223> OTHER INFORMATION: Xaa = Any Amino Acid

<400> SEQUENCE: 58

Ala Pro Gly Leu Xaa
1               5

<210> SEQ ID NO 59
<211> LENGTH: 7
<212> TYPE: PRT
<213> ORGANISM: Artificial Sequence
<220> FEATURE:
<223> OTHER INFORMATION: Collagenase-cleavable amino acid linker
      sequence
<220> FEATURE:
<221> NAME/KEY: VARIANT
<222> LOCATION: (5)..(5)
<223> OTHER INFORMATION: Xaa = Any Amino Acid
<220> FEATURE:
<221> NAME/KEY: VARIANT
<222> LOCATION: (7)..(7)
<223> OTHER INFORMATION: Xaa = Any Amino Acid

<400> SEQUENCE: 59

Pro Leu Gly Pro Xaa Arg Xaa
1               5

<210> SEQ ID NO 60
<211> LENGTH: 7
<212> TYPE: PRT
<213> ORGANISM: Artificial Sequence
<220> FEATURE:
<223> OTHER INFORMATION: Collagenase-cleavable amino acid linker
      sequence
<220> FEATURE:
```

```
<221> NAME/KEY: VARIANT
<222> LOCATION: (7)..(7)
<223> OTHER INFORMATION: Xaa = Any Amino Acid

<400> SEQUENCE: 60

Pro Leu Gly Leu Leu Gly Xaa
1               5

<210> SEQ ID NO 61
<211> LENGTH: 7
<212> TYPE: PRT
<213> ORGANISM: Artificial Sequence
<220> FEATURE:
<223> OTHER INFORMATION: Collagenase-cleavable amino acid linker
      sequence

<400> SEQUENCE: 61

Pro Gln Gly Ile Ala Gly Trp
1               5

<210> SEQ ID NO 62
<211> LENGTH: 5
<212> TYPE: PRT
<213> ORGANISM: Artificial Sequence
<220> FEATURE:
<223> OTHER INFORMATION: Collagenase-cleavable amino acid linker
      sequence

<400> SEQUENCE: 62

Pro Leu Gly Cys His
1               5

<210> SEQ ID NO 63
<211> LENGTH: 6
<212> TYPE: PRT
<213> ORGANISM: Artificial Sequence
<220> FEATURE:
<223> OTHER INFORMATION: Collagenase-cleavable amino acid linker
      sequence

<400> SEQUENCE: 63

Pro Leu Gly Leu Tyr Ala
1               5

<210> SEQ ID NO 64
<211> LENGTH: 7
<212> TYPE: PRT
<213> ORGANISM: Artificial Sequence
<220> FEATURE:
<223> OTHER INFORMATION: Collagenase-cleavable amino acid linker
      sequence

<400> SEQUENCE: 64

Pro Leu Ala Leu Trp Ala Arg
1               5

<210> SEQ ID NO 65
<211> LENGTH: 7
<212> TYPE: PRT
<213> ORGANISM: Artificial Sequence
<220> FEATURE:
<223> OTHER INFORMATION: Collagenase-cleavable amino acid linker
      sequence

<400> SEQUENCE: 65

Pro Leu Ala Tyr Trp Ala Arg
1               5
```

```
<210> SEQ ID NO 66
<211> LENGTH: 7
<212> TYPE: PRT
<213> ORGANISM: Artificial Sequence
<220> FEATURE:
<223> OTHER INFORMATION: Stromelysin-cleavable amino acid linker
      sequence

<400> SEQUENCE: 66

Pro Tyr Ala Tyr Tyr Met Arg
1               5

<210> SEQ ID NO 67
<211> LENGTH: 7
<212> TYPE: PRT
<213> ORGANISM: Artificial Sequence
<220> FEATURE:
<223> OTHER INFORMATION: Gelatinase-cleavable amino acid linker
      sequence

<400> SEQUENCE: 67

Pro Leu Gly Met Tyr Ser Arg
1               5

<210> SEQ ID NO 68
<211> LENGTH: 4
<212> TYPE: PRT
<213> ORGANISM: Artificial Sequence
<220> FEATURE:
<223> OTHER INFORMATION: Angiotensin converting enzyme-cleavable amino
      acid linker sequence

<400> SEQUENCE: 68

Gly Asp Lys Pro
1

<210> SEQ ID NO 69
<211> LENGTH: 5
<212> TYPE: PRT
<213> ORGANISM: Artificial Sequence
<220> FEATURE:
<223> OTHER INFORMATION: Angiotensin converting enzyme-cleavable amino
      acid linker sequence

<400> SEQUENCE: 69

Gly Ser Asp Lys Pro
1               5

<210> SEQ ID NO 70
<211> LENGTH: 4
<212> TYPE: PRT
<213> ORGANISM: Artificial Sequence
<220> FEATURE:
<223> OTHER INFORMATION: Cathepsin B-cleavable amino acid linker
      sequence

<400> SEQUENCE: 70

Ala Leu Ala Leu
1

<210> SEQ ID NO 71
<211> LENGTH: 4
<212> TYPE: PRT
<213> ORGANISM: Artificial Sequence
<220> FEATURE:
<223> OTHER INFORMATION: Cathepsin B-cleavable amino acid linker
      sequence
```

```
<400> SEQUENCE: 71

Gly Phe Leu Gly
1

<210> SEQ ID NO 72
<211> LENGTH: 14
<212> TYPE: PRT
<213> ORGANISM: Artificial Sequence
<220> FEATURE:
<223> OTHER INFORMATION: V5 tag sequence

<400> SEQUENCE: 72

Gly Lys Pro Ile Pro Asn Pro Leu Leu Gly Leu Asp Ser Thr
1               5                   10

<210> SEQ ID NO 73
<211> LENGTH: 8
<212> TYPE: PRT
<213> ORGANISM: Artificial Sequence
<220> FEATURE:
<223> OTHER INFORMATION: Flag tag sequence

<400> SEQUENCE: 73

Asp Tyr Lys Asp Asp Asp Asp Lys
1               5

<210> SEQ ID NO 74
<211> LENGTH: 182
<212> TYPE: PRT
<213> ORGANISM: Homo sapiens

<400> SEQUENCE: 74

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
        130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn
            180

<210> SEQ ID NO 75
<211> LENGTH: 180
<212> TYPE: PRT
```

<213> ORGANISM: Homo sapiens

<400> SEQUENCE: 75

```
Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu
            180
```

<210> SEQ ID NO 76
<211> LENGTH: 178
<212> TYPE: PRT
<213> ORGANISM: Homo sapiens

<400> SEQUENCE: 76

```
Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175
```

```
                165                 170                 175
Asp Thr

<210> SEQ ID NO 77
<211> LENGTH: 176
<212> TYPE: PRT
<213> ORGANISM: Homo sapiens

<400> SEQUENCE: 77

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

<210> SEQ ID NO 78
<211> LENGTH: 174
<212> TYPE: PRT
<213> ORGANISM: Homo sapiens

<400> SEQUENCE: 78

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140
```

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val
                165                 170

<210> SEQ ID NO 79
<211> LENGTH: 172
<212> TYPE: PRT
<213> ORGANISM: Homo sapiens

<400> SEQUENCE: 79

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala
                165                 170

<210> SEQ ID NO 80
<211> LENGTH: 170
<212> TYPE: PRT
<213> ORGANISM: Homo sapiens

<400> SEQUENCE: 80

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly
                165                 170

<210> SEQ ID NO 81
<211> LENGTH: 168
<212> TYPE: PRT
<213> ORGANISM: Homo sapiens

<400> SEQUENCE: 81

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu
                165

<210> SEQ ID NO 82
<211> LENGTH: 166
<212> TYPE: PRT
<213> ORGANISM: Homo sapiens

<400> SEQUENCE: 82

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

```
Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
        130                 135                 140

Ile Ser Leu Ala Glu Pro Arg Leu Pro Leu Gln Leu Asp Asp Ala Val
145                 150                 155                 160

Arg Pro Glu Ala Glu Gly
                165

<210> SEQ ID NO 83
<211> LENGTH: 164
<212> TYPE: PRT
<213> ORGANISM: Homo sapiens

<400> SEQUENCE: 83

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
                35                  40                  45

Arg Asp Leu Thr Ile Gln Lys Ala Asp Glu Val Val Trp Val Arg Ala
50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
        130                 135                 140

Ile Ser Leu Ala Glu Pro Arg Leu Pro Leu Gln Leu Asp Asp Ala Val
145                 150                 155                 160

Arg Pro Glu Ala

<210> SEQ ID NO 84
<211> LENGTH: 162
<212> TYPE: PRT
<213> ORGANISM: Homo sapiens

<400> SEQUENCE: 84

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
                35                  40                  45

Arg Asp Leu Thr Ile Gln Lys Ala Asp Glu Val Val Trp Val Arg Ala
50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95
```

```
Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro

<210> SEQ ID NO 85
<211> LENGTH: 160
<212> TYPE: PRT
<213> ORGANISM: Homo sapiens

<400> SEQUENCE: 85

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
            85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

<210> SEQ ID NO 86
<211> LENGTH: 158
<212> TYPE: PRT
<213> ORGANISM: Homo sapiens

<400> SEQUENCE: 86

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
            85                  90                  95

Ala Ser Lys Gln Met Val Lys Phe Ala Ala Asn Ile Asn Lys Glu Ser
```

```
                100             105                 110
Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
            130                 135             140

Ile Ser Leu Ala Glu Pro Arg Leu Pro Leu Gln Leu Asp Asp
145                 150                 155
```

<210> SEQ ID NO 87
<211> LENGTH: 156
<212> TYPE: PRT
<213> ORGANISM: Homo sapiens

<400> SEQUENCE: 87

```
Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
            130                 135             140

Ile Ser Leu Ala Glu Pro Arg Leu Pro Leu Gln Leu
145                 150                 155
```

<210> SEQ ID NO 88
<211> LENGTH: 154
<212> TYPE: PRT
<213> ORGANISM: Homo sapiens

<400> SEQUENCE: 88

```
Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
```

```
            115                 120                 125
Ser Cys Thr Gln Gln Asp Val Glu Leu His Val Gln Lys Ile Tyr Val
    130                 135                 140
Ile Ser Leu Ala Glu Pro Arg Leu Pro Leu
145                 150

<210> SEQ ID NO 89
<211> LENGTH: 152
<212> TYPE: PRT
<213> ORGANISM: Homo sapiens

<400> SEQUENCE: 89

Met Pro Ser Ala Ser Ala Ser Arg Lys Ser Gln Glu Lys Pro Arg Glu
1               5                   10                  15
Ile Met Asp Ala Ala Glu Asp Tyr Ala Lys Glu Arg Tyr Gly Ile Ser
            20                  25                  30
Ser Met Ile Gln Ser Gln Glu Lys Pro Asp Arg Val Leu Val Arg Val
        35                  40                  45
Arg Asp Leu Thr Ile Gln Lys Ala Asp Glu Val Val Trp Val Arg Ala
    50                  55                  60
Arg Val His Thr Ser Arg Ala Lys Gly Lys Gln Cys Phe Leu Val Leu
65                  70                  75                  80
Arg Gln Gln Gln Phe Asn Val Gln Ala Leu Val Ala Val Gly Asp His
                85                  90                  95
Ala Ser Lys Gln Met Val Lys Phe Ala Ala Asn Ile Asn Lys Glu Ser
            100                 105                 110
Ile Val Asp Val Glu Gly Val Val Arg Lys Val Asn Gln Lys Ile Gly
        115                 120                 125
Ser Cys Thr Gln Gln Asp Val Glu Leu His Val Gln Lys Ile Tyr Val
    130                 135                 140
Ile Ser Leu Ala Glu Pro Arg Leu
145                 150

<210> SEQ ID NO 90
<211> LENGTH: 150
<212> TYPE: PRT
<213> ORGANISM: Homo sapiens

<400> SEQUENCE: 90

Met Pro Ser Ala Ser Ala Ser Arg Lys Ser Gln Glu Lys Pro Arg Glu
1               5                   10                  15
Ile Met Asp Ala Ala Glu Asp Tyr Ala Lys Glu Arg Tyr Gly Ile Ser
            20                  25                  30
Ser Met Ile Gln Ser Gln Glu Lys Pro Asp Arg Val Leu Val Arg Val
        35                  40                  45
Arg Asp Leu Thr Ile Gln Lys Ala Asp Glu Val Val Trp Val Arg Ala
    50                  55                  60
Arg Val His Thr Ser Arg Ala Lys Gly Lys Gln Cys Phe Leu Val Leu
65                  70                  75                  80
Arg Gln Gln Gln Phe Asn Val Gln Ala Leu Val Ala Val Gly Asp His
                85                  90                  95
Ala Ser Lys Gln Met Val Lys Phe Ala Ala Asn Ile Asn Lys Glu Ser
            100                 105                 110
Ile Val Asp Val Glu Gly Val Val Arg Lys Val Asn Gln Lys Ile Gly
        115                 120                 125
Ser Cys Thr Gln Gln Asp Val Glu Leu His Val Gln Lys Ile Tyr Val
```

Ile Ser Leu Ala Glu Pro
145                 150

<210> SEQ ID NO 91
<211> LENGTH: 148
<212> TYPE: PRT
<213> ORGANISM: Homo sapiens

<400> SEQUENCE: 91

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
    130                 135                 140

Ile Ser Leu Ala
145

<210> SEQ ID NO 92
<211> LENGTH: 146
<212> TYPE: PRT
<213> ORGANISM: Homo sapiens

<400> SEQUENCE: 92

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
    130                 135                 140

Ile Ser

145

<210> SEQ ID NO 93
<211> LENGTH: 151
<212> TYPE: PRT
<213> ORGANISM: Homo sapiens

<400> SEQUENCE: 93

```
Ala Ser Ala Ser Arg Lys Ser Gln Glu Lys Pro Arg Glu Ile Met Asp
1               5                   10                  15
Ala Ala Glu Asp Tyr Ala Lys Glu Arg Tyr Gly Ile Ser Ser Met Ile
                20                  25                  30
Gln Ser Gln Glu Lys Pro Asp Arg Val Leu Val Arg Val Arg Asp Leu
            35                  40                  45
Thr Ile Gln Lys Ala Asp Glu Val Val Trp Val Arg Ala Arg Val His
50                  55                  60
Thr Ser Arg Ala Lys Gly Lys Gln Cys Phe Leu Val Leu Arg Gln Gln
65                  70                  75                  80
Gln Phe Asn Val Gln Ala Leu Val Ala Val Gly Asp His Ala Ser Lys
                85                  90                  95
Gln Met Val Lys Phe Ala Ala Asn Ile Asn Lys Glu Ser Ile Val Asp
            100                 105                 110
Val Glu Gly Val Val Arg Lys Val Asn Gln Lys Ile Gly Ser Cys Thr
                115                 120                 125
Gln Gln Asp Val Glu Leu His Val Gln Lys Ile Tyr Val Ile Ser Leu
        130                 135                 140
Ala Glu Pro Arg Leu Pro Leu
145                 150
```

<210> SEQ ID NO 94
<211> LENGTH: 149
<212> TYPE: PRT
<213> ORGANISM: Homo sapiens

<400> SEQUENCE: 94

```
Ala Ser Arg Lys Ser Gln Glu Lys Pro Arg Glu Ile Met Asp Ala Ala
1               5                   10                  15
Glu Asp Tyr Ala Lys Glu Arg Tyr Gly Ile Ser Ser Met Ile Gln Ser
                20                  25                  30
Gln Glu Lys Pro Asp Arg Val Leu Val Arg Val Arg Asp Leu Thr Ile
            35                  40                  45
Gln Lys Ala Asp Glu Val Val Trp Val Arg Ala Arg Val His Thr Ser
50                  55                  60
Arg Ala Lys Gly Lys Gln Cys Phe Leu Val Leu Arg Gln Gln Gln Phe
65                  70                  75                  80
Asn Val Gln Ala Leu Val Ala Val Gly Asp His Ala Ser Lys Gln Met
                85                  90                  95
Val Lys Phe Ala Ala Asn Ile Asn Lys Glu Ser Ile Val Asp Val Glu
            100                 105                 110
Gly Val Val Arg Lys Val Asn Gln Lys Ile Gly Ser Cys Thr Gln Gln
                115                 120                 125
Asp Val Glu Leu His Val Gln Lys Ile Tyr Val Ile Ser Leu Ala Glu
        130                 135                 140
Pro Arg Leu Pro Leu
145
```

<210> SEQ ID NO 95
<211> LENGTH: 147
<212> TYPE: PRT
<213> ORGANISM: Homo sapiens

<400> SEQUENCE: 95

Arg Lys Ser Gln Glu Lys Pro Arg Glu Ile Met Asp Ala Ala Glu Asp
1               5                   10                  15

Tyr Ala Lys Glu Arg Tyr Gly Ile Ser Ser Met Ile Gln Ser Gln Glu
            20                  25                  30

Lys Pro Asp Arg Val Leu Val Arg Val Arg Asp Leu Thr Ile Gln Lys
        35                  40                  45

Ala Asp Glu Val Val Trp Val Arg Ala Arg Val His Thr Ser Arg Ala
    50                  55                  60

Lys Gly Lys Gln Cys Phe Leu Val Leu Arg Gln Gln Gln Phe Asn Val
65                  70                  75                  80

Gln Ala Leu Val Ala Val Gly Asp His Ala Ser Lys Gln Met Val Lys
                85                  90                  95

Phe Ala Ala Asn Ile Asn Lys Glu Ser Ile Val Asp Val Glu Gly Val
            100                 105                 110

Val Arg Lys Val Asn Gln Lys Ile Gly Ser Cys Thr Gln Gln Asp Val
        115                 120                 125

Glu Leu His Val Gln Lys Ile Tyr Val Ile Ser Leu Ala Glu Pro Arg
    130                 135                 140

Leu Pro Leu
145

<210> SEQ ID NO 96
<211> LENGTH: 145
<212> TYPE: PRT
<213> ORGANISM: Homo sapiens

<400> SEQUENCE: 96

Ser Gln Glu Lys Pro Arg Glu Ile Met Asp Ala Ala Glu Asp Tyr Ala
1               5                   10                  15

Lys Glu Arg Tyr Gly Ile Ser Ser Met Ile Gln Ser Gln Glu Lys Pro
            20                  25                  30

Asp Arg Val Leu Val Arg Val Arg Asp Leu Thr Ile Gln Lys Ala Asp
        35                  40                  45

Glu Val Val Trp Val Arg Ala Arg Val His Thr Ser Arg Ala Lys Gly
    50                  55                  60

Lys Gln Cys Phe Leu Val Leu Arg Gln Gln Gln Phe Asn Val Gln Ala
65                  70                  75                  80

Leu Val Ala Val Gly Asp His Ala Ser Lys Gln Met Val Lys Phe Ala
                85                  90                  95

Ala Asn Ile Asn Lys Glu Ser Ile Val Asp Val Glu Gly Val Val Arg
            100                 105                 110

Lys Val Asn Gln Lys Ile Gly Ser Cys Thr Gln Gln Asp Val Glu Leu
        115                 120                 125

His Val Gln Lys Ile Tyr Val Ile Ser Leu Ala Glu Pro Arg Leu Pro
    130                 135                 140

Leu
145

<210> SEQ ID NO 97
<211> LENGTH: 143
<212> TYPE: PRT

-continued

<213> ORGANISM: Homo sapiens

<400> SEQUENCE: 97

Glu Lys Pro Arg Glu Ile Met Asp Ala Ala Glu Asp Tyr Ala Lys Glu
1               5                   10                  15

Arg Tyr Gly Ile Ser Ser Met Ile Gln Ser Gln Glu Lys Pro Asp Arg
            20                  25                  30

Val Leu Val Arg Val Arg Asp Leu Thr Ile Gln Lys Ala Asp Glu Val
        35                  40                  45

Val Trp Val Arg Ala Arg Val His Thr Ser Arg Ala Lys Gly Lys Gln
    50                  55                  60

Cys Phe Leu Val Leu Arg Gln Gln Gln Phe Asn Val Gln Ala Leu Val
65                  70                  75                  80

Ala Val Gly Asp His Ala Ser Lys Gln Met Val Lys Phe Ala Ala Asn
                85                  90                  95

Ile Asn Lys Glu Ser Ile Val Asp Val Glu Gly Val Val Arg Lys Val
            100                 105                 110

Asn Gln Lys Ile Gly Ser Cys Thr Gln Gln Asp Val Glu Leu His Val
        115                 120                 125

Gln Lys Ile Tyr Val Ile Ser Leu Ala Glu Pro Arg Leu Pro Leu
    130                 135                 140

<210> SEQ ID NO 98
<211> LENGTH: 141
<212> TYPE: PRT
<213> ORGANISM: Homo sapiens

<400> SEQUENCE: 98

Pro Arg Glu Ile Met Asp Ala Ala Glu Asp Tyr Ala Lys Glu Arg Tyr
1               5                   10                  15

Gly Ile Ser Ser Met Ile Gln Ser Gln Glu Lys Pro Asp Arg Val Leu
            20                  25                  30

Val Arg Val Arg Asp Leu Thr Ile Gln Lys Ala Asp Glu Val Val Trp
        35                  40                  45

Val Arg Ala Arg Val His Thr Ser Arg Ala Lys Gly Lys Gln Cys Phe
    50                  55                  60

Leu Val Leu Arg Gln Gln Gln Phe Asn Val Gln Ala Leu Val Ala Val
65                  70                  75                  80

Gly Asp His Ala Ser Lys Gln Met Val Lys Phe Ala Ala Asn Ile Asn
                85                  90                  95

Lys Glu Ser Ile Val Asp Val Glu Gly Val Val Arg Lys Val Asn Gln
            100                 105                 110

Lys Ile Gly Ser Cys Thr Gln Gln Asp Val Glu Leu His Val Gln Lys
        115                 120                 125

Ile Tyr Val Ile Ser Leu Ala Glu Pro Arg Leu Pro Leu
    130                 135                 140

<210> SEQ ID NO 99
<211> LENGTH: 139
<212> TYPE: PRT
<213> ORGANISM: Homo sapiens

<400> SEQUENCE: 99

Glu Ile Met Asp Ala Ala Glu Asp Tyr Ala Lys Glu Arg Tyr Gly Ile
1               5                   10                  15

Ser Ser Met Ile Gln Ser Gln Glu Lys Pro Asp Arg Val Leu Val Arg
            20                  25                  30

```
Val Arg Asp Leu Thr Ile Gln Lys Ala Asp Glu Val Val Trp Val Arg
        35                  40                  45

Ala Arg Val His Thr Ser Arg Ala Lys Gly Lys Gln Cys Phe Leu Val
 50                  55                  60

Leu Arg Gln Gln Gln Phe Asn Val Gln Ala Leu Val Ala Val Gly Asp
65                  70                  75                  80

His Ala Ser Lys Gln Met Val Lys Phe Ala Ala Asn Ile Asn Lys Glu
                85                  90                  95

Ser Ile Val Asp Val Glu Gly Val Val Arg Lys Val Asn Gln Lys Ile
                100                 105                 110

Gly Ser Cys Thr Gln Gln Asp Val Glu Leu His Val Gln Lys Ile Tyr
            115                 120                 125

Val Ile Ser Leu Ala Glu Pro Arg Leu Pro Leu
        130                 135

<210> SEQ ID NO 100
<211> LENGTH: 137
<212> TYPE: PRT
<213> ORGANISM: Homo sapiens

<400> SEQUENCE: 100

Met Asp Ala Ala Glu Asp Tyr Ala Lys Glu Arg Tyr Gly Ile Ser Ser
1               5                   10                  15

Met Ile Gln Ser Gln Glu Lys Pro Asp Arg Val Leu Val Arg Val Arg
                20                  25                  30

Asp Leu Thr Ile Gln Lys Ala Asp Glu Val Val Trp Val Arg Ala Arg
        35                  40                  45

Val His Thr Ser Arg Ala Lys Gly Lys Gln Cys Phe Leu Val Leu Arg
 50                  55                  60

Gln Gln Gln Phe Asn Val Gln Ala Leu Val Ala Val Gly Asp His Ala
65                  70                  75                  80

Ser Lys Gln Met Val Lys Phe Ala Ala Asn Ile Asn Lys Glu Ser Ile
                85                  90                  95

Val Asp Val Glu Gly Val Val Arg Lys Val Asn Gln Lys Ile Gly Ser
                100                 105                 110

Cys Thr Gln Gln Asp Val Glu Leu His Val Gln Lys Ile Tyr Val Ile
            115                 120                 125

Ser Leu Ala Glu Pro Arg Leu Pro Leu
        130                 135

<210> SEQ ID NO 101
<211> LENGTH: 135
<212> TYPE: PRT
<213> ORGANISM: Homo sapiens

<400> SEQUENCE: 101

Met Asp Ala Ala Glu Asp Tyr Ala Lys Glu Arg Tyr Gly Ile Ser Ser
1               5                   10                  15

Met Ile Gln Ser Gln Glu Lys Pro Asp Arg Val Leu Val Arg Val Arg
                20                  25                  30

Asp Leu Thr Ile Gln Lys Ala Asp Glu Val Val Trp Val Arg Ala Arg
        35                  40                  45

Val His Thr Ser Arg Ala Lys Gly Lys Gln Cys Phe Leu Val Leu Arg
 50                  55                  60

Gln Gln Gln Phe Asn Val Gln Ala Leu Val Ala Val Gly Asp His Ala
65                  70                  75                  80
```

```
Ser Lys Gln Met Val Lys Phe Ala Ala Asn Ile Asn Lys Glu Ser Ile
            85                  90                  95

Val Asp Val Glu Gly Val Val Arg Lys Val Asn Gln Lys Ile Gly Ser
            100                 105                 110

Cys Thr Gln Gln Asp Val Glu Leu His Val Gln Lys Ile Tyr Val Ile
            115                 120                 125

Ser Leu Ala Glu Pro Arg Leu
            130             135

<210> SEQ ID NO 102
<211> LENGTH: 135
<212> TYPE: PRT
<213> ORGANISM: Homo sapiens

<400> SEQUENCE: 102

Met Asp Ala Ala Glu Asp Tyr Ala Lys Glu Arg Tyr Gly Ile Ser Ser
1               5                   10                  15

Met Ile Gln Ser Gln Glu Lys Pro Asp Arg Val Leu Val Arg Val Arg
            20                  25                  30

Asp Leu Thr Ile Gln Lys Ala Asp Glu Val Val Trp Val Arg Ala Arg
            35                  40                  45

Val His Thr Ser Arg Ala Lys Gly Lys Gln Cys Phe Leu Val Leu Arg
        50                  55                  60

Gln Gln Gln Phe Asn Val Gln Ala Leu Val Ala Val Gly Asp His Ala
65                  70                  75                  80

Ser Lys Gln Met Val Lys Phe Ala Ala Asn Ile Asn Lys Glu Ser Ile
            85                  90                  95

Val Asp Val Glu Gly Val Val Arg Lys Val Asn Gln Lys Ile Gly Ser
            100                 105                 110

Cys Thr Gln Gln Asp Val Glu Leu His Val Gln Lys Ile Tyr Val Ile
            115                 120                 125

Ser Leu Ala Glu Pro Arg Leu
            130             135

<210> SEQ ID NO 103
<211> LENGTH: 133
<212> TYPE: PRT
<213> ORGANISM: Homo sapiens

<400> SEQUENCE: 103

Ala Ala Glu Asp Tyr Ala Lys Glu Arg Tyr Gly Ile Ser Ser Met Ile
1               5                   10                  15

Gln Ser Gln Glu Lys Pro Asp Arg Val Leu Val Arg Val Arg Asp Leu
            20                  25                  30

Thr Ile Gln Lys Ala Asp Glu Val Val Trp Val Arg Ala Arg Val His
            35                  40                  45

Thr Ser Arg Ala Lys Gly Lys Gln Cys Phe Leu Val Leu Arg Gln Gln
        50                  55                  60

Gln Phe Asn Val Gln Ala Leu Val Ala Val Gly Asp His Ala Ser Lys
65                  70                  75                  80

Gln Met Val Lys Phe Ala Ala Asn Ile Asn Lys Glu Ser Ile Val Asp
            85                  90                  95

Val Glu Gly Val Val Arg Lys Val Asn Gln Lys Ile Gly Ser Cys Thr
            100                 105                 110

Gln Gln Asp Val Glu Leu His Val Gln Lys Ile Tyr Val Ile Ser Leu
            115                 120                 125
```

Ala Glu Pro Arg Leu
       130

<210> SEQ ID NO 104
<211> LENGTH: 137
<212> TYPE: PRT
<213> ORGANISM: Homo sapiens

<400> SEQUENCE: 104

Met Gln Glu Lys Pro Arg Glu Ile Met Asp Ala Ala Glu Asp Tyr Ala
1               5                   10                  15

Lys Glu Arg Tyr Gly Ile Ser Ser Met Ile Gln Ser Gln Glu Lys Pro
            20                  25                  30

Asp Arg Val Leu Val Arg Val Arg Asp Leu Thr Ile Gln Lys Ala Asp
        35                  40                  45

Glu Val Val Trp Val Arg Ala Arg Val His Thr Ser Arg Ala Lys Gly
    50                  55                  60

Lys Gln Cys Phe Leu Val Leu Arg Gln Gln Phe Asn Val Gln Ala
65                  70                  75                  80

Leu Val Ala Val Gly Asp His Ala Ser Lys Gln Met Val Lys Phe Ala
                85                  90                  95

Cys Asn Ile Asn Lys Glu Ser Ile Val Asp Val Glu Gly Val Val Arg
            100                 105                 110

Lys Val Asn Gln Lys Ile Gly Ser Cys Thr Gln Gln Asp Val Glu Leu
        115                 120                 125

His Val Gln Lys Ile Tyr Val Ile Ser
    130                 135

<210> SEQ ID NO 105
<211> LENGTH: 135
<212> TYPE: PRT
<213> ORGANISM: Homo sapiens

<400> SEQUENCE: 105

Met Lys Pro Arg Glu Ile Met Asp Ala Ala Glu Asp Tyr Ala Lys Glu
1               5                   10                  15

Arg Tyr Gly Ile Ser Ser Met Ile Gln Ser Gln Glu Lys Pro Asp Arg
            20                  25                  30

Val Leu Val Arg Val Arg Asp Leu Thr Ile Gln Lys Ala Asp Glu Val
        35                  40                  45

Val Trp Val Arg Ala Arg Val His Thr Ser Arg Ala Lys Gly Lys Gln
    50                  55                  60

Cys Phe Leu Val Leu Arg Gln Gln Phe Asn Val Gln Ala Leu Val
65                  70                  75                  80

Ala Val Gly Asp His Ala Ser Lys Gln Met Val Lys Phe Ala Cys Asn
                85                  90                  95

Ile Asn Lys Glu Ser Ile Val Asp Val Glu Gly Val Val Arg Lys Val
            100                 105                 110

Asn Gln Lys Ile Gly Ser Cys Thr Gln Gln Asp Val Glu Leu His Val
        115                 120                 125

Gln Lys Ile Tyr Val Ile Ser
    130                 135

<210> SEQ ID NO 106
<211> LENGTH: 135
<212> TYPE: PRT
<213> ORGANISM: Homo sapiens

<400> SEQUENCE: 106

Met Lys Pro Arg Glu Ile Met Asp Ala Ala Glu Asp Tyr Ala Lys Glu
1               5                   10                  15

Arg Tyr Gly Ile Ser Ser Met Ile Gln Ser Gln Glu Lys Pro Asp Arg
                20                  25                  30

Val Leu Val Arg Val Arg Asp Leu Thr Ile Gln Lys Ala Asp Glu Val
            35                  40                  45

Val Trp Val Arg Ala Arg Val His Thr Ser Arg Ala Lys Gly Lys Gln
    50                  55                  60

Cys Phe Leu Val Leu Arg Gln Gln Gln Phe Asn Val Gln Ala Leu Val
65                  70                  75                  80

Ala Val Gly Asp His Ala Ser Lys Gln Met Val Lys Phe Ala Cys Asn
                85                  90                  95

Ile Asn Lys Glu Ser Ile Val Asp Val Glu Gly Val Val Arg Lys Val
            100                 105                 110

Asn Gln Lys Ile Gly Ser Cys Thr Gln Gln Asp Val Glu Leu His Val
        115                 120                 125

Gln Lys Ile Tyr Val Ile Ser
    130                 135

<210> SEQ ID NO 107
<211> LENGTH: 131
<212> TYPE: PRT
<213> ORGANISM: Homo sapiens

<400> SEQUENCE: 107

Met Ile Met Asp Ala Ala Glu Asp Tyr Ala Lys Glu Arg Tyr Gly Ile
1               5                   10                  15

Ser Ser Met Ile Gln Ser Gln Glu Lys Pro Asp Arg Val Leu Val Arg
                20                  25                  30

Val Arg Asp Leu Thr Ile Gln Lys Ala Asp Glu Val Val Trp Val Arg
            35                  40                  45

Ala Arg Val His Thr Ser Arg Ala Lys Gly Lys Gln Cys Phe Leu Val
    50                  55                  60

Leu Arg Gln Gln Gln Phe Asn Val Gln Ala Leu Val Ala Val Gly Asp
65                  70                  75                  80

His Ala Ser Lys Gln Met Val Lys Phe Ala Cys Asn Ile Asn Lys Glu
                85                  90                  95

Ser Ile Val Asp Val Glu Gly Val Arg Lys Val Asn Gln Lys Ile
            100                 105                 110

Gly Ser Cys Thr Gln Gln Asp Val Glu Leu His Val Gln Lys Ile Tyr
        115                 120                 125

Val Ile Ser
    130

<210> SEQ ID NO 108
<211> LENGTH: 127
<212> TYPE: PRT
<213> ORGANISM: Homo sapiens

<400> SEQUENCE: 108

Met Ala Glu Asp Tyr Ala Lys Glu Arg Tyr Gly Ile Ser Ser Met Ile
1               5                   10                  15

Gln Ser Gln Glu Lys Pro Asp Arg Val Leu Val Arg Val Arg Asp Leu
                20                  25                  30

Thr Ile Gln Lys Ala Asp Glu Val Val Trp Val Arg Ala Arg Val His
        35                  40                  45

Thr Ser Arg Ala Lys Gly Lys Gln Cys Phe Leu Val Leu Arg Gln Gln
 50                  55                  60

Gln Phe Asn Val Gln Ala Leu Val Ala Val Gly Asp His Ala Ser Lys
 65                  70                  75                  80

Gln Met Val Lys Phe Ala Cys Asn Ile Asn Lys Glu Ser Ile Val Asp
                 85                  90                  95

Val Glu Gly Val Val Arg Lys Val Asn Gln Lys Ile Gly Ser Cys Thr
                100                 105                 110

Gln Gln Asp Val Glu Leu His Val Gln Lys Ile Tyr Val Ile Ser
            115                 120                 125

<210> SEQ ID NO 109
<211> LENGTH: 501
<212> TYPE: PRT
<213> ORGANISM: Artificial Sequence
<220> FEATURE:
<223> OTHER INFORMATION: DRS polypeptide variant with reduced cysteine
      content

<400> SEQUENCE: 109

Met Pro Ser Ala Ser Ala Ser Arg Lys Ser Gln Glu Lys Pro Arg Glu
 1               5                  10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
 50                  55                  60

Arg Val His Thr Ser Arg Ala Lys Gly Lys Gln Cys Phe Leu Val Leu
 65                  70                  75                  80

Arg Gln Gln Gln Phe Asn Val Gln Ala Leu Val Ala Val Gly Asp His
                 85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val Ile Asp Leu Arg Thr Ser Thr Ser
            180                 185                 190

Gln Ala Val Phe Arg Leu Gln Ser Gly Ile Cys His Leu Phe Arg Glu
        195                 200                 205

Thr Leu Ile Asn Lys Gly Phe Val Glu Ile Gln Thr Pro Lys Ile Ile
210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Cys Ala Asp Phe Glu Lys Val Phe Ser Ile Gly Pro Val Phe
            260                 265                 270

-continued

```
Arg Ala Glu Asp Ser Asn Thr His Arg His Leu Thr Glu Phe Val Gly
            275                 280                 285

Leu Asp Ile Glu Met Ala Phe Asn Tyr His Tyr His Glu Val Met Glu
    290                 295                 300

Glu Ile Ala Asp Thr Met Val Gln Ile Phe Lys Gly Leu Gln Glu Arg
305                 310                 315                 320

Phe Gln Thr Glu Ile Gln Thr Val Asn Lys Gln Phe Pro Ser Glu Pro
                325                 330                 335

Phe Lys Phe Leu Glu Pro Thr Leu Arg Leu Glu Tyr Cys Glu Ala Leu
            340                 345                 350

Ala Met Leu Arg Glu Ala Gly Val Glu Met Gly Asp Glu Asp Asp Leu
        355                 360                 365

Ser Thr Pro Asn Glu Lys Leu Leu Gly His Leu Val Lys Glu Lys Tyr
    370                 375                 380

Asp Thr Asp Phe Tyr Ile Leu Asp Lys Tyr Pro Leu Ala Val Arg Pro
385                 390                 395                 400

Phe Tyr Thr Met Pro Asp Pro Arg Asn Pro Lys Gln Ser Asn Ser Tyr
                405                 410                 415

Asp Met Phe Met Arg Gly Glu Glu Ile Leu Ser Gly Ala Gln Arg Ile
            420                 425                 430

His Asp Pro Gln Leu Leu Thr Glu Arg Ala Leu His His Gly Ile Asp
        435                 440                 445

Leu Glu Lys Ile Lys Ala Tyr Ile Asp Ser Phe Arg Phe Gly Ala Pro
    450                 455                 460

Pro His Ala Gly Gly Gly Ile Gly Leu Glu Arg Val Thr Met Leu Phe
465                 470                 475                 480

Leu Gly Leu His Asn Val Arg Gln Thr Ser Met Phe Pro Arg Asp Pro
                485                 490                 495

Lys Arg Leu Thr Pro
            500

<210> SEQ ID NO 110
<211> LENGTH: 501
<212> TYPE: PRT
<213> ORGANISM: Artificial Sequence
<220> FEATURE:
<223> OTHER INFORMATION: DRS polypeptide variant with reduced cysteine
      content

<400> SEQUENCE: 110

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
```

```
            115                 120                 125
Ser Cys Thr Gln Gln Asp Val Glu Leu His Val Gln Lys Ile Tyr Val
130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val Ile Asp Leu Arg Thr Ser Thr Ser
            180                 185                 190

Gln Ala Val Phe Arg Leu Gln Ser Gly Ile Cys His Leu Phe Arg Glu
            195                 200                 205

Thr Leu Ile Asn Lys Gly Phe Val Glu Ile Gln Thr Pro Lys Ile Ile
            210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Cys Ala Asp Phe Glu Lys Val Phe Ser Ile Gly Pro Val Phe
                260                 265                 270

Arg Ala Glu Asp Ser Asn Thr His Arg His Leu Thr Glu Phe Val Gly
            275                 280                 285

Leu Asp Ile Glu Met Ala Phe Asn Tyr His Tyr His Glu Val Met Glu
            290                 295                 300

Glu Ile Ala Asp Thr Met Val Gln Ile Phe Lys Gly Leu Gln Glu Arg
305                 310                 315                 320

Phe Gln Thr Glu Ile Gln Thr Val Asn Lys Gln Phe Pro Cys Glu Pro
                325                 330                 335

Phe Lys Phe Leu Glu Pro Thr Leu Arg Leu Glu Tyr Ser Glu Ala Leu
            340                 345                 350

Ala Met Leu Arg Glu Ala Gly Val Glu Met Gly Asp Glu Asp Asp Leu
            355                 360                 365

Ser Thr Pro Asn Glu Lys Leu Leu Gly His Leu Val Lys Glu Lys Tyr
            370                 375                 380

Asp Thr Asp Phe Tyr Ile Leu Asp Lys Tyr Pro Leu Ala Val Arg Pro
385                 390                 395                 400

Phe Tyr Thr Met Pro Asp Pro Arg Asn Pro Lys Gln Ser Asn Ser Tyr
                405                 410                 415

Asp Met Phe Met Arg Gly Glu Glu Ile Leu Ser Gly Ala Gln Arg Ile
                420                 425                 430

His Asp Pro Gln Leu Leu Thr Glu Arg Ala Leu His His Gly Ile Asp
            435                 440                 445

Leu Glu Lys Ile Lys Ala Tyr Ile Asp Ser Phe Arg Phe Gly Ala Pro
            450                 455                 460

Pro His Ala Gly Gly Gly Ile Gly Leu Glu Arg Val Thr Met Leu Phe
465                 470                 475                 480

Leu Gly Leu His Asn Val Arg Gln Thr Ser Met Phe Pro Arg Asp Pro
            485                 490                 495

Lys Arg Leu Thr Pro
            500

<210> SEQ ID NO 111
<211> LENGTH: 501
<212> TYPE: PRT
<213> ORGANISM: Artificial Sequence
```

<220> FEATURE:
<223> OTHER INFORMATION: DRS polypeptide variant with reduced cysteine content

<400> SEQUENCE: 111

```
Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val Ile Asp Leu Arg Thr Ser Thr Ser
            180                 185                 190

Gln Ala Val Phe Arg Leu Gln Ser Gly Ile Cys His Leu Phe Arg Glu
        195                 200                 205

Thr Leu Ile Asn Lys Gly Phe Val Glu Ile Gln Thr Pro Lys Ile Ile
        210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Cys Ala Asp Phe Glu Lys Val Phe Ser Ile Gly Pro Val Phe
            260                 265                 270

Arg Ala Glu Asp Ser Asn Thr His Arg His Leu Thr Glu Phe Val Gly
        275                 280                 285

Leu Asp Ile Glu Met Ala Phe Asn Tyr His Tyr His Glu Val Met Glu
290                 295                 300

Glu Ile Ala Asp Thr Met Val Gln Ile Phe Lys Gly Leu Gln Glu Arg
305                 310                 315                 320

Phe Gln Thr Glu Ile Gln Thr Val Asn Lys Gln Phe Pro Ser Glu Pro
                325                 330                 335

Phe Lys Phe Leu Glu Pro Thr Leu Arg Leu Glu Tyr Ser Glu Ala Leu
            340                 345                 350

Ala Met Leu Arg Glu Ala Gly Val Glu Met Gly Asp Glu Asp Asp Leu
        355                 360                 365

Ser Thr Pro Asn Glu Lys Leu Leu Gly His Leu Val Lys Glu Lys Tyr
        370                 375                 380

Asp Thr Asp Phe Tyr Ile Leu Asp Lys Tyr Pro Leu Ala Val Arg Pro
```

```
                385                 390                 395                 400
            Phe Tyr Thr Met Pro Asp Pro Arg Asn Pro Lys Gln Ser Asn Ser Tyr
                            405                 410                 415

Asp Met Phe Met Arg Gly Glu Glu Ile Leu Ser Gly Ala Gln Arg Ile
                            420                 425                 430

His Asp Pro Gln Leu Leu Thr Glu Arg Ala Leu His His Gly Ile Asp
                            435                 440                 445

Leu Glu Lys Ile Lys Ala Tyr Ile Asp Ser Phe Arg Phe Gly Ala Pro
                            450                 455                 460

Pro His Ala Gly Gly Gly Ile Gly Leu Glu Arg Val Thr Met Leu Phe
            465                 470                 475                 480

Leu Gly Leu His Asn Val Arg Gln Thr Ser Met Phe Pro Arg Asp Pro
                            485                 490                 495

Lys Arg Leu Thr Pro
                            500

<210> SEQ ID NO 112
<211> LENGTH: 501
<212> TYPE: PRT
<213> ORGANISM: Artificial Sequence
<220> FEATURE:
<223> OTHER INFORMATION: DRS polypeptide variant with reduced cysteine
      content

<400> SEQUENCE: 112

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val Ile Asp Leu Arg Thr Ser Thr Ser
                180                 185                 190

Gln Ala Val Phe Arg Leu Gln Ser Gly Ile Ala His Leu Phe Arg Glu
            195                 200                 205

Thr Leu Ile Asn Lys Gly Phe Val Glu Ile Gln Thr Pro Lys Ile Ile
            210                 215                 220

Ser Ala Ala Ser Glu Gly Gly Ala Asn Val Phe Thr Val Ser Tyr Phe
225                 230                 235                 240
```

```
Lys Asn Asn Ala Tyr Leu Ala Gln Ser Pro Gln Leu Tyr Lys Gln Met
                245                 250                 255

Cys Ile Cys Ala Asp Phe Glu Lys Val Phe Ser Ile Gly Pro Val Phe
            260                 265                 270

Arg Ala Glu Asp Ser Asn Thr His Arg His Leu Thr Glu Phe Val Gly
        275                 280                 285

Leu Asp Ile Glu Met Ala Phe Asn Tyr His Tyr His Glu Val Met Glu
    290                 295                 300

Glu Ile Ala Asp Thr Met Val Gln Ile Phe Lys Gly Leu Gln Glu Arg
305                 310                 315                 320

Phe Gln Thr Glu Ile Gln Thr Val Asn Lys Gln Phe Pro Cys Glu Pro
                325                 330                 335

Phe Lys Phe Leu Glu Pro Thr Leu Arg Leu Glu Tyr Cys Glu Ala Leu
            340                 345                 350

Ala Met Leu Arg Glu Ala Gly Val Glu Met Gly Asp Glu Asp Asp Leu
        355                 360                 365

Ser Thr Pro Asn Glu Lys Leu Leu Gly His Leu Val Lys Glu Lys Tyr
    370                 375                 380

Asp Thr Asp Phe Tyr Ile Leu Asp Lys Tyr Pro Leu Ala Val Arg Pro
385                 390                 395                 400

Phe Tyr Thr Met Pro Asp Pro Arg Asn Pro Lys Gln Ser Asn Ser Tyr
                405                 410                 415

Asp Met Phe Met Arg Gly Glu Glu Ile Leu Ser Gly Ala Gln Arg Ile
            420                 425                 430

His Asp Pro Gln Leu Leu Thr Glu Arg Ala Leu His His Gly Ile Asp
        435                 440                 445

Leu Glu Lys Ile Lys Ala Tyr Ile Asp Ser Phe Arg Phe Gly Ala Pro
    450                 455                 460

Pro His Ala Gly Gly Gly Ile Gly Leu Glu Arg Val Thr Met Leu Phe
465                 470                 475                 480

Leu Gly Leu His Asn Val Arg Gln Thr Ser Met Phe Pro Arg Asp Pro
                485                 490                 495

Lys Arg Leu Thr Pro
            500

<210> SEQ ID NO 113
<211> LENGTH: 501
<212> TYPE: PRT
<213> ORGANISM: Artificial Sequence
<220> FEATURE:
<223> OTHER INFORMATION: DRS polypeptide variant with reduced cysteine
      content

<400> SEQUENCE: 113

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95
```

```
Ala Ser Lys Gln Met Val Lys Phe Ala Ala Asn Ile Asn Lys Glu Ser
            100                 105                 110
Ile Val Asp Val Glu Gly Val Arg Lys Val Asn Gln Lys Ile Gly
        115                 120                 125
Ser Cys Thr Gln Gln Asp Val Glu Leu His Val Gln Lys Ile Tyr Val
130                 135                 140
Ile Ser Leu Ala Glu Pro Arg Leu Pro Leu Gln Leu Asp Asp Ala Val
145                 150                 155                 160
Arg Pro Glu Ala Glu Gly Glu Glu Gly Arg Ala Thr Val Asn Gln
            165                 170                 175
Asp Thr Arg Leu Asp Asn Arg Val Ile Asp Leu Arg Ser Thr Ser
        180                 185                 190
Gln Ala Val Phe Arg Leu Gln Ser Gly Ile Val His Leu Phe Arg Glu
        195                 200                 205
Thr Leu Ile Asn Lys Gly Phe Val Glu Ile Gln Thr Pro Lys Ile Ile
        210                 215                 220
Ser Ala Ala Ser Glu Gly Gly Ala Asn Val Phe Thr Val Ser Tyr Phe
225                 230                 235                 240
Lys Asn Asn Ala Tyr Leu Ala Gln Ser Pro Gln Leu Tyr Lys Gln Met
                245                 250                 255
Cys Ile Cys Ala Asp Phe Glu Lys Val Phe Ser Ile Gly Pro Val Phe
            260                 265                 270
Arg Ala Glu Asp Ser Asn Thr His Arg His Leu Thr Glu Phe Val Gly
        275                 280                 285
Leu Asp Ile Glu Met Ala Phe Asn Tyr His Tyr His Glu Val Met Glu
        290                 295                 300
Glu Ile Ala Asp Thr Met Val Gln Ile Phe Lys Gly Leu Gln Glu Arg
305                 310                 315                 320
Phe Gln Thr Glu Ile Gln Thr Val Asn Lys Gln Phe Pro Cys Glu Pro
                325                 330                 335
Phe Lys Phe Leu Glu Pro Thr Leu Arg Leu Glu Tyr Cys Glu Ala Leu
            340                 345                 350
Ala Met Leu Arg Glu Ala Gly Val Glu Met Gly Asp Glu Asp Leu
        355                 360                 365
Ser Thr Pro Asn Glu Lys Leu Leu Gly His Leu Val Lys Glu Lys Tyr
        370                 375                 380
Asp Thr Asp Phe Tyr Ile Leu Asp Lys Tyr Pro Leu Ala Val Arg Pro
385                 390                 395                 400
Phe Tyr Thr Met Pro Asp Pro Arg Asn Pro Lys Gln Ser Asn Ser Tyr
                405                 410                 415
Asp Met Phe Met Arg Gly Glu Glu Ile Leu Ser Gly Ala Gln Arg Ile
            420                 425                 430
His Asp Pro Gln Leu Leu Thr Glu Arg Ala Leu His His Gly Ile Asp
        435                 440                 445
Leu Glu Lys Ile Lys Ala Tyr Ile Asp Ser Phe Arg Phe Gly Ala Pro
        450                 455                 460
Pro His Ala Gly Gly Gly Ile Gly Leu Glu Arg Val Thr Met Leu Phe
465                 470                 475                 480
Leu Gly Leu His Asn Val Arg Gln Thr Ser Met Phe Pro Arg Asp Pro
                485                 490                 495
Lys Arg Leu Thr Pro
            500
```

<210> SEQ ID NO 114
<211> LENGTH: 501
<212> TYPE: PRT
<213> ORGANISM: Artificial Sequence
<220> FEATURE:
<223> OTHER INFORMATION: DRS polypeptide variant with reduced cysteine content

<400> SEQUENCE: 114

```
Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val Ile Asp Leu Arg Thr Ser Thr Ser
            180                 185                 190

Gln Ala Val Phe Arg Leu Gln Ser Gly Ile Ala His Leu Phe Arg Glu
        195                 200                 205

Thr Leu Ile Asn Lys Gly Phe Val Glu Ile Gln Thr Pro Lys Ile Ile
210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Cys Ala Asp Phe Glu Lys Val Phe Ser Ile Gly Pro Val Phe
            260                 265                 270

Arg Ala Glu Asp Ser Asn Thr His Arg His Leu Thr Glu Phe Val Gly
        275                 280                 285

Leu Asp Ile Glu Met Ala Phe Asn Tyr His Tyr His Glu Val Met Glu
290                 295                 300

Glu Ile Ala Asp Thr Met Val Gln Ile Phe Lys Gly Leu Gln Glu Arg
305                 310                 315                 320

Phe Gln Thr Glu Ile Gln Thr Val Asn Lys Gln Phe Pro Ser Glu Pro
                325                 330                 335

Phe Lys Phe Leu Glu Pro Thr Leu Arg Leu Glu Tyr Ser Glu Ala Leu
            340                 345                 350

Ala Met Leu Arg Glu Ala Gly Val Glu Met Gly Asp Glu Asp Leu
        355                 360                 365
```

```
Ser Thr Pro Asn Glu Lys Leu Leu Gly His Leu Val Lys Glu Lys Tyr
    370                 375                 380

Asp Thr Asp Phe Tyr Ile Leu Asp Lys Tyr Pro Leu Ala Val Arg Pro
385                 390                 395                 400

Phe Tyr Thr Met Pro Asp Pro Arg Asn Pro Lys Gln Ser Asn Ser Tyr
                405                 410                 415

Asp Met Phe Met Arg Gly Glu Glu Ile Leu Ser Gly Ala Gln Arg Ile
                420                 425                 430

His Asp Pro Gln Leu Leu Thr Glu Arg Ala Leu His His Gly Ile Asp
            435                 440                 445

Leu Glu Lys Ile Lys Ala Tyr Ile Asp Ser Phe Arg Phe Gly Ala Pro
    450                 455                 460

Pro His Ala Gly Gly Gly Ile Gly Leu Glu Arg Val Thr Met Leu Phe
465                 470                 475                 480

Leu Gly Leu His Asn Val Arg Gln Thr Ser Met Phe Pro Arg Asp Pro
                485                 490                 495

Lys Arg Leu Thr Pro
            500

<210> SEQ ID NO 115
<211> LENGTH: 501
<212> TYPE: PRT
<213> ORGANISM: Artificial Sequence
<220> FEATURE:
<223> OTHER INFORMATION: DRS polypeptide variant with reduced cysteine
      content

<400> SEQUENCE: 115

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val Ile Asp Leu Arg Thr Ser Thr Ser
            180                 185                 190

Gln Ala Val Phe Arg Leu Gln Ser Gly Ile Val His Leu Phe Arg Glu
        195                 200                 205

Thr Leu Ile Asn Lys Gly Phe Val Glu Ile Gln Thr Pro Lys Ile Ile
```

210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Ala Ala Asp Phe Glu Lys Val Phe Ser Ile Gly Pro Val Phe
            260                 265                 270

Arg Ala Glu Asp Ser Asn Thr His Arg His Leu Thr Glu Phe Val Gly
        275                 280                 285

Leu Asp Ile Glu Met Ala Phe Asn Tyr His Tyr His Glu Val Met Glu
    290                 295                 300

Glu Ile Ala Asp Thr Met Val Gln Ile Phe Lys Gly Leu Gln Glu Arg
305                 310                 315                 320

Phe Gln Thr Glu Ile Gln Thr Val Asn Lys Gln Phe Pro Ser Glu Pro
                325                 330                 335

Phe Lys Phe Leu Glu Pro Thr Leu Arg Leu Glu Tyr Ser Glu Ala Leu
            340                 345                 350

Ala Met Leu Arg Glu Ala Gly Val Glu Met Gly Asp Glu Asp Asp Leu
        355                 360                 365

Ser Thr Pro Asn Glu Lys Leu Leu Gly His Leu Val Lys Glu Lys Tyr
    370                 375                 380

Asp Thr Asp Phe Tyr Ile Leu Asp Lys Tyr Pro Leu Ala Val Arg Pro
385                 390                 395                 400

Phe Tyr Thr Met Pro Asp Pro Arg Asn Pro Lys Gln Ser Asn Ser Tyr
                405                 410                 415

Asp Met Phe Met Arg Gly Glu Glu Ile Leu Ser Gly Ala Gln Arg Ile
            420                 425                 430

His Asp Pro Gln Leu Leu Thr Glu Arg Ala Leu His His Gly Ile Asp
        435                 440                 445

Leu Glu Lys Ile Lys Ala Tyr Ile Asp Ser Phe Arg Phe Gly Ala Pro
    450                 455                 460

Pro His Ala Gly Gly Gly Ile Gly Leu Glu Arg Val Thr Met Leu Phe
465                 470                 475                 480

Leu Gly Leu His Asn Val Arg Gln Thr Ser Met Phe Pro Arg Asp Pro
                485                 490                 495

Lys Arg Leu Thr Pro
            500

<210> SEQ ID NO 116
<211> LENGTH: 501
<212> TYPE: PRT
<213> ORGANISM: Artificial Sequence
<220> FEATURE:
<223> OTHER INFORMATION: DRS polypeptide variant with reduced cysteine
      content

<400> SEQUENCE: 116

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

-continued

```
Arg Val His Thr Ser Arg Ala Lys Gly Lys Gln Cys Phe Leu Val Leu
 65                  70                  75                  80

Arg Gln Gln Gln Phe Asn Val Gln Ala Leu Val Ala Val Gly Asp His
                 85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val Ile Asp Leu Arg Thr Ser Thr Ser
                180                 185                 190

Gln Ala Val Phe Arg Leu Gln Ser Gly Ile Ala His Leu Phe Arg Glu
            195                 200                 205

Thr Leu Ile Asn Lys Gly Phe Val Glu Ile Gln Thr Pro Lys Ile Ile
        210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Ala Ala Asp Phe Glu Lys Val Phe Ser Ile Gly Pro Val Phe
            260                 265                 270

Arg Ala Glu Asp Ser Asn Thr His Arg His Leu Thr Glu Phe Val Gly
        275                 280                 285

Leu Asp Ile Glu Met Ala Phe Asn Tyr His Tyr His Glu Val Met Glu
    290                 295                 300

Glu Ile Ala Asp Thr Met Val Gln Ile Phe Lys Gly Leu Gln Glu Arg
305                 310                 315                 320

Phe Gln Thr Glu Ile Gln Thr Val Asn Lys Gln Phe Pro Ser Glu Pro
                325                 330                 335

Phe Lys Phe Leu Glu Pro Thr Leu Arg Leu Glu Tyr Ser Glu Ala Leu
            340                 345                 350

Ala Met Leu Arg Glu Ala Gly Val Glu Met Gly Asp Glu Asp Asp Leu
        355                 360                 365

Ser Thr Pro Asn Glu Lys Leu Leu Gly His Leu Val Lys Glu Lys Tyr
    370                 375                 380

Asp Thr Asp Phe Tyr Ile Leu Asp Lys Tyr Pro Leu Ala Val Arg Pro
385                 390                 395                 400

Phe Tyr Thr Met Pro Asp Pro Arg Asn Pro Lys Gln Ser Asn Ser Tyr
                405                 410                 415

Asp Met Phe Met Arg Gly Glu Glu Ile Leu Ser Gly Ala Gln Arg Ile
            420                 425                 430

His Asp Pro Gln Leu Leu Thr Glu Arg Ala Leu His His Gly Ile Asp
        435                 440                 445

Leu Glu Lys Ile Lys Ala Tyr Ile Asp Ser Phe Arg Phe Gly Ala Pro
    450                 455                 460

Pro His Ala Gly Gly Gly Ile Gly Leu Glu Arg Val Thr Met Leu Phe
465                 470                 475                 480

Leu Gly Leu His Asn Val Arg Gln Thr Ser Met Phe Pro Arg Asp Pro
```

```
                        485                 490                 495
Lys Arg Leu Thr Pro
                500

<210> SEQ ID NO 117
<211> LENGTH: 501
<212> TYPE: PRT
<213> ORGANISM: Artificial Sequence
<220> FEATURE:
<223> OTHER INFORMATION: RS polypeptide variant with reduced cysteine
      content

<400> SEQUENCE: 117

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val Ile Asp Leu Arg Thr Ser Thr Ser
            180                 185                 190

Gln Ala Val Phe Arg Leu Gln Ser Gly Ile Val His Leu Phe Arg Glu
        195                 200                 205

Thr Leu Ile Asn Lys Gly Phe Val Glu Ile Gln Thr Pro Lys Ile Ile
        210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Ala Ala Asp Phe Glu Lys Val Phe Ser Ile Gly Pro Val Phe
            260                 265                 270

Arg Ala Glu Asp Ser Asn Thr His Arg His Leu Thr Glu Phe Val Gly
        275                 280                 285

Leu Asp Ile Glu Met Ala Phe Asn Tyr His Tyr His Glu Val Met Glu
        290                 295                 300

Glu Ile Ala Asp Thr Met Val Gln Ile Phe Lys Gly Leu Gln Glu Arg
305                 310                 315                 320

Phe Gln Thr Glu Ile Gln Thr Val Asn Lys Gln Phe Pro Ser Glu Pro
                325                 330                 335
```

```
Phe Lys Phe Leu Glu Pro Thr Leu Arg Leu Glu Tyr Ser Glu Ala Leu
            340                 345                 350

Ala Met Leu Arg Glu Ala Gly Val Glu Met Gly Asp Glu Asp Asp Leu
        355                 360                 365

Ser Thr Pro Asn Glu Lys Leu Leu Gly His Leu Val Lys Glu Lys Tyr
    370                 375                 380

Asp Thr Asp Phe Tyr Ile Leu Asp Lys Tyr Pro Leu Ala Val Arg Pro
385                 390                 395                 400

Phe Tyr Thr Met Pro Asp Pro Arg Asn Pro Lys Gln Ser Asn Ser Tyr
                405                 410                 415

Asp Met Phe Met Arg Gly Glu Glu Ile Leu Ser Gly Ala Gln Arg Ile
            420                 425                 430

His Asp Pro Gln Leu Leu Thr Glu Arg Ala Leu His His Gly Ile Asp
        435                 440                 445

Leu Glu Lys Ile Lys Ala Tyr Ile Asp Ser Phe Arg Phe Gly Ala Pro
    450                 455                 460

Pro His Ala Gly Gly Gly Ile Gly Leu Glu Arg Val Thr Met Leu Phe
465                 470                 475                 480

Leu Gly Leu His Asn Val Arg Gln Thr Ser Met Phe Pro Arg Asp Pro
                485                 490                 495

Lys Arg Leu Thr Pro
            500

<210> SEQ ID NO 118
<211> LENGTH: 1503
<212> TYPE: DNA
<213> ORGANISM: Artificial Sequence
<220> FEATURE:
<223> OTHER INFORMATION: DRS polynucleotide encoding polypetide variant
      with reduced cysteine content

<400> SEQUENCE: 118
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgcttc ttagtcccta     240
cgtcagcagc agtttaatgt ccaggctctt gtggcggtgg agaccatgc aagcaagcag      300 atggttaaat tgctgccaa catcaacaaa gagagcattg tggatgtaga aggtgttgtg      360
agaaaagtga atcagaaaat ggaagctgt acacagcaag acgttgagtt acatgttcag      420
aagatttatg tgatcagttt ggctgaaccc cgtctgcccc tgcagctgga tgatgctgtt     480
cggcctgagg cagaaggaga agaggaagga agagctactg ttaaccagga tacaagatta     540
gacaacagag tcattgatct taggacatca actagtcagg cagtcttccg tctccagtct     600
ggcatctgcc atctcttccg agaaacttta attaacaaag gttttgtgga aatccaaact     660
cctaaaatta tttcagctgc cagtgaagga ggagccaatg ttttactgt gtcatatttt      720 aaaaataatg catacctggc tcagtcccca cagctatata agcaaatgtg catttgtgct     780
gattttgaga aggtttttctc tattggacca gtattcagag cggaagactc taatacccat     840
agacatctaa ctgagtttgt tggtttggac attgaaatgg cttttaatta ccattaccac     900
gaagttatgg aagaaattgc tgacaccatg gtacaaatat caaaggact tcaagaaagg     960 tttcagactg aaattcaaac agtgaataaa cagttcccat ctgagccatt caaattttg     1020 gagccaactc taagactaga atattgtgaa gcattggcta tgcttaggga agctggagtc     1080
```

```
gaaatgggag atgaagacga tctgagcaca ccaaatgaaa agctgttggg tcatttggta    1140
aaggaaaagt atgatacaga tttttatatt cttgataaat atccattggc tgtaagacct    1200
ttctatacca tgcctgaccc aagaaatccc aaacagtcca actcttacga tatgttcatg    1260
agaggagaag aaatattgtc aggagctcaa agaatacatg atcctcaact gctaacagag    1320
agagctttac atcatggaat tgatttggag aaaattaagg cttacattga ttccttccgc    1380
tttggagccc ctcctcatgc tggtggaggc attggattgg aacgagttac tatgctgttt    1440
ctgggattgc ataatgttcg tcagacctcc atgttccctc gtgatcccaa acgactcact    1500
cct                                                                  1503
```

<210> SEQ ID NO 119
<211> LENGTH: 1503
<212> TYPE: DNA
<213> ORGANISM: Artificial Sequence
<220> FEATURE:
<223> OTHER INFORMATION: DRS polynucleotide encoding polypetide variant
      with reduced cysteine content

<400> SEQUENCE: 119

```
atgcccagcg ccagcgccag ccgcaagagt caggagaagc cgcgggagat catggacgcg     60
gcggaagatt atgctaaaga gagatatgga atatcttcaa tgatacaatc acaagaaaaa    120
ccagatcgag ttttggttcg ggttagagac ttgacaatac aaaaagctga tgaagttgtt    180
tgggtacgtg caagagttca tacaagcaga gctaaaggga acagtgctt cttagtccta    240 cgtcagcagc agtttaatgt ccaggctctt gtggcggtgg agaccatgc aagcaagcag    300 atggttaaat ttgctgccaa catcaacaaa gagagcattg tggatgtaga aggtgttgtg    360
agaaaagtga atcagaaaat tggaagctgt acacagcaag acgttgagtt acatgttcag    420
aagatttatg tgatcagttt ggctgaaccc cgtctgcccc tgcagctgga tgatgctgtt    480
cggcctgagg cagaaggaga agaggaagga agagctactg ttaaccagga tacaagatta    540
gacaacagag tcattgatct taggacatca actagtcagg cagtcttccg tctccagtct    600
ggcatctgcc atctcttccg agaaacttta attaacaaag gttttgtgga atccaaact    660 cctaaaatta tttcagctgc cagtgaagga ggagccaatg ttttactgt gtcatatttt    720 aaaaataatg cataccctgg ctcagtcccca cagctatata agcaaatgtg catttgtgct    780
gattttgaga aggttttctc tattggacca gtattcagag cggaagactc taatacccat    840
agacatctaa ctgagtttgt tggtttggac attgaaatgg ctttaattaa ccattaccac    900
gaagttatgg aagaaattgc tgacaccatg gtacaaatat tcaaaggact tcaagaaagg    960
tttcagactg aaattcaaac agtgaataaa cagttcccat gtgagccatt caaattttg    1020 gagccaactc taagactaga atattctgaa gcattggcta tgcttaggga agctggagtc    1080
gaaatgggag atgaagacga tctgagcaca ccaaatgaaa agctgttggg tcatttggta    1140
aaggaaaagt atgatacaga tttttatatt cttgataaat atccattggc tgtaagacct    1200
ttctatacca tgcctgaccc aagaaatccc aaacagtcca actcttacga tatgttcatg    1260
agaggagaag aaatattgtc aggagctcaa agaatacatg atcctcaact gctaacagag    1320
agagctttac atcatggaat tgatttggag aaaattaagg cttacattga ttccttccgc    1380
tttggagccc ctcctcatgc tggtggaggc attggattgg aacgagttac tatgctgttt    1440
ctgggattgc ataatgttcg tcagacctcc atgttccctc gtgatcccaa acgactcact    1500
cct                                                                  1503
```

<210> SEQ ID NO 120
<211> LENGTH: 1503
<212> TYPE: DNA
<213> ORGANISM: Artificial Sequence
<220> FEATURE:
<223> OTHER INFORMATION: DRS polynucleotide encoding polypetide variant with reduced cysteine content

<400> SEQUENCE: 120

| | | | | | |
|---|---|---|---|---|---|
| atgcccagcg | ccagcgccag | ccgcaagagt | caggagaagc | cgcgggagat | catggacgcg | 60 |
| gcggaagatt | atgctaaaga | gagatatgga | atatcttcaa | tgatacaatc | acaagaaaaa | 120 |
| ccagatcgag | ttttggttcg | ggttagagac | ttgacaatac | aaaaagctga | tgaagttgtt | 180 |
| tgggtacgtg | caagagttca | tacaagcaga | gctaaaggga | acagtgctt | cttagtccta | 240 |
| cgtcagcagc | agtttaatgt | ccaggctctt | gtggcggtgg | gagaccatgc | aagcaagcag | 300 |
| atggttaaat | ttgctgccaa | catcaacaaa | gagagcattg | tggatgtaga | aggtgttgtg | 360 |
| agaaaagtga | atcagaaaat | tggaagctgt | acacagcaag | acgttgagtt | acatgttcag | 420 |
| aagatttatg | tgatcagttt | ggctgaaccc | cgtctgcccc | tgcagctgga | tgatgctgtt | 480 |
| cggcctgagg | cagaaggaga | agaggaagga | agagctactt | taaccagga | tacaagatta | 540 |
| gacaacagag | tcattgatct | taggacatca | actagtcagg | cagtcttccg | tctccagtct | 600 |
| ggcatctgcc | atctcttccg | agaaacttta | attaacaaag | ttttgtgga | aatccaaact | 660 |
| cctaaaatta | tttcagctgc | cagtgaagga | ggagccaatg | ttttactgt | gtcatatttt | 720 |
| aaaaataatg | catacctggc | tcagtcccca | cagctatata | agcaaatgtg | catttgtgct | 780 |
| gattttgaga | aggttttctc | tattggacca | gtattcagag | cggaagactc | taatacccat | 840 |
| agacatctaa | ctgagtttgt | tggttttggac | attgaaatgg | cttttaatta | ccattaccac | 900 |
| gaagttatgg | aagaaattgc | tgacaccatg | gtacaaatat | caaaggact | tcaagaaagg | 960 |
| tttcagactg | aaattcaaac | agtgaataaa | cagttcccat | ctgagccatt | caaattttg | 1020 |
| gagccaactc | taagactaga | atattctgaa | gcattggcta | tgcttaggga | agctggagtc | 1080 |
| gaaatgggag | atgaagacga | tctgagcaca | ccaaatgaaa | agctgttggg | tcatttggta | 1140 |
| aaggaaaagt | atgatacaga | tttttatatt | cttgataaat | atccattggc | tgtaagacct | 1200 |
| ttctatacca | tgcctgaccc | aagaaatccc | aaacagtcca | actcttacga | tatgttcatg | 1260 |
| agaggagaag | aaatattgtc | aggagctcaa | agaatacatg | atcctcaact | gctaacagag | 1320 |
| agagctttac | atcatggaat | tgatttggag | aaaattaagg | cttacattga | ttccttccgc | 1380 |
| tttggagccc | ctcctcatgc | tggtggaggc | attggattgg | aacgagttac | tatgctgttt | 1440 |
| ctgggattgc | ataatgttcg | tcagacctcc | atgttccctc | gtgatcccaa | acgactcact | 1500 |
| cct | | | | | | 1503 |

<210> SEQ ID NO 121
<211> LENGTH: 1503
<212> TYPE: DNA
<213> ORGANISM: Artificial Sequence
<220> FEATURE:
<223> OTHER INFORMATION: DRS polynucleotide encoding polypetide variant with reducedcysteine content

<400> SEQUENCE: 121

| | | | | | |
|---|---|---|---|---|---|
| atgcccagcg | ccagcgccag | ccgcaagagt | caggagaagc | cgcgggagat | catggacgcg | 60 |
| gcggaagatt | atgctaaaga | gagatatgga | atatcttcaa | tgatacaatc | acaagaaaaa | 120 |

```
ccagatcgag ttttggttcg ggttagagac ttgacaatac aaaaagctga tgaagttgtt      180
tgggtacgtg caagagttca tacaagcaga gctaaaggga aacagtgctt cttagtccta      240
cgtcagcagc agtttaatgt ccaggctctt gtggcggtgg gagaccatgc aagcaagcag      300
atggttaaat ttgctgccaa catcaacaaa gagagcattg tggatgtaga aggtgttgtg      360
agaaaagtga atcagaaaat tggaagctgt acacagcaag acgttgagtt acatgttcag      420
aagatttatg tgatcagttt ggctgaaccc cgtctgcccc tgcagctgga tgatgctgtt      480
cggcctgagg cagaaggaga agaggaagga agagctactg ttaaccagga tacaagatta      540
gacaacagag tcattgatct taggacatca actagtcagg cagtcttccg tctccagtct      600
ggcatcgccc atctcttccg agaaacttta attaacaaag ttttgtgga aatccaaact       660 cctaaaatta tttcagctgc cagtgaagga ggagccaatg tttttactgt gtcatatttt      720
aaaaataatg catacctggc tcagtcccca cagctatata agcaaatgtg catttgtgct      780
gattttgaga aggttttctc tattggacca gtattcagag cggaagactc taatacccat      840
agacatctaa ctgagtttgt tggtttggac attgaaatgg cttttaatta ccattaccac      900
gaagttatgg aagaaattgc tgacaccatg gtacaaatat caaaggact tcaagaaagg       960 tttcagactg aaattcaaac agtgaataaa cagttcccat gtgagccatt caaatttttg     1020
gagccaactc taagactaga atattgtgaa gcattggcta tgcttaggga agctggagtc     1080
gaaatgggag atgaagacga tctgagcaca ccaaatgaaa agctgttggg tcatttggta     1140
aaggaaaagt atgatacaga ttttatatt cttgataaat atccattggc tgtaagacct      1200
ttctatacca tgcctgaccc aagaaatccc aacagtcca actcttacga tatgttcatg      1260
agaggagaag aaatattgtc aggagctcaa agaatacatg atcctcaact gctaacagag     1320
agagctttac atcatggaat tgatttggag aaaattaagg cttacattga ttccttccgc     1380
tttggagccc ctcctcatgc tggtggaggc attggattgg aacgagttac tatgctgttt     1440
ctgggattgc ataatgttcg tcagacctcc atgttccctc gtgatcccaa acgactcact     1500
cct                                                                    1503
```

<210> SEQ ID NO 122
<211> LENGTH: 1503
<212> TYPE: DNA
<213> ORGANISM: Artificial Sequence
<220> FEATURE:
<223> OTHER INFORMATION: DRS polynucleotide encoding polypetide variant
      with reduced cysteine content

<400> SEQUENCE: 122

```
atgcccagcg ccagcgccag ccgcaagagt caggagaagc cgcgggagat catggacgcg       60
gcggaagatt atgctaaaga gagatatgga atatcttcaa tgatacaatc acaagaaaaa      120
ccagatcgag ttttggttcg ggttagagac ttgacaatac aaaaagctga tgaagttgtt      180
tgggtacgtg caagagttca tacaagcaga gctaaaggga aacagtgctt cttagtccta      240
cgtcagcagc agtttaatgt ccaggctctt gtggcggtgg gagaccatgc aagcaagcag      300
atggttaaat ttgctgccaa catcaacaaa gagagcattg tggatgtaga aggtgttgtg      360
agaaaagtga atcagaaaat tggaagctgt acacagcaag acgttgagtt acatgttcag      420
aagatttatg tgatcagttt ggctgaaccc cgtctgcccc tgcagctgga tgatgctgtt      480
cggcctgagg cagaaggaga agaggaagga agagctactg ttaaccagga tacaagatta      540
gacaacagag tcattgatct taggacatca actagtcagg cagtcttccg tctccagtct      600
```

-continued

```
ggcatcgtcc atctcttccg agaaacttta attaacaaag gttttgtgga aatccaaact    660
cctaaaatta tttcagctgc cagtgaagga ggagccaatg tttttactgt gtcatatttt    720
aaaaataatg catacctggc tcagtcccca cagctatata agcaaatgtg catttgtgct    780
gattttgaga aggttttctc tattggacca gtattcagag cggaagactc taatacccat    840
agacatctaa ctgagtttgt tggtttggac attgaaatgg cttttaatta ccattaccac    900
gaagttatgg aagaaattgc tgacaccatg gtacaaatat caaaggact  tcaagaaagg    960
tttcagactg aaattcaaac agtgaataaa cagttcccat gtgagccatt caaatttttg   1020
gagccaactc taagactaga atattgtgaa gcattggcta tgcttaggga agctggagtc   1080
gaaatgggag atgaagacga tctgagcaca ccaaatgaaa agctgttggg tcatttggta   1140
aaggaaaagt atgatacaga ttttatatt  cttgataaat atccattggc tgtaagacct   1200
ttctatacca tgcctgaccc aagaaatccc aaacagtcca actcttacga tatgttcatg   1260
agaggagaag aaatattgtc aggagctcaa agaatacatg atcctcaact gctaacagag   1320
agagctttac atcatggaat tgatttggag aaaattaagg cttacattga ttccttccgc   1380
tttggagccc ctcctcatgc tggtggaggc attggattgg aacgagttac tatgctgttt   1440
ctgggattgc ataatgttcg tcagacctcc atgttccctc gtgatcccaa acgactcact   1500
cct                                                                1503
```

<210> SEQ ID NO 123
<211> LENGTH: 1503
<212> TYPE: DNA
<213> ORGANISM: Artificial Sequence
<220> FEATURE:
<223> OTHER INFORMATION: DRS polynucleotide encoding polypetide variant
      with reduced cysteine content

<400> SEQUENCE: 123

```
atgcccagcg ccagcgccag ccgcaagagt caggagaagc cgcgggagat catggacgcg     60
gcggaagatt atgctaaaga gagatatgga atatcttcaa tgatacaatc acaagaaaaa    120
ccagatcgag ttttggttcg ggttagagac ttgacaatac aaaaagctga tgaagttgtt    180
tgggtacgtg caagagttca tacaagcaga gctaaaggga acagtgctt  cttagtccta    240
cgtcagcagc agtttaatgt ccaggctctt gtggcggtgg agaccatgc  aagcaagcag    300
atggttaaat ttgctgccaa catcaacaaa gagagcattg tggatgtaga aggtgttgtg    360
agaaaagtga atcagaaaat tggaagctgt acacagcaag acgttgagtt acatgttcag    420
aagatttatg tgatcagttt ggctgaaccc cgtctgcccc tgcagctgga tgatgctgtt    480
cggcctgagg cagaaggaga agaggaagga agagctactg ttaaccagga tacaagatta    540
gacaacagag tcattgatct taggacatca actagtcagg cagtcttccg tctccagtct    600
ggcatcgccc atctcttccg agaaacttta attaacaaag gttttgtgga aatccaaact    660
cctaaaatta tttcagctgc cagtgaagga ggagccaatg tttttactgt gtcatatttt    720
aaaaataatg catacctggc tcagtcccca cagctatata agcaaatgtg catttgtgct    780
gattttgaga aggttttctc tattggacca gtattcagag cggaagactc taatacccat    840
agacatctaa ctgagtttgt tggtttggac attgaaatgg cttttaatta ccattaccac    900
gaagttatgg aagaaattgc tgacaccatg gtacaaatat caaaggact  tcaagaaagg    960
tttcagactg aaattcaaac agtgaataaa cagttcccat ctgagccatt caaatttttg   1020
gagccaactc taagactaga atattctgaa gcattggcta tgcttaggga agctggagtc   1080
```

```
gaaatgggag atgaagacga tctgagcaca ccaaatgaaa agctgttggg tcatttggta    1140
aaggaaaagt atgatacaga tttttatatt cttgataaat atccattggc tgtaagacct    1200
ttctatacca tgcctgaccc aagaaatccc aacagtcca actcttacga tatgttcatg    1260
agaggagaag aaatattgtc aggagctcaa agaatacatg atcctcaact gctaacagag    1320
agagctttac atcatggaat tgatttggag aaaattaagg cttacattga ttccttccgc    1380
tttggagccc ctcctcatgc tggtggaggc attggattgg aacgagttac tatgctgttt    1440
ctgggattgc ataatgttcg tcagacctcc atgttccctc gtgatccaa acgactcact    1500 cct                                                                  1503

<210> SEQ ID NO 124
<211> LENGTH: 1503
<212> TYPE: DNA
<213> ORGANISM: Artificial Sequence
<220> FEATURE:
<223> OTHER INFORMATION: DRS polynucleotide encoding polypetide variant
      with reduced cysteine content

<400> SEQUENCE: 124
atgcccagcg ccagcgccag ccgcaagagt caggagaagc cgcgggagat catggacgcg      60
gcggaagatt atgctaaaga gagatatgga atatcttcaa tgatacaatc acaagaaaaa    120
ccagatcgag ttttggttcg ggttagagac ttgacaatac aaaaagctga tgaagttgtt    180
tgggtacgtg caagagttca tacaagcaga gctaaaggga acagtgctt cttagtccta    240 cgtcagcagc agtttaatgt ccaggctctt gtggcggtgg agaccatgc aagcaagcag    300 atggttaaat tgctgccaa catcaacaaa gagagcattg tggatgtaga aggtgttgtg    360
agaaaagtga atcagaaaat tggaagctgt acacagcaag acgttgagtt acatgttcag    420
aagatttatg tgatcagttt ggctgaaccc cgtctgcccc tgcagctgga tgatgctgtt    480
cggcctgagg cagaaggaga agaggaagga agagctactg ttaaccagga tacaagatta    540
gacaacagag tcattgatct taggacatca actagtcagg cagtcttccg tctccagtct    600
ggcatcgtcc atctcttccg agaaactta attaacaaag ttttgtgga atccaaact    660 cctaaaatta tttcagctgc cagtgaagga ggagccaatg tttttactgt gtcatatttt    720
aaaaataatg cataccctggc tcagtcccca cagctatata agcaaatgtg catttgtgct    780
gattttgaga aggttttctc tattggacca gtattcagag cggaagactc taatacccat    840
agacatctaa ctgagtttgt tggttggac attgaaatgg ctttaaatta ccattaccac    900
gaagttatgg aagaaattgc tgacaccatg gtacaaatat tcaaaggact tcaagaaagg    960
tttcagactg aaattcaaac agtgaataaa cagttcccat ctgagccatt caaattttg   1020 gagccaactc taagactaga atattctgaa gcattggcta tgcttaggga agctggagtc   1080
gaaatgggag atgaagacga tctgagcaca ccaaatgaaa agctgttggg tcatttggta   1140
aaggaaaagt atgatacaga tttttatatt cttgataaat atccattggc tgtaagacct   1200
ttctatacca tgcctgaccc aagaaatccc aacagtcca actcttacga tatgttcatg   1260
agaggagaag aaatattgtc aggagctcaa agaatacatg atcctcaact gctaacagag   1320
agagctttac atcatggaat tgatttggag aaaattaagg cttacattga ttccttccgc   1380
tttggagccc ctcctcatgc tggtggaggc attggattgg aacgagttac tatgctgttt   1440
ctgggattgc ataatgttcg tcagacctcc atgttccctc gtgatccaa acgactcact   1500 cct                                                                  1503
```

<210> SEQ ID NO 125
<211> LENGTH: 1503
<212> TYPE: DNA
<213> ORGANISM: Artificial Sequence
<220> FEATURE:
<223> OTHER INFORMATION: DRS polynucleotide encoding polypetide variant
      with reduced cysteine content

<400> SEQUENCE: 125

| | | | | | |
|---|---|---|---|---|---|
| atgcccagcg | ccagcgccag | ccgcaagagt | caggagaagc | cgcgggagat | catggacgcg | 60 |
| gcggaagatt | atgctaaaga | gagatatgga | atatcttcaa | tgatacaatc | acaagaaaaa | 120 |
| ccagatcgag | ttttggttcg | ggttagagac | ttgacaatac | aaaaagctga | tgaagttgtt | 180 |
| tgggtacgtg | caagagttca | tacaagcaga | gctaaaggga | acagtgctt | cttagtccta | 240 |
| cgtcagcagc | agtttaatgt | ccaggctctt | gtggcggtgg | gagaccatgc | aagcaagcag | 300 |
| atggttaaat | ttgctgccaa | catcaacaaa | gagagcattg | tggatgtaga | aggtgttgtg | 360 |
| agaaaagtga | atcagaaaat | tggaagctgt | acacagcaag | acgttgagtt | acatgttcag | 420 |
| aagatttatg | tgatcagttt | ggctgaaccc | cgtctgcccc | tgcagctgga | tgatgctgtt | 480 |
| cggcctgagg | cagaaggaga | agaggaagga | agagctactt | ttaaccagga | tacaagatta | 540 |
| gacaacagag | tcattgatct | taggacatca | actagtcagg | cagtcttccg | tctccagtct | 600 |
| ggcatcgccc | atctcttccg | agaaactta | attaacaaag | ttttgtggaa | atccaaact | 660 |
| cctaaaatta | tttcagctgc | cagtgaagga | ggagccaatg | tttttactgt | gtcatatttt | 720 |
| aaaaataatg | catacctggc | tcagtcccca | cagctatata | agcaaatgtg | cattgcggct | 780 |
| gattttgaga | aggttttctc | tattggacca | gtattcagag | cggaagactc | taatacccat | 840 |
| agacatctaa | ctgagtttgt | tggtttggac | attgaaatgg | cttttaatta | ccattaccac | 900 |
| gaagttatgg | aagaaattgc | tgacaccatg | gtacaaatat | caaaggact | tcaagaaagg | 960 |
| tttcagactg | aaattcaaac | agtgaataaa | cagttcccat | ctgagccatt | caaattttttg | 1020 |
| gagccaactc | taagactaga | atattctgaa | gcattggcta | tgcttaggga | agctggagtc | 1080 |
| gaaatgggag | atgaagacga | tctgagcaca | ccaaatgaaa | agctgttggg | tcatttggta | 1140 |
| aaggaaaagt | atgatacaga | tttttatatt | cttgataaat | atccattggc | tgtaagacct | 1200 |
| ttctatacca | tgcctgaccc | aagaaatccc | aaacagtcca | actcttacga | tatgttcatg | 1260 |
| agaggagaag | aaatattgtc | aggagctcaa | agaatacatg | atcctcaact | gctaacagag | 1320 |
| agagctttac | atcatggaat | tgatttggag | aaaattaagg | cttacattga | ttccttccgc | 1380 |
| tttggagccc | ctcctcatgc | tggtggaggc | attggattgg | aacgagttac | tatgctgttt | 1440 |
| ctgggattgc | ataatgttcg | tcagacctcc | atgttccctc | gtgatcccaa | acgactcact | 1500 |
| cct | | | | | | 1503 |

<210> SEQ ID NO 126
<211> LENGTH: 1503
<212> TYPE: DNA
<213> ORGANISM: Artificial Sequence
<220> FEATURE:
<223> OTHER INFORMATION: DRS polynucleotide encoding polypetide variant
      with reduced cysteine content

<400> SEQUENCE: 126

| | | | | | |
|---|---|---|---|---|---|
| atgcccagcg | ccagcgccag | ccgcaagagt | caggagaagc | cgcgggagat | catggacgcg | 60 |
| gcggaagatt | atgctaaaga | gagatatgga | atatcttcaa | tgatacaatc | acaagaaaaa | 120 |

```
ccagatcgag ttttggttcg ggttagagac ttgacaatac aaaaagctga tgaagttgtt        180
tgggtacgtg caagagttca tacaagcaga gctaaaggga aacagtgctt cttagtccta        240
cgtcagcagc agtttaatgt ccaggctctt gtggcggtgg gagaccatgc aagcaagcag        300
atggttaaat ttgctgccaa catcaacaaa gagagcattg tggatgtaga aggtgttgtg        360
agaaaagtga atcagaaaat tggaagctgt acacagcaag acgttgagtt acatgttcag        420
aagatttatg tgatcagttt ggctgaaccc cgtctgcccc tgcagctgga tgatgctgtt        480
cggcctgagg cagaaggaga agaggaagga agagctactg ttaaccagga tacaagatta        540
gacaacagag tcattgatct taggacatca actagtcagg cagtcttccg tctccagtct        600
ggcatcgtcc atctcttccg agaaacttta attaacaaag gttttgtgga aatccaaact        660
cctaaaatta tttcagctgc cagtgaagga ggagccaatg ttttactgt gtcatatttt         720 aaaaataatg catacctggc tcagtcccca cagctatata agcaaatgtg cattgcggct        780
gattttgaga aggttttctc tattggacca gtattcagag cggaagactc taatacccat        840
agacatctaa ctgagtttgt tggtttggac attgaaatgg cttttaatta ccattaccac        900
gaagttatgg aagaaattgc tgacaccatg gtacaaatat caaaggact tcaagaaagg         960 tttcagactg aaattcaaac agtgaataaa cagttcccat ctgagccatt caaatttttg       1020
gagccaactc taagactaga atattctgaa gcattggcta tgcttaggga agctggagtc       1080
gaaatgggag atgaagacga tctgagcaca ccaaatgaaa agctgttggg tcatttggta       1140
aaggaaaagt atgatacaga tttttatatt cttgataaat atccattggc tgtaagacct       1200
ttctatacca tgcctgaccc aagaaatccc aacagtcca actcttacga tatgttcatg       1260
agaggagaag aaatattgtc aggagctcaa agaatacatg atcctcaact gctaacagag       1320
agagctttac atcatggaat tgatttggag aaaattaagg cttacattga ttccttccgc       1380
tttggagccc ctcctcatgc tggtggaggc attggattgg aacgagttac tatgctgttt       1440
ctgggattgc ataatgttcg tcagacctcc atgttccctc gtgatcccaa acgactcact       1500
cct                                                                     1503

<210> SEQ ID NO 127
<211> LENGTH: 546
<212> TYPE: DNA
<213> ORGANISM: Homo sapiens

<400> SEQUENCE: 127
atgcccagcg ccagcgccag ccgcaagagt caggagaagc cgcgggagat catggacgcg         60
gcggaagatt atgctaaaga gagatatgga atatcttcaa tgatacaatc acaagaaaaa        120
ccagatcgag ttttggttcg ggttagagac ttgacaatac aaaaagctga tgaagttgtt        180
tgggtacgtg caagagttca tacaagcaga gctaaaggga aacagtgctt cttagtccta        240
cgtcagcagc agtttaatgt ccaggctctt gtggcggtgg gagaccatgc aagcaagcag        300
atggttaaat ttgctgccaa catcaacaaa gagagcattg tggatgtaga aggtgttgtg        360
agaaaagtga atcagaaaat tggaagctgt acacagcaag acgttgagtt acatgttcag        420
aagatttatg tgatcagttt ggctgaaccc cgtctgcccc tgcagctgga tgatgctgtt        480
cggcctgagg cagaaggaga agaggaagga agagctactg ttaaccagga tacaagatta        540
gacaac                                                                   546

<210> SEQ ID NO 128
<211> LENGTH: 540
```

<212> TYPE: DNA
<213> ORGANISM: Homo sapiens

<400> SEQUENCE: 128

```
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgcttc ttagtccta      240
cgtcagcagc agtttaatgt ccaggctctt gtggcggtgg agaccatgc aagcaagcag      300
atggttaaat tgctgccaa catcaacaaa gagagcattg tggatgtaga aggtgttgtg      360
agaaaagtga atcagaaaat tggaagctgt acacagcaag acgttgagtt acatgttcag     420
aagatttatg tgatcagttt ggctgaaccc cgtctgcccc tgcagctgga tgatgctgtt     480
cggcctgagg cagaaggaga agaggaagga agagctactg ttaaccagga tacaagatta    540
```

<210> SEQ ID NO 129
<211> LENGTH: 534
<212> TYPE: DNA
<213> ORGANISM: Homo sapiens

<400> SEQUENCE: 129

```
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgcttc ttagtccta      240
cgtcagcagc agtttaatgt ccaggctctt gtggcggtgg agaccatgc aagcaagcag      300
atggttaaat tgctgccaa catcaacaaa gagagcattg tggatgtaga aggtgttgtg      360
agaaaagtga atcagaaaat tggaagctgt acacagcaag acgttgagtt acatgttcag     420
aagatttatg tgatcagttt ggctgaaccc cgtctgcccc tgcagctgga tgatgctgtt     480
cggcctgagg cagaaggaga agaggaagga agagctactg ttaaccagga taca          534
```

<210> SEQ ID NO 130
<211> LENGTH: 528
<212> TYPE: DNA
<213> ORGANISM: Homo sapiens

<400> SEQUENCE: 130

```
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgcttc ttagtccta      240
cgtcagcagc agtttaatgt ccaggctctt gtggcggtgg agaccatgc aagcaagcag      300
atggttaaat tgctgccaa catcaacaaa gagagcattg tggatgtaga aggtgttgtg      360
agaaaagtga atcagaaaat tggaagctgt acacagcaag acgttgagtt acatgttcag     420
aagatttatg tgatcagttt ggctgaaccc cgtctgcccc tgcagctgga tgatgctgtt     480
cggcctgagg cagaaggaga agaggaagga agagctactg ttaaccag                528
```

<210> SEQ ID NO 131
<211> LENGTH: 522
<212> TYPE: DNA

<213> ORGANISM: Homo sapiens

<400> SEQUENCE: 131

```
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgctt cttagtccta      240
cgtcagcagc agtttaatgt ccaggctctt gtggcggtgg agaccatgc aagcaagcag      300
atggttaaat ttgctgccaa catcaacaaa gagagcattg tggatgtaga aggtgttgtg     360
agaaaagtga atcagaaaat tggaagctgt acacagcaag acgttgagtt acatgttcag     420
aagatttatg tgatcagttt ggctgaaccc cgtctgcccc tgcagctgga tgatgctgtt     480
cggcctgagg cagaaggaga agaggaagga agagctactg tt                       522
```

<210> SEQ ID NO 132
<211> LENGTH: 516
<212> TYPE: DNA
<213> ORGANISM: Homo sapiens

<400> SEQUENCE: 132

```
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgctt cttagtccta      240
cgtcagcagc agtttaatgt ccaggctctt gtggcggtgg agaccatgc aagcaagcag      300
atggttaaat ttgctgccaa catcaacaaa gagagcattg tggatgtaga aggtgttgtg     360
agaaaagtga atcagaaaat tggaagctgt acacagcaag acgttgagtt acatgttcag     420
aagatttatg tgatcagttt ggctgaaccc cgtctgcccc tgcagctgga tgatgctgtt     480
cggcctgagg cagaaggaga agaggaagga agagct                              516
```

<210> SEQ ID NO 133
<211> LENGTH: 510
<212> TYPE: DNA
<213> ORGANISM: Homo sapiens

<400> SEQUENCE: 133

```
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgctt cttagtccta      240
cgtcagcagc agtttaatgt ccaggctctt gtggcggtgg agaccatgc aagcaagcag      300
atggttaaat ttgctgccaa catcaacaaa gagagcattg tggatgtaga aggtgttgtg     360
agaaaagtga atcagaaaat tggaagctgt acacagcaag acgttgagtt acatgttcag     420
aagatttatg tgatcagttt ggctgaaccc cgtctgcccc tgcagctgga tgatgctgtt     480
cggcctgagg cagaaggaga agaggaagga                                     510
```

<210> SEQ ID NO 134
<211> LENGTH: 504
<212> TYPE: DNA
<213> ORGANISM: Homo sapiens

<400> SEQUENCE: 134

```
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgctt cttagtccta     240
cgtcagcagc agtttaatgt ccaggctctt gtggcggtgg gagaccatgc aagcaagcag     300
atggttaaat ttgctgccaa catcaacaaa gagagcattg tggatgtaga aggtgttgtg     360
agaaaagtga atcagaaaat tggaagctgt acacagcaag acgttgagtt acatgttcag     420
aagatttatg tgatcagttt ggctgaaccc cgtctgcccc tgcagctgga tgatgctgtt     480
cggcctgagg cagaaggaga agag                                            504
```

<210> SEQ ID NO 135
<211> LENGTH: 498
<212> TYPE: DNA
<213> ORGANISM: Homo sapiens

<400> SEQUENCE: 135

```
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgctt cttagtccta     240
cgtcagcagc agtttaatgt ccaggctctt gtggcggtgg gagaccatgc aagcaagcag     300
atggttaaat ttgctgccaa catcaacaaa gagagcattg tggatgtaga aggtgttgtg     360
agaaaagtga atcagaaaat tggaagctgt acacagcaag acgttgagtt acatgttcag     420
aagatttatg tgatcagttt ggctgaaccc cgtctgcccc tgcagctgga tgatgctgtt     480
cggcctgagg cagaagga                                                   498
```

<210> SEQ ID NO 136
<211> LENGTH: 492
<212> TYPE: DNA
<213> ORGANISM: Homo sapiens

<400> SEQUENCE: 136

```
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgctt cttagtccta     240
cgtcagcagc agtttaatgt ccaggctctt gtggcggtgg gagaccatgc aagcaagcag     300
atggttaaat ttgctgccaa catcaacaaa gagagcattg tggatgtaga aggtgttgtg     360
agaaaagtga atcagaaaat tggaagctgt acacagcaag acgttgagtt acatgttcag     420
aagatttatg tgatcagttt ggctgaaccc cgtctgcccc tgcagctgga tgatgctgtt     480
cggcctgagg ca                                                         492
```

<210> SEQ ID NO 137
<211> LENGTH: 486
<212> TYPE: DNA
<213> ORGANISM: Homo sapiens

<400> SEQUENCE: 137

```
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgctt cttagtccta     240
cgtcagcagc agtttaatgt ccaggctctt gtggcggtgg agaccatgc aagcaagcag     300
atggttaaat ttgctgccaa catcaacaaa gagagcattg tggatgtaga aggtgttgtg     360
agaaaagtga atcagaaaat ggaagctgt acacagcaag acgttgagtt acatgttcag     420
aagatttatg tgatcagttt ggctgaaccc cgtctgcccc tgcagctgga tgatgctgtt     480
cggcct                                                                486
```

<210> SEQ ID NO 138
<211> LENGTH: 480
<212> TYPE: DNA
<213> ORGANISM: Homo sapiens

<400> SEQUENCE: 138

```
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgctt cttagtccta     240
cgtcagcagc agtttaatgt ccaggctctt gtggcggtgg agaccatgc aagcaagcag     300
atggttaaat ttgctgccaa catcaacaaa gagagcattg tggatgtaga aggtgttgtg     360
agaaaagtga atcagaaaat ggaagctgt acacagcaag acgttgagtt acatgttcag     420
aagatttatg tgatcagttt ggctgaaccc cgtctgcccc tgcagctgga tgatgctgtt     480
```

<210> SEQ ID NO 139
<211> LENGTH: 474
<212> TYPE: DNA
<213> ORGANISM: Homo sapiens

<400> SEQUENCE: 139

```
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgctt cttagtccta     240
cgtcagcagc agtttaatgt ccaggctctt gtggcggtgg agaccatgc aagcaagcag     300
atggttaaat ttgctgccaa catcaacaaa gagagcattg tggatgtaga aggtgttgtg     360
agaaaagtga atcagaaaat ggaagctgt acacagcaag acgttgagtt acatgttcag     420
aagatttatg tgatcagttt ggctgaaccc cgtctgcccc tgcagctgga tgat           474
```

<210> SEQ ID NO 140
<211> LENGTH: 468
<212> TYPE: DNA
<213> ORGANISM: Homo sapiens

<400> SEQUENCE: 140

```
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
```

```
ccagatcgag ttttggttcg ggttagagac ttgacaatac aaaaagctga tgaagttgtt      180
tgggtacgtg caagagttca tacaagcaga gctaaaggga aacagtgctt cttagtccta      240
cgtcagcagc agtttaatgt ccaggctctt gtggcggtgg gagaccatgc aagcaagcag      300
atggttaaat ttgctgccaa catcaacaaa gagagcattg tggatgtaga aggtgttgtg      360
agaaaagtga atcagaaaat tggaagctgt acacagcaag acgttgagtt acatgttcag      420
aagatttatg tgatcagttt ggctgaaccc cgtctgcccc tgcagctg                   468
```

<210> SEQ ID NO 141
<211> LENGTH: 462
<212> TYPE: DNA
<213> ORGANISM: Homo sapiens

<400> SEQUENCE: 141

```
atgcccagcg ccagcgccag ccgcaagagt caggagaagc cgcgggagat catggacgcg      60
gcggaagatt atgctaaaga gagatatgga atatcttcaa tgatacaatc acaagaaaaa      120
ccagatcgag ttttggttcg ggttagagac ttgacaatac aaaaagctga tgaagttgtt      180
tgggtacgtg caagagttca tacaagcaga gctaaaggga aacagtgctt cttagtccta      240
cgtcagcagc agtttaatgt ccaggctctt gtggcggtgg gagaccatgc aagcaagcag      300
atggttaaat ttgctgccaa catcaacaaa gagagcattg tggatgtaga aggtgttgtg      360
agaaaagtga atcagaaaat tggaagctgt acacagcaag acgttgagtt acatgttcag      420
aagatttatg tgatcagttt ggctgaaccc cgtctgcccc tg                        462
```

<210> SEQ ID NO 142
<211> LENGTH: 456
<212> TYPE: DNA
<213> ORGANISM: Homo sapiens

<400> SEQUENCE: 142

```
atgcccagcg ccagcgccag ccgcaagagt caggagaagc cgcgggagat catggacgcg      60
gcggaagatt atgctaaaga gagatatgga atatcttcaa tgatacaatc acaagaaaaa      120
ccagatcgag ttttggttcg ggttagagac ttgacaatac aaaaagctga tgaagttgtt      180
tgggtacgtg caagagttca tacaagcaga gctaaaggga aacagtgctt cttagtccta      240
cgtcagcagc agtttaatgt ccaggctctt gtggcggtgg gagaccatgc aagcaagcag      300
atggttaaat ttgctgccaa catcaacaaa gagagcattg tggatgtaga aggtgttgtg      360
agaaaagtga atcagaaaat tggaagctgt acacagcaag acgttgagtt acatgttcag      420
aagatttatg tgatcagttt ggctgaaccc cgtctg                               456
```

<210> SEQ ID NO 143
<211> LENGTH: 450
<212> TYPE: DNA
<213> ORGANISM: Homo sapiens

<400> SEQUENCE: 143

```
atgcccagcg ccagcgccag ccgcaagagt caggagaagc cgcgggagat catggacgcg      60
gcggaagatt atgctaaaga gagatatgga atatcttcaa tgatacaatc acaagaaaaa      120
ccagatcgag ttttggttcg ggttagagac ttgacaatac aaaaagctga tgaagttgtt      180
tgggtacgtg caagagttca tacaagcaga gctaaaggga aacagtgctt cttagtccta      240
cgtcagcagc agtttaatgt ccaggctctt gtggcggtgg gagaccatgc aagcaagcag      300
```

```
atggttaaat tgctgccaa catcaacaaa gagagcattg tggatgtaga aggtgttgtg      360
agaaaagtga atcagaaaat tggaagctgt acacagcaag acgttgagtt acatgttcag      420
aagatttatg tgatcagttt ggctgaaccc                                       450
```

```
<210> SEQ ID NO 144
<211> LENGTH: 444
<212> TYPE: DNA
<213> ORGANISM: Homo sapiens

<400> SEQUENCE: 144
atgcccagcg ccagcgccag ccgcaagagt caggagaagc cgcgggagat catggacgcg       60
gcggaagatt atgctaaaga gagatatgga atatcttcaa tgatacaatc acaagaaaaa      120
ccagatcgag ttttggttcg ggttagagac ttgacaatac aaaaagctga tgaagttgtt      180
tgggtacgtg caagagttca tacaagcaga gctaaaggga acagtgctt cttagtccta       240 cgtcagcagc agtttaatgt ccaggctctt gtggcggtgg agaccatgc aagcaagcag        300 atggttaaat tgctgccaa catcaacaaa gagagcattg tggatgtaga aggtgttgtg        360
agaaaagtga atcagaaaat tggaagctgt acacagcaag acgttgagtt acatgttcag      420
aagatttatg tgatcagttt ggct                                             444
```

```
<210> SEQ ID NO 145
<211> LENGTH: 438
<212> TYPE: DNA
<213> ORGANISM: Homo sapiens

<400> SEQUENCE: 145
atgcccagcg ccagcgccag ccgcaagagt caggagaagc cgcgggagat catggacgcg       60
gcggaagatt atgctaaaga gagatatgga atatcttcaa tgatacaatc acaagaaaaa      120
ccagatcgag ttttggttcg ggttagagac ttgacaatac aaaaagctga tgaagttgtt      180
tgggtacgtg caagagttca tacaagcaga gctaaaggga acagtgctt cttagtccta       240 cgtcagcagc agtttaatgt ccaggctctt gtggcggtgg agaccatgc aagcaagcag        300 atggttaaat tgctgccaa catcaacaaa gagagcattg tggatgtaga aggtgttgtg        360
agaaaagtga atcagaaaat tggaagctgt acacagcaag acgttgagtt acatgttcag      420
aagatttatg tgatcagt                                                    438
```

```
<210> SEQ ID NO 146
<211> LENGTH: 453
<212> TYPE: DNA
<213> ORGANISM: Homo sapiens

<400> SEQUENCE: 146
gccagcgcca gccgcaagag tcaggagaag ccgcgggaga tcatggacgc ggcggaagat       60
tatgctaaag agagatatgg aatatcttca atgatacaat cacaagaaaa accagatcga      120
gttttggttc gggttagaga cttgacaata caaaaagctg atgaagttgt ttgggtacgt      180
gcaagagttc atacaagcag agctaaaggg aacagtgct tcttagtcct acgtcagcag        240
cagtttaatg tccaggctct gtggcggtg ggagaccatg caagcaagca gatggttaaa        300
tttgctgcca acatcaacaa agagagcatt gtggatgtag aaggtgttgt gagaaaagtg      360
aatcagaaaa ttggaagctg tacacagcaa gacgttgagt tacatgttca gaagatttat      420
gtgatcagtt tggctgaacc ccgtctgccc ctg                                   453
```

<210> SEQ ID NO 147
<211> LENGTH: 447
<212> TYPE: DNA
<213> ORGANISM: Homo sapiens

<400> SEQUENCE: 147

```
gccagccgca agagtcagga gaagccgcgg gagatcatgg acgcggcgga agattatgct    60
aaagagagat atggaatatc ttcaatgata caatcacaag aaaaaccaga tcgagttttg   120
gttcgggtta gagacttgac aatacaaaaa gctgatgaag ttgtttgggt acgtgcaaga   180
gttcatacaa gcagagctaa agggaaacag tgcttcttag tcctacgtca gcagcagttt   240
aatgtccagg ctcttgtggc ggtgggagac catgcaagca agcagatggt taaatttgct   300
gccaacatca acaaagagag cattgtggat gtagaaggtg ttgtgagaaa agtgaatcag   360
aaaattggaa gctgtacaca gcaagacgtt gagttacatg ttcagaagat ttatgtgatc   420
agtttggctg aaccccgtct gcccctg                                       447
```

<210> SEQ ID NO 148
<211> LENGTH: 441
<212> TYPE: DNA
<213> ORGANISM: Homo sapiens

<400> SEQUENCE: 148

```
cgcaagagtc aggagaagcc gcgggagatc atggacgcgg cggaagatta tgctaaagag    60
agatatggaa tatcttcaat gatacaatca agaaaaaac cagatcgagt tttggttcgg   120
gttagagact tgacaataca aaaagctgat gaagttgttt gggtacgtgc aagagttcat   180
acaagcagag ctaaagggaa acagtgcttc ttagtcctac gtcagcagca gtttaatgtc   240
caggctcttg tggcggtggg agaccatgca agcaagcaga tggttaaatt tgctgccaac   300
atcaacaaag agagcattgt ggatgtagaa ggtgttgtga gaaaagtgaa tcagaaaatt   360
ggaagctgta cacagcaaga cgttgagtta catgttcaga gatttatgt gatcagtttg   420
gctgaacccc gtctgcccct g                                             441
```

<210> SEQ ID NO 149
<211> LENGTH: 435
<212> TYPE: DNA
<213> ORGANISM: Homo sapiens

<400> SEQUENCE: 149

```
agtcaggaga agccgcggga gatcatggac gcggcggaag attatgctaa agagagatat    60
ggaatatctt caatgataca atcacaagaa aaaccagatc gagttttggt tcgggttaga   120
gacttgacaa tacaaaaagc tgatgaagtt gtttgggtac gtgcaagagt tcatacaagc   180
agagctaaag ggaaacagtg cttcttagtc ctacgtcagc agcagtttaa tgtccaggct   240
cttgtggcgg tgggagacca tgcaagcaag cagatggtta aatttgctgc caacatcaac   300
aaagagagca ttgtggatgt agaaggtgtt gtgagaaaag tgaatcagaa aattggaagc   360
tgtacacagc aagacgttga gttacatgtt cagaagattt atgtgatcag tttggctgaa   420
ccccgtctgc ccctg                                                    435
```

<210> SEQ ID NO 150
<211> LENGTH: 429
<212> TYPE: DNA
<213> ORGANISM: Homo sapiens

<400> SEQUENCE: 150

```
gagaagccgc gggagatcat ggacgcggcg aagattatg  ctaaagagag atatggaata      60
tcttcaatga tacaatcaca agaaaaacca gatcgagttt tggttcgggt tagagacttg     120
acaatacaaa aagctgatga agttgtttgg gtacgtgcaa gagttcatac aagcagagct     180
aaagggaaac agtgcttctt agtcctacgt cagcagcagt ttaatgtcca ggctcttgtg     240
gcggtgggag accatgcaag caagcagatg gttaaatttg ctgccaacat caacaaagag     300
agcattgtgg atgtagaagg tgttgtgaga aaagtgaatc agaaaattgg aagctgtaca     360
cagcaagacg ttgagttaca tgttcagaag atttatgtga tcagtttggc tgaaccccgt     420
ctgcccctg                                                             429

<210> SEQ ID NO 151
<211> LENGTH: 423
<212> TYPE: DNA
<213> ORGANISM: Homo sapiens

<400> SEQUENCE: 151
ccgcgggaga tcatggacgc ggcggaagat tatgctaaag agagatatgg aatatcttca      60
atgatacaat cacaagaaaa accagatcga gttttggttc gggttagaga cttgacaata     120
caaaaagctg atgaagttgt tgggtacgt gcaagagttc atacaagcag agctaaaggg     180
aaacagtgct tcttagtcct acgtcagcag cagtttaatg tccaggctct tgtggcggtg     240
ggagaccatg caagcaagca gatggttaaa tttgctgcca acatcaacaa agagagcatt     300
gtggatgtag aaggtgttgt gagaaaagtg aatcagaaaa ttggaagctg tacacagcaa     360
gacgttgagt tacatgttca agagatttat gtgatcagtt tggctgaacc ccgtctgccc     420
ctg                                                                   423

<210> SEQ ID NO 152
<211> LENGTH: 417
<212> TYPE: DNA
<213> ORGANISM: Homo sapiens

<400> SEQUENCE: 152
gagatcatgg acgcggcgga agattatgct aaagagagat atggaatatc ttcaatgata      60
caatcacaag aaaaaccaga tcgagttttg gttcgggtta gagacttgac aatacaaaaa     120
gctgatgaag ttgtttgggt acgtgcaaga gttcatacaa gcagagctaa agggaaacag     180
tgcttcttag tcctacgtca gcagcagttt aatgtccagg ctcttgtggc ggtgggagac     240
catgcaagca agcagatggt taaatttgct gccaacatca acaaagagag cattgtggat     300
gtagaaggtg ttgtgagaaa agtgaatcag aaaattggaa gctgtacaca gcaagacgtt     360
gagttacatg ttcagaagat ttatgtgatc agtttggctg aaccccgtct gcccctg        417

<210> SEQ ID NO 153
<211> LENGTH: 411
<212> TYPE: DNA
<213> ORGANISM: Homo sapiens

<400> SEQUENCE: 153
atggacgcgg cggaagatta tgctaaagag agatatggaa tatcttcaat gatacaatca      60
caagaaaaac cagatcgagt tttggttcgg gttagagact tgacaataca aaaagctgat     120
gaagttgttt gggtacgtgc aagagttcat acaagcagag ctaaagggaa acagtgcttc     180
ttagtcctac gtcagcagca gtttaatgtc caggctcttg tggcggtggg agaccatgca     240
agcaagcaga tggttaaatt tgctgccaac atcaacaaag agagcattgt ggatgtagaa     300
```

```
ggtgttgtga gaaaagtgaa tcagaaaatt ggaagctgta cacagcaaga cgttgagtta      360
catgttcaga agatttatgt gatcagtttg gctgaacccc gtctgcccct g               411

<210> SEQ ID NO 154
<211> LENGTH: 405
<212> TYPE: DNA
<213> ORGANISM: Homo sapiens

<400> SEQUENCE: 154
gcggcggaag attatgctaa agagagatat ggaatatctt caatgataca atcacaagaa       60
aaaccagatc gagttttggt tcgggttaga gacttgacaa tacaaaaagc tgatgaagtt      120
gtttgggtac gtgcaagagt tcatacaagc agagctaaag ggaaacagtg cttcttagtc      180
ctacgtcagc agcagtttaa tgtccaggct cttgtggcgg tgggagacca tgcaagcaag      240
cagatggtta aatttgctgc caacatcaac aaagagagca ttgtggatgt agaaggtgtt      300
gtgagaaaag tgaatcagaa aattggaagc tgtacacagc aagacgttga gttacatgtt      360
cagaagattt atgtgatcag tttggctgaa ccccgtctgc ccctg                      405

<210> SEQ ID NO 155
<211> LENGTH: 399
<212> TYPE: DNA
<213> ORGANISM: Homo sapiens

<400> SEQUENCE: 155
gcggcggaag attatgctaa agagagatat ggaatatctt caatgataca atcacaagaa       60
aaaccagatc gagttttggt tcgggttaga gacttgacaa tacaaaaagc tgatgaagtt      120
gtttgggtac gtgcaagagt tcatacaagc agagctaaag ggaaacagtg cttcttagtc      180
ctacgtcagc agcagtttaa tgtccaggct cttgtggcgg tgggagacca tgcaagcaag      240
cagatggtta aatttgctgc caacatcaac aaagagagca ttgtggatgt agaaggtgtt      300
gtgagaaaag tgaatcagaa aattggaagc tgtacacagc aagacgttga gttacatgtt      360
cagaagattt atgtgatcag tttggctgaa ccccgtctg                             399

<210> SEQ ID NO 156
<211> LENGTH: 393
<212> TYPE: DNA
<213> ORGANISM: Homo sapiens

<400> SEQUENCE: 156
gcggcggaag attatgctaa agagagatat ggaatatctt caatgataca atcacaagaa       60
aaaccagatc gagttttggt tcgggttaga gacttgacaa tacaaaaagc tgatgaagtt      120
gtttgggtac gtgcaagagt tcatacaagc agagctaaag ggaaacagtg cttcttagtc      180
ctacgtcagc agcagtttaa tgtccaggct cttgtggcgg tgggagacca tgcaagcaag      240
cagatggtta aatttgctgc caacatcaac aaagagagca ttgtggatgt agaaggtgtt      300
gtgagaaaag tgaatcagaa aattggaagc tgtacacagc aagacgttga gttacatgtt      360
cagaagattt atgtgatcag tttggctgaa ccc                                   393

<210> SEQ ID NO 157
<211> LENGTH: 411
<212> TYPE: DNA
<213> ORGANISM: Homo sapiens

<400> SEQUENCE: 157
```

```
atgcaggaga agccgcggga gatcatggac gcggcggaag attatgctaa agagagatat    60
ggaatatctt caatgataca atcacaagaa aaaccagatc gagttttggt tcgggttaga   120
gacttgacaa tacaaaaagc tgatgaagtt gtttgggtac gtgcaagagt tcatacaagc   180
agagctaaag ggaaacagtg cttcttagtc ctacgtcagc agcagtttaa tgtccaggct   240
cttgtggcgg tgggagacca tgcaagcaag cagatggtta aatttgcttg caacatcaac   300
aaagagagca ttgtggatgt agaaggtgtt gtgagaaaag tgaatcagaa aattggaagc   360
tgtacacagc aagacgttga gttacatgtt cagaagattt atgtgatcag t            411
```

<210> SEQ ID NO 158
<211> LENGTH: 405
<212> TYPE: DNA
<213> ORGANISM: Homo sapiens

<400> SEQUENCE: 158

```
atgaagccgc gggagatcat ggacgcggcg gaagattatg ctaaagagag atatggaata    60
tcttcaatga tacaatcaca agaaaaacca gatcgagttt tggttcgggt tagagacttg   120
acaatacaaa aagctgatga agttgtttgg gtacgtgcaa gagttcatac aagcagagct   180
aaagggaaac agtgcttctt agtcctacgt cagcagcagt ttaatgtcca ggctcttgtg   240
gcggtgggag accatgcaag caagcagatg gttaaatttg cttgcaacat caacaaagag   300
agcattgtgg atgtagaagg tgttgtgaga aagtgaatc agaaaattgg aagctgtaca   360
cagcaagacg ttgagttaca tgttcagaag atttatgtga tcagt                   405
```

<210> SEQ ID NO 159
<211> LENGTH: 405
<212> TYPE: DNA
<213> ORGANISM: Homo sapiens

<400> SEQUENCE: 159

```
atgaagccgc gggagatcat ggacgcggcg gaagattatg ctaaagagag atatggaata    60
tcttcaatga tacaatcaca agaaaaacca gatcgagttt tggttcgggt tagagacttg   120
acaatacaaa aagctgatga agttgtttgg gtacgtgcaa gagttcatac aagcagagct   180
aaagggaaac agtgcttctt agtcctacgt cagcagcagt ttaatgtcca ggctcttgtg   240
gcggtgggag accatgcaag caagcagatg gttaaatttg cttgcaacat caacaaagag   300
agcattgtgg atgtagaagg tgttgtgaga aagtgaatc agaaaattgg aagctgtaca   360
cagcaagacg ttgagttaca tgttcagaag atttatgtga tcagt                   405
```

<210> SEQ ID NO 160
<211> LENGTH: 393
<212> TYPE: DNA
<213> ORGANISM: Homo sapiens

<400> SEQUENCE: 160

```
atgatcatgg acgcggcgga agattatgct aaagagagat atggaatatc ttcaatgata    60
caatcacaag aaaaaccaga tcgagttttg gttcgggtta gagacttgac aatacaaaaa   120
gctgatgaag ttgtttgggt acgtgcaaga gttcatacaa gcagagctaa agggaaacag   180
tgcttcttag tcctacgtca gcagcagttt aatgtccagg ctcttgtggc ggtgggagac   240
catgcaagca agcagatggt taaatttgct tgcaacatca acaaagagag cattgtggat   300
gtagaaggtg ttgtgagaaa agtgaatcag aaaattggaa gctgtacaca gcaagacgtt   360
gagttacatg ttcagaagat ttatgtgatc agt                                 393
```

<210> SEQ ID NO 161
<211> LENGTH: 381
<212> TYPE: DNA
<213> ORGANISM: Homo sapiens

<400> SEQUENCE: 161

```
atggcggaag attatgctaa agagagatat ggaatatctt caatgataca atcacaagaa      60
aaaccagatc gagttttggt tcggttaga  gacttgacaa tacaaaaagc tgatgaagtt     120
gtttgggtac gtgcaagagt tcatacaagc agagctaaag ggaaacagtg cttcttagtc     180
ctacgtcagc agcagtttaa tgtccaggct cttgtggcgg tgggagacca tgcaagcaag     240
cagatggtta aatttgcttg caacatcaac aaagagagca ttgtggatgt agaaggtgtt     300
gtgagaaaag tgaatcagaa aattggaagc tgtacacagc aagacgttga gttacatgtt     360
cagaagattt atgtgatcag t                                               381
```

<210> SEQ ID NO 162
<211> LENGTH: 21
<212> TYPE: DNA
<213> ORGANISM: Artificial Sequence
<220> FEATURE:
<223> OTHER INFORMATION: Primer

<400> SEQUENCE: 162

```
cagttcccat ctgagccatt c                                                21
```

<210> SEQ ID NO 163
<211> LENGTH: 25
<212> TYPE: DNA
<213> ORGANISM: Artificial Sequence
<220> FEATURE:
<223> OTHER INFORMATION: Primer

<400> SEQUENCE: 163

```
gactagaata ttctgaagca ttggc                                            25
```

<210> SEQ ID NO 164
<211> LENGTH: 26
<212> TYPE: DNA
<213> ORGANISM: Artificial Sequence
<220> FEATURE:
<223> OTHER INFORMATION: Primer

<400> SEQUENCE: 164

```
ccagtctggc atcgcccatc tcttcc                                           26
```

<210> SEQ ID NO 165
<211> LENGTH: 26
<212> TYPE: DNA
<213> ORGANISM: Artificial Sequence
<220> FEATURE:
<223> OTHER INFORMATION: Primer

<400> SEQUENCE: 165

```
ccagtctggc atcgtccatc tcttcc                                           26
```

<210> SEQ ID NO 166
<211> LENGTH: 42
<212> TYPE: DNA
<213> ORGANISM: Artificial Sequence
<220> FEATURE:
<223> OTHER INFORMATION: Primer

```
<400> SEQUENCE: 166
ccacagctat ataagcaaat gtgcattgcg gctgattttg ag                    42

<210> SEQ ID NO 167
<211> LENGTH: 42
<212> TYPE: DNA
<213> ORGANISM: Artificial Sequence
<220> FEATURE:
<223> OTHER INFORMATION: Primer

<400> SEQUENCE: 167
gggttaggga taggcttacc agccaaactg atcacataaa tc                    42

<210> SEQ ID NO 168
<211> LENGTH: 41
<212> TYPE: DNA
<213> ORGANISM: Artificial Sequence
<220> FEATURE:
<223> OTHER INFORMATION: Primer

<400> SEQUENCE: 168
gggttaggga taggcttacc gggttcagcc aaactgatca c                     41

<210> SEQ ID NO 169
<211> LENGTH: 40
<212> TYPE: DNA
<213> ORGANISM: Artificial Sequence
<220> FEATURE:
<223> OTHER INFORMATION: Primer

<400> SEQUENCE: 169
gggttaggga taggcttacc cagacggggt tcagccaaac                       40

<210> SEQ ID NO 170
<211> LENGTH: 41
<212> TYPE: DNA
<213> ORGANISM: Artificial Sequence
<220> FEATURE:
<223> OTHER INFORMATION: Primer

<400> SEQUENCE: 170
gggttaggga taggcttacc cagctgcagg ggcagacggg g                     41

<210> SEQ ID NO 171
<211> LENGTH: 41
<212> TYPE: DNA
<213> ORGANISM: Artificial Sequence
<220> FEATURE:
<223> OTHER INFORMATION: Primer

<400> SEQUENCE: 171
gggttaggga taggcttacc atcatccagc tgcaggggca g                     41

<210> SEQ ID NO 172
<211> LENGTH: 42
<212> TYPE: DNA
<213> ORGANISM: Artificial Sequence
<220> FEATURE:
<223> OTHER INFORMATION: Primer

<400> SEQUENCE: 172
gggttaggga taggcttacc aacagcatca tccagctgca gg                    42

<210> SEQ ID NO 173
<211> LENGTH: 41
```

```
<212> TYPE: DNA
<213> ORGANISM: Artificial Sequence
<220> FEATURE:
<223> OTHER INFORMATION: Primer

<400> SEQUENCE: 173
gggttaggga taggcttacc aggccgaaca gcatcatcca g                  41

<210> SEQ ID NO 174
<211> LENGTH: 41
<212> TYPE: DNA
<213> ORGANISM: Artificial Sequence
<220> FEATURE:
<223> OTHER INFORMATION: Primer

<400> SEQUENCE: 174
gggttaggga taggcttacc tgcctcaggc cgaacagcat c                  41

<210> SEQ ID NO 175
<211> LENGTH: 41
<212> TYPE: DNA
<213> ORGANISM: Artificial Sequence
<220> FEATURE:
<223> OTHER INFORMATION: Primer

<400> SEQUENCE: 175
gggttaggga taggcttacc tccttctgcc tcaggccgaa c                  41

<210> SEQ ID NO 176
<211> LENGTH: 41
<212> TYPE: DNA
<213> ORGANISM: Artificial Sequence
<220> FEATURE:
<223> OTHER INFORMATION: Primer

<400> SEQUENCE: 176
gggttaggga taggcttacc ctcttctcct tctgcctcag g                  41

<210> SEQ ID NO 177
<211> LENGTH: 41
<212> TYPE: DNA
<213> ORGANISM: Artificial Sequence
<220> FEATURE:
<223> OTHER INFORMATION: Primer

<400> SEQUENCE: 177
gggttaggga taggcttacc tccttcctct tctccttctg c                  41

<210> SEQ ID NO 178
<211> LENGTH: 41
<212> TYPE: DNA
<213> ORGANISM: Artificial Sequence
<220> FEATURE:
<223> OTHER INFORMATION: Primer

<400> SEQUENCE: 178
gggttaggga taggcttacc agctcttcct tcctcttctc c                  41

<210> SEQ ID NO 179
<211> LENGTH: 41
<212> TYPE: DNA
<213> ORGANISM: Artificial Sequence
<220> FEATURE:
<223> OTHER INFORMATION: Primer

<400> SEQUENCE: 179
```
gggttaggga taggcttacc ctggttaaca gtagctcttc c					41

<210> SEQ ID NO 180
<211> LENGTH: 41
<212> TYPE: DNA
<213> ORGANISM: Artificial Sequence
<220> FEATURE:
<223> OTHER INFORMATION: Primer

<400> SEQUENCE: 180
gggttaggga taggcttacc tgtatcctgg ttaacagtag c					41

<210> SEQ ID NO 181
<211> LENGTH: 41
<212> TYPE: DNA
<213> ORGANISM: Artificial Sequence
<220> FEATURE:
<223> OTHER INFORMATION: Primer

<400> SEQUENCE: 181
gggttaggga taggcttacc taatcttgta tcctggttaa c					41

<210> SEQ ID NO 182
<211> LENGTH: 42
<212> TYPE: DNA
<213> ORGANISM: Artificial Sequence
<220> FEATURE:
<223> OTHER INFORMATION: Primer

<400> SEQUENCE: 182
gggttaggga taggcttacc gttgtctaat cttgtatcct gg					42

<210> SEQ ID NO 183
<211> LENGTH: 34
<212> TYPE: DNA
<213> ORGANISM: Artificial Sequence
<220> FEATURE:
<223> OTHER INFORMATION: Primer

<400> SEQUENCE: 183
gaaggagata taccatgagc gccagcgcca gccg					34

<210> SEQ ID NO 184
<211> LENGTH: 34
<212> TYPE: DNA
<213> ORGANISM: Artificial Sequence
<220> FEATURE:
<223> OTHER INFORMATION: Primer

<400> SEQUENCE: 184
gaaggagata taccatgagc gccagccgca agag					34

<210> SEQ ID NO 185
<211> LENGTH: 35
<212> TYPE: DNA
<213> ORGANISM: Artificial Sequence
<220> FEATURE:
<223> OTHER INFORMATION: Primer

<400> SEQUENCE: 185
gaaggagata taccatgagc cgcaagagtc aggag					35

<210> SEQ ID NO 186
<211> LENGTH: 34
<212> TYPE: DNA
<213> ORGANISM: Artificial Sequence

```
<220> FEATURE:
<223> OTHER INFORMATION: Primer

<400> SEQUENCE: 186
gaaggagata taccatgaag agtcaggaga agcc                                34

<210> SEQ ID NO 187
<211> LENGTH: 35
<212> TYPE: DNA
<213> ORGANISM: Artificial Sequence
<220> FEATURE:
<223> OTHER INFORMATION: Primer

<400> SEQUENCE: 187
gaaggagata tcatatgcag gagaagccgc gggag                               35

<210> SEQ ID NO 188
<211> LENGTH: 35
<212> TYPE: DNA
<213> ORGANISM: Artificial Sequence
<220> FEATURE:
<223> OTHER INFORMATION: Primer

<400> SEQUENCE: 188
gaaggagata tcatatgaag ccgcgggaga tcatg                               35

<210> SEQ ID NO 189
<211> LENGTH: 36
<212> TYPE: DNA
<213> ORGANISM: Artificial Sequence
<220> FEATURE:
<223> OTHER INFORMATION: Primer

<400> SEQUENCE: 189
gaaggagata tcatatgcgg gagatcatgg acgcgg                              36

<210> SEQ ID NO 190
<211> LENGTH: 33
<212> TYPE: DNA
<213> ORGANISM: Artificial Sequence
<220> FEATURE:
<223> OTHER INFORMATION: Primer

<400> SEQUENCE: 190
gaaggagata tcatatgatc atggacgcgg cgg                                 33

<210> SEQ ID NO 191
<211> LENGTH: 36
<212> TYPE: DNA
<213> ORGANISM: Artificial Sequence
<220> FEATURE:
<223> OTHER INFORMATION: Primer

<400> SEQUENCE: 191
gaaggagata tcatatggcg gaagattatg ctaaag                              36

<210> SEQ ID NO 192
<211> LENGTH: 30
<212> TYPE: DNA
<213> ORGANISM: Artificial Sequence
<220> FEATURE:
<223> OTHER INFORMATION: Primer

<400> SEQUENCE: 192
gaaggagata tcatatggat tatgctaaag                                     30
```

```
<210> SEQ ID NO 193
<211> LENGTH: 40
<212> TYPE: DNA
<213> ORGANISM: Artificial Sequence
<220> FEATURE:
<223> OTHER INFORMATION: Primer

<400> SEQUENCE: 193
accgatcaca tatgcaggag aagccgcggg agatcatgga                          40

<210> SEQ ID NO 194
<211> LENGTH: 39
<212> TYPE: DNA
<213> ORGANISM: Artificial Sequence
<220> FEATURE:
<223> OTHER INFORMATION: Primer

<400> SEQUENCE: 194
aagcttacgc atatgaagcc gcgggagatc atggacgcg                           39

<210> SEQ ID NO 195
<211> LENGTH: 40
<212> TYPE: DNA
<213> ORGANISM: Artificial Sequence
<220> FEATURE:
<223> OTHER INFORMATION: Primer

<400> SEQUENCE: 195
aactgttacc atatgatcat ggacgcggcg gaagattatg                          40

<210> SEQ ID NO 196
<211> LENGTH: 42
<212> TYPE: DNA
<213> ORGANISM: Artificial Sequence
<220> FEATURE:
<223> OTHER INFORMATION: Primer

<400> SEQUENCE: 196
aactgtcatc atatggcgga agattatgct aaagagagat at                       42

<210> SEQ ID NO 197
<211> LENGTH: 33
<212> TYPE: DNA
<213> ORGANISM: Artificial Sequence
<220> FEATURE:
<223> OTHER INFORMATION: Primer

<400> SEQUENCE: 197
tgacggctcg agactgatca cataaatctt ctg                                 33

<210> SEQ ID NO 198
<211> LENGTH: 47
<212> TYPE: DNA
<213> ORGANISM: Artificial Sequence
<220> FEATURE:
<223> OTHER INFORMATION: Primer

<400> SEQUENCE: 198
gcagatggtt aaatttgctt gcaacatcaa caaagagagc attgtgg                  47
```

PEGYLATED ASPARTYL-TRNA SYNTHETASE POLYPEPTIDES

CROSS-REFERENCE TO RELATED APPLICATIONS

This application claims benefit under 35 U.S.C. §119(e) of U.S. Provisional Application No. 61/567,602, filed Dec. 6, 2011, which is incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ATYR_108_01WO_ST25.txt. The text file is about 203 KB, was created on Dec. 6, 2012, and is being submitted electronically via EFS-Web.

BACKGROUND

Technical Field

The present invention relates generally to PEGylated aspartyl-tRNA synthetase (DRS) polypeptides, compositions comprising the same, and methods of using such polypeptides and compositions for treating or diagnosing a variety of conditions.

Description of the Related Art

Aspartyl-tRNA synthetases (DRS), and fragments and variants thereof, (collectively DRS polypeptides) have recently been shown to possess a variety of non-canonical activities of therapeutic and diagnostic relevance. In particular it has been established that certain aspartyl-tRNA synthetase fragments are highly potent, endogenously produced, Toll-like receptor modulators. Without being bound to any one specific theory of operation, it is believed that such DRS polypeptides are released from macrophage cells upon proteolytic cleavage, or through alternative splicing of the full length AspRS tRNA synthetase and are capable of binding to and modulating the activity of immunomodulatory, and other cell types. Such DRS polypeptides when administered, provide for a novel mechanism of selectively modulating inflammatory responses, without the side effect profiles typically associated with traditional anti-inflammatory agents such as steroids Toll-like receptors (TLRs) are a family of pattern recognition receptors that play a key role in initiating the rapid innate immune response in an organism. TLRs recognize certain pathogen or host derived cellular components which can be generally characterized as being either pathogen associated molecular patterns, (PAMPs), or damage-associated molecular pattern molecules, (DAMPS) respectively. PAMPS are typically unique to a given class of pathogen, and include for example bacterial components such as the lipopolysaccharide of Gram negative bacteria, and viral specific nucleic acid motifs or viral specific modifications of RNA or DNA. By contrast DAMPS are typically endogenous molecules released from dying host cells upon cellular stress or tissue damage.

TLRs are implicated in several chronic inflammatory and immune mediated disorders by various potential mechanisms, including those in which infectious agents have been proposed to initiate disease progression. For example in scenarios in which endogenous damage signals or self-antigens cause chronic inflammation in a TLR dependent manner, or where TLRs may be involved in the breakdown of immune tolerance. TLRs have been implicated in the pathogenesis of chronic inflammatory diseases such as inflammatory bowel disease, rheumatoid arthritis, psoriasis, and multiple sclerosis.

It is now increasingly recognized that the successful treatment of some autoimmune and inflammatory conditions of tissues requires effective control of the inflammatory reaction in order to preserve tissue integrity and function, without immune-compromising the patient. Recent experimental evidence has shown that specific modulation of TLR pathways induces an improvement in several inflammatory conditions, without comprising tissue function, or enhancing bacterial or viral infections, suggesting the potential for new therapeutic anti-inflammatory strategies with significantly improved side effect profiles. Moreover TLR agonists have already proved useful in clinical trials in allergic, infectious and autoimmune diseases and are under development for a broad range of other diseases including cancer, arthritis, multiple sclerosis, inflammatory bowel disease, see generally Zhu and Mohan (2010) Mediators of Inflammation doi:10.1155/2010/781235; Hennessy et al., Nat. Rev. 9:293-307, 2010). Therefore TLRs are becoming increasingly recognized as novel potential therapeutic targets for the modulation of a broad variety of diseases and disorders.

To best exploit these and other activities in therapeutic or diagnostic settings, there is a need in the art for DRS polypeptides having improved pharmacokinetic properties. The present invention is focused on the development of DRS polypeptides that have been modified through the addition of water soluble polymers, which retain the biological activity of the native DRS polypeptides and exhibit superior pharmacokinetic and other properties.

Although many suitable water soluble polymers exist, polyethylene glycol (PEG) is typically preferred as a water soluble polymer for attachment because it has good solubility in both water and in many organic solvents, lacks of toxicity, and immunogenicity, and is also clear, colorless, odorless, and chemically stable.

The term "PEGylation" refers to the modification of biological molecules by covalent conjugation with polyethylene glycol (PEG). PEGylation can change the physical and chemical properties of a biological molecule, such as its conformation, electrostatic binding, hydrophobicity, and pharmacokinetic profile. In general, PEGylation improves drug solubility and decreases immunogenicity. PEGylation also increases drug stability and the retention time of the conjugates in blood, and reduces proteolysis and renal excretion, thereby allowing a reduced dosing frequency. In order to benefit from these favorable pharmacokinetic consequences, a variety of therapeutic proteins, peptides, and antibody fragments, as well as small molecule drugs, have been PEGylated.

These improved therapeutic forms of the DRS polypeptides enable the development of more effective therapeutic regimens for the treatment of various diseases and disorders, and require significantly less frequent administration than the unmodified proteins.

AspRS1$^{N1}$ (DRS(1-154)) lot # D-N1-V5H-047, lanes 3 and 6: AspRS1$^{N1}$ (C76S) lot # D-N1:1-V5H-048.

Figure 2:
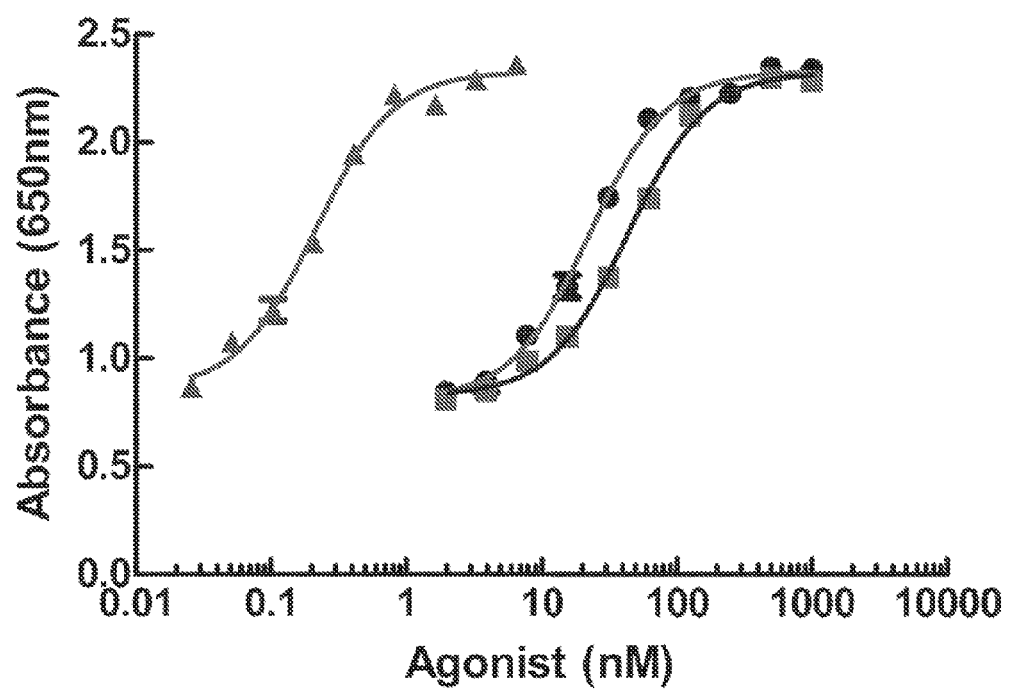

FIG. 2 shows a direct comparison of AspRS1$^{N1}$ (grey squares) and AspRS1$^{N1}$ (C76S) (black circles) on their ability to stimulate reporter gene activity mediated by the TLR2 receptor in HEK—Blue 2 cells. Grey triangles—Pam3C SK4.

Figure 3:
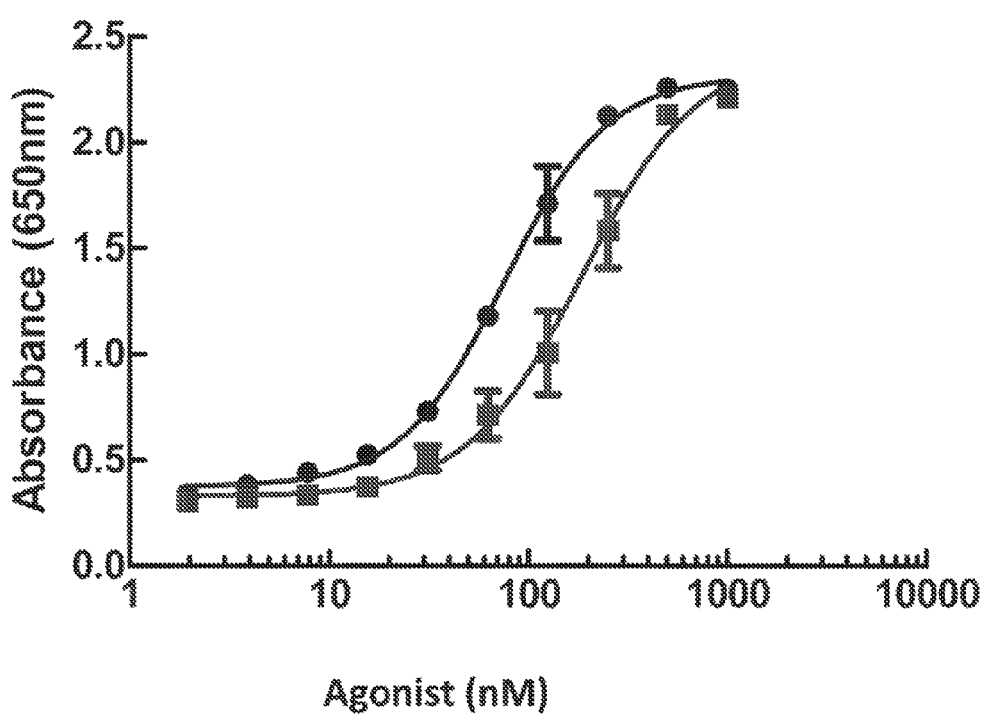

FIG. 3 shows a direct comparison of AspRS1$^{N1}$ (grey squares) and AspRS1$^{N1}$ (C76S) (Black circles) on their ability to stimulate reporter gene activity mediated by the TLR4 receptor in HEK-Blue 4 cells.

Figure 4A:
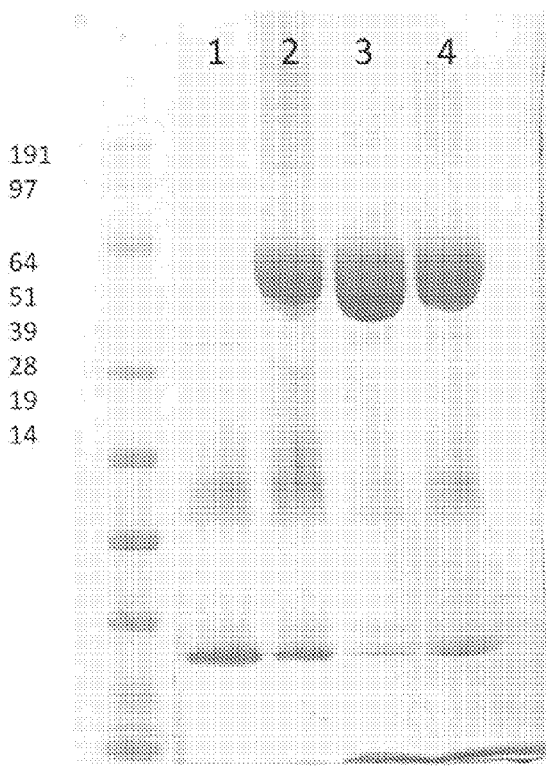
Figure 4B:
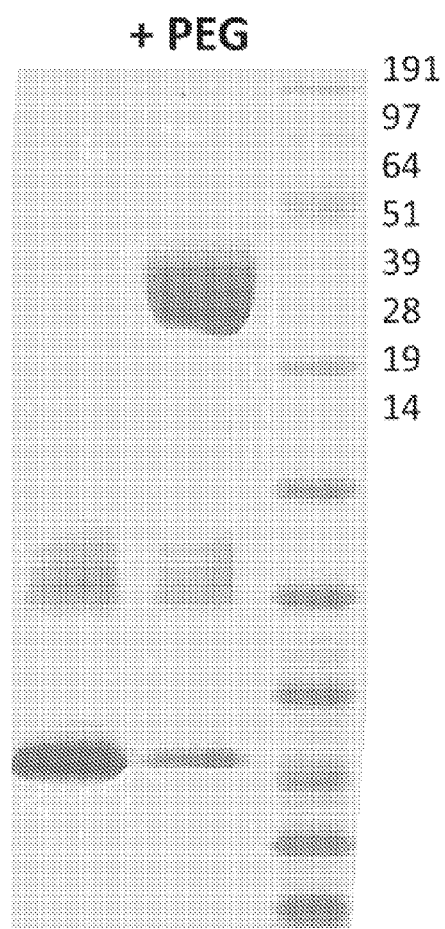

FIG. 4 shows the SDS-PAGE analysis of samples of AspRS1$^{N1}$ C76S) PEGylated with different PEGylation reagents. A Lane 1, AspRS1$^{N1}$ C76S); Lane 2, reaction mix after PEGylation with SUNBRIGHT 40 K PEG (NOF ME-400MA); Lane 3 purified reaction product from (2); Lane 4 Pool of purified product from lane 2. FIG. 4B PEGylated and unPEGylated samples of AspRS1$^{N1}$ C76S) after PEGylated with JemKem 40K PEG (Cat # A3042-1).

Figure 5:
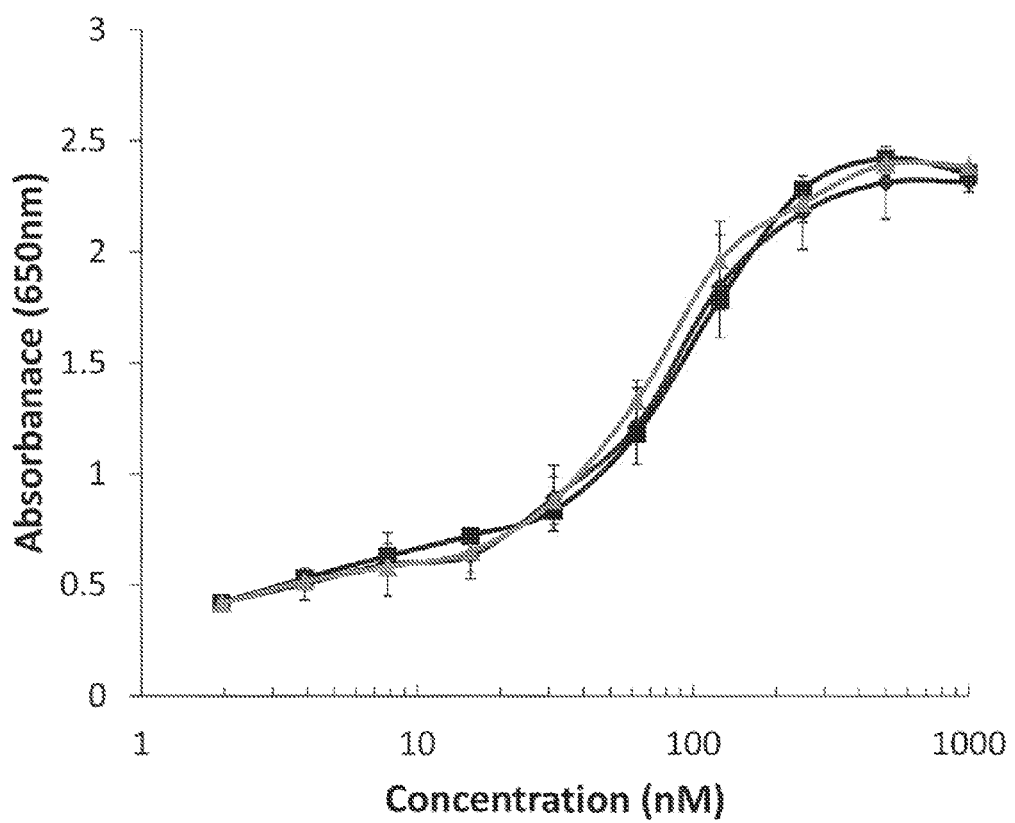

FIG. 5 shows the activity of the PEGylated and unPEGylated AspRS1$^{N1}$(C76S) in a TLR2 reporter gene assay. Diamonds and triangles=UnPEGylated AspRS1$^{N1}$ C76S); Squares=PEGylated AspRS1$^{N1}$ C76S).

Figure 6:
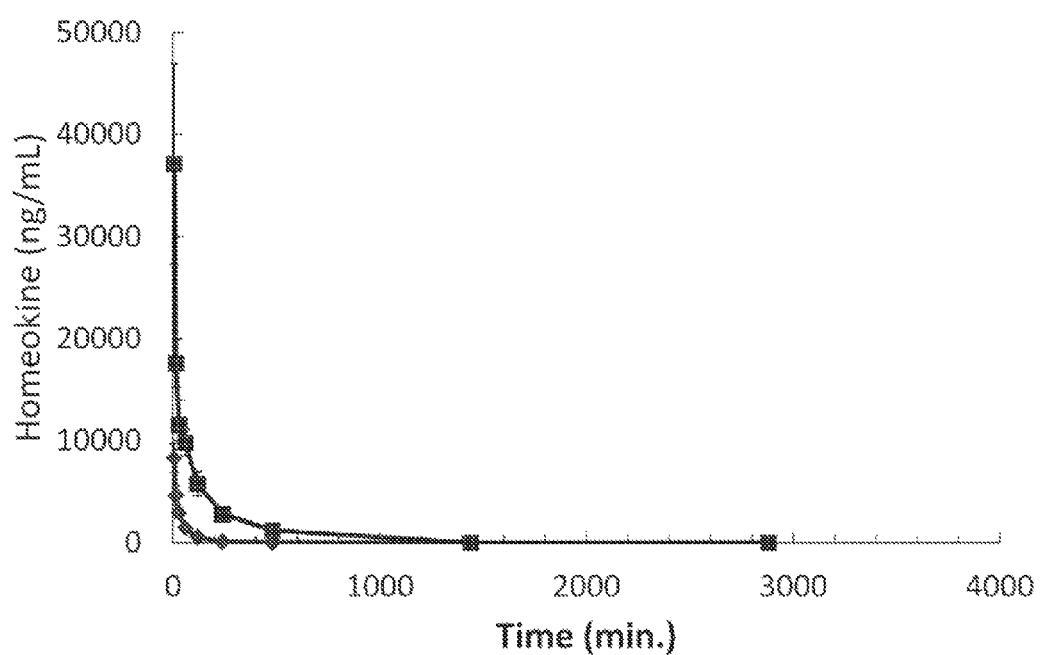

FIG. 6 shows the results of PK analysis of the PEGylated and unPEGylated samples of AspRS1$^{N1}$ C76S) in rats. Diamonds=unPEGylated and Squares=PEGylated.

Figure 7:
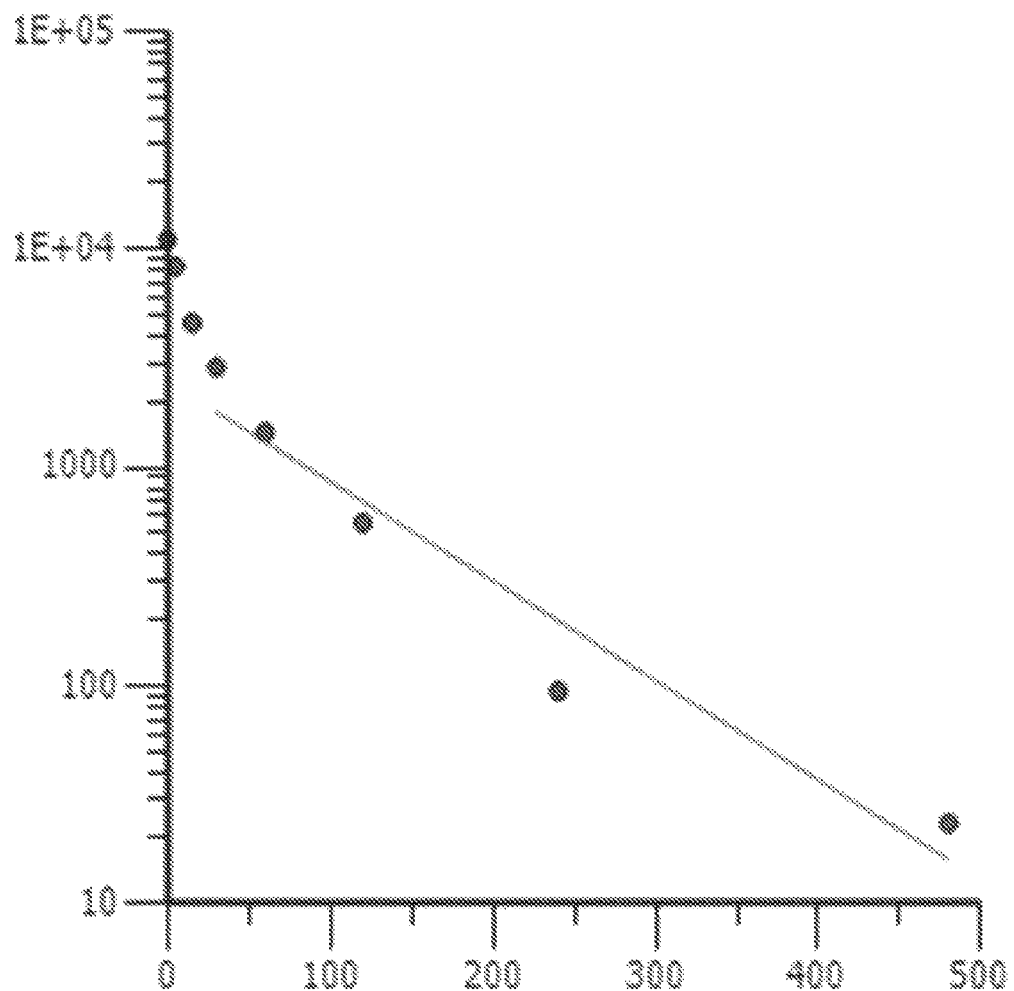

FIG. 7 shows the WinNonLin analysis of the unPEGylated AspRS1$^{N1}$(C76S) rat PK data.

Figure 8:
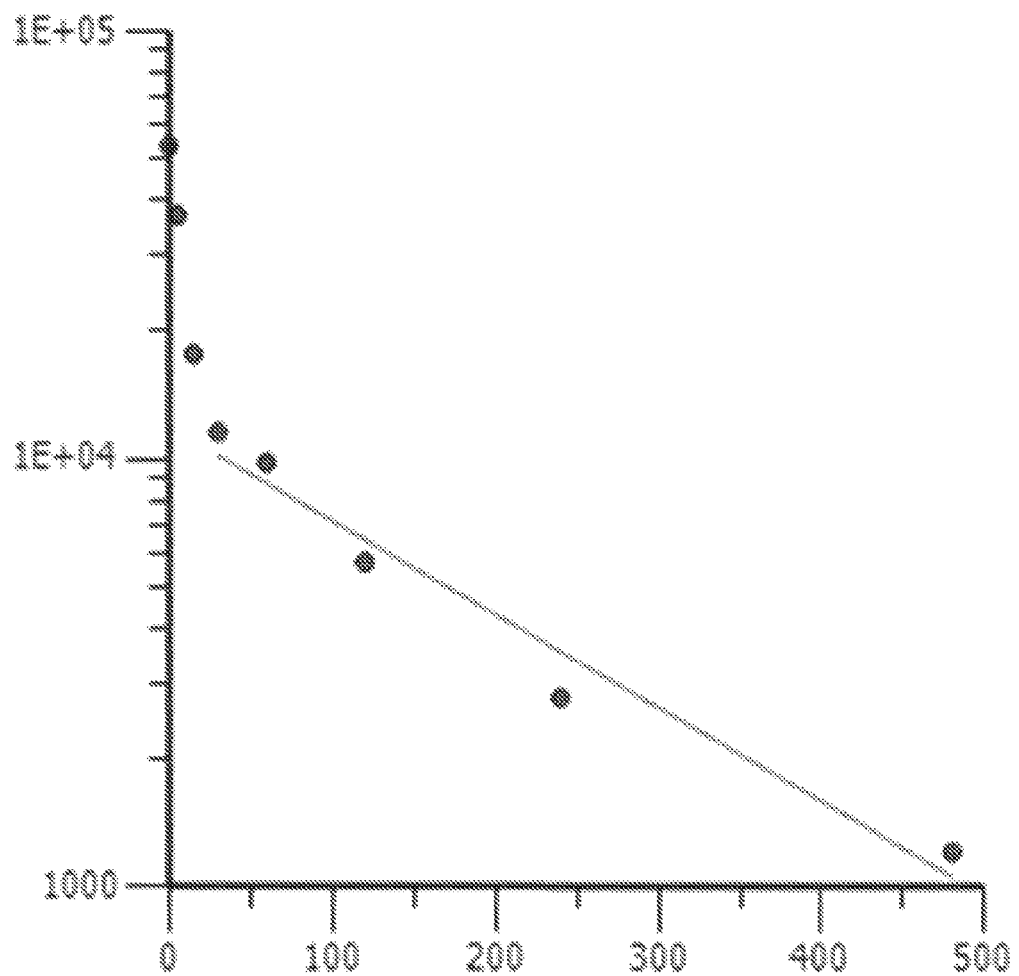

FIG. 8 shows the WinNonLin analysis of the PEGylated AspRS1$^{N1}$(C76S) rat PK data.

Figure 9:
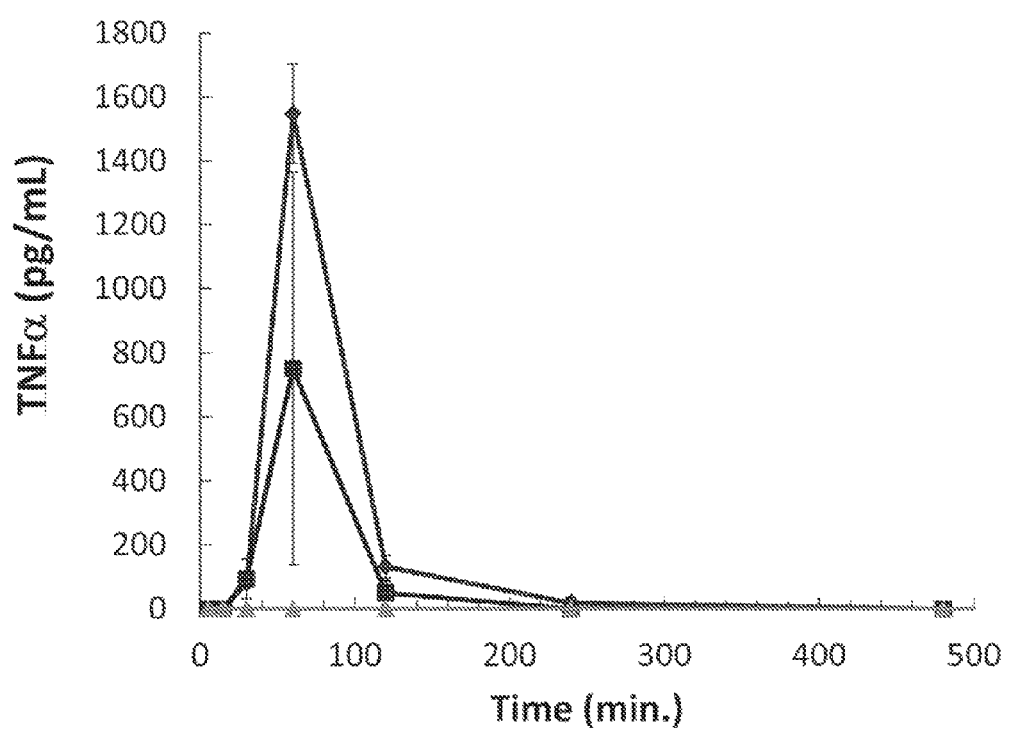

FIG. 9 shows the results of PD analysis with respect to TNF-alpha secretion in response to the injection of PEGylated and unPEGylated AspRS1$^{N1}$ C76S) in rats. Diamonds=unPEGylated AspRS1$^{N1}$(C76S); Squares=PEGylated AspRS1$^{N1}$(C76S); triangles=vehicle control.

Figure 10:
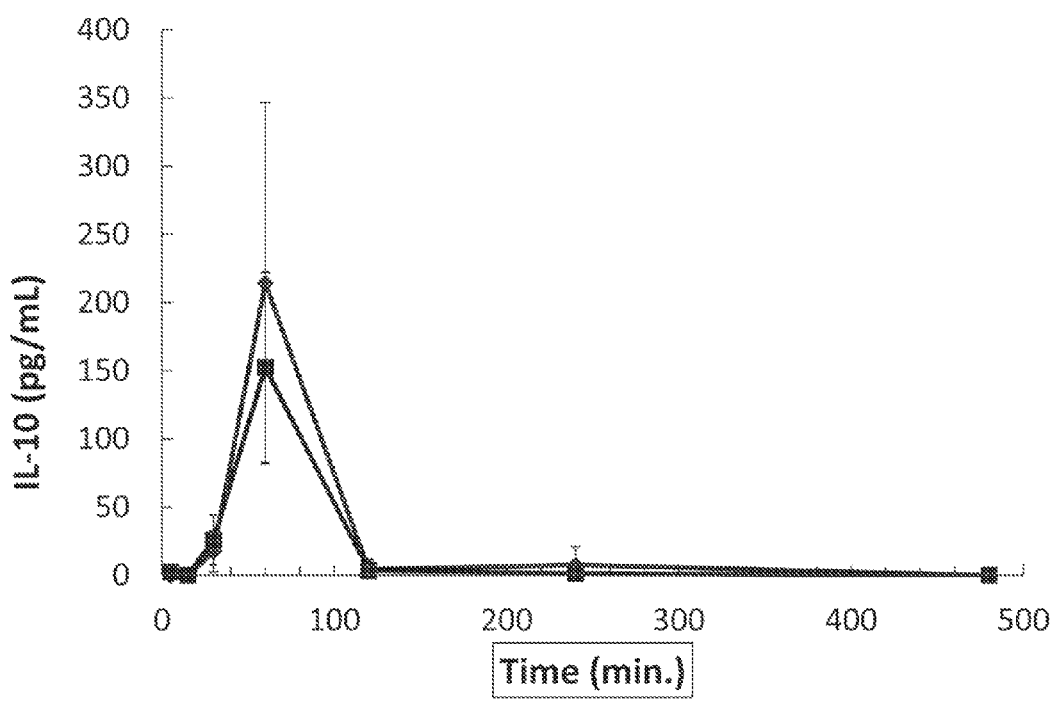

FIG. 10 shows the results of PD analysis with respect to IL-10 secretion in response to the injection of the PEGylated AspRS1$^{N1}$(C76S) and unPEGylated AspRS1$^{N1}$(C76S) in rats. Diamonds=unPEGylated; Squares=PEGylated; triangles=vehicle control.

Figure 11:
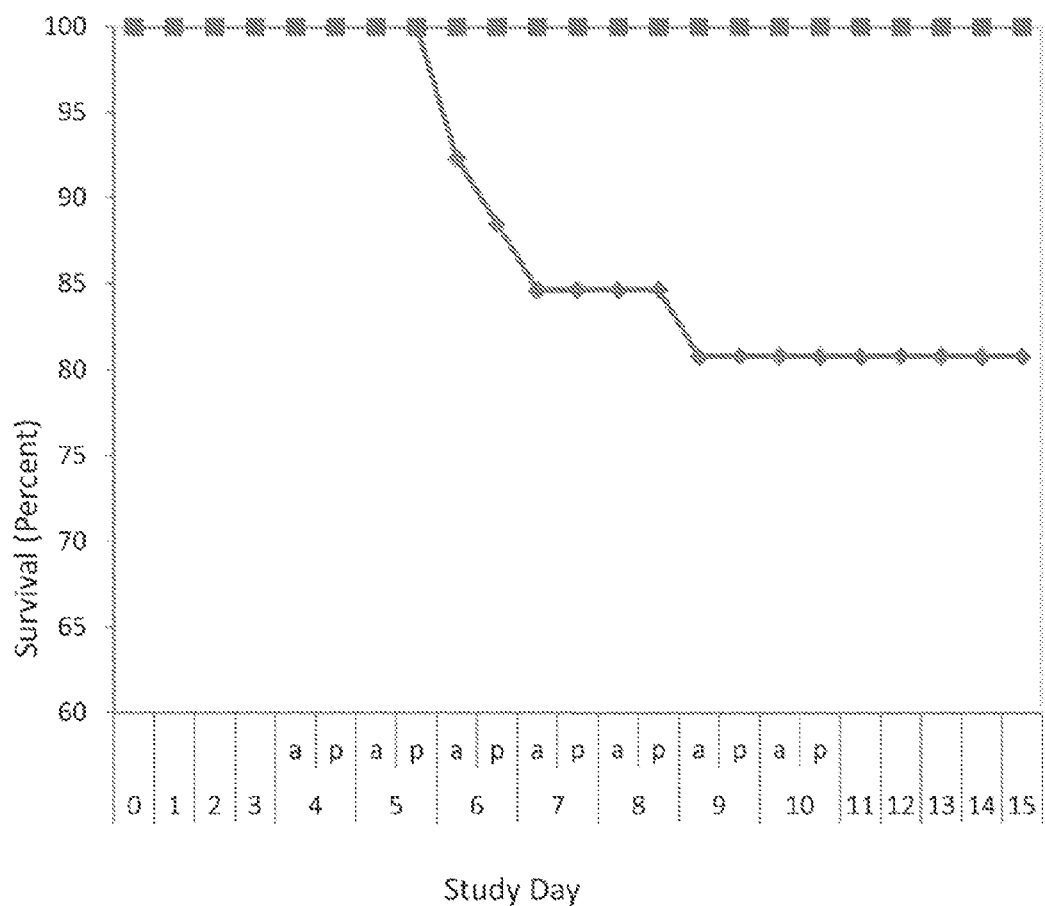

FIG. 11 shows the results of the administration of AspRS1$^{N1}$(C76S) in a partial body irradiation survival model; AspRS1$^{N1}$(C76S) shown in squares and the PBS control shown as diamonds.

Figure 12A:
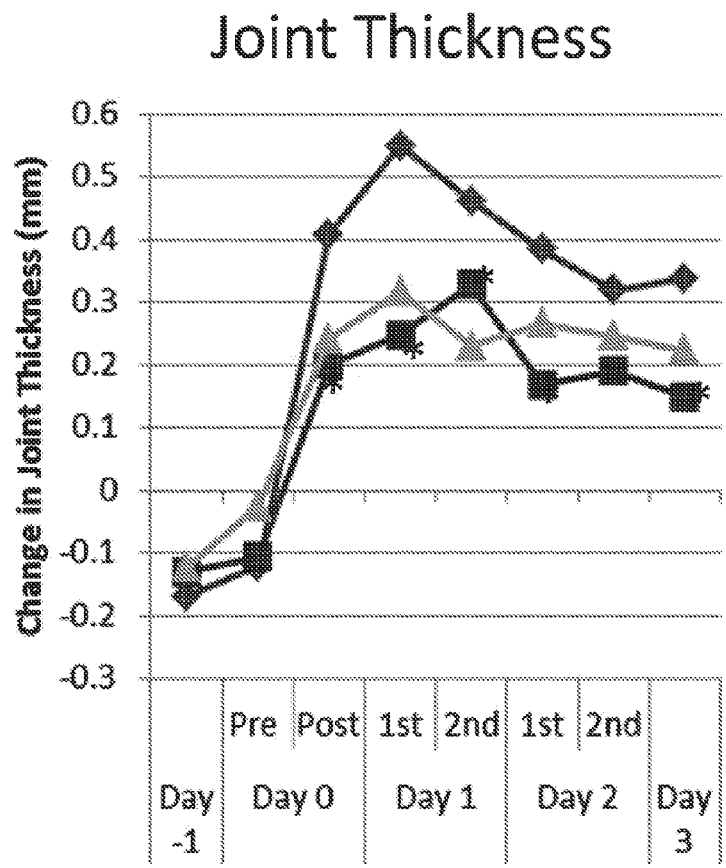
Figure 12B:
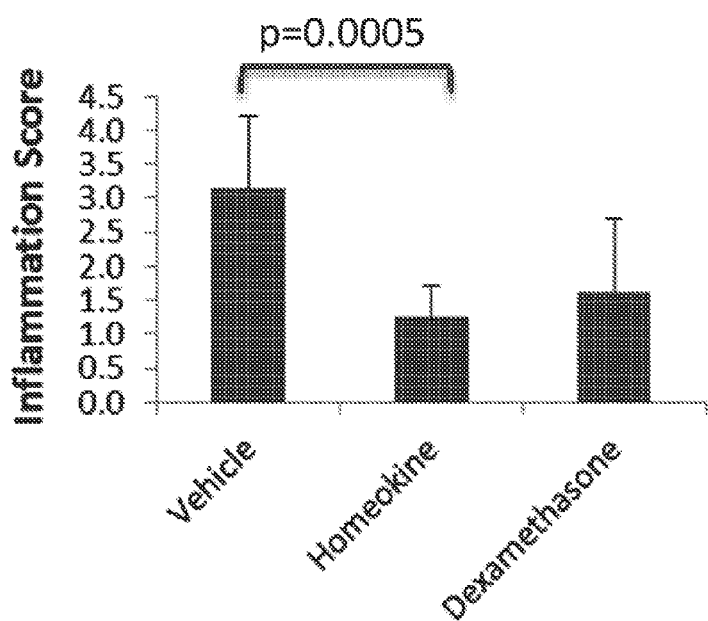

FIG. 12 shows the results of the administration of AspRS1$^{N1}$(C76S) in an MSU induced model of gout inflammation (squares), compared to vehicle control (PBS) diamonds, and a positive control (dexamethasone (triangles) The insert shows the statistical significance for AspRS1$^{N1}$ (C76S) ("Homeokine") compared to the vehicle control.

BRIEF SUMMARY OF THE INVENTION

Embodiments of the present invention relate generally to PEGylated aspartyl-tRNA synthetase (DRS) polypeptides, pharmaceutical compositions comprising such molecules, and methods for their therapeutic use. In one embodiment the invention includes a PEGylated aspartyl-tRNA synthetase (DRS) polypeptide, comprising an amino acid sequence at least 80% identical as that set forth in any of SEQ ID NOS:1, 3-24, 29, 31, or 74-117, comprising at least one PEG moiety covalently attached to an amino acid residue within about 10 amino acid residues of the C-terminus or the N-terminus, or a solvent accessible surface amino acid of the DRS polypeptide or any combination thereof. In some embodiments, at least one endogenous cysteine residue has been modified to another amino acid residue.

In some embodiments of the PEGylated DRS polypeptide, the DRS polypeptide is about 50-200 amino acids in length and comprises amino acid residues 1-154, 11-146, 13-146, 23-154, 1-171, or 1-174 of SEQ ID NO:1. In one aspect the PEGylated DRS polypeptide comprises amino acid residues 1-154. In one aspect the PEGylated DRS polypeptide comprises amino acid residues 13-146. In some embodiments, the Cys76 residue has been selectively mutated to another amino acid. In some embodiments, the Cys130 residue has been selectively mutated to another amino acid. In some embodiments both the Cys76 residue and the Cys130 residue have been mutated to another amino acid.

In some embodiments the PEGylated DRS polypeptide comprises a PEG moiety which has a molecular weight of between about 1 KDa and about 80 KDa. In some embodiments the PEG moiety has a molecular weight of between about 20 KDa and about 60 KDa. In some embodiments the PEG moiety has a molecular weight of between about 30 KDa and about 50 KDa. In some embodiments the PEG moiety has a molecular weight has a molecular weight of about 40 KDa. In some embodiments the PEG moiety has a molecular weight has a molecular weight of about 20 KDa. In some embodiments the PEG moiety has a molecular weight has a molecular weight of about 10 KDa. In some embodiments the PEG moiety has a molecular weight has a molecular weight of about 5 KDa. In some embodiments the PEG moiety has a molecular weight has a molecular weight of about 2 KDa. In some embodiments the PEG moiety has a molecular weight has a molecular weight of about 2 KDa. In some embodiments the PEG moiety has a molecular weight has a molecular weight of less than 2 KDa.

In some embodiments of the PEGylated DRS polypeptide the PEG moiety is attached to an amino acid residue within about 10 amino acid residues of the N-terminus of the DRS polypeptide. In some embodiments the PEG moiety is attached to the N-terminal amino acid of the DRS polypeptide. In some embodiments the PEG moiety is attached to an amino acid residue within about 10 amino acid residues of the C-terminus. In some embodiments the PEG moiety is attached to the C-terminal amino acid of the DRS polypeptide.

In some embodiments of the PEGylated DRS polypeptide the PEG moiety is attached to a cysteine (C) residue. In some embodiments the cysteine residue is naturally occurring. In one aspect, the naturally occurring cysteine residue is C76 or C130. In one aspect it is attached to C130.

In some embodiments the cysteine residue is introduced into, or appended onto the DRS polypeptide. In some embodiments of the PEGylated DRS polypeptide, the PEGylated DRS polypeptide comprises an inserted cysteine residue within about 10 amino acids of the N terminus, the C-terminus, a solvent accessible surface amino acid of the DRS polypeptide or any combination thereof. In some embodiments of the PEGylated DRS polypeptide, the solvent accessible surface amino acids of the DRS polypeptide used for the insertion of the cysteine residue are selected from the group consisting of: S130, G129, A107, A72, or G95. In some embodiments of the PEGylated DRS polypeptide, the PEGylated DRS polypeptide comprises a substituted cysteine residue wherein the substituted amino acid is introduced at an amino acid position corresponding to any amino acid selected from 154-184 of SEQ ID NO:1. In some embodiments of the PEGylated DRS polypeptide at least one endogenous cysteine residue has been substituted with another amino acid to block PEGylation at that position. In some embodiments the endogenous cysteine residue has been substituted with a conservative amino acid. In some embodiments the endogenous cysteine residue is selected from C76 and C130.

In some embodiments of the PEGylated DRS polypeptide the PEG moiety is attached to a non-naturally occurring amino acid. In some embodiments the non-naturally occurring amino acid comprises a side chain having a functional group selected from the group consisting of: an alkyl, aryl, aryl halide, vinyl halide, alkyl halide, acetyl, ketone, aziridine, nitrile, nitro, halide, acyl, keto, azido, hydroxyl, hydrazine, cyano, halo, hydrazide, alkenyl, alkynyl, ether, thio ether, epoxide, sulfone, boronic acid, boronate ester, borane, phenylboronic acid, thiol, seleno, sulfonyl, borate, boronate, phospho, phosphono, phosphine, heterocyclic-, pyridyl, naphthyl, benzophenone, a constrained ring such as a cyclooctyne, thio ester, enone, imine, aldehyde, ester, thioacid, hydroxylamine, amino, carboxylic acid, alpha-keto carboxylic acid, alpha or beta unsaturated acids and amides, glyoxylamide, and organosilane group. In some embodiments the non-naturally occurring amino acid is selected from the group consisting of: p-acetyl-L-phenylalanine, O-methyl-L-tyrosine, L-3-(2-naphthyealanine, 3-methylphenylalanine, O-4-allyl-L-tyrosine, 4-propyl-L-tyrosine, tri-O-acetyl-GlcNAcβ-serine, β-O-GlcNAc-L-serine, tri-O-acetyl-GalNAc-α-threonine, α-GalNAc-L-threonine, L-Dopa, a fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, and isopropyl-L-phenylalanine.

In some embodiments of the PEGylated DRS polypeptide, the PEGylated DRS polypeptide has the following structure (I):

X-L-Y-DRS wherein:
X is the PEG moiety;
L is an optional linker;
Y is a covalent linkage; and
DRS is the DRS polypeptide.

In some embodiments, X, in formula (I) is $R_1$—$(CH_2CH_2O)_n$ or $R_1$—$(OCH_2CH_2)_n$, wherein $R_1$=alkyl, alkoxy, aryl, glucose, or galactose; and n is 20 to 800.

In some embodiments, $R_1$ is an alkoxy selected from the group consisting of: methoxy, ethoxy, and benzyloxy.

In some embodiments, L in formula (I) comprises a chain of 1 to 20 atoms selected from the group consisting of: C, S, N, P, and O.

In some embodiments, L in formula (I) comprises one or more of the following linkages: —O—, —NH—, —S—, —C(O)—, C(O)—NH, NH—C(O)—NH, O—C(O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—C(O)—NH—CH$_2$—, —CH$_2$—CH$_2$—CH$_2$—CH$_2$—C(O)—NH—, —NH—C(O)—CH$_2$—, —CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—, —C(O)—NH—CH$_2$—, —C(O)—NH—CH$_2$—CH$_2$, —O—C(O)—NH—CH$_2$—, —O—C(O)—NH—CH$_2$—CH$_2$—, —NH—CH$_2$—, —NH—CH$_2$—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, bivalent cycloalkyl group, —$N(R^6)$—, $R^6$ is H or an organic radical selected from the group consisting of alkyl, substituted alkyl, alkenyl, substituted alkenyl, alkynyl, substituted alkynyl, aryl and substituted aryl.

In some embodiments, L in formula (I) comprises a releasable linkage. In some embodiments, the releasable linkage is selected from the group consisting of: carboxylate ester, phosphate ester, anhydride, acetal, ketal, acyloxyalkyl ether, imine, orthoester, thio ester, thiol ester, carbonate, and hydrazone.

In some embodiments, L in formula (I) comprises a stable linkage. In some embodiments, the stable linkage is selected from the group consisting of: succinimide, propionic acid, carboxymethylate linkages, ethers, carbamates, amides, amines, carbamides, imides, aliphatic C—C bonds, and thio ethers.

In some embodiments, Y in formula (I) is selected from the group consisting of: amide, secondary amine, carbonyl, carboxylate, carbamate, carbamide, ester, formyl, acyl, thiocarbonyl, thio ester, thioacetate, thioformate, thio ether, alkoxyl, phosphoryl, phosphonate, phosphinate, amino, amido, amidine, imine, cyano, nitro, azido, disulfide, sulthydryl, sulfate, sulfonate, sulfamoyl, sulfonamido, sulfonyl, heterocyclyl, aralkyl, aromatic moiety, hydrazone, heteroaromatic moiety, imino, sulfamoyl, sulfonate, silyl, ether, and alkylthio.

In some embodiments, the PEGylated DRS polypeptides of formula (I) comprise a structure selected from the group consisting of:

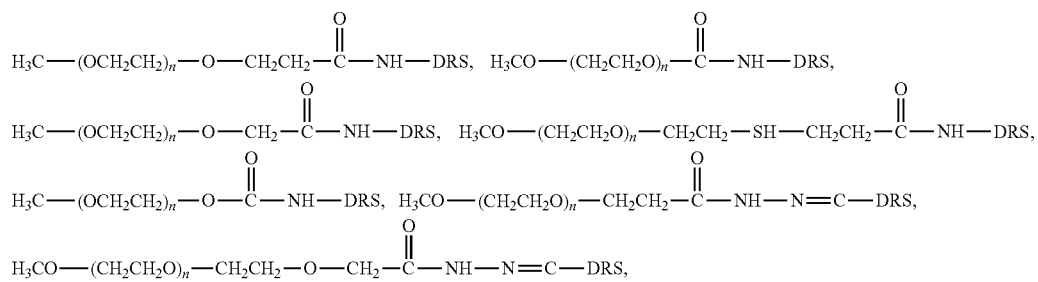

-continued
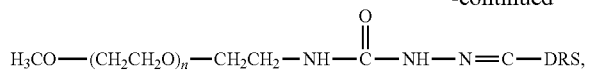
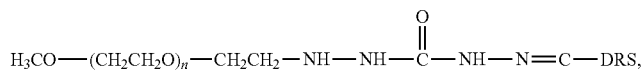
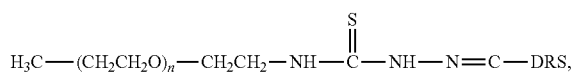
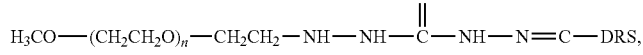
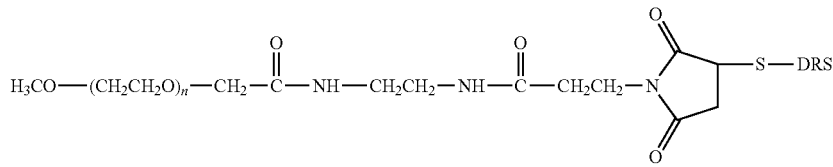
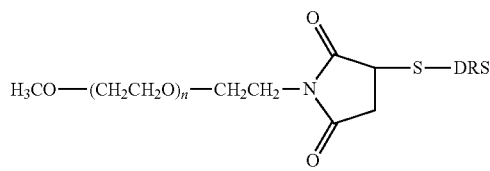
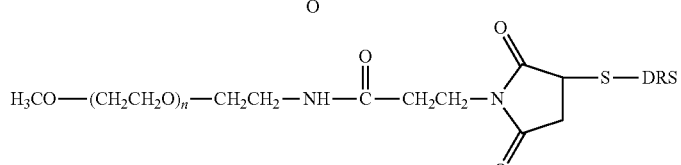
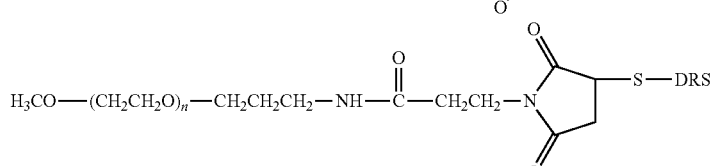
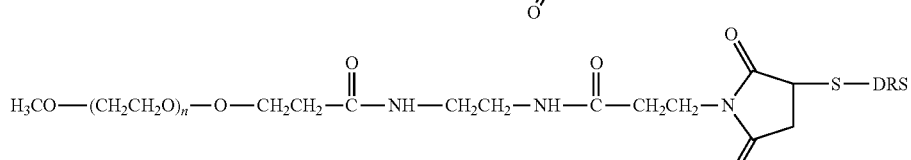
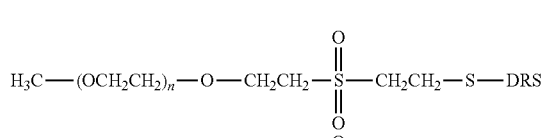
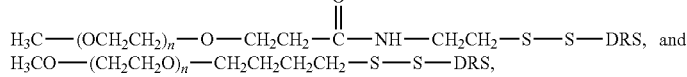
wherein n=20-800.
In one aspect, the PEGylated DRS polypeptides of formula (I) have the structure:
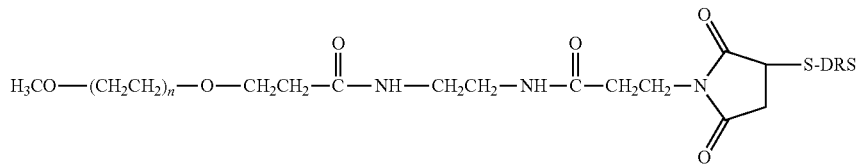

In some embodiments of the PEGylated DRS polypeptide, the PEGylated DRS polypeptide comprises a branched PEG polymer. In some embodiments of the PEGylated DRS polypeptide, the PEGylated DRS polypeptide has the following structure (II):

(X-L$_1$)$_m$-B-L$_2$-Y-DRS wherein:
X is an independently selected PEG moiety for each m;
L$_1$ and L$_2$ are independently selected optional linkers, wherein L$_1$ is also independently selected for each m;
m is 2, 3, 4, or 5;
B is a branching moiety;
Y is a covalent linkage; and
DRS is the DRS polypeptide.

In some embodiments of the PEGylated DRS polypeptide, the PEGylated DRS polypeptide has the following structure (IIA):

$$\begin{array}{l} X-L_1-CH_2 \\ \phantom{X-L_1-}| \\ X-L_2-CH \\ \phantom{X-L_2-}| \\ \phantom{X-L_2-}CH_2-L_3-Y-DRS \end{array}$$

wherein:
X is an independently selected water soluble polymer moiety;
L$_1$, L$_2$ and L$_3$ are independently selected optional linkers;
Y is a covalent linkage between the DRS polypeptide and the remainder of the conjugate; and
DRS refers to a DRS polypeptide as disclosed herein.

In some embodiments of the PEGylated DRS polypeptide, the PEGylated DRS polypeptide has the following structure (IIB):

$$\begin{array}{l} X-L_1-CH_2 \\ \phantom{X-L_1-}| \\ \phantom{X-L_1}HC-L_3-Y-DRS \\ \phantom{X-L_1-}| \\ X-L_2-CH_2 \end{array}$$

wherein:
X is an independently selected water soluble polymer moiety;
L$_1$, L$_2$ and L$_3$ are independently selected optional linkers;
Y is a covalent linkage between the DRS polypeptide and the remainder of the conjugate; and
DRS refers to a DRS polypeptide as disclosed herein.

In some embodiments of the PEGylated DRS polypeptide, the PEGylated DRS polypeptide has the following structure (IIC):

$$\begin{array}{l} X-L_1 \\ \phantom{X-L_1}\backslash \\ \phantom{X-L_1-}\text{Lysine-}L_3-Y-DRS \\ \phantom{X-L_1}/ \\ X-L_2 \end{array}$$

wherein:
X is an independently selected water soluble polymer moiety;
L$_1$, L$_2$ and L$_3$ are independently selected optional linkers, and wherein the linkers connecting the lysine residue to the water soluble polymer moiety are connected via the amino groups of the lysine molecule, and the linker connecting the lysine molecule to the DRS polypeptide is attached via the C-terminal carboxylate group of the lysine molecule;
Y is a covalent linkage between the DRS polypeptide and the remainder of the conjugate; and DRS refers to a DRS polypeptide as disclosed herein.

In some embodiments of the PEGylated DRS polypeptide, the PEGylated DRS polypeptide has the following structure (IID):

$$\begin{array}{l} X-L_1 \\ \phantom{X-L_1}\backslash \\ \phantom{X-L_1-}N-L_3-Y-DRS \\ \phantom{X-L_1}/ \\ X-L_2 \end{array}$$

wherein:
X is an independently selected water soluble polymer moiety;
L$_1$, L$_2$ and L$_3$ are independently selected optional linkers;
Y is a covalent linkage between the DRS polypeptide and the remainder of the conjugate; and DRS refers to a DRS polypeptide as disclosed herein.

In some embodiments in any of formulae (II), (IIA), (IIB), (IIC), or (IID) each X is independently $R_1-(CH_2CH_2O)_n$ or $R_1-(OCH_2CH_2)_n$,
wherein R$_1$=alkyl, alkoxy, aryl, glucose, or galactose; and n is 20 to 800. In some embodiments, R$_1$ is an alkoxy selected from the group consisting of: methoxy, ethoxy, and benzyloxy.

In some embodiments in any of formulae (II), (IIA), (IIB), (IIC), or (IID) L$_2$ and each of L$_1$ independently comprise a chain of 1 to 20 atoms selected from the group consisting of: C, S, N, P, and O.

In some embodiments in any of formulae (II), (IIA), (IIB), (IIC), or (IID) L$_2$ and each of L$_1$ independently comprise one or more of the following linkages: —O—, —NH—, —S—, —C(O)—, C(O)—NH, NH—C(O)—NH, O—C(O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—C(O)—NH—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, bivalent cycloalkyl group, —N(R$^6$)—, R$^6$ is H or an organic radical selected from the group consisting of alkyl, substituted alkyl, alkenyl, substituted alkenyl, alkynyl, substituted alkynyl, aryl and substituted aryl.

In some embodiments of the PEGylated DRS polypeptide of formulae (II), (IIA), (IIB), (IIC), or (IID) L$_2$ and each of L$_1$ independently comprise a releasable linkage or a stable linkage.

In some embodiments of the PEGylated DRS polypeptide of formulae (II), (IIA), (IIB), (IIC), or (IID) L$_2$ and each of L$_1$ independently comprise a releasable linkage.

In some embodiments of the PEGylated DRS polypeptide of formulae (II), (IIA), (IIB), (IIC), or (IID) L$_2$ and each of L$_1$ independently comprise a stable linkage.

In some embodiments of the PEGylated DRS polypeptide of formulae (II), (IIA), (IIB), (IIC), or (IID) the stable linkage is selected from the group consisting of: succinimide, propionic acid, carboxymethylate linkages, ethers, carbamates, amides, amines, carbamides, imides, aliphatic C—C bonds, and thio ethers.

In some embodiments of the PEGylated DRS polypeptide of formulae (II), (IIA), (IIB), (IIC), or (IID) Y is selected from the group consisting of: amide, secondary amine, carbonyl, carboxylate, carbamate, carbamide, ester, formyl, acyl, thiocarbonyl, thio ester, thioacetate, thioformate, thio ether, alkoxyl, phosphoryl, phosphonate, phosphinate, amino, amido, amidine, imine, cyano, nitro, azido, disulfide, sulthydryl, sulfate, sulfonate, sulfamoyl, sulfonamido, sulfonyl, heterocyclyl, aralkyl, aromatic moiety, hydrazone, heteroaromatic moiety, imino, sulfamoyl, sulfonate, silyl, ether, and alkylthio.

In some embodiments of the PEGylated DRS polypeptide of formulae (II), (IIA), (IIB), (IIC), or (IID), and B is selected from the group consisting of: an amino acid linkage or an aliphatic hydrocarbon chain of 3 to 6 carbons.

In some embodiments of the PEGylated DRS polypeptide of formula (II), B is selected from arginine, histidine, lysine, glutamine, serine, threonine, asparagine, aspartic acid, glutamic acid, cysteine, and seleno cysteine. In one aspect, B is lysine. In some embodiments of the PEGylated DRS polypeptide of formula (II), B is an aliphatic hydrocarbon chain is derived from propane, butane, pentane, or hexane. In some embodiments of the PEGylated DRS polypeptide of formula (II), B is an aliphatic hydrocarbon chain derived from a polyol selected from the groups consisting of: glycerol, erythritol, xylitol, and sorbitol. In some embodiments of the PEGylated DRS polypeptide of formula (II), B is an aliphatic hydrocarbon chain is derived from glycerol or propane.

In some embodiments of the PEGylated DRS polypeptide of formulae (II), (IIA), (IIB), (IIC), or (IID) comprise a structure selected from the group consisting of:

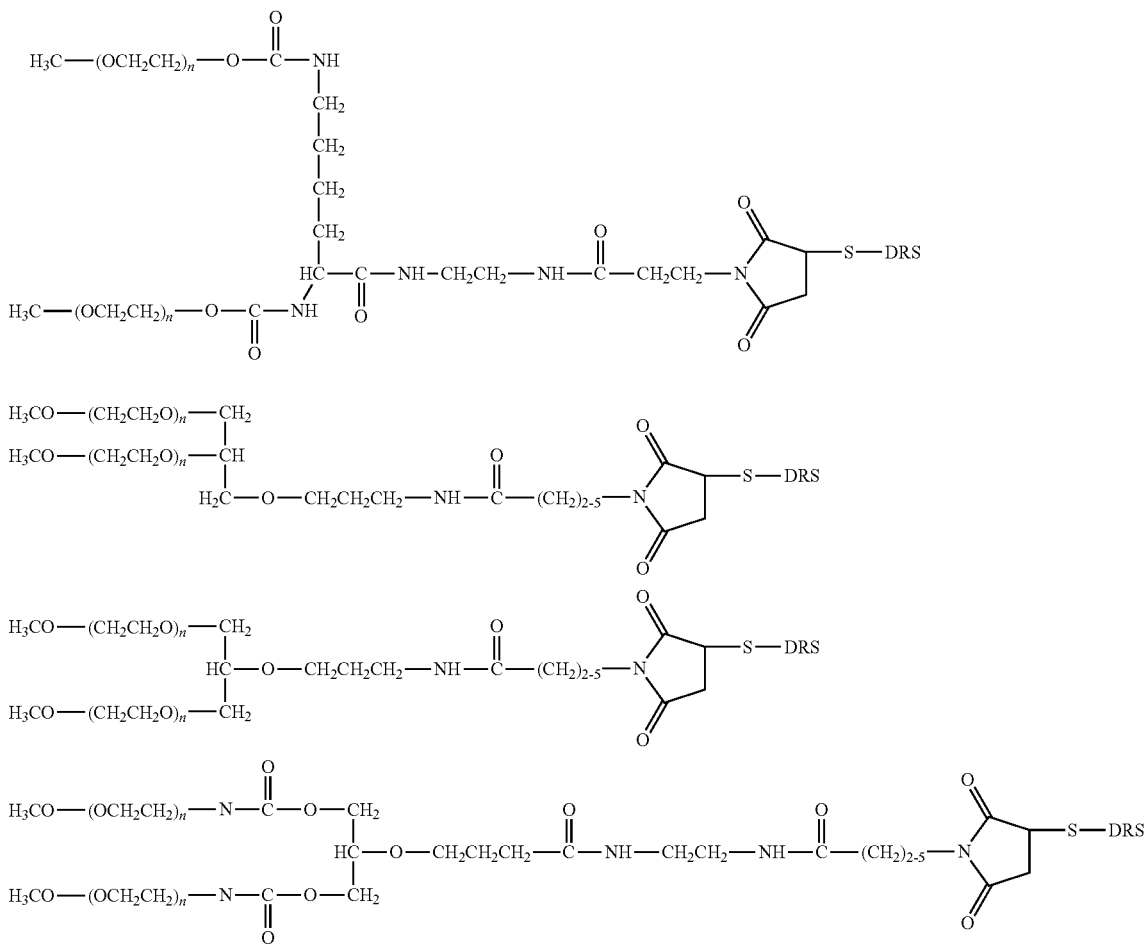

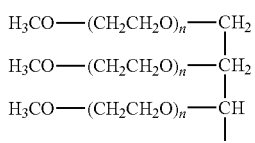
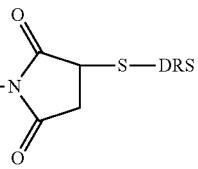

and

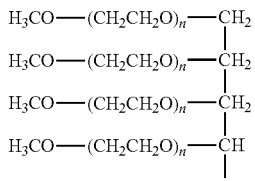
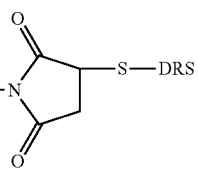

wherein n is independently any integer from 20 to 800.

In some embodiments of the PEGylated DRS polypeptide, the PEGylated DRS polypeptide, is about 50-200 amino acids in length and comprises amino acid residues 1-154, 11-146, 13-146, 23-154, 1-171, or 1-174 of SEQ ID NO:1 which is modified by C76S, and a maleimide monomethoxy polyethylene glycol (mPEG) derivative is covalently attached via a thio ether linkage to C130.

In some embodiments of the PEGylated DRS polypeptide, the PEGylated DRS polypeptide, is about 50-200 amino acids in length and comprises amino acid residues 1-154, 11-146, 13-146, 23-154, 1-171, or 1-174 of SEQ ID NO:1 which is modified by C76S, and C130S and a maleimide monomethoxy polyethylene glycol (mPEG) derivative is covalently attached via a thio ether linkage to an inserted cysteine residue inserted within about 10 amino acids of the C-terminus In some embodiments of the PEGylated DRS polypeptide, the PEGylated DRS polypeptide is about 50-200 amino acids in length and comprises amino acid residues 1-154, 11-146, 13-146, 23-154, 1-171, or 1-174 of SEQ ID NO:1 which is modified by C76S, and C130S and a maleimide monomethoxy polyethylene glycol (mPEG) derivative is covalently attached via a thio ether linkage to an inserted cysteine residue inserted into a surface exposed amino acid listed in Table D9.

In some embodiments of the PEGylated DRS polypeptide, the PEGylated DRS polypeptide is a full-length DRS polypeptide comprising the sequence set forth in SEQ ID NO:1, which is modified by at least one cysteine modification selected from the group consisting of C76, C203, C259, C334, and C349, where a maleimide monomethoxy polyethylene glycol (mPEG) derivative of about 40,000 Daltons is covalently attached to a solvent exposed cysteine residue. In certain embodiments, the DRS polypeptide further comprises at least one cysteine modification selected from Cys76 and Cys130. In some embodiments, the DRS polypeptide comprises a mutation of Cys203, where a maleimide monomethoxy polyethylene glycol (mPEG) derivative of about 40,000 Daltons is covalently attached to an amino acid residue within about 1, 2, 3, 4, 5, 6, 7, 8, 9, or 10 amino acid residues of the C-terminus or the N-terminus of the DRS polypeptide.

In particular embodiments, the amino acid residue to which the mPEG derivative is attached is introduced into the DRS polypeptide. In specific embodiments, the amino acid to which the mPEG derivative is attached is a cysteine residue.

In some of the PEGylated DRS polypeptides, the DRS polypeptide comprises a mutation of Cys203, where a maleimide monomethoxy polyethylene glycol (mPEG) derivative of about 40,000 Daltons is covalently attached to a cysteine residue selected from the group consisting of Cys76, Cys130, Cys259, Cys334, and Cys349. In certain embodiments, the DRS polypeptide comprises cysteine modifications at positions Cys203, Cys334 and Cys349. In specific embodiments, the mPEG derivative is attached to Cys130.

In some aspects, the full-length PEGylated DRS polypeptide is modified by at least one cysteine modification selected from the group consisting of C76S, C203S, C259S, C334S, and C349S substitution(s), where a maleimide monomethoxy polyethylene glycol (mPEG) derivative of about 40,000 Daltons is covalently attached via a thio ether linkage to C130. In specific aspects, the full-length PEGylated DRS polypeptide is modified by C76S, C203S, C259S, C334S, and C349S substitutions, where a maleimide monomethoxy polyethylene glycol (mPEG) derivative of about 40,000 Daltons is covalently attached via a thio ether linkage to C130. In some aspects, the PEGylated polypeptide exhibits a higher stability compared to a corresponding non-PEGylated polypeptide.

In one aspect the PEGylated DRS polypeptide comprises the structure:

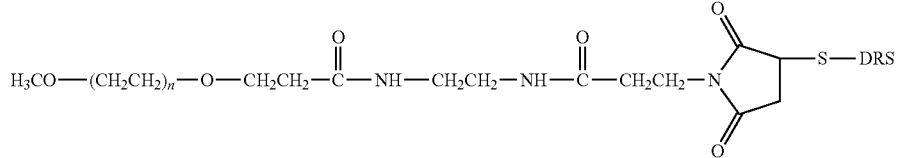

In one aspect the PEGylated DRS polypeptide comprises the structure:

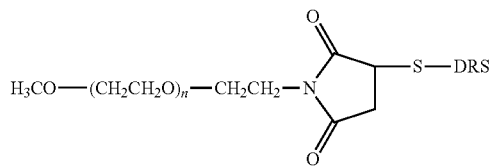

In one aspect the PEGylated DRS polypeptide comprises the structure:

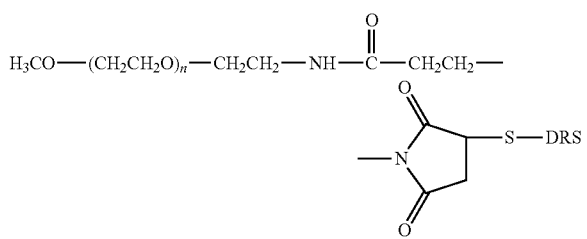

In one aspect the PEGylated DRS polypeptide comprises the structure:

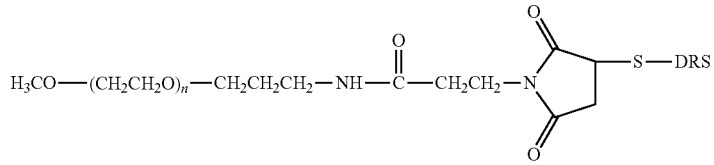

In one aspect of any of these PEGylated DRS polypeptides, the PEGylated DRS polypeptide has substantially the same secondary structure as unmodified DRS polypeptide, as determined via UV circular dichroism analysis.

In one aspect of any of these PEGylated DRS polypeptides, the PEGylated DRS polypeptide has a plasma or sera pharmacokinetic AUC profile at least 5-fold greater than unmodified DRS polypeptide when administered to rats.

In one aspect of any of these PEGylated DRS polypeptides, the PEGylated DRS polypeptide has substantially the same activity of the unPEGylated protein in a TLR 2 or TLR 4 based assay.

In one aspect of any of these PEGylated DRS polypeptides, the PEGylated DRS polypeptide has greater than 2 fold the activity of the unPEGylated protein in a TLR 2 or TLR 4.

In one aspect of any of these PEGylated DRS polypeptides, the PEGylated DRS polypeptide has a stability which is at least 30% greater than unmodified DRS polypeptide when compared under similar conditions at room temperature, for 7 days in PBS at pH 7.4.

In one embodiment the invention includes a dosing regimen which maintains an average steady-state concentration of DRS polypeptide in the subjects' plasma of between about 0.3 µg/ml and about 3 µg/ml when using a dosing interval of 3 days or longer, comprising administering to the patient a therapeutic dose of any of the PEGylated DRS polypeptides described herein.

In one embodiment the invention includes a method for maintaining DRS polypeptide levels above the minimum effective therapeutic level in a subject in need thereof, comprising administering to the subject a therapeutic dose of any of the PEGylated DRS polypeptides described herein.

In another aspect, the invention includes a method for treating an inflammatory response in a subject, comprising administering any of the herein disclosed PEGylated DRS polypeptides to a subject in need thereof.

In another aspect, the invention includes a method for treating a TLR associated disease in a subject in need thereof, comprising administering to the subject a therapeutic dose of any of the herein disclosed PEGylated DRS polypeptides.

In another aspect, the invention includes a method for method for modulating TLR activity in a subject, comprising administering to the subject a therapeutic dose of any of the herein disclosed PEGylated DRS polypeptides.

In another aspect, the invention includes a method for method for killing cancer cells, comprising administering a vaccine or immunogenic composition comprising any of the previously disclosed PEGylated DRS polypeptides to a subject in need thereof.

In another aspect, the invention includes a method for treating a subject with cancer, or preventing the development of cancer in a subject, comprising administering a vaccine or immunogenic composition comprising any of the previously disclosed PEGylated DRS polypeptides to a subject in need thereof.

DETAILED DESCRIPTION OF THE INVENTION

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al., *Molecular Cloning: A Laboratory Manual* (3$^{rd}$ Edition, 2000); *DNA Cloning: A Practical Approach*, vol. I & II (D. Glover, ed.); *Oligonucleotide Synthesis* (N. Gait, ed., 1984); *Oligonucleotide Synthesis: Methods and Applications* (P. Herdewijn, ed., 2004); *Nucleic Acid Hybridization* (B. Hames & S. Higgins, eds., 1985); *Nucleic Acid Hybridization: Modern Applications* (Buzdin and Lukyanov, eds., 2009); *Transcription and Translation* (B. Hames & S. Higgins, eds., 1984); *Animal Cell Culture* (R. Freshney, ed., 1986); Freshney, R. I. (2005) *Culture of Animal Cells, a Manual of Basic Technique*, 5$^{th}$ Ed. Hoboken N.J., John Wiley & Sons; B. Perbal, *A Practical Guide to Molecular Cloning* (3$^{rd}$ Edition 2010); Farrell, R., *RNA Methodologies: A Laboratory Guide for Isolation and Characterization* (3$^{rd}$ Edition 2005). *Poly(ethylene glycol), Chemistry and Biological Applications*, ACS, Washington, 1997; Veronese, F., and J. M. Harris, Eds., *Peptide and protein PEGylation, Advanced Drug Delivery Reviews*, 54(4) 453-609 (2002); Zalipsky, S., et al., "*Use of functionalized Poly(Ethylene Glycols) for modification of polypeptides*" in Polyethylene Glycol Chemistry: Biotechnical and Biomedical Applications.

All publications, patents and patent applications cited herein are hereby incorporated by reference in their entirety.

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

An "alkyl" or "alkylene" group, depending upon its position in a molecule and the number of points of attachment of the group to atoms other than hydrogen, refers to a hydrocarbon chain or moiety, typically ranging from about 1 to 50 atoms in length. Such hydrocarbon chains are preferably but not necessarily saturated unless so indicated and may be branched or straight chain, although typically straight chain is preferred in particular embodiments. Exemplary alkyl groups include methyl, ethyl, propyl, butyl, pentyl, 1-methylbutyl, 1-ethylpropyl, 3-methylpentyl, and the like.

"Alicyclic" refers to any aliphatic compound that contains a ring of carbon atoms. An alicyclic group is one that contains a "cycloalkyl" or "cycloalkylene" group as defined above that is substituted with one or more alkyl or alkylenes.

"Alkoxy" refers to an —O—R group, wherein R is alkyl or substituted alkyl, preferably $C_1$-$C_{20}$ alkyl (e.g., methoxy, ethoxy, propyloxy, benzyl, etc.), and in some embodiments, preferably $C_1$-$C_5$.

As used herein, "alkenyl" refers to a branched or unbranched hydrocarbon group of 1 to 15 atoms in length, containing at least one double bond, such as ethenyl, n-propenyl, isopropenyl, n-butenyl, isobutenyl, octenyl, decenyl, tetradecenyl, and the like.

The term "alkynyl" as used herein refers to a branched or unbranched hydrocarbon group of 2 to 15 atoms in length, containing at least one triple bond, ethynyl, n-propynyl, isopropynyl, n-butynyl, isobutynyl, octynyl, decynyl, and so forth.

As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like, which are known to a person skilled in the art. Amino acid analogs include modified forms of naturally and non-naturally occurring amino acids. Such modifications can include, for example, substitution or replacement of chemical groups and moieties on the amino acid or by derivitization of the amino acid Amino acid mimetics include, for example, organic structures which exhibit functionally similar properties such as charge and charge spacing characteristic of the reference amino acid. For example, an organic structure which mimics Arginine (Arg or R) would have a positive charge moiety located in similar molecular space and having the same degree of mobility as the e-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Atom length" or "chain length" refers to the number of atoms making up a particular fragment, spacer, linker or the like. By chain length is meant the number of atoms in a single chain, not counting substituents. For instance, —$CH_2$— counts as one atom with respect to chain length, —$CH_2CH_2CH_2$— counts as 3 atoms with respect to chain length, and so on.

"Bifunctional" in the context of a polymer of the invention refers to a PEG polymer possessing two reactive functional groups which may be the same or different.

"Branched" in reference to the geometry or overall structure of a PEG polymer refers to polymer having 2 or more PEG polymer "arms." A branched polymer may possess 2, 3, 4, 5, 6, 7, 8, 9, 10 or more PEG polymer arms.

"Branch moiety" refers to a moiety comprising one or more atoms at which a PEG polymer splits or branches from a linear structure into one or more additional PEG polymer arms.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The term "conjugate" is intended to refer to the entity formed as a result of covalent attachment of a molecule, e.g., a biologically active molecule, to a reactive polymer molecule, preferably a branched reactive polymer of the invention.

"Cycloalkyl" or "cycloalkylene", depending upon its position in a molecule and the number of points of attachment to atoms other than hydrogen, refers to a saturated or unsaturated cyclic hydrocarbon chain, including polycyclics such as bridged, fused, or spiro cyclic compounds, preferably made up of 3 to about 12 carbon atoms, more preferably 3 to about 8.

The recitation "endotoxin free" or "substantially endotoxin free" relates generally to compositions, solvents, and/or vessels that contain at most trace amounts (e.g., amounts having no clinically adverse physiological effects to a subject) of endotoxin, and preferably undetectable amounts of endotoxin. Endotoxins are toxins associated with certain bacteria, typically gram-negative bacteria, although endotoxins may be found in gram-positive bacteria, such as *Listeria monocytogenes*. The most prevalent endotoxins are lipopolysaccharides (LPS) or lipo-oligo-saccharides (LOS) found in the outer membrane of various Gram-negative bacteria, and which represent a central pathogenic feature in the ability of these bacteria to cause disease. Small amounts of endotoxin in humans may produce fever, a lowering of the blood pressure, and activation of inflammation and coagulation, among other adverse physiological effects.

Therefore, in pharmaceutical production, it is often desirable to remove most or all traces of endotoxin from drug products and/or drug containers, because even small amounts may cause adverse effects in humans. A depyrogenation oven may be used for this purpose, as temperatures in excess of 300° C. are typically required to break down most endotoxins. For instance, based on primary packaging material such as syringes or vials, the combination of a glass temperature of 250° C. and a holding time of 30 minutes is often sufficient to achieve a 3 log reduction in endotoxin levels. Other methods of removing endotoxins are contemplated, including, for example, chromatography and filtration methods, as described herein and known in the art. Also included are methods of producing DRS polypeptides in and isolating them from eukaryotic cells such as mammalian cells to reduce, if not eliminate, the risk of endotoxins being present in a composition of the invention. Preferred are methods of producing DRS polypeptides in and isolating them from serum free cells.

Endotoxins can be detected using routine techniques known in the art. For example, the *Limulus* Ameobocyte Lysate assay, which utilizes blood from the horseshoe crab, is a very sensitive assay for detecting presence of endotoxin. In this test, very low levels of LPS can cause detectable coagulation of the *limulus* lysate due a powerful enzymatic cascade that amplifies this reaction. Endotoxins can also be quantitated by enzyme-linked immunosorbent assay (ELISA). To be substantially endotoxin free, endotoxin levels may be less than about 0.001, 0.005, 0.01, 0.02, 0.03, 0.04, 0.05, 0.06, 0.08, 0.09, 0.1, 0.5, 1.0, 1.5, 2, 2.5, 3, 4, 5, 6, 7, 8, 9, or 10 EU/ml. Typically, 1 ng lipopolysaccharide (LPS) corresponds to about 1-10 EU.

"Electrophile" refers to an ion, atom, or collection of atoms that may be ionic, having an electrophilic center, i.e., a center that is electron seeking, capable of reacting with a nucleophile.

The terms "end-capped" and "terminally capped" are interchangeably used herein to refer to a terminal or endpoint of a polymer having an end-capping moiety. Typically, although not necessarily, the end-capping moiety comprises a hydroxy or an alkoxy group, more preferably a $C_{1-10}$ alkoxy group, and still more preferably a $C_{1-5}$ alkoxy group. Thus, examples of end-capping moieties include alkoxy (e.g., methoxy, ethoxy and benzyloxy), as well as aryl, heteroaryl, cycloalkyl, heterocyclo, and the like. In particular embodiments, the end-capping moiety may include one or more atoms of the terminal monomer in the polymer [e.g., the end-capping moiety "methoxy" in $CH_3O(CH_2CH_2O)_n$— and $CH_3(OCH_2CH_2)_n$—]. In addition, saturated, unsaturated, substituted and unsubstituted forms of each of the foregoing are envisioned. Moreover, the end-capping group can also be a silane or acrylate. In certain embodiments, the end-capping group can also comprise a phospholipid. When the polymer has an end-capping group comprising a phospholipid, unique properties can be imparted to the polymer and the resulting conjugate, e.g., DRS polypeptide. Exemplary phospholipids include, without limitation, phosphatidylcholines, such as, for example, dilauroylphosphatidylcholine, dioleylphosphatidylcholine, dipalmitoylphosphatidylcholine, disteroylphosphatidylcholine, behenoylphosphatidylcholine, arachidoylphosphatidylcholine, and lecithin.

As used herein, the terms "function" and "functional" and the like refer to a biological, enzymatic, or therapeutic function.

"Homology" refers to the percentage number of amino acids that are identical or constitute conservative substitutions. Homology may be determined using sequence comparison programs such as GAP (Deveraux et al., 1984, *Nucleic Acids Research* 12, 387-395), which is incorporated herein by reference. In this way sequences of a similar or substantially different length to those cited herein could be compared by insertion of gaps into the alignment, such gaps being determined, for example, by the comparison algorithm used by GAP.

A "hydrolytically stable" linkage or bond refers to a linker, or chemical bond, that is substantially stable in water, that is to say, does not undergo hydrolysis under physiological conditions to any appreciable extent over an extended period of time. Examples of hydrolytically stable linkages include, but are not limited to, the following: succinimide, propionic acid, carboxymethylate linkages, ethers, carbamates, amides, amines, carbamides, imides, aliphatic C—C bonds, thio ethers, thiocarbamates, thiocarbamides, and the like. Generally, a hydrolytically stable linkage is one that exhibits a rate of hydrolysis of less than about 0.5%, about 1%, about 2%, about 3%, about 4%, or about 5% per day under physiological conditions.

By "isolated" is meant material that is substantially or essentially free from components that normally accompany it in its native state. For example, an "isolated peptide" or an "isolated polypeptide" and the like, as used herein, includes the in vitro isolation and/or purification of a peptide or polypeptide molecule from its natural cellular environment, and from association with other components of the cell; i.e., it is not significantly associated with in vivo substances.

The term "half maximal effective concentration" or "$EC_{50}$" refers to the concentration of a PEGylated DRS polypeptide agent described herein at which it induces a response halfway between the baseline and maximum after some specified exposure time; the $EC_{50}$ of a graded dose response curve therefore represents the concentration of a compound at which 50% of its maximal effect is observed. In certain embodiments, the $EC_{50}$ of an agent provided herein is indicated in relation to a "non-canonical" activity, as noted above. $EC_{50}$ also represents the plasma concentration required for obtaining 50% of a maximum effect in vivo. Similarly, the "$EC_{90}$" refers to the concentration of an agent or composition at which 90% of its maximal effect is observed. The "$EC_{90}$" can be calculated from the "$EC_{50}$" and the Hill slope, or it can be determined from the data directly, using routine knowledge in the art. In some embodiments, the $EC_{50}$ of a PEGylated DRS protein is less than about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 40, 50, 60, 70, 80, 90, or 100 nM. Preferably, biotherapeutic composition will have an $EC_{50}$ value of about 1 nM or less.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom which is not a carbon. Preferred heteroatoms include sulfur, oxygen, and nitrogen.

The terms "functional group," "active moiety," "reactive site," "chemically reactive group," and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules. The term "active," when used in conjunction with a functional group, is intended to include those functional groups that react readily with electrophilic or nucleophilic groups on other molecules, in contrast to those groups that require strong catalysts or highly impractical reaction conditions in order to react (i.e., "non-reactive" or "inert" groups).

The term "linkage," "linker," "linker moiety," or "L" is used herein to refer to an atom or a collection of atoms used to link, preferably by one or more covalent bonds, interconnecting moieties such as two polymer segments or a terminus of a polymer and a reactive functional group present on a polypeptide, e.g., a DRS polypeptide. The linker may be hydrolytically stable or may include a releasable linkage such as a physiologically hydrolyzable or enzymatically degradable linkage.

"Lower alkyl" or "lower alkylene" refers to an alkyl or alkylene group as defined above containing from 1 to 6 carbon atoms, and may be straight chain or branched, as exemplified by methyl, ethyl, n-butyl, i-butyl, t-butyl.

"Lower cycloalkyl" or "lower cycloalkylene" refers to a cycloalkyl group or cycloalkylene group containing from 1 to 6 carbon atoms.

The term "modulating" includes "increasing," "enhancing" or "stimulating," as well as "decreasing" or "reducing," typically in a statistically significant or a physiologically significant amount as compared to a control. An "increased," "stimulated" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the amount produced by no composition (e.g., in the absence of any of the PEGylated DRS polypeptides of the invention) or a control composition, sample or test subject. A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease in the amount produced by no composition (the absence of an agent or compound) or a control composition, including all integers in between. As one non-limiting example, a control in comparing canonical and non-canonical activities could include the PEGylated DRS polypeptide of interest compared to a corresponding un-PEGylated DRS polypeptide. Other examples of "statistically significant" amounts are described herein.

"Monofunctional" in the context of a polymer of the invention refers to a PEG polymer possessing a single reactive functional group.

"Multifunctional" in the context of a polymer of the invention means a PEG polymer having 3 or more functional groups attached thereto, where the functional groups may be the same or different. Multifunctional polymers of the invention will typically comprise from about 3 to 100 functional groups, or from 3 to 50 functional groups, or from 3 to 25 functional groups, or from 3 to 15 functional groups, or from 3 to 10 functional groups, or will contain 3, 4, 5, 6, 7, 8, 9 or 10 functional groups attached to the polymer backbone.

"Non-canonical" activity as used herein, refers generally to either i) a new activity possessed by DRS polypeptide of the invention that is not possessed to any significant degree by the intact native full length parental protein, or ii) an activity that was possessed by the by the intact native full length parental protein, where the DRS polypeptide either exhibits a significantly higher (i.e., at least 20% greater) specific activity with respect to the non-canonical activity compared to the intact native full length parental protein, or exhibits the activity in a new context; for example by isolating the activity from other activities possessed by the intact native full length parental protein. In the case of DRS polypeptides, non-limiting examples of non-canonical activities include extracellular signaling including the modulation of TLRs, modulation of cell proliferation, modulation of cell migration, modulation of cell differentiation (e.g., hematopoiesis, neurogenesis, myogenesis, osteogenesis, and adipogenesis), modulation of gene transcription, modulation of apoptosis or other forms of cell death, modulation of cell signaling, modulation of cellular uptake, or secretion, modulation of angiogenesis, modulation of cell binding, modulation of cellular metabolism, modulation of cytokine production or activity, modulation of cytokine receptor activity, modulation of inflammation, immunogenicity, and the like.

"Non-interfering substituents" are those groups that, when present in a molecule, are typically non-reactive with other functional groups contained within the molecule.

"Nucleophile" refers to an ion or atom or collection of atoms that may be ionic, having a nucleophilic center, i.e., a center that is seeking an electrophilic center, and capable of reacting with an electrophile.

As used herein, the term "polyalkylene glycol" or "poly (alkene glycol)" refers to polyethylene glycol (poly(ethylene glycol)), polypropylene glycol, polybutylene glycol, and derivatives thereof. The term "polyalkylene glycol" encompasses both linear and branched polymers and average molecular weights of between 0.1 kDa and 100 kDa. Other exemplary embodiments are listed, for example, in commercial supplier catalogs, such as Shearwater Corporation's catalog "Polyethylene Glycol and Derivatives for Biomedical Applications" (2001).

As used herein, the terms "PEG," "polyethylene glycol" and "poly(ethylene glycol)" as used herein, are interchangeable and meant to encompass any water-soluble poly(ethylene oxide) derivative. PEG is a well-known polymer with good solubility in many aqueous and organic solvents, which exhibits low toxicity, lack of immunogenicity, and is clear, colorless, odorless, and stable. For these reasons and others, PEG has been selected as the preferred polymer for attachment, but it has been employed solely for purposes of illustration and not limitation. Similar products may be obtained with other water-soluble polymers, as described herein, including without limitation; polyvinyl alcohol, other poly(alkylene oxides) such as poly(propylene glycol) and the like, poly(oxyethylated polyols) such as poly(oxyethylated glycerol) and the like, carboxymethylcellulose, dextran, polyvinyl alcohol, polyvinyl purrolidone, poly-1,3-dioxolane, poly-1,3,6-trioxane, ethylene/maleic anhydride, and polyaminoacids. One skilled in the art will be able to select the desired polymer based on the desired dosage, circulation time, resistance to proteolysis, and other considerations.

Typically, PEGs for use in accordance with the invention comprise the following structure "—$(OCH_2CH_2)_n$—" where (n) is about 1 to 4000, alternatively from about 20 to 1400, or about 20-800. In particular embodiments, PEG also includes "—O—$(CH_2CH_2O)_n$—$CH_2CH_2$—" and "—$(OCH_2CH_2)_n$—O—" depending upon whether or not the terminal oxygens have been displaced. Throughout the specification and claims, it should be understood that in certain embodiments, the term "PEG" includes structures having various terminal or "end capping" groups and so forth. The term "PEG" also means a polymer that contains a majority, that is to say, greater than 50%, of —$OCH_2CH_2$— repeating subunits. With respect to specific forms, the PEG can take any number of a variety of molecular weights, as well as structures or geometries such as "branched," "linear," "forked," "multifunctional," and the like, to be described in greater detail below.

Representative polymeric reagents and methods for conjugating such polymers to an active moiety are described in Harris, J. M. and Zalipsky, S., Eds, Poly(ethylene glycol), *Chemistry and Biological Applications*, ACS, Washington, 1997; Veronese, F., and J. M. Harris, Eds., *Peptide and Protein PEGylation, Advanced Drug Delivery Reviews*, 54(4); 453-609 (2002); Zalipsky, S., et al., "Use of Functionalized Poly Ethylene Glycols) for Modification of Polypeptides" in *Polyethylene Glycol Chemistry: Biotechnical and Biomedical Applications*, J. M. Harris, ed., Plenus Press, New York (1992); Zalipsky (1995) *Advanced Drug Reviews* 16:157-182; and in Roberts et al., *Adv. Drug Delivery Reviews*, 54, 459-476 (2002).

A wide variety of PEG derivatives are both commercially available and suitable for use in the preparation of the PEG-conjugates of the invention. For example, NOF Corp.'s SUNBRIGHT® Series provides numerous PEG derivatives, including methoxypolyethylene glycols and activated PEG derivatives such as succinimidyl ester, methoxy-PEG amines, maleimides, and carboxylic acids, for coupling by various methods to DRS polypeptides and Nektar Therapeutics' Advanced PEGylation also offers diverse PEG-coupling technologies to improve the safety and efficacy of therapeutics. Additional PEGs for use in forming a DRS polypeptide conjugate of the invention include those available from Polypure (Norway), from QuantaBioDesign LTD (Ohio) JenKem Technology, Nanocs Corporation, and Sunbio, Inc (South Korea). Further PEG reagents suitable for use in forming a conjugate of the invention, and methods of conjugation are described in the Pasut. G., et al., *Expert Opin. Ther. Patents* (2004),14(6) 859-893.

A number of investigators have disclosed the preparation of linear or branched PEG polymers and derivatives or conjugates thereof (see, e.g., U.S. Pat. Nos. 4,904,584; 5,428,128; 5,621,039; 5,622,986; 5,643,575; 5,728,560; 5,730,990; 5,738,846; 5,811,076; 5,824,701; 5,840,900; 5,880,131; 5,900,402; 5,902,588; 5,919,455; 5,951,974; 5,965,119; 5,965,566; 5,969,040; 5,981,709; 6,011,042; 6,042,822; 6,113,906; 6,127,355; 6,132,713; 6,177,087; 6,180,095; 6,448,369; 6,495,659; 6,602,498; 6,858,736; 6,828,401; 7,026,440; 7,608,678; 7,655,747; 7,786,221; 7,872,072; and 7,910,661, each of which is incorporated herein by reference in its entirety.

In certain embodiments, the "purity" of any given agent (e.g., PEGylated DRS polypeptide) in a composition may be specifically defined. For instance, certain compositions may comprise an agent that is at least 80, 85, 90, 91, 92, 93, 94, 95, 96, 97, 98, 99, or 100% pure, including all decimals in between, as measured, for example and by no means limiting, by high pressure liquid chromatography (HPLC), a well-known form of column chromatography used frequently in biochemistry and analytical chemistry to separate, identify, and quantify compounds.

A "physiologically cleavable" or "hydrolyzable" or "degradable" bond is a bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include, but are not limited to: carboxylate ester, phosphate ester, anhydride, acetal, ketal, acyloxyalkyl ether, imine, orthoester, thio ester, thiol ester, carbonate, and hydrazone, peptides and oligonucleotides. Without wishing to be bound to any particular theory, an "enzymatically degradable linkage" means a linkage, e.g., amino acid sequence, that is subject to degradation by one or more enzymes, e.g., peptidases or proteases.

The terms "polypeptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers.

A "releasable linkage" includes, but is not limited to, a physiologically cleavable bond, a hydrolyzable bond, and an enzymatically degradable linkage. Thus, a "releasable linkage" is a linkage that may undergo either spontaneous hydrolysis, or cleavage by some other mechanism (e.g., enzyme-catalyzed, acid-catalyzed, base-catalyzed, and so forth) under physiological conditions. For example, a "releasable linkage" can involve an elimination reaction that has a base abstraction of a proton, (e.g., an ionizable hydrogen atom, Ha), as the driving force. For purposes herein, a "releasable linkage" is synonymous with a "degradable linkage." In particular embodiments, a releasable linkage has a half life at pH 7.4, 25° C., e.g., a physiological pH, human body temperature, of about 30 min., about 1 hour, about 2 hour, about 3 hours, about 4 hours, about 5 hours, about 6 hours, about 12 hours, about 18 hours, about 24 hours, about 36 hours, about 48 hours, about 72 hours, or about 96 hours or more.

By "statistically significant", it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

The term "substituted" as in, for example, "substituted alkyl," refers to a moiety (e.g., an alkyl group) substituted with one or more non-interfering substituents, such as, but not limited to: $C_3$-$C_8$ cycloalkyl, e.g., cyclopropyl, cyclobutyl, and the like; halo, e.g., fluoro, chloro, bromo, and iodo; cyano; alkoxy, lower phenyl; substituted phenyl; and the like. For substitutions on a phenyl ring, the substituents may be in any orientation (i.e., ortho, meta, or par "Substituted heteroaryl" is heteroaryl having one or more non-interfering groups as substituents.

"Substituted heterocycle" is a heterocycle having one or more side chains formed from non-interfering substituents.

The term "solubility" refers to the property of a PEGylated DRS polypeptide provided herein to dissolve in a liquid solvent and form a homogeneous solution. Solubility is typically expressed as a concentration, either by mass of solute per unit volume of solvent (g of solute per kg of solvent, g per dL (100 mL), mg/ml, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 5.0, pH 6.0, pH 7.0, or pH 7.4. In certain embodiments, solubility is measured in water or a physiological buffer such as PBS or NaCl (with or without NaP). In specific embodiments, solubility is measured at relatively lower pH (e.g., pH 6.0) and relatively higher salt (e.g., 500 mM NaCl and 10 mM NaP). In certain embodiments, solubility is measured in a biological fluid (solvent) such as blood or serum. In certain embodiments, the temperature can be about room temperature (e.g., about 20, 21, 22, 23, 24, 25° C.) or about body temperature (37° C.). In certain embodiments, a PEGylated DRS polypeptide has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, or 30 mg/ml at room temperature or at 37° C.

A "subject," as used herein, includes any animal that exhibits a symptom, or is at risk for exhibiting a symptom, which can be treated or diagnosed with a PEGylated DRS polypeptide of the invention. Suitable subjects (patients) include laboratory animals (such as mouse, rat, rabbit, or guinea pig), farm animals, and domestic animals or pets (such as a cat or dog). Non-human primates and, preferably, human patients, are included.

"Substantially" or "essentially" means nearly totally or completely, for instance, 95% or greater of some given quantity.

"Treatment" or "treating," as used herein, includes any desirable effect on the symptoms or pathology of a disease or condition, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

As used herein, the term "water soluble polymer" refers to any polymer that is soluble in aqueous solvents. Linkage of water soluble polymers to DRS polypeptides can result in changes including, but not limited to, increased or modulated serum half-life, or increased or modulated therapeutic half-life relative to the unmodified form, modulated immunogenicity, modulated physical association characteristics such as aggregation and multimer formation, altered receptor binding, altered receptor dimerization or multimerization, modulated toxicity, and modulation of one or more the biological activities of DRS polypeptides including side effects found with current DRS therapeutics. The water soluble polymer may or may not have its own biological activity, and may be utilized as a linker for attaching DRS polypeptides to other substances, including but not limited to one or more DRS polypeptides, and/or one or more biologically active molecules. Suitable polymers include, but are not limited to, polyethylene glycol, polyethylene glycol propionaldehyde, mono $C_1$-$C_{10}$ alkoxy or aryloxy derivatives thereof (described in U.S. Pat. No. 5,252,714 which is incorporated by reference), monomethoxy-polyethylene glycol, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, starch and starch derivatives, polypeptides, polyalkylene glycol and derivatives thereof, copolymers of polyalkylene glycols and derivatives thereof, polyvinyl ethyl ethers, and alpha-beta-poly[(2-hydroxyethyl)-DL-aspartamide, and the like, or mixtures thereof.

Specific examples of such water soluble polymers include, but are not limited to, polyalkyl ethers and alkoxy-capped analogs thereof (e.g., polyoxyethylene glycol, polyoxyethylene/propylene glycol, and methoxy or ethoxy-capped analogs thereof, especially polyoxyethylene glycol, the latter is also known as polyethyleneglycol or PEG); polyvinylpyrrolidones; polyvinylalkyl ethers; polyoxazolines, polyalkyl oxazolines and polyhydroxyalkyl oxazolines; polyacrylamides, polyalkyl acrylamides, and polyhydroxyalkyl acrylamides (e.g., polyhydroxypropylmethacrylamide and derivatives thereof); polyhydroxyalkyl acrylates; polysialic acids and analogs thereof; hydrophilic peptide sequences; polysaccharides and their derivatives, including dextran and dextran derivatives, e.g., carboxymethyldextran, dextran sulfates, aminodextran; cellulose and its derivatives, e.g., carboxymethyl cellulose, hydroxyalkyl celluloses; chitin and its derivatives, e.g., chitosan, succinyl chitosan, carboxymethylchitin, carboxymethylchitosan; hyaluronic acid and its derivatives; starches; alginates; chondroitin sulfate; albumin; pullulan and carboxymethyl pullulan; polyaminoacids and derivatives thereof, e.g., polyglutamic acids, polylysines, polyaspartic acids, polyaspartamides; maleic anhydride copolymers such as: styrene maleic anhydride copolymer, divinylethyl ether maleic anhydride copolymer;

polyvinyl alcohols; copolymers thereof; terpolymers thereof; mixtures thereof; and derivatives of the foregoing.

Aspartyl-tRNA Synthetase Derived Polypeptides

Embodiments of the present invention relate to the use of non-naturally occurring Aspartyl-tRNA synthetase derived polypeptides with altered cysteine content ("DRS polypeptides"). Aspartyl-tRNA synthetases belong to the class I tRNA synthetase family, which has two highly conserved sequence motifs at the active site, HIGH (SEQ ID NO:42) and KMSKS (SEQ ID NO:43). Class I tRNA synthetases are widely recognized as being responsible the specific attachment of an amino acid to its cognate tRNA in a 2 step reaction: the amino acid (AA) is first activated by ATP to form AA-AMP and then transferred to the acceptor end of the tRNA. The full length Aspartyl-tRNA synthetases typically exists as a homodimer; and also forms part of a multisubunit complex that typically includes the proteins AIMP1, AIMP2, EEF1A1 and the tRNA synthetases for Arg, Asp, Glu, Gln, Ile, Leu, Lys, Met and Pro.

More recently it has been established that some biological fragments, or alternatively spliced isoforms of eukaryotic aspartyl-tRNA synthetases, or in some contexts the intact synthetase, can dissociate from the multisubunit complex, and activate certain cell-signaling pathways, or act within the nucleus to modulate transcription. These activities, which are distinct from the classical role of tRNA synthetases in protein synthesis, are collectively referred to herein as "non canonical activities". These DRS polypeptides may be produced naturally by either alternative splicing or proteolysis, and can act in a cell autonomous (i.e., within the host cell), or non-cell autonomous fashion (i.e., outside the host cell) to regulate a variety of homeostatic mechanisms. For example, as provided in the present invention, the N-terminal fragment of Aspartyl-tRNA synthetase, DRS (1-154), is capable of modulating the activity of certain TLRs in vivo. In addition, certain mutations or deletions relative to the full-length DRS polypeptide sequence confer increased TLR binding or other non-canonical activities. The sequences of various exemplary DRS polypeptides are provided in Tables D1 to D8.

TABLE D1

| Name | Amino Acid Residue Range of SEQ ID NO: 1 | Amino acid and nucleic acid sequence | SEQ ID NO: |
|---|---|---|---|
| Exemplary DRS Polypeptides | | | |
| Full length AspRS sequence | Protein / Human / 1-501 | MPSASASRKSQEKPREIMDAAEDYAKERYGISSMIQS QEKPDRVLVRVRDLTIQKADEVVWVRARVHTSRAK GKQCFLVLRQQQFNVQALVAVGDHASKQMVKFAA NINKESIVDVEGVVRKVNQKIGSCTQQDVELHVQKI YVISLAEPRLPLQLDDAVRPEAEGEEEGRATVNQDT RLDNRVIDLRTSTSQAVFRLQSGICHLFRETLINKGFV EIQTPKIISAASEGGANVFTVSYFKNNAYLAQSPQLY KQMCICADFEKVFSIGPVFRAEDSNTHRHLTEFVGLD IEMAFNYHYHEVMEEIADTMVQIFKGLQERFQTEIQ TVNKQFPCEPFKFLEPTLRLEYCEALAMLREAGVEM GDEDDLSTPNEKLLGHLVKEKYDTDFYILDKYPLAV RPFYTMPDPRNPKQSNSYDMFMRGEEILSGAQRIHD PQLLTERALHHGIDLEKIKAYIDSFRFGAPPHAGGGI GLERVTMLFLGLHNVRQTSMFPRDPKRLTP | 1 |
| Exemplary AspRS nucleic Acids | | | |
| Full length AspRS sequence Human codon usage | DNA / Human / 1-1506 | ATGCCCAGCGCCAGCGCCAGCCGCAAGAGTCAGGAGA AGCCGCGGGAGATCATGGACGCGGCGGAAGATTATGCT AAAGAGAGATATGGAATATCTTCAATGATACAATCACA AGAAAAACCAGATCGAGTTTTGGTTCGGGTTAGAGACT TGACAATACAAAAAGCTGATGAAGTTGTTTGGGTACGT GCAAGAGTTCATACAAGCAGAGCTAAAGGGAAACAGT GCTTCTTAGTCCTACGTCAGCAGCAGTTTAATGTCCAGG CTCTTGTGGCGGTGGGAGACCATGCAAGCAAGCAGATG GTTAAATTTGCTGCCAACATCAACAAAGAGAGCATTGT GGATGTAGAAGGTGTTGTGAGAAAAGTGAATCAGAAA ATTGGAAGCTGTACACAGCAAGACGTTGAGTTACATGT TCAGAAGATTTATGTGATCAGTTTGGCTGAACCCCGTCT GCCCCTGCAGCTGGATGATGCTGTTCGGCCTGAGGCAG AAGGAGAAGAGGAAGGAAGAGCTACTGTTAACCAGGA TACAAGATTAGACAACAGAGTCATTGATCTTAGGACAT CAACTAGTCAGGCAGTCTTCCGTCTCCAGTCTGGCATCT GCCATCTCTTCCGAGAAACTTTAATTAACAAAGGTTTTG TGGAAATCCAAACTCCTAAAATTATTTCAGCTGCCAGT GAAGGAGGAGCCAATGTTTTTACTGTGTCATATTTTAA AAATAATGCATACCTGGCTCAGTCCCCACAGCTATATA AGCAAATGTGCATTTGTGCTGATTTTGAGAAGGTTTTCT CTATTGGACCAGTATTCAGAGCGGAAGACTCTAATACC CATAGACATCTAACTGAGTTTGTTGGTTTGGACATTGAA ATGGCTTTTAATTACCATTACCACGAAGTTATGGAAGA AATTGCTGACACCATGGTACAAATATTCAAAGGACTTC AAGAAAGGTTTCAGACTGAAATTCAAACAGTGAATAAA CAGTTCCCATGTGAGCCATTCAAATTTTTGGAGCCAACT CTAAGACTAGAATATTGTGAAGCATTGGCTATGCTTAG GGAAGCTGGAGTCGAAATGGGAGATGAAGACGATCTG AGCACACCAAATGAAAAGCTGTTGGGTCATTTGGTAAA | 2 |

TABLE D1-continued

| Name | Amino Acid Residue Range of SEQ ID NO: 1 | Amino acid and nucleic acid sequence | SEQ ID NO: |
|---|---|---|---|
| | | GGAAAAGTATGATACAGATTTTTATATTCTTGATAAAT ATCCATTGGCTGTAAGACCTTTCTATACCATGCCTGACC CAAGAAATCCCAAACAGTCCAACTCTTACGATATGTTC ATGAGAGGAGAAGAAATATTGTCAGGAGCTCAAAGAA TACATGATCCTCAACTGCTAACAGAGAGAGCTTTACAT CATGGAATTGATTTGGAGAAAATTAAGGCTTACATTGA TTCCTTCCGCTTTGGAGCCCCTCCTCATGCTGGTGGAGG CATTGGATTGGAACGAGTTACTATGCTGTTTCTGGGATT GCATAATGTTCGTCAGACCTCCATGTTCCCTCGTGATCC CAAACGACTCACTCCTTAG | |

TABLE D2

Exemplary N-terminal DRS polypeptide Fragments

| Name | Amino Acid Residue Range of SEQ ID NO: 1 | Amino acid sequence | SEQ ID NO: |
|---|---|---|---|
| AspRS1$^{N1}$ | Protein / Human /1- 154 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPL | 3 |
| AspRS1$^{N11}$ | Protein / Human /1-171 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGR | 4 |
| AspRS1$^{N12}$ | Protein / Human /1-174 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATV | 5 |
| AspRS1$^{N13}$ | Protein / Human /1-182 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATVNQDTRLDN | 6 |
| AspRS1$^{N4}$ | Protein / Human /1-184 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATVNQDTRLDNRV | 7 |
| AspRS1$^{N2}$ | Protein / Human /1-274 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAFGEEEGRATVNQDTRLDNRVIDLRTSTSQAVF RLQSGICHLFRETLINKGFVEIQTPKIISAASEGGANVFTVS YFKNNAYLAQSPQLYKQMCICADFEKVFSIGPVFRA | 8 |
| AspRS1$^{N3}$ | Protein / Human /1-224 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKKVNQKIGSCTQQDVELHVQKIYVISLAEPRLPLQL DDAVRPEAFGEEEGRATVNQDTRLDNRVIDLRTSTSQAVF RLQSGICHLFRETLINKGFVEIQTPKII | 9 |
| DRS 1-182 | 1-182 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAFGEEEGRATVNQDTRLDN | 74 |
| DRS 1-180 | 1-180 | MPSASASRKSQEKPREIMDAAEDYAKERYGISSMIQSQEK PDRVLVRVRDLTIQKADEVVWVRARVHTSRAKGKQCFL | 75 |

TABLE D2-continued

Exemplary N-terminal DRS polypeptide Fragments

| Name | Amino Acid Residue Range of SEQ ID NO: 1 | Amino acid sequence | SEQ ID NO: |
|---|---|---|---|
| | | VLRQQQFNVQALVAVGDHASKQMVKFAANINKESIVDV EGVVRKVNQKIGSCTQQDVELHVQKIYVISLAEPRLPLQL DDAVRPEAFGEEKGRATVNQDTRL | |
| DRS 1-178 | 1-178 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATVNQDT | 76 |
| DRS 1-176 | 1-176 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATVNQ | 77 |
| DRS 1-174 | 1-174 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATV | 78 |
| DRS 1-172 | 1-172 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRA | 79 |
| DRS 1-170 | 1-170 | MPSASASRKSQEKPREIMDAAEDYAKERYGISSMIQSQEK PDRVLRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEG | 80 |
| DRS 1-168 | 1-168 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEE | 81 |
| DRS 1-166 | 1-166 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEG | 82 |
| DRS 1-164 | 1-164 | MPSASASRKSQEKPREIMDAAFDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEA | 83 |
| DRS 1-162 | 1-162 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRP | 84 |
| DRS 1-160 | 1-160 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKKIGCTQQDVELHVQKIYVISLAEPRLPLQL DDAV | 85 |
| DRS 1-158 | 1-158 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DD | 86 |
| DRS 1-156 | 1-156 | MPSASASRKSQEKPREIMDAAEDYAKERYGISSMIQSQEK PDRVLVRVRDLTIQKADEVVWVRARVHTSRAKGKQCFL | 87 |

TABLE D2-continued

Exemplary N-terminal DRS polypeptide Fragments

| Name | Amino Acid Residue Range of SEQ ID NO: 1 | Amino acid sequence | SEQ ID NO: |
|---|---|---|---|
| | | VLRQQQFNVQALVAVGDHASKQMVKFAANINKESIVDV EGVVRKVNQKIGSCTQQDVELHVQKIYVISLAEPRLPLQL | |
| DRS 1-154 | 1-154 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPL | 88 |
| DRS 1-152 | 1-152 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRL | 89 |
| DRS 1-150 | 1-150 | MPSASASRKSQEKPREIMDAAEDYAKERYGISSMIQSQEK PDRVLVRVRDLTIQKADEVVWVRARVHTSRAKGKQCFL FLRQQQFNVQALVAVGDHASKQMVKFAANINKESIVDV EGVVRKVNQKIGSCTQQDVELHVQKIYVISLAEP | 90 |
| DRS 1-148 | 148 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLA | 91 |
| DRS 1-146 | 1-146 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVIS | 92 |
| DRS 3-154 | 3-154 | ASASRKSQEKPREIMDAAEDYAKERYGISSMIQSQEKPDR VLVRVRDLTIQKADEVVWVRARVHTSRAKGKQCFLVLR QQQFNVQALVAVGDHASKQMVKFAANINKESIVDVEGV VRKVNQKIGSCTQQDVELHVQKIYVISLAEPRLPL | 93 |
| DRS 5-154 | 5-154 | ASRKSQEKPREIMDAAEDYAKERYGISSMIQSQEKPDRVL VRVRDLTIQKADEVVWVRARVHTSRAKGKQCFLVLRQQ QFNVQALVAVGDHASKQMVKFAANINKESIVDVEGVVR KVNQKIGSCTQQDVELHVQKIYVISLAEPRLPL | 94 |
| DRS 7-154 | 7-154 | TKSQEKPREIMDAAEDYAKERYGISSMIQSQEKPDRVLVR VRDLTIQKADEVVWVRARVHTSRAKGKQCFLVLRQQQF NVQALVAVGDHASKQMVKFAANINKESIVDVEGVVRKV NQKIGSCTQQDVELHVQKIYVISLAEPRLPL | 95 |
| DRS 9-154 | 9-154 | SQEKPREIMDAAEDYAKERYGISSMIQSQEKPDRVLVRVR DLTIQKADEVVWVRARVHTSRAKGKQCFLVLERQQQFNV QALVAVGDHASKQMVKFAANINKESIVDVEGVVRKVNQ KIGSCTQQDVELHVQKIYVISLAEPRLPL | 96 |
| DRS 11-154 | 11-154 | EKPREIMDAAEDYAKERYGISSMIQSQEKPDRVLVRVRDL TIQKADEVVWVRARVHTSRAKGKQCFLVLRQQQFNVQA LVAVGDHASKQMVKFAANINKESIVDVEGVVRKVNQKIG SCTQQDVELHVQKIYVISLAEPRLPL | 97 |
| DRS 13-154 | 13-154 | PREIMDAAEDYAKERYGISSMIQSQEKPDRVLVRVRDLTI QKADEVVWVRARVHTSRAKGKQCFLVLRQQQFNVQALV AVGDHASKQMVKFAANINKESIVDVEGVVRKVNQKIGSC TQQDVELHVQKIYVISLAEPRLPL | 98 |
| DRS15 -154 | 15 -154 | EIMDAAEDYAKERYGISSMIQSQEKPDRVLVRVRDLTIQK ADEVVWVRARVHTSRAKGKQCFLVLRQQQFNVQALVAVG GDHASKQMVKFAANINKESIVDVEGVVRKVNQKIGSCTQ QDVELHVQKIYVISLAEPRLPL | 99 |
| DRS 17-154 | 17-154 | MDAAEDYAKERYGISSMIQSQEKPDRVLVRVRDLTIQKA DEVVWVRARVHTSRAKGKQCFLVLRQQQFNVQALVAVG DHASKQMVKFAANINKESIVDVEGVVRKVNQKIGSCTQQ DVELHVQKIYVISLAEPRLPL | 100 |
| DRS 19-154 | 19-154 | MDAAEDYAKERYGISSMIQSQEKPDRVLVRVRDLTIQKA DEVVWVRARVHTSRAKGKQCFLVLRQQQFNVQALVAVG DHASKQMVKFAANINKESIVDVEGVVRKVNQKIGSCTQQ DVELHVQKIYVISLAEPRL | 101 |

TABLE D2-continued

Exemplary N-terminal DRS polypeptide Fragments

| Name | Amino Acid Residue Range of SEQ ID NO: 1 | Amino acid sequence | SEQ ID NO: |
|---|---|---|---|
| DRS 21-154 | 21-154 | MDAAEDYAKERYGISSMIQSQEKPDRVLVRVRDLTIQKA DEVVWVRARVHTSRAKGKQCFLVLRQQQFNVQALVAVG DHASKQMVKFAANINKESIVDVEGVVRKVNQKIGSCTQQ DVELHVQKIYVISLAEPRL | 102 |
| DRS 23-154 | 23-154 | AAEDYAKERYGISSMIQSQEKPDRVLVRVRDLTIQKADEV VWVRARVHTSRAKGKQCFLVLRQQQFNVQALVAVGDH ASKQMVKFAANINKESIVDVEGVVRKVNQKIGSCTQQDV ELHVQKIYVISLAEPRL | 103 |
| DRS 11-146 | 11-146 | MQEKPREIMDAAEDYAKERYGISSMIQSQEKPDRVLVRV RDLTIQKADEVVWVRARVHTSRAKGKQCFLVLRQQQFN VQALVAVGDHASKQMVKFACNINKESIVDVEGVVRKVN QKIGSCTQQDVELHVQKIYVIS | 104 |
| DRS 13-146 | 13-146 | MKPREIMDAAEDYAKERYGISSMIQSQEKPDRVLVRVRD LTIQKADEVVWVRARVHTSRAKGKQCFLVLERQQQFNVQ ALVAVGDHASKQMVKFACNINKESIVDVEGVVRKVNQKI GSCTQQDVELHVQKIYVIS | 105 |
| DRS 13-146/A106C | 13-146 | MKPREIMDAAEDYAKERYGISSMIQSQEKPDRVLVRVRD LTIQKADEVVWVRARVHTSRAKGKQCFLVLERQQQFNVQ ALVAVGDHASKQMVKFACNINKESIVDVEGVVRKVNQKI GSCTQQDVELHVQKIYVIS | 106 |
| DRS 17-146 | 17-146 | MIMDAAEDYAKERYGISSMIQSQEKPDRVLVRVRDLTIQK ADEVVWVRARVHTSRAKGKQCFLVLRQQQFNVQALVAV GDHASKQMVKFACNINKESIVDVEGVVRKVNQKIGSCTQ QDVELHVQKIYVIS | 107 |
| DRS 21-146 | 21-146 | MAEDYAKERYGISSMIQSQEKPDRVLVRVRDLTIQKADE VVWVRARVHTSRAKGKQCFLVLRQQQFNVQALVAVGD HASKQMVKFACNINKESIVDVEGVVRKVNQKIGSCTQQD VELHVQKIYVIS | 108 |

TABLE D3

Exemplary Internal DRS polypeptide Fragments

| Name | Amino Acid Residue Range of SEQ ID NO: | Amino acid sequence | SEQ ID NO: |
|---|---|---|---|
| AspRS1[f1] | Protein / Human / 38-292 | QEKPDRVLVRVRDLTIQKADEVVWVRARVHTSRAKGKQ CFLVLRQQQFNVQALVAVGDHASKQMVKFAANINKESIV DVEGVVRKVNQKIGSCTQQDVELHVQKIYVISLAEPRLPL QLDDAVRPEAEGEEEGRATVNQDTRLDNRVIDLRTSTSQ AVFRLQSGICHLFRETLINKGFVEIQTPKIISAASEGGANVF TVSYFKNNAYLAQSPQLYKQMCICADFEKVFSIGPVFRAE DSNTHRHLTEFVGLDIE | 10 |
| AspRS1[f2] | Protein / Human / 23-154 | DYAKERYGISSMIQSQEKPDRVLVRVRDLTIQKADEVVW VRARVHTSRAKGKQCFLVLRQQQFNVQALVAVGDHASK QMVKFAANINKESIVDVEGVVRKVNQKIGSCTQQDVELH VQKIYVISLAEPRLPL | 11 |
| AspRS1[f3] | Protein / Human / 33-154 | SMIQSQEKPDRVLVRVRDLTIQKADEVVWVRARVHTSRA KGKQCFLVLRQQQFNVQALVAVGDHASKQMVKFAANIN KESIVDVEGVVRKVNQKIGSCTQQDVELHVQKIYVISLAE PRLPL | 12 |

TABLE D4

Exemplary C-Terminal DRS polypeptide Fragments

| Name | Amino Acid Residue Range of SEQ ID NO: 1 | Amino acid sequence | SEQ ID NO: |
|---|---|---|---|
| AspRS1$^{C1}$ | Protein / Human / 297-501 | YHYHEVMEEIADTMVQIFKGLQERFQTEIQTVNKQFPCEP FKFLEPTLRLEYCEALAMLREAGVEMGDEDDLSTPNEKLL GHLVKEKYDTDFYILDKYPLAVRPFYTMPDPRNPKQSNS YDMFMRGEEILSGAQRIHDPQLLTERALHHGIDLEKIKAYI DSFRFGAPPHAGGGIGLERVTMLFLGLHNVRQTSMFPRDP KRLTP | 13 |
| AspRS1$^{C2}$ | Protein / Human / 101-501 | MVKFAANINKESIVDVEGVVRKVNQKIGSCTQQDVELHV QKIYVISLAEPRLPLQLDDAVRPEAEGEEEGRATVNQDTR LDNRVIDLRTSTSQAVFRLQSGICHLFRETLINKGFVEIQTP KIISAASEGGANVFTVSYFKNNAYLAQSPQLYKQMCICAD FEKVFSIGPVFRAEDSNTHRHLTEFVGLDIEMAFNYHYHE VMEEIADTMVQIFKGLQERFQTEIQTVNKQFPCEPFKFLEP TLRLEYCEALAMLREAGVEMGDEDDLSTPNEKLLGHLVK EKYDTDFYILDKYPLAVRPFYTMPDPRNPKQSNSYDMFM RGEEILSGAQRIHDPQLLTERALHHGIDLEKIKAYIDSFRFG APPHAGGGIGLERVTMLFLGLHNVRQTSMFPRDPKRLTP | 14 |

TABLE D5

Exemplary Alternatively Spliced DRS polypeptide Variants

| Name | Amino Acid Residue Range of SEQ ID NO: 1 | Amino acid sequence | SEQ ID NO: |
|---|---|---|---|
| AspRS1$^{N6}$ | Protein / Human / 1-41 + 73-501 | MPSASASRKSQEKPREIMDAAEDYAKERYGISSMIQSQEK PGKQCFLVLRQQQFNVQALVAVGDHASKQMVKFAANIN KESIVDVEGVVRKVNQKIGSCTQQDVELHVQKIYVISLAE PRLPLQLDDAVRPEAEGEEEGRATVNQDTRLDNRVIDLRT STSQAVFRLQSGICHLFRETLINKGFVEIQTPKIISAASEGG ANVFTVSYFKNNAYLAQSPQLYKQMCICADFEKVFSIGPV FRAEDSNTHRHLTEFVGLDIEMAFNYHYHEVMEEIADTM VQIFKGLQERFQTEIQTVNKQFPCEPFKFLEPTLRLEYCEA LAMLREAGVEMGDEDDLSTPNEKLLGHLVKEKYDTDFYI LDKYPLAVRPFYTMPDPRNPKQSNSYDMFMRGEEILSGA QRIHDPQLLTERALHHGIDLEKIKAYIDSFRFGAPPHAGGG IGLERVTMLFLGLHNVRQTSMFPRDPKRLTP | 15 |
| AspRS1$^{N7}$ | Protein / Human / 1-141 + 189-501 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKTSTSQAVFRLQSGIC HLFRETLINKGFVEIQTPKIISAASEGGANVFTVSYFKNNA YLAQSPQLYKQMCICADFEKVFSIGPVFRAEDSNTHRHLT EFVGLDIEMAFNYHYHEVMEEIADTMVQIFKGLQERFQTE IQTVNKQFPCEPFKFLEPTLRLEYCEALAMLREAGVEMGD EDDLSTPNEKLLGHLVKEKYDTDFYILDKYPLAVRPFYTM PDPRNPKQSNSYDMFMRGEEILSGAQRIHDPQLLTERALH HGIDLEKIKAYIDSFRFGAPPHAGGGIGLERVTMLFLGLHN VRQTSMFPRDPKRLTP | 16 |
| AspRS1$^{N8}$ | Protein / Human / 1-319 + 369-501 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATVNQDTRLDNRVIDLRTSTSQAVF RLQSGICHLFRETLINKGFVEIQTPKIISAASEGGANVFTVS YFKNNAYLAQSPQLYKQMCICADFEKVFSIGPVFRAEDSN THRHLTEFVGLDIEMAFNYHYHEVMEEIADTMVQIFKGL QESTPNEKLLGHLVKEKYDTDFYILDKYPLAVRPFYTMPD PRNPKQSNSYDMFMRGEEILSGAQRIHDPQLLTERALHHG IDLEKIKAYIDSFRFGAPPHAGGGIGLERVTMLFLGLHNVR QTSMFPRDPKRLTP | 17 |
| AspRS1$^{N9}$ DRS (1-22 + 63 aa) | Protein / Human / 1-22 + 63 aa | MPSASASRKSQEKPREIMDAAEDWNELLCCFWDCIMFVR PPCSLVIPNDSLLKFTLCHLTPVWMTERDPASKKKKKKES HTYSFQ | 18 |

TABLE D5-continued

Exemplary Alternatively Spliced DRS polypeptide Variants

| Name | Amino Acid Residue Range of SEQ ID NO: 1 | Amino acid sequence | SEQ ID NO: |
|---|---|---|---|
| AspRS1N[10] DRS (1-22 + 5 aa) | Protein / Human / 1-22 + 5 aa | MPSASASRKSQEKPREIMDAAEGNSAS | 19 |
| AspRS1[C2] | Protein / Human / 101-501 | MVKFAANINKESIVDVEGVVRKVNQKIGSCTQQDVELHV QKIYVISLAEPRLPLQLDDAVRPEAEGEEEGRATVNQDTR LDNRVIDLRTSTSQAVFRLQSGICHLFRETLINKGFVEIQTP KIISAASEGGANVFTVSYFKNNAYLAQSPQLYKQMCICAD FEKVFSIGPVFRAEDSNTHRHLTEFVGLDIEMAFNYHYHE VMEEIADTMVQIFKGLQERFQTEIQTVNKQFPCEPFKFLEP TLRLEYCEALAMLREAGVEMGDEDDLSTPNEKLLGHLVK EKYDTDFYILDKYPLAVRPFYTMPDPRNPKQSNSYDMFM RGEEILSGAQRIHDPQLLTERALHHGIDLEKIKAYIDSFRFG APPHAGGGIGLERVTMLFLGLHNVRQTSMFPRDPKRLTP | 20 |
| AspRS1[C3] DRS (478-501) | Protein / Human / 478-501 | MLFLGLHNVRQTSMFPRDPKRLTP | 21 |

A number of naturally occurring aspartyl-tRNA synthetase single nucleotide polymorphisms (SNPs) and naturally occurring variants of the human gene have been sequenced, and are known in the art to be at least partially functionally interchangeable. Additionally homologs and orthologs of the human gene exist in other species, and it would thus be a routine matter to select a naturally occurring variant such as a DRS polypeptide encoded by a SNP, or other naturally occurring variant in place of any of the DRS polypeptide sequences listed in Tables D1-D5. Several such variants of aspartyl-tRNA synthetase (i.e., representative aspartyl-tRNA synthetase SNPs) are shown in Table D6.

TABLE D6

Human Aspartyl-tRNA synthetase SNPs

| Gene Bank Accession Number | Nucleotide Change | Gene Bank Accession Number | Nucleotide Change |
|---|---|---|---|
| rs118100102 | C/T | rs2164332 | C/G |
| rs117859527 | C/G | rs2164331 | C/T |
| rs117847055 | A/G | rs1867632 | A/G |
| rs117843158 | A/C | rs1803167 | C/T |
| rs117754321 | A/C | rs1803166 | C/T |
| rs117605910 | C/G | rs1803165 | G/T |
| rs117587018 | A/G | rs1347442 | C/T |
| rs117448010 | A/C | rs895285 | A/G |
| rs117438984 | A/G | rs834734 | C/T |
| rs117395206 | G/T | rs689002 | A/G |
| rs117045416 | C/T | rs687670 | C/T |
| rs116899241 | C/T | rs661562 | A/C |
| rs116807764 | C/T | rs660002 | C/T |
| rs116756668 | C/T | rs640727 | A/T |
| rs116755289 | C/T | rs567363 | C/T |
| rs116723553 | A/G | rs561980 | A/G |
| rs116719241 | C/T | rs522086 | C/T |
| rs116626412 | C/T | rs309172 | C/T |
| rs116599033 | A/G | rs309171 | C/G |
| rs116528963 | C/T | rs309170 | C/T |
| rs116504104 | A/G | rs309169 | C/T |
| rs116503734 | A/T | rs309168 | C/T |
| rs116471228 | G/T | rs309167 | C/T |
| rs116460118 | A/T | rs309166 | C/T |
| rs116376572 | A/G | rs309165 | C/T |
| rs116373537 | G/T | rs309164 | A/G |
| rs116190965 | C/T | rs309163 | C/T |
| rs116114585 | A/T | rs309162 | A/T |
| rs116069651 | C/T | rs309161 | C/T |
| rs116013288 | C/T | rs309160 | A/G |
| rs115947325 | C/T | rs309159 | A/G |
| rs115876148 | C/T | rs309158 | C/T |
| rs115771261 | C/T | rs309157 | A/G |
| rs115749352 | A/G | rs309156 | C/G |
| rs115704588 | C/T | rs309155 | A/G |
| rs115691888 | A/C | rs309154 | C/T |

TABLE D6-continued

Human Aspartyl-tRNA synthetase SNPs

| Gene Bank Accession Number | Nucleotide Change | Gene Bank Accession Number | Nucleotide Change |
|---|---|---|---|
| rs115651129 | C/G | rs309153 | A/G |
| rs115572299 | C/T | rs309150 | A/T |
| rs115553816 | A/G | rs309149 | C/T |
| rs115530645 | C/T | rs7587285 | C/T |
| rs115475999 | C/T | rs7585928 | C/G |
| rs115469964 | A/C | rs7573555 | C/T |
| rs115332530 | A/G | rs6760465 | A/T |
| rs115330084 | C/G | rs6757965 | A/G |
| rs115316382 | A/G | rs6754311 | C/T |
| rs115306423 | C/T | rs6752967 | A/G |
| rs115253602 | A/G | rs6750549 | A/G |
| rs115249754 | C/T | rs6743537 | A/G |
| rs115248017 | C/G | rs6742701 | C/T |
| rs114986027 | C/T | rs6740254 | C/G |
| rs114977327 | C/T | rs6738266 | C/T |
| rs114851922 | C/T | rs6733398 | A/G |
| rs114841878 | A/G | rs6724595 | A/G |
| rs114832662 | A/G | rs6711493 | A/G |
| rs114830940 | A/G | rs6430594 | A/G |
| rs114489290 | C/T | rs5834455 | −/T |
| rs114428384 | C/T | rs5834454 | −/AA |
| rs114422751 | C/T | rs5834453 | −/AAAAT |
| rs114414669 | A/C | rs4954551 | A/G |
| rs114412783 | C/T | rs4597591 | A/T |
| rs114399267 | C/T | rs4538260 | A/G |
| rs114398361 | A/G | rs4278979 | C/T |
| rs114345514 | C/T | rs3820789 | C/G |
| rs114337780 | A/C | rs3768999 | C/G |
| rs114164361 | C/G | rs3768998 | A/C |
| rs114162105 | A/T | rs3768997 | A/G |
| rs114126158 | A/G | rs3768996 | C/G |
| rs114110228 | A/C | rs3112496 | C/T |
| rs114058841 | G/T | rs3098104 | A/T |
| rs113998842 | G/T | rs2839741 | A/T |
| rs113995718 | A/C | rs2556175 | C/T |
| rs113884130 | C/T | rs2322725 | C/T |
| rs113882668 | A/C | rs2307720 | −/TTAG |
| rs113853485 | G/T | rs2305101 | G/T |
| rs113759327 | C/G | rs2278683 | A/C |
| rs113676252 | C/T | rs2278682 | C/G |
| rs113641203 | G/T | rs2278681 | C/T |
| rs113342018 | G/T | rs2164333 | A/T |
| rs113328159 | −/C | rs13397074 | A/C |
| rs113316632 | A/T | rs13392680 | A/T |
| rs113200654 | A/T | rs13388887 | C/T |
| rs113155677 | A/G | rs13034773 | A/C |
| rs113148022 | AAAAAAAAAAAA AAAAAAATCCAA | rs13025460 | A/T |
| rs113012086 | A/G | rs13007697 | G/T |
| rs112923773 | A/G | rs13004546 | C/T |
| rs112910626 | C/T | rs12999871 | A/C |
| rs112868187 | C/T | rs12990346 | G/T |
| rs112849402 | A/G | rs12990316 | C/T |
| rs112848056 | C/T | rs12624144 | C/T |
| rs112835147 | C/T | rs12623506 | A/G |
| rs112767522 | C/T | rs12617586 | C/T |
| rs112396243 | C/T | rs12615624 | A/G |
| rs112369881 | A/T | rs12613540 | C/T |
| rs112319042 | C/T | rs12613074 | G/T |
| rs112300736 | G/T | rs12477103 | A/C |
| rs112205661 | C/T | rs12474975 | A/T |
| rs112205423 | G/T | rs12471430 | A/T |
| rs112138368 | C/T | rs11895669 | G/T |
| rs112136466 | C/T | rs11895436 | A/G |
| rs111956746 | A/G | rs11892136 | G/T |
| rs111909933 | C/T | rs11889473 | A/C |
| rs111766943 | A/G | rs11548872 | C/G |
| rs111731189 | C/T | rs11548870 | A/G |
| rs111716305 | C/T | rs11375996 | −/A |
| rs111670530 | C/T | rs11345750 | −/A |
| rs111613855 | A/G | rs11340194 | −/A |
| rs111608134 | C/T | rs11319623 | −/A |
| rs111600480 | A/G | rs11297201 | −/T |
| rs111578911 | A/C | rs10610928 | −/CTCT |

TABLE D6-continued

Human Aspartyl-tRNA synthetase SNPs

| Gene Bank Accession Number | Nucleotide Change | Gene Bank Accession Number | Nucleotide Change |
|---|---|---|---|
| rs111533002 | –/T | rs10606646 | –/AAAA |
| rs111432741 | C/T | rs10598545 | –/AAAA |
| rs111346414 | C/T | rs10566195 | –/TGA |
| rs111261866 | C/T | rs10546948 | –/TT |
| rs80342688 | A/C | rs10205844 | C/G |
| rs80296238 | A/C | rs35332762 | –/C |
| rs80290607 | G/T | rs35323281 | –/A |
| rs80201497 | A/C | rs35250856 | –/C |
| rs80160510 | C/T | rs35207721 | –/C |
| rs80095420 | C/T | rs35180509 | –/A |
| rs79933222 | A/C | rs35066766 | –/T |
| rs79908186 | G/T | rs34855029 | –/A |
| rs79826902 | A/G | rs34818704 | –/G |
| rs79811988 | G/T | rs34764820 | –/T |
| rs79778906 | C/T | rs34762161 | –/T |
| rs79745746 | C/T | rs34744196 | –/A |
| rs79719188 | C/T | rs34739918 | –/T |
| rs79715594 | C/T | rs34719779 | –/T |
| rs79685879 | –/TT | rs34713850 | –/A |
| rs79613305 | A/C | rs34698626 | –/AA |
| rs79513920 | C/T | rs34675243 | –/A |
| rs79507949 | A/G | rs34613097 | –/A |
| rs79494100 | A/T | rs34442772 | –/C |
| rs79478181 | A/T | rs34398897 | –/G |
| rs79327246 | C/G | rs34215176 | –/G |
| rs79301888 | C/T | rs34180776 | –/G |
| rs79274257 | A/G | rs34142242 | –/T |
| rs79268627 | A/T | rs34050823 | –/T |
| rs79238496 | A/G | rs17718194 | C/T |
| rs79231002 | C/T | rs16832417 | C/T |
| rs79227800 | C/T | rs16832413 | A/C |
| rs79173488 | A/G | rs16832394 | A/C |
| rs79161420 | –/A | rs16832326 | A/G |
| rs79139071 | A/G | rs16832275 | C/G |
| rs79137850 | C/T | rs16832274 | C/T |
| rs79121686 | C/T | rs16832248 | C/G |
| rs79078468 | G/T | rs16832243 | C/T |

TABLE D6-continued

Human Aspartyl-tRNA synthetase SNPs

| Gene Bank Accession Number | Nucleotide Change | Gene Bank Accession Number | Nucleotide Change |
|---|---|---|---|
| rs79018926 | C/T | rs16832221 | C/T |
| rs78993580 | A/G | rs16832205 | A/G |
| rs78943662 | –/A | rs16832200 | C/T |
| rs78919277 | G/T | rs16832172 | C/T |
| rs78915112 | A/C | rs16832162 | A/T |
| rs78898735 | A/T | rs13404551 | C/T |
| rs78793088 | A/G | rs13399128 | A/G |
| rs78784878 | G/T | rs71417582 | C/T |
| rs78770570 | C/T | rs71417581 | C/G |
| rs78700806 | C/G | rs71400535 | –/A |
| rs78638278 | C/T | rs67636722 | –/A |
| rs78629157 | A/G | rs67591467 | –/A |
| rs78628013 | C/T | rs66527494 | –/A |
| rs78577601 | A/T | rs66508408 | –/AA |
| rs78537103 | C/T | rs62159056 | A/C |
| rs78518056 | A/C | rs62159055 | A/T |
| rs78512447 | A/T | rs61569739 | –/AA |
| rs78497838 | –/TTT | rs61297566 | –/AAATA |
| rs78383997 | A/T | rs61222539 | C/T |
| rs78283445 | C/G | rs61133344 | C/T |
| rs78275586 | G/T | rs60878223 | –/T |
| rs78274583 | C/T | rs60538468 | A/C |
| rs78258066 | A/G | rs60485095 | –/TT |
| rs78168253 | C/T | rs60318326 | C/T |
| rs78143716 | A/G | rs59584448 | –/A |
| rs78130363 | A/G | rs59505882 | –/A |
| rs78083497 | A/C | rs59464486 | G/T |
| rs78081965 | G/T | rs59199326 | –/TT |
| rs78076875 | C/T | rs58805013 | A/C |
| rs78026280 | A/G | rs58799551 | –/G |
| rs78015725 | G/T | rs58666594 | G/T |
| rs77987440 | C/T | rs57046249 | –/A |
| rs77972711 | A/G | rs56721192 | –/AA |
| rs77930020 | A/C | rs56100046 | A/T |
| rs77902883 | C/T | rs55951873 | A/G |
| rs77883526 | A/T | rs55815289 | –/A |
| rs77862927 | –/TT | rs55759471 | G/T |

TABLE D6-continued

Human Aspartyl-tRNA synthetase SNPs

| Gene Bank Accession Number | Nucleotide Change | Gene Bank Accession Number | Nucleotide Change | Gene Bank Accession Number | Nucleotide Change | Gene Bank Accession Number | Nucleotide Change |
|---|---|---|---|---|---|---|---|
| rs77837755 | A/C | rs55641281 | A/G | rs76677887 | C/T | rs71930676 | —/A |
| rs77793053 | C/T | rs41269823 | A/G | rs76672039 | C/T | rs71746189 | —/A |
| rs77774340 | A/C | rs41269821 | A/G | rs76496496 | A/G | rs71701797 | —/AAAA |
| rs77753457 | C/T | rs36023868 | —/T | rs76460134 | A/C | rs71697066 | —/A |
| rs77752694 | A/T | rs35921927 | A/G | rs76456107 | A/G | rs71535212 | A/T |
| rs77743403 | G/T | rs35814998 | —/C | rs76448970 | A/G | rs71535211 | C/T |
| rs77707512 | C/T | rs35760856 | —/C | rs76433055 | C/T | rs71417587 | A/C |
| rs77697045 | C/T | rs35460584 | —/C | rs76392392 | A/G | rs71417586 | A/C |
| rs77694994 | A/G | rs35363362 | C/G | rs76357426 | C/T | rs71417585 | C/G |
| rs77654242 | G/T | rs74661004 | C/T | rs76350348 | A/G | rs71417584 | C/G |
| rs77546304 | C/T | rs74527665 | C/T | rs76337990 | C/T | rs71417583 | A/C |
| rs77516029 | C/T | rs74479926 | C/T | rs76306255 | G/T | rs309148 | C/T |
| rs77511888 | A/C | rs74462337 | G/T | rs76302219 | C/T | rs309147 | C/T |
| rs77507602 | A/T | rs74399174 | A/C | rs76296777 | A/G | rs309146 | A/G |
| rs77390314 | A/G | rs74398392 | C/T | rs76285313 | A/T | rs309145 | A/G |
| rs77341293 | A/C | rs74266318 | G/T | rs76189476 | A/G | rs309144 | C/T |
| rs77340433 | C/T | rs73957079 | C/T | rs76089705 | G/T | rs309143 | A/G |
| rs77244692 | A/G | rs73957078 | C/T | rs76047098 | C/T | rs309142 | C/T |
| rs77241600 | C/T | rs73957074 | A/C | rs75999734 | C/T | rs309141 | A/C |
| rs77194466 | A/T | rs73957073 | A/G | rs75990169 | A/G | rs309140 | A/C |
| rs77182879 | A/G | rs73957072 | A/G | rs75935955 | C/T | rs309120 | C/G |
| rs77177301 | G/T | rs73957071 | A/G | rs75874749 | C/T | rs309119 | A/G |
| rs77147958 | A/G | rs73957070 | A/G | rs75843843 | C/G | rs309115 | C/T |
| rs77144439 | A/T | rs73957069 | C/G | rs75843510 | C/T | rs309114 | A/T |
| rs77113180 | A/G | rs73957068 | C/T | rs75842188 | A/G | rs309113 | A/C |
| rs77092452 | A/G | rs72974121 | A/G | rs75800473 | G/T | rs309112 | G/T |
| rs77052188 | G/T | rs72974120 | C/G | rs75794936 | A/C | rs192822 | A/T |
| rs77051588 | C/T | rs72974119 | A/G | rs75753154 | C/T | rs177917 | C/T |
| rs76986930 | A/C | rs72974109 | A/G | rs75732042 | C/G | rs167442 | G/T |
| rs76946722 | —/AA | rs72423998 | —/A | rs75683158 | G/T | rs71518151 | ACTTTTTGATGGGGTTGT (SEQ ID NO: 44)/CCTTTTTCATGGGCTTGTTTTTTCTTGTAAATTTGTTT (SEQ ID NO: 45) |
| rs76862952 | A/C | rs72366475 | —/T | | | | |
| rs76856516 | G/T | rs72355283 | —/A | | | | |
| rs76798249 | A/C | rs72313616 | —/TT | | | | |
| rs76793136 | A/G | rs72270342 | —/A | rs75667274 | C/T | rs75123144 | —/AG |
| rs76792531 | A/G | rs72268157 | —/A | rs75657010 | A/T | rs75071131 | A/T |
| rs76732000 | G/T | rs72097458 | —/A | rs75647121 | C/T | rs74959174 | C/T |
| rs76729798 | C/T | rs71937749 | —/AA | rs75572938 | A/T | rs74833182 | A/T |

TABLE D6-continued

Human Aspartyl-tRNA synthetase SNPs

| Gene Bank Accession Number | Nucleotide Change | Gene Bank Accession Number | Nucleotide Change |
|---|---|---|---|
| rs75560320 | A/G | rs74777619 | C/T |
| rs75524146 | C/T | rs74771413 | C/G |
| rs75437018 | C/G | rs74674565 | C/T |
| rs75402079 | A/C | rs75346069 | C/T |
| rs75394224 | C/G | rs75298650 | A/G |
| rs75365510 | A/G | rs75214175 | A/G |

Accordingly, the terms "DRS polypeptide" "DRS protein" or "DRS protein fragment" as used herein includes all naturally-occurring and synthetic forms of the aspartyl-tRNA synthetase that retain non canonical activity. Such DRS polypeptides include the full length human protein, as well as the DRS peptides derived from the full length protein listed in Tables D1-D5, as well as naturally occurring variants, for example as disclosed in Table D6, exemplary cysteine mutants listed in Table D7, and synthetic codon optimized forms and other coding sequences as exemplified by the nucleic acid sequences in Table D8. In some embodiments, the term DRS polypeptide refers to a polypeptide sequence derived from human aspartyl-tRNA synthetase (SEQ ID NO:1 in Table D1) comprising at least one mutation at either Cys76 or Cys130.

DRS Variants

Thus all such homologues, orthologs, and naturally-occurring, or synthetic isoforms of aspartyl-tRNA synthetase (e.g., any of the proteins or nucleic acids listed in Tables D1 to D8) are included in any of the methods, kits and pharmaceutical compositions of the invention, as long as they retain detectable non canonical activity.

The DRS polypeptides may be in their native form, i.e., as different variants as they appear in nature in different species which may be viewed as functionally equivalent variants of human aspartyl-tRNA synthetase, or they may be functionally equivalent natural derivatives thereof, which may differ in their amino acid sequence, e.g., by truncation (e.g., from the N- or C-terminus or both) or other amino acid deletions, additions, insertions, substitutions, or post-translational modifications. Naturally-occurring chemical derivatives, including post-translational modifications and degradation products of any DRS polypeptide, are also specifically included in any of the methods and pharmaceutical compositions of the invention including, e.g., pyroglutamyl, isoaspartyl, proteolytic, phosphorylated, glycosylated, oxidatized, isomerized, and deaminated variants of a DRS polypeptide.

It is known in the art to synthetically modify the sequences of proteins or peptides, while retaining their useful activity, and this may be achieved using techniques which are standard in the art and widely described in the literature, e.g., random or site-directed mutagenesis, cleavage, and ligation of nucleic acids, or via the chemical synthesis or modification of amino acids or polypeptide chains. Similarly it is within the skill in the art to address and/or mitigate immunogenicity concerns if they arise using a DRS polypeptide or variant thereof, e.g., by the use of automated computer recognition programs to identify potential T cell epitopes, and directed evolution approaches to identify less immunogenic forms.

As noted above, embodiments of the present invention include all homologues, orthologs, and naturally-occurring isoforms of aspartyl-tRNA synthetase (e.g., any of the proteins, or their corresponding nucleic acids listed in Tables D1 to D8 which i) retain detectable non canonical activity.

Also included are "variants" of these DRS reference polypeptides. The recitation polypeptide "variant" refers to polypeptides that are distinguished from a reference DRS polypeptide by the addition, deletion, and/or substitution of at least one amino acid residue, and which typically retain (e.g., mimic) or modulate (e.g., antagonize) one or more non-canonical activities of a reference DRS polypeptide. The structure of human aspartyl-tRNA synthetase has been determined to a resolution of 1.7A. (WO2010/120509) providing a detailed physical description of the protein, which in conjunction with the primary amino acid sequence provides precise insights into the roles played by specific amino acids within the protein. Accordingly it is within the skill of those in the art to identify amino acids suitable for substitution and to design variants with substantially unaltered, improved, or decreased activity with no more than routine experimentation.

In certain embodiments, a polypeptide variant is distinguished from a reference polypeptide by one or more substitutions, which may be conservative or non-conservative, as described herein and known in the art. In certain embodiments, the polypeptide variant comprises conservative substitutions and, in this regard, it is well understood in the art that some amino acids may be changed to others with broadly similar properties without changing the nature of the activity of the polypeptide.

Specific examples of DRS polypeptide variants useful in any of the methods and compositions of the invention include full-length DRS polypeptides, or truncations or splice variants thereof (e.g., any of the proteins or nucleic acids listed in Tables D1 to D8 which i) retain detectable non canonical activity and ii) have one or more additional amino acid substitutions. In certain embodiments, a variant polypeptide includes an amino acid sequence having at least about 50%, 55%, 60%, 65%, 70%, 75%, 80%, 85%, 90%, 91%, 92%, 93%, 94%, 95%, 96%, 97%, 98% or more sequence identity or similarity to a corresponding sequence of a DRS reference polypeptide, as described herein, (e.g., any of the proteins or nucleic acids listed in Tables D1 to D8 and substantially retains the non-canonical activity of that reference polypeptide. Also included are sequences differing from the reference DRS sequences by the addition, deletion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150 or more amino acids but which retain the properties of the reference DRS polypeptide. In certain embodiments, the amino acid additions or deletions occur at the C-terminal end and/or the N-terminal end of the DRS reference polypeptide. In certain embodiments, the amino acid additions include 1, 2, 3, 4, 5, 6, 7, 8, 9, 10, 11, 12, 13, 14, 15, 16, 17, 18, 19, 20, 30, 40, 50 or more wild-type residues (i.e., from the corresponding full-length DRS polypeptide) that are proximal to the C-terminal end and/or the N-terminal end of the DRS reference polypeptide.

In some embodiments, the DRS polypeptides comprise a polypeptide fragment of the full length Aspartyl-tRNA synthetase of about 50 to 250 amino acids, which comprises, or consists essentially of the amino acids 1-224, 1-184, 1-174, 1-171, 11-146, 13-146, 1-154 or 23-154 of the DRS polypeptide sequence set forth in SEQ ID NO:1, comprising at least one mutation at either Cys76 or Cys130 (using the numbering of SEQ ID NO:1), and variants thereof.

In certain embodiments, a DRS polypeptide of the invention comprises the minimal active fragment of a full-length DRS polypeptide capable of modulating TLR activity etc., in vivo or having other desirable non-canonical aspartyl-tRNA synthetase activities. In one aspect, such a minimal active fragment consists essentially of the anticodon binding domain, (i.e., about amino acids 23-154 of SEQ ID NO:1). In some aspects, the minimal active fragment consists essentially of the anticodon binding domain anticodon binding domain, and N-terminal amphiphilic helix (i.e., about amino acids 1-154 of SEQ ID NO:1. In some aspects, of either of these embodiments, the minimal active fragment consists essentially of the anticodon binding domain anticodon binding domain, and N-terminal amphiphilic helix and a variable amount of the flexible 29 amino acid linker (amino acids 154 to 182 of SEQ ID NO:1). In different embodiments, such minimal active fragments may comprise 1, 2, 3, 4, 5, 6, 7, 8, 9, 10, 11, 12, 13, 14, 15, 16, 17, 18, 19, 20, 21, 22, 23, 24, 25, 26, 27, 28, or all 29 amino acids of the flexible linker.

Without wishing to be bound by any one theory, the unique orientation, or conformation, of the anticodon-recognition domain in certain DRS polypeptides may contribute to the enhanced non canonical activities observed in these proteins. In certain embodiments, non-canonical activity may be modulated by the selective deletion, in whole or part of the Amphiphilic helix domain, anticodon-recognition domain, or the aminoacylation domain. Specific examples of splice variants that accomplish such embodiments include for example AspRS1$^{N6}$ and AspRS1$^{C2}$ (partial deletion of the anticodon binding domain), AspRS1$^{N7}$ (partial deletion of both the anticodon binding domain and aminoacylation domain), AspRS1$^{N7}$ (partial deletion of the aminoacylation domain). In some embodiments of the present invention, all such DRS polypeptides comprise at least one mutation at either Cys76 or Cys130 (using the numbering of SEQ ID NO:1).

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, H is, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polypeptides include "reference sequence," "comparison window," "sequence identity," "percentage of sequence identity" and "substantial identity." A "reference sequence" is at least 12 but frequently 15 to 18 and often at least 25 monomer units, inclusive of nucleotides and amino acid residues, in length. Because two polypeptides may each comprise (1) a sequence (i.e., only a portion of the complete polypeptides sequence) that is similar between the two polypeptides, and (2) a sequence that is divergent between the two polypeptides, sequence comparisons between two (or more) polypeptides are typically performed by comparing sequences of the two polypeptides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology," John Wiley & Sons Inc, 1994-1998, Chapter 15.

Calculations of sequence similarity or sequence identity between sequences (the terms are used interchangeably herein) can be performed as follows. To determine the percent identity of two amino acid sequences, or of two nucleic acid sequences, the sequences can be aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (1970, *J. Mol. Biol.* 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller (1989, *Cabios,* 4: 11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, *J. Mol. Biol,* 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997, *Nucleic Acids Res,* 25: 3389-3402). When utilizing BLAST and Gapped BLAST programs, the default parameters of the respective programs (e.g., XBLAST and NBLAST) can be used.

In certain embodiments, variant polypeptides differ from the corresponding DRS reference sequences by at least 1% but less than 20%, 15%, 10% or 5% of the residues. (If this comparison requires alignment, the sequences should be aligned for maximum similarity. "Looped" out sequences from deletions or insertions, or mismatches, are considered differences.) The differences are, suitably, differences or changes at a non-essential residue or a conservative substitution. In certain embodiments, the molecular weight of a variant DRS polypeptide differs from that of the DRS reference polypeptide by about 1%, 2%, 3%, 4%, 5%, 6%, 7%, 8%, 9%, 10%, 11%, 12%, 13%, 14%, 15%, 16%, 17%, 18%, 19%, 20%, or more.

In one embodiment, as noted above, polynucleotides and/or polypeptides can be evaluated using a BLAST alignment tool. A local alignment consists simply of a pair of sequence segments, one from each of the sequences being compared. A modification of Smith-Waterman or Sellers algorithms will find all segment pairs whose scores cannot be improved by extension or trimming, called high-scoring segment pairs (HSPs). The results of the BLAST alignments include statistical measures to indicate the likelihood that the BLAST score can be expected from chance alone.

The raw score, S, is calculated from the number of gaps and substitutions associated with each aligned sequence wherein higher similarity scores indicate a more significant alignment. Substitution scores are given by a look-up table (see PAM, BLOSUM).

Gap scores are typically calculated as the sum of G, the gap opening penalty and L, the gap extension penalty. For a gap of length n, the gap cost would be G+Ln. The choice of gap costs, G and L is empirical, but it is customary to choose a high value for G (10-15), e.g., 11, and a low value for L (1-2) e.g., 1.

The bit score, S', is derived from the raw alignment score S in which the statistical properties of the scoring system used have been taken into account. Bit scores are normalized with respect to the scoring system, therefore they can be used to compare alignment scores from different searches. The terms "bit score" and "similarity score" are used interchangeably. The bit score gives an indication of how good the alignment is; the higher the score, the better the alignment.

The E-Value, or expected value, describes the likelihood that a sequence with a similar score will occur in the database by chance. It is a prediction of the number of different alignments with scores equivalent to or better than S that are expected to occur in a database search by chance. The smaller the E-Value, the more significant the alignment. For example, an alignment having an E value of $e^{-117}$ means that a sequence with a similar score is very unlikely to occur simply by chance. Additionally, the expected score for aligning a random pair of amino acids is required to be negative, otherwise long alignments would tend to have high score independently of whether the segments aligned were related. Additionally, the BLAST algorithm uses an appropriate substitution matrix, nucleotide or amino acid and for gapped alignments uses gap creation and extension penalties. For example, BLAST alignment and comparison of polypeptide sequences are typically done using the BLOSUM62 matrix, a gap existence penalty of 11 and a gap extension penalty of 1.

In one embodiment, sequence similarity scores are reported from BLAST analyses done using the BLOSUM62 matrix, a gap existence penalty of 11 and a gap extension penalty of 1.

In a particular embodiment, sequence identity/similarity scores provided herein refer to the value obtained using GAP Version 10 (GCG, Accelrys, San Diego, Calif.) using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix (Henikoff and Henikoff (1992) Proc Natl Acad Sci USA 89:10915-10919). GAP uses the algorithm of Needleman and Wunsch (1970) J Mol Biol 48:443-453, to find the alignment of two complete sequences that maximizes the number of matches and minimizes the number of gaps.

In one particular embodiment, the DRS polypeptides comprise an amino acid sequence that can be optimally aligned with a DRS reference polypeptide sequence (e.g., amino acids 1-224, 1-184, 1-174, 1-171, 1-154 or 23-154 of the DRS polypeptide sequence set forth in SEQ ID NO:1, optionally comprising at least one mutation at either Cys76 or Cys130 (using the numbering of SEQ ID NO:1); any one of SEQ ID NOs: 1, 3-24, 29, 31, or 74-117) to generate a BLAST bit scores or sequence similarity scores of at least about 50, 60, 70, 80, 90, 100, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or more, including all integers and ranges in between, wherein the BLAST alignment used the BLOSUM62 matrix, a gap existence penalty of 11, and a gap extension penalty of 1.

Also included are biologically active "fragments" of the DRS reference polypeptides, i.e., biologically active fragments of the DRS protein fragments. Representative biologically active fragments generally participate in an interaction, e.g., an intramolecular or an inter-molecular interaction. An inter-molecular interaction can be a specific binding interaction or an enzymatic interaction. An inter-molecular interaction can be between a DRS polypeptide and a cellular binding partner, such as a cellular receptor or other host molecule that participates in the non-canonical activity of the DRS polypeptide.

A biologically active fragment of an DRS reference polypeptide can be a polypeptide fragment which is, for example, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 38, 359, 360, 361, 362, 363, 364, 365, 380, 400, 450, 500 or more contiguous or non-contiguous amino acids, including all integers (e.g., 101, 102, 103) and ranges (e.g., 50-100, 50-150, 50-200) in between, of the amino acid sequences set forth in any one of the DRS reference polypeptides described herein. In certain embodiments, a biologically active fragment comprises a non-canonical activity-related sequence, domain, or motif. In certain embodiments, the C-terminal or N-terminal region of any DRS reference polypeptide may be truncated by about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 130, 140, 150, 160, 170, 180, 190, 200, 250, 300, 350, 400, 450, 500 or more amino acids, or by about 10-50, 20-50, 50-100, 100-150, 150-200, 200-250, 250-300, 300-350, 350-400, 400-450, 450-500 or more amino acids, including all integers and ranges in between (e.g., 101, 102, 103, 104, 105), so long as the truncated DRS polypeptide retains the non-canonical activity of the reference polypeptide. Typically, the biologically-active fragment has no less than about 1%, 10%, 25%, or 50% of an activity of the biologically-active (i.e., non-canonical activity) DRS reference polypeptide from which it is derived. Exemplary methods for measuring such non-canonical activities are described in the Examples.

In some embodiments, DRS proteins, variants, and biologically active fragments thereof, bind to one or more cellular binding partners with an affinity of at least about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 100, or 150 nM. In some embodiments, the binding affinity of a DRS protein fragment for a selected cellular binding partner, particularly a binding partner that participates in a non-canonical activity, can be stronger than that of the corresponding full length DRS polypeptide or a specific alternatively spliced DRS polypeptide variant, by at least about 1.5×, 2×, 2.5×, 3×, 3.5×, 4×, 4.5×, 5×, 6×, 7×, 8×, 9×, 10×, 15×, 20×, 25×, 30×, 40×, 50×, 60×, 70×, 80×, 90×, 100×, 200×, 300×, 400×, 500×, 600×, 700×, 800×, 900×, 1000× or more (including all integers in between).

As noted above, a DRS polypeptide may be altered in various ways including amino acid substitutions, deletions, truncations, and insertions. Methods for such manipulations are generally known in the art. For example, amino acid sequence variants of a DRS reference polypeptide can be prepared by mutations in the DNA. Methods for mutagenesis and nucleotide sequence alterations are well known in the art. See, for example, Kunkel (1985, *Proc. Natl. Acad. Sci. USA.* 82: 488-492), Kunkel et al., (1987, *Methods in Enzymol,* 154: 367-382), U.S. Pat. No. 4,873,192, Watson, J. D. et al., ("Molecular Biology of the Gene", Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Biologically active truncated and/or variant DRS polypeptides may contain conservative amino acid substitutions at various locations along their sequence, as compared to a reference DRS amino acid residue, and such additional substitutions may further enhance the activity or stability of the DRS polypeptides with altered cysteine content. A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices are known in the art (see e.g., PAM120 matrix and PAM250 matrix as disclosed for example by Dayhoff et al., 1978, A model of evolutionary change in proteins). Matrices for determining distance relationships In M. O. Dayhoff, (ed.), Atlas of protein sequence and structure, Vol. 5, pp. 345-358, National Biomedical Research Foundation, Washington D.C.; and by Gonnet et al., (*Science,* 256: 14430-1445, 1992), however, include proline in the same group as glycine, serine, alanine and threonine. Accordingly, for the purposes of the present invention, proline is classified as a "small" amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always non-aromatic. Dependent on their structural properties, amino acid residues may fall in two or more classes. For the naturally-occurring protein amino acids, sub-classification according to this scheme is presented in Table A.

TABLE A

Amino acid sub-classification

| Sub-classes | Amino acids |
| --- | --- |
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional truncated and/or variant DRS polypeptide can readily be determined by assaying its non-canonical activity, as described herein. Conservative substitutions are shown in Table B under the heading of exemplary substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, (c) the bulk of the side chain, or (d) the biological function. After the substitutions are introduced, the variants are screened for biological activity.

TABLE B

Exemplary Amino Acid Substitutions

| Original Residue | Exemplary Substitutions | Preferred Substitutions |
| --- | --- | --- |
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., *Biochemistry*, third edition, Wm. C. Brown Publishers (1993).

Thus, a predicted non-essential amino acid residue in a truncated and/or variant DRS polypeptide is typically replaced with another amino acid residue from the same side chain family. Alternatively, mutations can be introduced randomly along all or part of a DRS coding sequence, such as by saturation mutagenesis, and the resultant mutants can be screened for an activity of the parent polypeptide to identify mutants which retain that activity. Following mutagenesis of the coding sequences, the encoded peptide can be expressed recombinantly and the activity of the peptide can be determined A "non-essential" amino acid residue is a residue that can be altered from the reference sequence of an embodiment polypeptide without abolishing or substantially altering one or more of its non canonical activities. Suitably, the alteration does not substantially abolish one of these activities, for example, the activity is at least 20%, 40%, 60%, 70% or 80% 100%, 500%, 1000% or more of the reference DRS sequence. An "essential" amino acid residue is a residue that, when altered from the reference sequence of a DRS polypeptide, results in abolition of an activity of the parent molecule such that less than 20% of the reference activity is present. For example, such essential amino acid residues include those that are conserved in DRS polypeptides across different species, including those sequences that are conserved in the active binding site(s) or motif(s) of DRS polypeptides from various sources.

For certain types of site-specific PEGylation, described below, DRS polypeptides may have one or more cysteine substitutions, where one or more naturally-occurring (non-cysteine) residues are substituted with cysteine, for example, to facilitate thiol-based attachment of PEG molecules. In some embodiments, cysteine substitutions are near the N-terminus and/or C-terminus of the DRS polypeptide (e.g., SEQ ID NOS:1, 3-24, 29, 31, or 74-117). Particular embodiments include where one or more of residues within 0, 1, 2, 3, 4, 5, 6, 7, 8, 9, 10, 11, 12, 13, 14, 15, 16, 17, 18, 19, 20, 21, 22, 23, 24, or 25 amino acids relative to the N-terminus and/or C-terminus of any one of SEQ ID NOS: 1, 3-24, 29, 31, or 74-117 are substituted with a cysteine residue. In some embodiments, cysteine residues may be added to the DRS polypeptide through the creation of N, or C-terminal fusion proteins. Such fusion proteins may be of any length, but will typically be about 1-5, or about 5-10, about 10 to 20, or about 20 to 30 amino acids in length. In some embodiments, fusion to the C-terminus is preferred.

Specific embodiments of such DRS polypeptides with an N-terminal cysteine substitution, include for example, those with a cysteine substitution within the first 23 amino acids, including the DRS polypeptides of any of SEQ ID NOs:1, 3-24, 29, 31, or 74-117. Specific embodiments of such DRS polypeptides with a C-terminal cysteine substitution include for example, those with a cysteine substitution with the last 20 amino acids, including the DRS polypeptides of any of SEQ ID NOs:1, 3-24, 29, 31, or 74-117.

These and related DRS polypeptides may also have additional substitutions at C76 and/or C130, to remove naturally-occurring cysteine residues, and to facilitate site-specific pegylation at the selectively introduced cysteine residue(s). Specific embodiments include any one of SEQ ID NOS:1, 3-24, 29, 31, or 74-117, or variants thereof, having at mutation at C76 and/or C130. Exemplary mutations at these positions include for example the mutation of cysteine to serine, alanine, leucine, or glycine. Various exemplary proteins with reduced cysteine content are listed in Table D7.

TABLE D7

Exemplary Variants with reduced cysteine content

| Name | Amino Acid Residue Range of SEQ ID NO: 1 | Amino acid sequence | SEQ ID NO: |
|---|---|---|---|
| AspRS1$^{N1}$ (C76S) | 1-154 | MPSASASRKSQEKPREIMDAAEDYAKERYGISSMIQSQEK PDRVLVRVRDLTIQKADEVVWVRARVHTSRAKGKQSFLV LRQQQFNVQALVAVGDHASKQMVKFAANINKESIVDVE GVVRKVNQKIGSCTQQDVELHVQKIYVISLAEPRLPL | 22 |
| AspRS1$^{N1}$ (C130S) | 1-154 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSSTQQDVELHVQKIYVISLAEPRLPL | 23 |
| AspRS1$^{N1}$ (C76S, C130S) | 1-154 | MPSASASRKSQEKPREIMDAAEDYAKERYGISSMIQSQEK PDRVLVRVRDLTIQKADEVVWVRARVHTSRAKGKQSFLV LRQQQFNVQALVAVGDHASKQMVKFAANINKESIVDVE GVVRKVNQKIGSSTQQDVELHVQKIYVISLAEPRLPL | 24 |
| DRS C334S | 1-501 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATVNQDTRLDNRVIDLRTSTSQAVF RLQSGICHLFRETLINKGFVEIQTPKIISAASEGGANVFTVS YFKNNAYLAQSPQLYKQMCICADFEKVFSIGPVFRAEDSN THRHLTEFVGLDIEMAFNYHYHEVMEEIADTMVQIFKGL QERFQTEIQTVNKQFPSEPFKFLEPTLRLEYCEALAMLREA GVEMGDEDDLSTPNEKLLGHLVKEKYDTDFYILDKYPLA VRPFYTMPDPRNPKQSNSYDMFMRGEEILSGAQRIHDPQL LTERALHHGIDLEKIKAYIDSFRFGAPPHAGGGIGLERVTM LFLGLHNVRQTSMFPRDPKRLTP | 109 |
| DRS C349S | 1-501 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATVNQDTRLDNRVIDLRTSTSQAVF RLQSGICHLFRETLINKGFVEIQTPKIISAASEGGANVFTVS YFKNNAYLAQSPQLYKQMCICADFEKVFSIGPVFRAEDSN THRHLTEFVGLDIEMAFNYHYHEVMEEIADTMVQIFKGL QERFQTEIQTVNKQFPCEPFKFLEPTLRLEYSEALAMLREA GVEMGDEDDLSTPNEKLLGHLVKEKYDTDFYILDKYPLA VRPFYTMPDPRNPKQSNSYDMFMRGEEILSGAQRIHDPQL LTERALHHGIDLEKIKAYIDSFRFGAPPHAGGGIGLERVTM LFLGLHNVRQTSMFPRDPKRLTP | 110 |
| DRS C334S/C349S | 1-501 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATVNQDTRLDNRVIDLRTSTSQAVF RLQSGICHLFRETLINKGFVEIQTPKIISAASEGGANVFTVS YFKNNAYLAQSPQLYKQMCICADFEKVFSIGPVFRAEDSN | 111 |

TABLE D7-continued

Exemplary Variants with reduced cysteine content

| Name | Amino Acid Residue Range of SEQ ID NO: 1 | Amino acid sequence | SEQ ID NO: |
|---|---|---|---|
| | | THRHLTEFVGLDIEMAFNYHYEVMEEIADTMVQIFKGL QERFQTEIQTVNKQFPSEPFKFLEPTLRLEYSEALAMLREA GVEMGDEDDLSTPNEKLLGHLVKEKYDTDFYILDKYPLA VRPFYTMPDPRNPKQSNSYDMFMRGEEILSGAQRIHDPQL LTERALHHGIDLEKIKAYIDSFRFGAPPHAGGGIGLERVTM LFLGLHNVRQTSMFPRDPKRLTP | |
| DRS C203A | 1-501 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATVNQDTRLDNRVIDLRTSTSQAVF RLQSGIAHLFRETLINKGFVEIQTPKIISAASEGGANVFTVS YFKNNAYLAQSPQLYKQMCICADFEKVFSIGPVFRAEDSN THRHLTEFVGLDIEMAFNYHYEVMEEIADTMVQIFKGL QERFQTEIQTVNKQFPCEPFKFLEPTLRLEYCEALAMLREA GVEMGDEDDLSTPNEKLLGHLVKEKYDTDFYILDKYPLA VRPFYTMPDPRNPKQSNSYDMFMRGEEILSGAQRIHDPQL LTERALHHGIDLEKIKAYIDSFRFGAPPHAGGGIGLERVTM LFLGLHNVRQTSMFPRDPKRLTP | 112 |
| DRS C203V | 1-501 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATVNQDTRLDNRVIDLRTSTSQAVF RLQSGIVHLFRETLINKGFVEIQTPKIISAASEGGANVFTVS YFKNNAYLAQSPQLYKQMCICADFEKVFSIGPVFRAEDSN THRHLTEFVGLDIEMAFNYHYEVMEEIADTMVQIFKGL QERFQTEIQTVNKQFPCEPFKFLEPTLRLEYCEALAMLREA GVEMGDEDDLSTPNEKLLGHLVKEKYDTDFYILDKYPLA VRPFYTMPDPRNPKQSNSYDMFMRGEEILSGAQRIHDPQL LTERALHHGIDLEKIKAYIDSFRFGAPPHAGGGIGLERVTM LFLGLHNVRQTSMFPRDPKRLTP | 113 |
| DRS C344S/C349S/C203A | 1-501 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATVNQDTRLDNRVIDLRTSTSQAVF RLQSGIAHLFRETLINKGFVEIQTPKIISAASEGGANVFTVS YFKNNAYLAQSPQLYKQMCICADFEKVFSIGPVFRAEDSN THRHLTEFVGLDIEMAFNYHYEVMEEIADTMVQIFKGL QERFQTEIQTVNKQFPSEPFKFLEPTLRLEYSEALAMLREA GVEMGDEDDLSTPNEKLLGHLVKEKYDTDFYILDKYPLA VRPFYTMPDPRNPKQSNSYDMFMRGEEILSGAQRIHDPQL LTERALHHGIDLEKIKAYIDSFRFGAPPHAGGGIGLERVTM LFLGLHNVRQTSMFPRDPKRLTP | 114 |
| DRS C334S/C349S/C203V | 1-501 | MPSASARKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATVNQDTRLDNRVIDLRTSTQAVF RLQSGIVHLFRETLINKGFVEIQTPKIISAASEGGANVFTVS YFKNNAYLAQSPQLYKQMCIAADFEKVFSIGPVFRAEDSN THRHLTEFVGLDIEMAFNYHYEVMEEIADTMVQIFKGL QERFQTEIQTVNKQFPSEPFKFLEPTLRLEYSEALAMLREA GVEMGDEDDLSTPNEKLLGHLVKEKYDTDFYILDKYPLA VRPFYTMPDPRNPKQSNSYDMFMRGEEILSGAQRIHDPQL LTERALHHGIDLEKIKAYIDSFRFGAPPHAGGGIGLERVTM LFLGLHNVRQTSMFPRDPKRLTP | 115 |
| DRS C334S/C349S/C259A/C203A | 1-501 | MPSASARKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATVNQDTRLDNRVIDLRTSTQAVF RLQSGIAHLFRETLINKGFVEIQTPKIISAASEGGANVFTVS YFKNNAYLAQSPQLYKQMCIAADFEKVFSIGPVFRAEDSN THRHLTEFVGLDIEMAFNYHYEVMEEIADTMVQIFKGL QERFQTEIQTVNKQFPSEPFKFLEPTLRLEYSEALAMLREA GVEMGDEDDLSTPNEKLLGHLVKEKYDTDFYILDKYPLA | 116 |

TABLE D7-continued

Exemplary Variants with reduced cysteine content

| Name | Amino Acid Residue Range of SEQ ID NO: 1 | Amino acid sequence | SEQ ID NO: |
|---|---|---|---|
| | | VRPFYTMPDPRNPKQSNSYDMFMRGEEILSGAQRIHDPQL LTERALHHGIDLEKIKAYIDSFRFGAPPHAGGGIGLERVTM LFLGLHNVRQTSMFPRDPKRLTP | |
| DRS C334S/C349S/ C259A/C203V | 1-501 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATVNQDTRLDNRVIDLRTSTSQAVF RLQSGIVHLFRETLINKGFVEIQTPKIISAASEGGANVFTVS YFKNNAYLAQSPQLYKQMCIAADFEKVFSIGPVFRAEDNS THRHLTEFVGLDIEMAFNYHYHEVMEEIADTMVQIFKGL QERFQTEIQTVNKQFPSEPFKFLEPTLRLEYSEALAMLREA GVEMGDEDDLSTPNEKLLGHLVKEKYDTDFYILDKYPLA VRPFYTMPDPRNPKQSNSYDMFMRGEEILSGAQRIHDPQL LTERALHHGIDLEKIKAYIDSFRFGAPPHAGGGIGLERVTM LFLGLHNVRQTSMFPRDPKRLTP | 117 |

For some types of site-specific pegylation, DRS polypeptides may have one or more glutamine substitutions, where one or more naturally-occurring (non-glutamine) residues are substituted with glutamine, for example, to facilitate transglutaminase-catalyzed attachment of PEG molecules to the glutamine's amide group. In some embodiments, glutamine substitutions are introduced near the N-terminus and/or C-terminus of the DRS polypeptide (e.g., SEQ ID NOS: 1, 3-24, 29, 31, or 74-117). Particular embodiments include where one or more of residues within 0, 1, 2, 3, 4, 5, 6, 7, 8, 9, 10, 11, 12, 13, 14, 15, 16, 17, 18, 19, 20, 21, 22, 23, 24 or 25 amino acids relative to the N-terminus and/or C-terminus of any one of SEQ ID NOS: 1, 3-24, 29, 31, or 74-117 are substituted with a glutamine residue. These and related DRS polypeptides can also include substitutions (e.g., conservative substitutions) to remove any naturally-occurring glutamine residues, if desired, and thereby regulate the degree of site-specific pegylation.

For other types of site-specific pegylation, DRS polypeptides may have one or more lysine substitutions, where one or more naturally-occurring (non-lysine) residues are substituted with lysine, for example, to facilitate acylation or alkylation-based attachment of PEG molecules to the lysine's amino group. These methods also typically result in attachment of PEG to the N-terminal residue. In some embodiments, lysine substations are near the N-terminus and/or C-terminus of the DRS polypeptide (e.g., SEQ ID NOS: 1, 3-24, 29, 31, or 74-117). Particular embodiments include where one or more of residues within 0, 1, 2, 3, 4, 5, 6, 7, 8, 9, 10, 11, 12, 13, 14, 15, 16, 17, 18, 19, 20, 21, 22, 23, 24 or 25 amino acids to the N-terminus and/or C-terminus of any one of SEQ ID NOS: 1, 3-24, 29, 31, or 74-117 are substituted with a lysine residue. These and related DRS polypeptides can also include substitutions (e.g., conservative substitutions) to remove any naturally-occurring lysine residues, if desired, and thereby regulate the degree of site-specific pegylation.

Site-specific PEGylation of DRS polypeptides may also be performed by substituting one or more solvent accessible surface amino acids of a DRS polypeptide. For example, suitable solvent accessible amino acids may be determined based on the predicted solvent accessibility using the SPIDDER server (http://sppider.cchmc.org/) using the published crystal structure of an exemplary DRS polypeptide (WO2010/120509). Based on this analysis several amino acids on the surface may potentially be used as mutation sites to introduce functional groups suitable for PEGylation. The following Table D9 lists the surface accessibility score of amino acids based on the crystal structure above. In this table, the higher scores represent better accessibility. Accordingly, higher scores (for example, >40) are preferred for better PEG-coupling efficiency. Accordingly in some embodiments an amino acid position selected from Table D9 may used to introduce a cysteine, lysine, glutamine, or non naturally occurring amino acid.

TABLE D9

Surface Exposed amino acids

| ID | Position | Amino Acid | Score |
|---|---|---|---|
| 1 | 125 | N | 63 |
| 2 | 55 | Q | 60 |
| 3 | 51 | D | 57 |
| 4 | 54 | I | 57 |
| 5 | 126 | Q | 57 |
| 6 | 58 | D | 56 |
| 7 | 96 | D | 55 |
| 8 | 43 | D | 53 |
| 9 | 104 | K | 53 |
| 10 | 108 | N | 53 |
| 11 | 130 | C | 53 |
| 12 | 132 | T | 53 |
| 13 | 151 | P | 53 |
| 14 | 152 | R | 52 |
| 15 | 40 | E | 52 |
| 16 | 97 | H | 52 |
| 17 | 127 | K | 52 |
| 18 | 129 | G | 51 |
| 19 | 50 | R | 50 |
| 20 | 107 | A | 50 |
| 21 | 72 | A | 49 |
| 22 | 39 | Q | 46 |
| 23 | 100 | K | 45 |
| 24 | 95 | G | 45 |

In particular embodiments, a solvent accessible surface amino acid from Table D9 is selected from the group consisting of: alanine, glycine, and serine, and can be substituted with naturally occurring amino acids including, but not limited to, cysteine, glutamine, or lysine, or a non-naturally occurring amino acid that is optimized for site specific PEGylation. In certain embodiments, one or more solvent accessible surface amino acids of the DRS polypeptide are selected from the group consisting of: C130, G129, A107, A72 and G95 are, substituted with cysteine, glutamine, lysine, or a non-naturally occurring amino acid.

In various embodiments, the present invention contemplates site-specific pegylation at any amino acid position in a DRS polypeptide by virtue of substituting a non-naturally occurring amino acid comprising a functional group that will form a covalent bond with the functional group attached to a PEG moiety. Non-natural amino acids can be inserted or substituted at, for example, one or more of residues within 0, 1, 2, 3, 4, 5, 6, 7, 8, 9, 10, 11, 12, 13, 14, 15, 16, 17, 18, 19, 20, 21, 22, 23, 24 or 25 amino acids relative to the N-terminus and/or C-terminus of any one of SEQ ID NOS: 1, 3-24, 29, 31, or 74-117; at the N-terminus and/or C-terminus of any one of SEQ ID NOS: 1, 3-24, 29, 31, or 74-117; or a solvent accessible surface amino acid residue as described in Table D9.

In particular embodiments, non-naturally occurring amino acids include, without limitation, any amino acid, modified amino acid, or amino acid analogue other than selenocysteine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by the following formula:

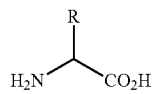

A non-natural amino acid is typically any structure having the foregoing formula wherein the R group is any substituent other than one used in the twenty natural amino acids. See, e.g., any biochemistry text such as Biochemistry by L. Stryer, 3rd ed. 1988, Freeman and Company, New York, for structures of the twenty natural amino acids. Note that the non-natural amino acids disclosed herein may be naturally occurring compounds other than the twenty alpha-amino acids above. Because the non-natural amino acids disclosed herein typically differ from the natural amino acids in side chain only, the non-natural amino acids form amide bonds with other amino acids, e.g., natural or non-natural, in the same manner in which they are formed in naturally occurring proteins. However, the non-natural amino acids have side chain groups that distinguish them from the natural amino acids. For example, R in foregoing formula optionally comprises an alkyl-, aryl-, aryl halide, vinyl halide, alkyl halide, acetyl, ketone, aziridine, nitrile, nitro, halide, acyl-, keto-, azido-, hydroxyl-, hydrazine, cyano-, halo-, hydrazide, alkenyl, alkynyl, ether, thio ether, epoxide, sulfone, boronic acid, boronate ester, borane, phenylboronic acid, thiol, seleno-, sulfonyl-, borate, boronate, phospho, phosphono, phosphine, heterocyclic-, pyridyl, naphthyl, benzophenone, a constrained ring such as a cyclooctyne, thio ester, enone, imine, aldehyde, ester, thioacid, hydroxylamine, amino, carboxylic acid, alpha-keto carboxylic acid, alpha or beta unsaturated acids and amides, glyoxylamide, or organosilane group, or the like or any combination thereof.

Specific examples of unnatural amino acids include, but are not limited to, p-acetyl-L-phenylalanine, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, β-O-GlcNAc-L-serine, a tri-O-acetyl-GalNAc-α-threonine, an α-GalNAc-L-threonine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, those listed below, or elsewhere herein, and the like.

Accordingly, one may select a non-naturally occurring amino acid comprising a functional group that forms a covalent bond with any preferred functional group of a PEG moiety. Non-natural amino acids, once selected, can either be purchased from vendors, or chemically synthesized. Any number of non-natural amino acids may be incorporated into the target molecule and may vary according to the number of desired water soluble polymers, e.g., PEG moieties, that are to be attached. The PEG moieties may be attached to all or only some of the non-natural amino acids. Further, the same or different non-natural amino acids may be incorporated into a DRS polypeptide, depending on the desired outcome. In certain embodiments, about 1, 2, 3, 4, 5, 6, 7, 8, 9, 10 or more non-natural amino acids are incorporated into a DRS polypeptide any or all of which may be conjugated to a PEG comprising a desired functional group.

In certain aspects, the use of non-natural amino acids can be utilized to modify (e.g., increase) a selected non-canonical activity of a DRS polypeptide, or to alter the in vivo or in vitro half-life of the protein. Non-natural amino acids can also be used to facilitate (selective) chemical modifications (e.g., pegylation) of a DRS protein, as described elsewhere herein. For instance, certain non-natural amino acids allow selective attachment of polymers such as PEG to a given protein, and thereby improve their pharmacokinetic properties.

Specific examples of amino acid analogs and mimetics can be found described in, for example, Roberts and Vellaccio, The Peptides: Analysis, Synthesis, Biology, Eds. Gross and Meinhofer, Vol. 5, p. 341, Academic Press, Inc., New York, N.Y. (1983), the entire volume of which is incorporated herein by reference. Other examples include peralkylated amino acids, particularly permethylated amino acids. See, for example, Combinatorial Chemistry, Eds. Wilson and Czarnik, Ch. 11, p. 235, John Wiley & Sons Inc., New York, N.Y. (1997), the entire book of which is incorporated herein by reference. Yet other examples include amino acids whose amide portion (and, therefore, the amide backbone of the resulting peptide) has been replaced, for example, by a sugar ring, steroid, benzodiazepine or carbo cycle. See, for instance, Burger's Medicinal Chemistry and Drug Discovery, Ed. Manfred E. Wolff, Ch. 15, pp. 619-620, John Wiley & Sons Inc., New York, N.Y. (1995), the entire book of which is incorporated herein by reference. Methods for synthesizing peptides, polypeptides, peptidomimetics and proteins are well known in the art (see, for example, U.S. Pat. No. 5,420,109; M. Bodanzsky, Principles of Peptide Synthesis (1st ed. & 2d rev. ed.), Springer-Verlag, New York, N.Y. (1984 & 1993), see Chapter 7; Stewart and Young, Solid Phase Peptide Synthesis, (2d ed.), Pierce Chemical Co., Rockford, Ill. (1984), each of which is incorporated herein by reference). Accordingly, the DRS polypeptides of the present invention may be composed of naturally occurring and non-naturally occurring amino acids as well as amino acid analogs and mimetics.

In one embodiment of any of these methods, compositions and kits, the DRS polypeptide is AspRS1$^{N1}$/DRS(1-154) comprising at least one mutation at either Cys76 or Cys130.

In some embodiments, the DRS polypeptide may comprise at mutation at Cys76 and/or Cys130, wherein the substituted amino acid is independently selected from the group consisting of all 19 alternative naturally occurring amino acids except Cys, or a non-naturally occurring amino acid.

In some embodiments, the DRS polypeptide may comprise at mutation at Cys76 and/or Cys130, wherein the substituted amino acid is independently selected from the group consisting of Ser, Ala, Gly, Met, Leu, Val; Ile and Thr.

In some embodiments, the DRS polypeptide may comprise at mutation at Cys76 and/or Cys130 wherein the substituted amino acid is independently selected from the group consisting of Ser and Ala.

In some embodiments, the DRS polypeptide may comprise at mutation at Cys76 and/or Cys130 wherein the substituted amino acid is independently selected from the group consisting of Asp, Glu, Arg, Lys, Gln, and Asn.

In some embodiments, the DRS polypeptide may comprise at mutation at Cys76 and/or Cys130 wherein the substituted amino acid is independently selected from the group consisting of His, Pro, Tyr, Trp and Phe.

In some embodiments, the DRS polypeptide may comprise at mutation at Cys76 and/or Cys130 wherein the substitution is a independently selected from Ser, Ala, Gly, Met, Leu, Val; Ile and Thr, and a non-naturally occurring amino acid.

In any of these various embodiments, Cys76 may be selectively modified, while Cys130 remains unmodified. Conversely, in some embodiments, Cys130 may be selectively modified, while Cys76 remains unmodified. In some embodiments both Cys76 and Cys130 may be independently modified using any combination of the sub-groupings listed above. In some embodiments, Cys76 may be selectively modified, and then the remaining free cysteine at position 130 used to selectively chemically couple another molecule.

Polynucleotides

Certain embodiments relate to polynucleotides that encode a DRS polypeptide. Among other uses, these embodiments may be utilized to recombinantly produce a desired DRS polypeptide or variant thereof, or to express the DRS polypeptide in a selected cell or subject. It will be appreciated by those of ordinary skill in the art that, as a result of the degeneracy of the genetic code, there are many nucleotide sequences that encode a DRS polypeptide as described herein. Some of these polynucleotides may bear minimal homology to the nucleotide sequence of any native gene. Nonetheless, polynucleotides that vary due to differences in codon usage are specifically contemplated by the present invention, for example polynucleotides that are optimized for human, yeast or bacterial codon selection.

Therefore, multiple polynucleotides can encode the DRS polypeptides of the invention. Moreover, the polynucleotide sequence can be manipulated for various reasons. Examples include but are not limited to the incorporation of preferred codons to enhance the expression of the polynucleotide in various organisms (see generally Nakamura et al., Nuc. Acid. Res. (2000) 28 (1): 292). In addition, silent mutations can be incorporated in order to introduce, or eliminate restriction sites, decrease the density of CpG dinucleotide motifs (see for example, Kameda et al., Biochem. Biophys. Res. Commun (2006) 349(4): 1269-1277) or reduce the ability of single stranded sequences to form stem-loop structures: (see, e.g., Zuker M., Nucl. Acid Res. (2003); 31(13): 3406-3415). In addition, mammalian expression can be further optimized by including a Kozak consensus sequence [i.e., (a/g)cc(a/g)ccATGg] at the start codon. Kozak consensus sequences useful for this purpose are known in the art (Mantyh et al. PNAS 92: 2662-2666 (1995); Mantyh et al. Prot. Exp. & Purif. 6,124 (1995)). Exemplary codon optimized versions of the wild type full length DRS polypeptide and AspRS1$^{N1}$ are provided in Table D8, below, as are other exemplary DRS coding sequences.

TABLE D8

DRS DNA Sequences

| Name | Amino Acid Residue Range of SEQ ID NO: 1 | Nucleic acid sequence | SEQ ID NO: |
|---|---|---|---|
| AspRS1$^{N1}$ | DNA / Synthetic / Codon optimized 1-462 | ATGCCGAGCGCGAGCGCCAGCCGTAAGAGCCAGGAAA AACCACGTGAGATTATGGATGCCGCAGAGGACTATGCG AAAGAACGTTACGGTATTTCCAGCATGATCCAATCTCA GGAGAAACCGGACCGCGTTCTGGTTCGTGTTCGCGATC TGACCATTCAGAAGGCGGACGAGGTGGTTTGGGTGCGT GCGCGCGTGCACACCAGCCGTGCAAAAGGCAAACAGT GCTTTCTGGTCCTGCGTCAGCAGCAATTCAACGTCCAG GCGCTGGTGGCAGTGGGTGACCACGCCAGCAAACAAAT GGTGAAGTTCGCTGCTAACATCAATAAAGAATCCATTG TTGATGTTGAAGGCGTCGTTCGCAAGGTCAATCAAAAG ATCGGCTCGTGTACGCAACAAGATGTCGAGCTGCATGT GCAGAAGATTTACGTCATCAGCCTGGCGGAGCCGCGTT TGCCGCTG | 25 |
| AspRS1$^{N1}$ (C76S) | DNA / Synthetic / Codon optimized 1-462 | ATGCCGAGCGCGAGCGCCAGCCGTAAGAGCCAGGAAA AACCACGTGAGATTATGGATGCCGCAGAGGACTATGCG AAAGAACGTTACGGTATTTCCAGCATGATCCAATCTCA GGAGAAACCGGACCGCGTTCTGGTTCGTGTTCGCGATC TGACCATTCAGAAGGCGGACGAGGTGGTTTGGGTGCGT GCGCGCGTGCACACCAGCCGTGCAAAAGGCAAACAGA GCTTTCTGGTCCTGCGTCAGCAGCAATTCAACGTCCAG GCGCTGGTGGCAGTGGGTGACCACGCCAGCAAACAAAT | 26 |

TABLE D8-continued

DRS DNA Sequences

| Name | Amino Acid Residue Range of SEQ ID NO: 1 | Nucleic acid sequence | SEQ ID NO: |
|---|---|---|---|
| | | GGTGAAGTTCGCTGCTAACATCAATAAAGAATCCATTG<br>TTGATGTTGAAGGCGTCGTTCGCAAGGTCAATCAAAAG<br>ATCGGCTCGTGTACGCAACAAGATGTCGAGCTGCATGT<br>GCAGAAGATTTACGTCATCAGCCTGGCGGAGCCGCGTT<br>TGCCGCTGGGTAAGCCGATCCCTAACCCGCTGTTGGGT<br>CTGGACAGCACGCATCACCATCACCACCACTAA | |
| Full length AspRS sequence | DNA/<br>Synthetic /<br>Codon<br>optimized 1-<br>1503 | ATGCCATCAGCCTCAGCATCTCGTAAAAGCCAGGAAAA<br>ACCGCGCGAAATCATGGACGCTGCCGAAGATTATGCCA<br>AAGAGCGCTATGGTATCAGTTCGATGATCAGTCACAA<br>GAGAAACCAGATCGTGTGCTGGTCCGTGTTCGTGACCT<br>GACCATCCAGAAAGCGGATGAAGTTGTTTGGGTCCGTG<br>CTCGTGTTCATACAAGCCGTGCCAAAGGCAAACAGTGC<br>TTCCTGGTTCTGCGTCAACAGCAGTTTAACGTTCAGGCC<br>CTGGTAGCCGTTGGTGATCACGCCTCAAAACAAATGGT<br>GAAATTCGCCGCCAACATCAACAAAGAGAGCATCGTCG<br>ACGTTGAAGGTGTCGTCCGTAAAGTGAATCAGAAAATC<br>GGCTCCTGTACACAGCAAGATGTGGAGCTGCATGTCCA<br>AAAAAATCTATGTCATCTCACTGGCCGAACCTCGTCTGCC<br>TCTGCAACTGGATGATGCTGTACGCCCTGAAGCTGAAG<br>GCGAAGAAGAAGGTCGTGCTACGGTTAATCAGGATACT<br>CGCCTGGACAACCGTGTCATTGATCTGCGCACCTCAAC<br>CTCTCAAGCGGTATTCCGCCTGCAATCCGGCATCTGTCA<br>CCTGTTCCGTGAAACGCTGATCAACAAAGGGTTTGTGG<br>AGATTCAGACCCCGAAAATCATTAGTGCCGCCAGCGAA<br>GGTGGAGCAAATGTGTTTACCGTGTCCTATTTCAAAAA<br>CAATGCCTATCTGGCACAGTCTCCTCAGCTGTATAAAC<br>AAATGTGTATCTGTGCTGACTTCGAGAAAGTGTTCTCA<br>ATCGGGCCGGTATTCCGTGCAGAGGATAGCAACACACA<br>CCGCCATCTGACCGAATTTGTAGGCCTGGACATCGAAA<br>TGGCCTTCAACTATCATTATCACGAGGTGATGGAAGAA<br>ATCGCTGATACAATGGTACAGATCTTTAAAGGGCTGCA<br>AGAACGCTTTCAAACAGAGATTCAAACCGTCAATAAAC<br>AGTTCCCGTGTGAACCGTTCAAATTTCTGAACCGACC<br>CTGCGTCTGGAATATTGTGAAGCACTGGCTATGCTGCG<br>CGAAGCTGGTGTCGAAATGGGTGATGAGGATGACCTGT<br>CTACCCCTAACGAAAAACTGCTGGGCCACCTGGTAAAA<br>GAAAAATATGACACAGACTTCTATATCCTGGACAAATA<br>TCCGCTGGCAGTTCGTCCGTTTTATACGATGCCTGATCC<br>TCGTAATCCGAAACAAAGCAACTCCTATGACATGTTCA<br>TGCGTGGTGAAGAGATCCTGTCTGGTGCTCAACGTATC<br>CATGATCCACAGCTGCTGACAGAACGTGCACTGCATCA<br>CGGTATTGATCTGGAGAAAATCAAAGCCTATATCGACT<br>CCTTTCGCTTTGGTGCCCCTCCACATGCCGGTGGTGGAA<br>TTGGGCTGGAGCGTGTAACAATGCTGTTCCTGGGACTG<br>CACAACGTCCGTCAAACCTCAATGTTTCCACGTGACCCT<br>AAACGTCTGACACCT | 27 |
| DRS-C334S | 1-1503/<br>Reduced<br>cysteine content | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGATGCTGTTCGGCCTGAGGCAG<br>AAGGAGAAGAGGAAGGAAGAGCTACTGTTAACCAGGA<br>TACAAGATTAGACAACAGAGTCATTGATCTTAGGACAT<br>CAACTAGTCAGGCAGTCTTCCGTCTCCAGTCTGGCATCT<br>GCCATCTCTTCCGAGAAACTTTAATTAACAAAGGTTTTG<br>TGGAAATCCAAACTCCTAAAATTATTTCAGCTGCCAGT<br>GAAGGAGGAGCCAATGTTTTTACTGTGTCATATTTTAA<br>AAATAATGCATACCTGGCTCAGTCCCCACAGCTATATA<br>AGCAAATGTGCATTTGTGCTGATTTTGAGAAGGTTTTCT<br>CTATTGGACCAGTATTCAGAGCGGAAGACTCTAATACC<br>CATAGACATCTAACTGAGTTTGTTGGTTTGGACATTGAA<br>ATGGCTTTTAATTACCATTACCACGAAGTTATGGAAGA<br>AATTGCTGACACCATGGTACAAATATTCAAAGGACTTC | 118 |

TABLE D8-continued

DRS DNA Sequences

| Name | Amino Acid Residue Range of SEQ ID NO: 1 | Nucleic acid sequence | SEQ ID NO: |
|---|---|---|---|
| | | AAGAAAGGTTTCAGACTGAAATTCAAACAGTGAATAAA CAGTTCCCATCTGAGCCATTCAAATTTTTGGAGCCAACT CTAAGACTAGAATATTGTGAAGCATTGGCTATGCTTAG GGAAGCTGGAGTCGAAATGGGAGATGAAGACGATCTG AGCACACCAAATGAAAAGCTGTTGGGTCATTTGGTAAA GGAAAAGTATGATACAGATTTTTATATTCTTGATAAAT ATCCATTGGCTGTAAGACCTTTCTATACCATGCCTGACC CAAGAAATCCCAAACAGTCCAACTCTTACGATATGTTC ATGAGAGGAGAAGAAATATTGTCAGGAGCTCAAAGAA TACATGATCCTCAACTGCTAACAGAGAGAGCTTTACAT CATGGAATTGATTTGGAGAAAATTAAGGCTTACATTGA TTCCTTCCGCTTTGGAGCCCCTCCTCATGCTGGTGGAGG CATTGGATTGGAACGAGTTACTATGCTGTTTCTGGGATT GCATAATGTTCGTCAGACCTCCATGTTCCCTCGTGATCC CAAACGACTCACTCCT | |
| DRS-C349S | 1-1503/ Reduced cysteine content | ATGCCCAGCGCCAGCGCCAGCCGCAAGAGTCAGGAGA AGCCGCGGGAGATCATGGACGCGGCGGAAGATTATGCT AAAGAGAGATATGGAATATCTTCAATGATACAATCACA AGAAAAACCAGATCGAGTTTTGGTTCGGGTTAGAGACT TGACAATACAAAAAGCTGATGAAGTTGTTTGGGTACGT GCAAGAGTTCATACAAGCAGAGCTAAAGGGAAACAGT GCTTCTTAGTCCTACGTCAGCAGCAGTTTAATGTCCAGG CTCTTGTGGCGGTGGGAGACCATGCAAGCAAGCAGATG GTTAAATTTGCTGCCAACATCAACAAAGAGAGCATTGT GGATGTAGAAGGTGTTGTGAGAAAAGTGAATCAGAAA ATTGGAAGCTGTACACAGCAAGACGTTGAGTTACATGT TCAGAAGATTTATGTGATCAGTTTGGCTGAACCCCGTCT GCCCCTGCAGCTGGATGATGCTGTTCGGCCTGAGGCAG AAGGAGAAGAGGAAGGAAGAGCTACTGTTAACCAGGA TACAAGATTAGACAACAGAGTCATTGATCTTAGGACAT CAACTAGTCAGGCAGTCTTCCGTCTCCAGTCTGGCATCT GCCATCTCTTCCGAGAAACTTTAATTAACAAAGGTTTTG TGGAAATCCAAACTCCTAAAATTATTTCAGCTGCCAGT GAAGGAGGAGCCAATGTTTTTACTGTGTCATATTTTAA AAATAATGCATACCTGGCTCAGTCCCCACAGCTATATA AGCAAATGTGCATTTGTGCTGATTTTGAGAAGGTTTTCT CTATTGGACCAGTATTCAGAGCGGAAGACTCTAATACC CATAGACATCTAACTGAGTTTGTTGGTTTGGACATTGAA ATGGCTTTTAATTACCATTACCACGAAGTTATGGAAGA AATTGCTGACACCATGGTACAAATATTCAAAGGACTTC AAGAAAGGTTTCAGACTGAAATTCAAACAGTGAATAAA CAGTTCCCATGTGAGCCATTCAAATTTTTGGAGCCAACT CTAAGACTAGAATATTCTGAAGCATTGGCTATGCTTAG GGAAGCTGGAGTCGAAATGGGAGATGAAGACGATCTG AGCACACCAAATGAAAAGCTGTTGGGTCATTTGGTAAA GGAAAAGTATGATACAGATTTTTATATTCTTGATAAAT ATCCATTGGCTGTAAGACCTTTCTATACCATGCCTGACC CAAGAAATCCCAAACAGTCCAACTCTTACGATATGTTC ATGAGAGGAGAAGAAATATTGTCAGGAGCTCAAAGAA TACATGATCCTCAACTGCTAACAGAGAGAGCTTTACAT CATGGAATTGATTTGGAGAAAATTAAGGCTTACATTGA TTCCTTCCGCTTTGGAGCCCCTCCTCATGCTGGTGGAGG CATTGGATTGGAACGAGTTACTATGCTGTTTCTGGGATT GCATAATGTTCGTCAGACCTCCATGTTCCCTCGTGATCC CAAACGACTCACTCCT | 119 |
| DRS C334S/C349S | 1-1503/ Reduced cysteine content | ATGCCCAGCGCCAGCGCCAGCCGCAAGAGTCAGGAGA AGCCGCGGGAGATCATGGACGCGGCGGAAGATTATGCT AAAGAGAGATATGGAATATCTTCAATGATACAATCACA AGAAAAACCAGATCGAGTTTTGGTTCGGGTTAGAGACT TGACAATACAAAAAGCTGATGAAGTTGTTTGGGTACGT GCAAGAGTTCATACAAGCAGAGCTAAAGGGAAACAGT GCTTCTTAGTCCTACGTCAGCAGCAGTTTAATGTCCAGG CTCTTGTGGCGGTGGGAGACCATGCAAGCAAGCAGATG GTTAAATTTGCTGCCAACATCAACAAAGAGAGCATTGT GGATGTAGAAGGTGTTGTGAGAAAAGTGAATCAGAAA ATTGGAAGCTGTACACAGCAAGACGTTGAGTTACATGT TCAGAAGATTTATGTGATCAGTTTGGCTGAACCCCGTCT GCCCCTGCAGCTGGATGATGCTGTTCGGCCTGAGGCAG AAGGAGAAGAGGAAGGAAGAGCTACTGTTAACCAGGA TACAAGATTAGACAACAGAGTCATTGATCTTAGGACAT CAACTAGTCAGGCAGTCTTCCGTCTCCAGTCTGGCATCT | 120 |

TABLE D8-continued

DRS DNA Sequences

| Name | Amino Acid Residue Range of SEQ ID NO: 1 | Nucleic acid sequence | SEQ ID NO: |
|---|---|---|---|
| | | GCCATCTCTTCCGAGAAACTTTAATTAACAAAGGTTTTG<br>TGGAAATCCAAACTCCTAAAATTATTTCAGCTGCCAGT<br>GAAGGAGGAGCCAATGTTTTTACTGTGTCATATTTTAA<br>AAATAATGCATACCTGGCTCAGTCCCCACAGCTATATA<br>AGCAAATGTGCATTTGTGCTGATTTTGAGAAGGTTTTCT<br>CTATTGGACCAGTATTCAGAGCGGAAGACTCTAATACC<br>CATAGACATCTAACTGAGTTTGTTGGTTTGGACATTGAA<br>ATGGCTTTTAATTACCATTACCACGAAGTTATGGAAGA<br>AATTGCTGACACCATGGTACAAATATTCAAAGGACTTC<br>AAGAAAGGTTTCAGACTGAAATTCAAACAGTGAATAAA<br>CAGTTCCCATCTGAGCCATTCAAATTTTTGGAGCCAACT<br>CTAAGACTAGAATATTCTGAAGCATTGGCTATGCTTAG<br>GGAAGCTGGAGTCGAAATGGGAGATGAAGACGATCTG<br>AGCACACCAAATGAAAAGCTGTTGGGTCATTTGGTAAA<br>GGAAAAGTATGATACAGATTTTTATATTCTTGATAAAT<br>ATCCATTGGCTGTAAGACCTTTCTATACCATGCCTGACC<br>CAAGAAATCCCAAACAGTCCAACTCTTACGATATGTTC<br>ATGAGAGGAGAAGAAATATTGTCAGGAGCTCAAAGAA<br>TACATGATCCTCAACTGCTAACAGAGAGAGCTTTACAT<br>CATGGAATTGATTTGGAGAAAATTAAGGCTTACATTGA<br>TTCCTTCCGCTTTGGAGCCCCTCCTCATGCTGGTGGAGG<br>CATTGGATTGGAACGAGTTACTATGCTGTTTCTGGGATT<br>GCATAATGTTCGTCAGACCTCCATGTTCCCTCGTGATCC<br>CAAACGACTCACTCCT | |
| DRS C203A | 1-501 /<br>Reduced<br>cysteine content | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGATGCTGTTCGGCCTGAGGCAG<br>AAGGAGAAGAGGAAGGAAGAGCTACTGTTAACCAGGA<br>TACAAGATTAGACAACAGAGTCATTGATCTTAGGACAT<br>CAACTAGTCAGGCAGTCTTCCGTCTCCAGTCTGGCATCG<br>CCCATCTCTTCCGAGAAACTTTAATTAACAAAGGTTTTG<br>TGGAAATCCAAACTCCTAAAATTATTTCAGCTGCCAGT<br>GAAGGAGGAGCCAATGTTTTTACTGTGTCATATTTTAA<br>AAATAATGCATACCTGCCTCAGTCCCCACAGCTATATA<br>AGCAAATGTGCATTTGTGCTGATTTTGAGAAGGTTTTCT<br>CTATTGGACCAGTATTCAGAGCGGAAGACTCTAATACC<br>CATAGACATCTAACTGAGTTTGTTGGTTTGGACATTGAA<br>ATGGCTTTTAATTACCATTACCACGAAGTTATGGAAGA<br>AATTGCTGACACCATGGTACAAATATTCAAAGGACTTC<br>AAGAAAGGTTTCAGACTGAAATTCAAACAGTGAATAAA<br>CAGTTCCCATGTGAGCCATTCAAATTTTTGGAGCCAACT<br>CTAAGACTAGAATATTGTGAAGCATTGGCTATGCTTAG<br>GGAAGCTGGAGTCGAAATGGGAGATGAAGACGATCTG<br>AGCACACCAAATGAAAAGCTGTTGGGTCATTTGGTAAA<br>GGAAAAGTATGATACAGATTTTTATATTCTTGATAAAT<br>ATCCATTGGCTGTAAGACCTTTCTATACCATGCCTGACC<br>CAAGAAATCCCAAACAGTCCAACTCTTACGATATGTTC<br>ATGAGAGGAGAAGAAATATTGTCAGGAGCTCAAAGAA<br>TACATGATCCTCAACTGCTAACAGAGAGAGCTTTACAT<br>CATGGAATTGATTTGGAGAAAATTAAGGCTTACATTGA<br>TTCCTTCCGCTTTGGAGCCCCTCCTCATGCTGGTGGAGG<br>CATTGGATTGGAACGAGTTACTATGCTGTTTCTGGGATT<br>GCATAATGTTCGTCAGACCTCCATGTTCCCTCGTGATCC<br>CAAACGACTCACTCCT | 121 |
| DRS C203V | 1-1503/<br>Reduced<br>cysteine content | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG | 122 |

TABLE D8-continued

DRS DNA Sequences

| Name | Amino Acid Residue Range of SEQ ID NO: 1 | Nucleic acid sequence | SEQ ID NO: |
|---|---|---|---|
| | | CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGATGCTGTTCGGCCTGAGGCAG<br>AAGGAGAAGAGGAAGGAAGAGCTACTGTTAACCAGGA<br>TACAAGATTAGACAACAGAGTCATTGATCTTAGGACAT<br>CAACTAGTCAGGCAGTCTTCCGTCTCCAGTCTGGCATCG<br>TCCATCTCTTCCGAGAAACTTTAATTAACAAAGGTTTTG<br>TGGAAATCCAAACTCCTAAAATTATTTCAGCTGCCAGT<br>GAAGGAGGAGCCAATGTTTTTACTGTGTCATATTTTAA<br>AAATAATGCATACCTGGCTCAGTCCCCACAGCTATATA<br>AGCAAATGTGCATTTGTGCTGATTTTGAGAAGGTTTTCT<br>CTATTGGACCAGTATTCAGAGCGGAAGACTCTAATACC<br>CATAGACATCTAACTGAGTTTGTTGGTTTGGACATTGAA<br>ATGGCTTTTAATTACCATTACCACGAAGTTATGGAAGA<br>AATTGCTGACACCATGGTACAAATATTCAAAGGACTTC<br>AAGAAAGGTTTCAGACTGAAATTCAAACAGTGAATAAA<br>CAGTTCCCATGTGAGCCATTCAAATTTTTGGAGCCAACT<br>CTAAGACTAGAATATTGTGAAGCATTGGCTATGCTTAG<br>GGAAGCTGGAGTCGAAATGGGAGATGAAGACGATCTG<br>AGCACACCAAATGAAAAGCTGTTGGGTCATTTGGTAAA<br>GGAAAAGTATGATACAGATTTTTATATTCTTGATAAAT<br>ATCCATTGGCTGTAAGACCTTTCTATACCATGCCTGACC<br>CAAGAAATCCCAAACAGTCCAACTCTTACGATATGTTC<br>ATGAGAGGAGAAGAAATATTGTCAGGAGCTCAAAGAA<br>TACATGATCCTCAACTGCTAACAGAGAGAGCTTTACAT<br>CATGGAATTGATTTGGAGAAAATTAAGGCTTACATTGA<br>TTCCTTCCGCTTTGGAGCCCCTCCTCATGCTGGTGGAGG<br>CATTGGATTGGAACGAGTTACTATGCTGTTTCTGGGATT<br>GCATAATGTTCGTCAGACCTCCATGTTCCCTCGTGATCC<br>CAAACGACTCACTCCT | |
| DRS<br>C334S/C349S/<br>C203A | 1-1503 /<br>Reduced<br>cysteine content | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGATGCTGTTCGGCCTGAGGCAG<br>AAGGAGAAGAGGAAGGAAGAGCTACTGTTAACCAGGA<br>TACAAGATTAGACAACAGAGTCATTGATCTTAGGACAT<br>CAACTAGTCAGGCAGTCTTCCGTCTCCAGTCTGGCATCG<br>CCCATCTCTTCCGAGAAACTTTAATTAACAAAGGTTTTG<br>TGGAAATCCAAACTCCTAAAATTATTTCAGCTGCCAGT<br>GAAGGAGGAGCCAATGTTTTTACTGTGTCATATTTTAA<br>AAATAATGCATACCTGGCTCAGTCCCCACAGCTATATA<br>AGCAAATGTGCATTTGTGCTGATTTTGAGAAGGTTTTCT<br>CTATTGGACCAGTATTCAGAGCGGAAGACTCTAATACC<br>CATAGACATCTAACTGAGTTTGTTGGTTTGGACATTGAA<br>ATGGCTTTTAATTACCATTACCACGAAGTTATGGAAGA<br>AATTGCTGACACCATGGTACAAATATTCAAAGGACTTC<br>AAGAAAGGTTTCAGACTGAAATTCAAACAGTGAATAAA<br>CAGTTCCCATCTGAGCCATTCAAATTTTTGGAGCCAACT<br>CTAAGACTAGAATATTCTGAAGCATTGGCTATGCTTAG<br>GGAAGCTGGAGTCGAAATGGGAGATGAAGACGATCTG<br>AGCACACCAAATGAAAAGCTGTTGGGTCATTTGGTAAA<br>GGAAAAGTATGATACAGATTTTTATATTCTTGATAAAT<br>ATCCATTGGCTGTAAGACCTTTCTATACCATGCCTGACC<br>CAAGAAATCCCAAACAGTCCAACTCTTACGATATGTTC<br>ATGAGAGGAGAAGAAATATTGTCAGGAGCTCAAAGAA<br>TACATGATCCTCAACTGCTAACAGAGAGAGCTTTACAT<br>CATGGAATTGATTTGGAGAAAATTAAGGCTTACATTGA<br>TTCCTTCCGCTTTGGAGCCCCTCCTCATGCTGGTGGAGG<br>CATTGGATTGGAACGAGTTACTATGCTGTTTCTGGGATT | 123 |

TABLE D8-continued

DRS DNA Sequences

| Name | Amino Acid Residue Range of SEQ ID NO: 1 | Nucleic acid sequence | SEQ ID NO: |
|---|---|---|---|
| | | GCATAATGTTCGTCAGACCTCCATGTTCCCTCGTGATCC CAAACGACTCACTCCT | |
| DRS C334S/C349S/ C203V | 1-501 / Reduced cysteine content | ATGCCCAGCGCCAGCGCCAGCCGCAAGAGTCAGGAGA AGCCGCGGGAGATCATGGACGCGGCGGAAGATTATGCT AAAGAGAGATATGGAATATCTTCAATGATACAATCACA AGAAAAACCAGATCGAGTTTTGGTTCGGGTTAGAGACT TGACAATACAAAAAGCTGATGAAGTTGTTTGGGTACGT GCAAGAGTTCATACAAGCAGAGCTAAAGGGAAACAGT GCTTCTTAGTCCTACGTCAGCAGCAGTTTAATGTCCAGG CTCTTGTGGCGGTGGGAGACCATGCAAGCAAGCAGATG GTTAAATTTGCTGCCAACATCAACAAAGAGAGCATTGT GGATGTAGAAGGTGTTGTGAGAAAAGTGAATCAGAAA ATTGGAAGCTGTACACAGCAAGACGTTGAGTTACATGT TCAGAAGATTTATGTGATCAGTTTGGCTGAACCCCGTCT GCCCCTGCAGCTGGATGATGCTGTTCGGCCTGAGGCAG AAGGAGAAGAGGAAGGAAGAGCTACTGTTAACCAGGA TACAAGATTAGACAACAGAGTCATTGATCTTAGGACAT CAACTAGTCAGGCAGTCTTCCGTCTCCAGTCTGGCATCG TCCATCTCTTCCGAGAAACTTTAATTAACAAAGGTTTTG TGGAAATCCAAACTCCTAAAATTATTTCAGCTGCCAGT GAAGGAGGAGCCAATGTTTTTACTGTGTCATATTTTAA AAATAATGCATACCTGGCTCAGTCCCCACAGCTATATA AGCAAATGTGCATTTGTGCTGATTTTGAGAAGGTTTTCT CTATTGGACCAGTATTCAGAGCGGAAGACTCTAATACC CATAGACATCTAACTGAGTTTGTTGGTTTGGACATTGAA ATGGCTTTTAATTACCATTACCACGAAGTTATGGAAGA AATTGCTGACACCATGGTACAAATATTCAAAGGACTTC AAGAAAGGTTTCAGACTGAAATTCAAACAGTGAATAAA CAGTTCCCATCTGAGCCATTCAAATTTTTGGAGCCAACT CTAAGACTAGAATATTCTGAAGCATTGGCTATGCTTAG GGAAGCTGGAGTCGAAATGGGAGATGAAGACGATCTG AGCACACCAAATGAAAAGCTGTTGGGTCATTTGGTAAA GGAAAAGTATGATACAGATTTTTATATTCTTGATAAAT ATCCATTGGCTGTAAGACCTTTCTATACCATGCCTGACC CAAGAAATCCCAAACAGTCCAACTCTTACGATATGTTC ATGAGAGGAGAAGAAATATTGTCAGGAGCTCAAAGAA TACATGATCCTCAACTGCTAACAGAGAGAGCTTTACAT CATGGAATTGATTTGGAGAAAATTAAGGCTTACATTGA TTCCTTCCGCTTTGGAGCCCCTCCTCATGCTGGTGGAGG CATTGGATTGGAACGAGTTACTATGCTGTTTCTGGGATT GCATAATGTTCGTCAGACCTCCATGTTCCCTCGTGATCC CAAACGACTCACTCCT | 124 |
| DRS C334S/C349S/ C259A/C203A | 1-1503 / Reduced cysteine content | ATGCCCAGCGCCAGCGCCAGCCGCAAGAGTCAGGAGA AGCCGCGGGAGATCATGGACGCGGCGGAAGATTATGCT AAAGAGAGATATGGAATATCTTCAATGATACAATCACA AGAAAAACCAGATCGAGTTTTGGTTCGGGTTAGAGACT TGACAATACAAAAAGCTGATGAAGTTGTTTGGGTACGT GCAAGAGTTCATACAAGCAGAGCTAAAGGGAAACAGT GCTTCTTAGTCCTACGTCAGCAGCAGTTTAATGTCCAGG CTCTTGTGGCGGTGGGAGACCATGCAAGCAAGCAGATG GTTAAATTTGCTGCCAACATCAACAAAGAGAGCATTGT GGATGTAGAAGGTGTTGTGAGAAAAGTGAATCAGAAA ATTGGAAGCTGTACACAGCAAGACGTTGAGTTACATGT TCAGAAGATTTATGTGATCAGTTTGGCTGAACCCCGTCT GCCCCTGCAGCTGGATGATGCTGTTCGGCCTGAGGCAG AAGGAGAAGAGGAAGGAAGAGCTACTGTTAACCAGGA TACAAGATTAGACAACAGAGTCATTGATCTTAGGACAT CAACTAGTCAGGCAGTCTTCCGTCTCCAGTCTGGCATCG CCCATCTCTTCCGAGAAACTTTAATTAACAAAGGTTTTG TGGAAATCCAAACTCCTAAAATTATTTCAGCTGCCAGT GAAGGAGGAGCCAATGTTTTTACTGTGTCATATTTTAA AAATAATGCATACCTGGCTCAGTCCCCACAGCTATATA AGCAAATGTGCATTGCGGCTGATTTTGAGAAGGTTTTCT CTATTGGACCAGTATTCAGAGCGGAAGACTCTAATACC CATAGACATCTAACTGAGTTTGTTGGTTTGGACATTGAA ATGGCTTTTAATTACCATTACCACGAAGTTATGGAAGA AATTGCTGACACCATGGTACAAATATTCAAAGGACTTC AAGAAAGGTTTCAGACTGAAATTCAAACAGTGAATAAA CAGTTCCCATCTGAGCCATTCAAATTTTTGGAGCCAACT CTAAGACTAGAATATTCTGAAGCATTGGCTATGCTTAG GGAAGCTGGAGTCGAAATGGGAGATGAAGACGATCTG | 125 |

TABLE D8-continued

DRS DNA Sequences

| Name | Amino Acid Residue Range of SEQ ID NO: 1 | Nucleic acid sequence | SEQ ID NO: |
|---|---|---|---|
| | | AGCACACCAAATGAAAAGCTGTTGGGTCATTTGGTAAA GGAAAAGTATGATACAGATTTTTATATTCTTGATAAAT ATCCATTGGCTGTAAGACCTTTCTATACCATGCCTGACC CAAGAAATCCCAAACAGTCCAACTCTTACGATATGTTC ATGAGAGGAGAAGAAATATTGTCAGGAGCTCAAAGAA TACATGATCCTCAACTGCTAACAGAGAGAGCTTTACAT CATGGAATTGATTTGGAGAAAATTAAGGCTTACATTGA TTCCTTCCGCTTTGGAGCCCCTCCTCATGCTGGTGGAGG CATTGGATTGGAACGAGTTACTATGCTGTTTCTGGGATT GCATAATGTTCGTCAGACCTCCATGTTCCCTCGTGATCC CAAACGACTCACTCCT | |
| DRS C334S/C349S/ C259A/C203V | 1-1503 / Reduced cysteine content | ATGCCCAGCGCCAGCGCCAGCCGCAAGAGTCAGGAGA AGCCGCGGGAGATCATGGACGCGGCGGAAGATTATGCT AAAGAGAGATATGGAATATCTTCAATGATACAATCACA AGAAAAACCAGATCGAGTTTTGGTTCGGGTTAGAGACT TGACAATACAAAAAGCTGATGAAGTTGTTTGGGTACGT GCAAGAGTTCATACAAGCAGAGCTAAAGGGAAACAGT GCTTCTTAGTCCTACGTCAGCAGCAGTTTAATGTCCAGG CTCTTGTGGCGGTGGGAGACCATGCAAGCAAGCAGATG GTTAAATTTGCTGCCAACATCAACAAAGAGAGCATTGT GGATGTAGAAGGTGTTGTGAGAAAAGTGAATCAGAAA ATTGGAAGCTGTACACAGCAAGACGTTGAGTTACATGT TCAGAAGATTTATGTGATCAGTTTGGCTGAACCCCGTCT GCCCCTGCAGCTGGATGATGCTGTTCGGCCTGAGGCAG AAGGAGAAGAGGAAGGAAGAGCTACTGTTAACCAGGA TACAAGATTAGACAACAGAGTCATTGATCTTAGGACAT CAACTAGTCAGGCAGTCTTCCGTCTCCAGTCTGGCATCG TCCATCTCTTCCGAGAAACTTTAATTAACAAAGGTTTTG TGGAAATCCAAACTCCTAAAATTATTTCAGCTGCCAGT GAAGGAGGAGCCAATGTTTTTACTGTGTCATATTTTAA AAATAATGCATACCTGGCTCAGTCCCCACAGCTATATA AGCAAATGTGCATTGCGGCTGATTTTGAGAAGGTTTTCT CTATTGGACCAGTATTCAGAGCGGAAGACTCTAATACC CATAGACATCTAACTGAGTTTGTTGGTTTGGACATTGAA ATGGCTTTAATTACCATTACCACGAAGTTATGGAAGA AATTGCTGACACCATGGTACAAATATTCAAAGGACTTC AAGAAAGGTTTCAGACTGAAATTCAAACAGTGAATAAA CAGTTCCCATCTGAGCCATTCAAATTTTTGGAGCCAACT CTAAGACTAGAATATTCTGAAGCATTGGCTATGCTTAG GGAAGCTGGAGTCGAAATGGGAGATGAAGACGATCTG AGCACACCAAATGAAAAGCTGTTGGGTCATTTGGTAAA GGAAAAGTATGATACAGATTTTTATATTCTTGATAAAT ATCCATTGGCTGTAAGACCTTTCTATACCATGCCTGACC CAAGAAATCCCAAACAGTCCAACTCTTACGATATGTTC ATGAGAGGAGAAGAAATATTGTCAGGAGCTCAAAGAA TACATGATCCTCAACTGCTAACAGAGAGAGCTTTACAT CATGGAATTGATTTGGAGAAAATTAAGGCTTACATTGA TTCCTTCCGCTTTGGAGCCCCTCCTCATGCTGGTGGAGG CATTGGATTGGAACGAGTTACTATGCTGTTTCTGGGATT GCATAATGTTCGTCAGACCTCCATGTTCCCTCGTGATCC CAAACGACTCACTCCT | 126 |
| DRS 1-182 | | ATGCCCAGCGCCAGCGCCAGCCGCAAGAGTCAGGAGA AGCCGCGGGAGATCATGGACGCGGCGGAAGATTATGCT AAAGAGAGATATGGAATATCTTCAATGATACAATCACA AGAAAAACCAGATCGAGTTTTGGTTCGGGTTAGAGACT TGACAATACAAAAAGCTGATGAAGTTGTTTGGGTACGT GCAAGAGTTCATACAAGCAGAGCTAAAGGGAAACAGT GCTTCTTAGTCCTACGTCAGCAGCAGTTTAATGTCCAGG CTCTTGTGGCGGTGGGAGACCATGCAAGCAAGCAGATG GTTAAATTTGCTGCCAACATCAACAAAGAGAGCATTGT GGATGTAGAAGGTGTTGTGAGAAAAGTGAATCAGAAA ATTGGAAGCTGTACACAGCAAGACGTTGAGTTACATGT TCAGAAGATTTATGTGATCAGTTTGGCTGAACCCCGTCT GCCCCTGCAGCTGGATGATGCTGTTCGGCCTGAGGCAG AAGGAGAAGAGGAAGGAAGAGCTACTGTTAACCAGGA TACAAGATTAGACAAC | 127 |
| DRS 1-180 | | ATGCCCAGCGCCAGCGCCAGCCGCAAGAGTCAGGAGA AGCCGCGGGAGATCATGGACGCGGCGGAAGATTATGCT AAAGAGAGATATGGAATATCTTCAATGATACAATCACA AGAAAAACCAGATCGAGTTTTGGTTCGGGTTAGAGACT | 128 |

TABLE D8-continued

DRS DNA Sequences

| Name | Amino Acid Residue Range of SEQ ID NO: 1 | Nucleic acid sequence | SEQ ID NO: |
|---|---|---|---|
| | | TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGATGCTGTTCGGCCTGAGGCAG<br>AAGGAGAAGAGGAAGGAAGAGCTACTGTTAACCAGGA<br>TACAAGATTA | |
| DRS 1-178 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGATGCTGTTCGGCCTGAGGCAG<br>AAGGAGAAGAGGAAGGAAGAGCTACTGTTAACCAGGA<br>TACA | 129 |
| DRS 1-176 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGATGCTGTTCGGCCTGAGGCAG<br>AAGGAGAAGAGGAAGGAAGAGCTACTGTTAACCAG | 130 |
| DRS 1-174 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGATGCTGTTCGGCCTGAGGCAG<br>AAGGAGAAGAGGAAGGAAGAGCTACTGTT | 131 |
| DRS 1-172 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGATGCTGTTCGGCCTGAGGCAG<br>AAGGAGAAGAGGAAGGAAGAGCT | 132 |

TABLE D8-continued

DRS DNA Sequences

| Name | Amino Acid Residue Range of SEQ ID NO: 1 | Nucleic acid sequence | SEQ ID NO: |
|---|---|---|---|
| DRS 1-170 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGATGCTGTTCGGCCTGAGGCAG<br>AAGGAGAAGAGGAAGGA | 133 |
| DRS 1-168 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGATGCTGTTCGGCCTGAGGCAG<br>AAGGAGAAGAG | 134 |
| DRS 1-166 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGATGCTGTTCGGCCTGAGGCAG<br>AAGGA | 135 |
| DRS 1-164 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGATGCTGTTCGGCCTGAGGCA | 136 |
| DRS 1-162 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGATGCTGTTCGGCCT | 137 |

US 9,822,353 B2

TABLE D8-continued

DRS DNA Sequences

| Name | Amino Acid Residue Range of SEQ ID NO: 1 | Nucleic acid sequence | SEQ ID NO: |
|---|---|---|---|
| DRS 1-160 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGATGCTGTT | 138 |
| DRS 1-158 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGAT | 139 |
| DRS 1-156 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTG | 140 |
| DRS 1-154 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTG | 141 |
| DRS 1-152 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>G | 142 |
| DRS 1-150 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA | 143 |

TABLE D8-continued

DRS DNA Sequences

| Name | Amino Acid Residue Range of SEQ ID NO: 1 | Nucleic acid sequence | SEQ ID NO: |
|---|---|---|---|
| | | AGAAAAACCAGATCGAGTTTTGGTTCGGGTTAGAGACT TGACAATACAAAAAGCTGATGAAGTTGTTTGGGTACGT GCAAGAGTTCATACAAGCAGAGCTAAAGGGAAACAGT GCTTCTTAGTCCTACGTCAGCAGCAGTTTAATGTCCAGG CTCTTGTGGCGGTGGGAGACCATGCAAGCAAGCAGATG GTTAAATTTGCTGCCAACATCAACAAAGAGAGCATTGT GGATGTAGAAGGTGTTGTGAGAAAAGTGAATCAGAAA ATTGGAAGCTGTACACAGCAAGACGTTGAGTTACATGT TCAGAAGATTTATGTGATCAGTTTGGCTGAACCC | |
| DRS 1-148 | | ATGCCCAGCGCCAGCGCCAGCCGCAAGAGTCAGGAGA AGCCGCGGGAGATCATGGACGCGGCGGAAGATTATGCT AAAGAGAGATATGGAATATCTTCAATGATACAATCACA AGAAAAACCAGATCGAGTTTTGGTTCGGGTTAGAGACT TGACAATACAAAAAGCTGATGAAGTTGTTTGGGTACGT GCAAGAGTTCATACAAGCAGAGCTAAAGGGAAACAGT GCTTCTTAGTCCTACGTCAGCAGCAGTTTAATGTCCAGG CTCTTGTGGCGGTGGGAGACCATGCAAGCAAGCAGATG GTTAAATTTGCTGCCAACATCAACAAAGAGAGCATTGT GGATGTAGAAGGTGTTGTGAGAAAAGTGAATCAGAAA ATTGGAAGCTGTACACAGCAAGACGTTGAGTTACATGT TCAGAAGATTTATGTGATCAGTTTGGCT | 144 |
| DRS 1-146 | | ATGCCCAGCGCCAGCGCCAGCCGCAAGAGTCAGGAGA AGCCGCGGGAGATCATGGACGCGGCGGAAGATTATGCT AAAGAGAGATATGGAATATCTTCAATGATACAATCACA AGAAAAACCAGATCGAGTTTTGGTTCGGGTTAGAGACT TGACAATACAAAAAGCTGATGAAGTTGTTTGGGTACGT GCAAGAGTTCATACAAGCAGAGCTAAAGGGAAACAGT GCTTCTTAGTCCTACGTCAGCAGCAGTTTAATGTCCAGG CTCTTGTGGCGGTGGGAGACCATGCAAGCAAGCAGATG GTTAAATTTGCTGCCAACATCAACAAAGAGAGCATTGT GGATGTAGAAGGTGTTGTGAGAAAAGTGAATCAGAAA ATTGGAAGCTGTACACAGCAAGACGTTGAGTTACATGT TCAGAAGATTTATGTGATCAGT | 145 |
| DRS 3-154 | | GCCAGCGCCAGCCGCAAGAGTCAGGAGAAGCCGCGGG AGATCATGGACGCGGCGGAAGATTATGCTAAAGAGAG ATATGGAATATCTTCAATGATACAATCACAAGAAAAAC CAGATCGAGTTTTGGTTCGGGTTAGAGACTTGACAATA CAAAAAGCTGATGAAGTTGTTTGGGTACGTGCAAGAGT TCATACAAGCAGAGCTAAAGGGAAACAGTGCTTCTTAG TCCTACGTCAGCAGCAGTTTAATGTCCAGGCTCTTGTGG CGGTGGGAGACCATGCAAGCAAGCAGATGGTTAAATTT GCTGCCAACATCAACAAAGAGAGCATTGTGGATGTAGA AGGTGTTGTGAGAAAAGTGAATCAGAAAATTGGAAGCT GTACACAGCAAGACGTTGAGTTACATGTTCAGAAGATT TATGTGATCAGTTTGGCTGAACCCCGTCTGCCCCTG | 146 |
| DRS 5-154 | | GCCAGCCGCAAGAGTCAGGAGAAGCCGCGGGAGATCA TGGACGCGGCGGAAGATTATGCTAAAGAGAGATATGG AATATCTTCAATGATACAATCACAAGAAAAACCAGATC GAGTTTTGGTTCGGGTTAGAGACTTGACAATACAAAAA GCTGATGAAGTTGTTTGGGTACGTGCAAGAGTTCATAC AAGCAGAGCTAAAGGGAAACAGTGCTTCTTAGTCCTAC GTCAGCAGCAGTTTAATGTCCAGGCTCTTGTGGCGGTG GGAGACCATGCAAGCAAGCAGATGGTTAAATTTGCTGC CAACATCAACAAAGAGAGCATTGTGGATGTAGAAGGT GTTGTGAGAAAAGTGAATCAGAAAATTGGAAGCTGTAC ACAGCAAGACGTTGAGTTACATGTTCAGAAGATTTATG TGATCAGTTTGGCTGAACCCCGTCTGCCCCTG | 147 |
| DRS 7-154 | | CGCAAGAGTCAGGAGAAGCCGCGGGAGATCATGGACG CGGCGGAAGATTATGCTAAAGAGAGATATGGAATATCT TCAATGATACAATCACAAGAAAAACCAGATCGAGTTTT GGTTCGGGTTAGAGACTTGACAATACAAAAAGCTGATG AAGTTGTTTGGGTACGTGCAAGAGTTCATACAAGCAGA GCTAAAGGGAAACAGTGCTTCTTAGTCCTACGTCAGCA GCAGTTTAATGTCCAGGCTCTTGTGGCGGTGGGAGACC ATGCAAGCAAGCAGATGGTTAAATTTGCTGCCAACATC AACAAAGAGAGCATTGTGGATGTAGAAGGTGTTGTGAG AAAAGTGAATCAGAAAATTGGAAGCTGTACACAGCAA | 148 |

TABLE D8-continued

DRS DNA Sequences

| Name | Amino Acid Residue Range of SEQ ID NO: 1 | Nucleic acid sequence | SEQ ID NO: |
|---|---|---|---|
| | | GACGTTGAGTTACATGTTCAGAAGATTTATGTGATCAG TTTGGCTGAACCCCGTCTGCCCCTG | |
| DRS 9-154 | | AGTCAGGAGAAGCCGCGGGAGATCATGGACGCGGCGG AAGATTATGCTAAAGAGAGATATGGAATATCTTCAATG ATACAATCACAAGAAAAACCAGATCGAGTTTTGGTTCG GGTTAGAGACTTGACAATACAAAAAGCTGATGAAGTTG TTTGGGTACGTGCAAGAGTTCATACAAGCAGAGCTAAA GGGAAACAGTGCTTCTTAGTCCTACGTCAGCAGCAGTT TAATGTCCAGGCTCTTGTGGCGGTGGGAGACCATGCAA GCAAGCAGATGGTTAAATTTGCTGCCAACATCAACAAA GAGAGCATTGTGGATGTAGAAGGTGTTGTGAGAAAAGT GAATCAGAAAATTGGAAGCTGTACACAGCAAGACGTTG AGTTACATGTTCAGAAGATTTATGTGATCAGTTTGGCTG AACCCCGTCTGCCCCTG | 149 |
| DRS 11-154 | | GAGAAGCCGCGGGAGATCATGGACGCGGCGGAAGATT ATGCTAAAGAGAGATATGGAATATCTTCAATGATACAA TCACAAGAAAAACCAGATCGAGTTTTGGTTCGGGTTAG AGACTTGACAATACAAAAAGCTGATGAAGTTGTTTGGG TACGTGCAAGAGTTCATACAAGCAGAGCTAAAGGGAA ACAGTGCTTCTTAGTCCTACGTCAGCAGCAGTTTAATGT CCAGGCTCTTGTGGCGGTGGGAGACCATGCAAGCAAGC AGATGGTTAAATTTGCTGCCAACATCAACAAAGAGAGC ATTGTGGATGTAGAAGGTGTTGTGAGAAAAGTGAATCA GAAAATTGGAAGCTGTACACAGCAAGACGTTGAGTTAC ATGTTCAGAAGATTTATGTGATCAGTTTGGCTGAACCCC GTCTGCCCCTG | 150 |
| DRS 13-154 | | CCGCGGGAGATCATGGACGCGGCGGAAGATTATGCTAA AGAGAGATATGGAATATCTTCAATGATACAATCACAAG AAAAACCAGATCGAGTTTTGGTTCGGGTTAGAGACTTG ACAATACAAAAAGCTGATGAAGTTGTTTGGGTACGTGC AAGAGTTCATACAAGCAGAGCTAAAGGGAAACAGTGC TTCTTAGTCCTACGTCAGCAGCAGTTTAATGTCCAGGCT CTTGTGGCGGTGGGAGACCATGCAAGCAAGCAGATGGT TAAATTTGCTGCCAACATCAACAAAGAGAGCATTGTGG ATGTAGAAGGTGTTGTGAGAAAAGTGAATCAGAAAATT GGAAGCTGTACACAGCAAGACGTTGAGTTACATGTTCA GAAGATTTATGTGATCAGTTTGGCTGAACCCCGTCTGCC CCTG | 151 |
| DRS15 -154 | | GAGATCATGGACGCGGCGGAAGATTATGCTAAAGAGA GATATGGAATATCTTCAATGATACAATCACAAGAAAAA CCAGATCGAGTTTTGGTTCGGGTTAGAGACTTGACAAT ACAAAAAGCTGATGAAGTTGTTTGGGTACGTGCAAGAG TTCATACAAGCAGAGCTAAAGGGAAACAGTGCTTCTTA GTCCTACGTCAGCAGCAGTTTAATGTCCAGGCTCTTGTG GCGGTGGGAGACCATGCAAGCAAGCAGATGGTTAAATT TGCTGCCAACATCAACAAAGAGAGCATTGTGGATGTAG AAGGTGTTGTGAGAAAAGTGAATCAGAAAATTGGAAG CTGTACACAGCAAGACGTTGAGTTACATGTTCAGAAGA TTTATGTGATCAGTTTGGCTGAACCCCGTCTGCCCCTG | 152 |
| DRS 17-154 | | ATGGACGCGGCGGAAGATTATGCTAAAGAGAGATATG GAATATCTTCAATGATACAATCACAAGAAAAACCAGAT CGAGTTTTGGTTCGGGTTAGAGACTTGACAATACAAAA AGCTGATGAAGTTGTTTGGGTACGTGCAAGAGTTCATA CAAGCAGAGCTAAAGGGAAACAGTGCTTCTTAGTCCTA CGTCAGCAGCAGTTTAATGTCCAGGCTCTTGTGGCGGT GGGAGACCATGCAAGCAAGCAGATGGTTAAATTTGCTG CCAACATCAACAAAGAGAGCATTGTGGATGTAGAAGGT GTTGTGAGAAAAGTGAATCAGAAAATTGGAAGCTGTAC ACAGCAAGACGTTGAGTTACATGTTCAGAAGATTTATG TGATCAGTTTGGCTGAACCCCGTCTGCCCCTG | 153 |
| DRS 19-154 | | GCGGCGGAAGATTATGCTAAAGAGAGATATGGAATATC TTCAATGATACAATCACAAGAAAAACCAGATCGAGTTT TGGTTCGGGTTAGAGACTTGACAATACAAAAAGCTGAT GAAGTTGTTTGGGTACGTGCAAGAGTTCATACAAGCAG AGCTAAAGGGAAACAGTGCTTCTTAGTCCTACGTCAGC AGCAGTTTAATGTCCAGGCTCTTGTGGCGGTGGGAGAC CATGCAAGCAAGCAGATGGTTAAATTTGCTGCCAACAT | 154 |

TABLE D8-continued

DRS DNA Sequences

| Name | Amino Acid Residue Range of SEQ ID NO: 1 | Nucleic acid sequence | SEQ ID NO: |
|---|---|---|---|
| | | CAACAAAGAGAGCATTGTGGATGTAGAAGGTGTTGTGA GAAAAGTGAATCAGAAAATTGGAAGCTGTACACAGCA AGACGTTGAGTTACATGTTCAGAAGATTTATGTGATCA GTTTGGCTGAACCCCGTCTGCCCCTG | |
| DRS 21-154 | | GCGGCGGAAGATTATGCTAAAGAGAGATATGGAATATC TTCAATGATACAATCACAAGAAAAACCAGATCGAGTTT TGGTTCGGGTTAGAGACTTGACAATACAAAAAGCTGAT GAAGTTGTTTGGGTACGTGCAAGAGTTCATACAAGCAG AGCTAAAGGGAAACAGTGCTTCTTAGTCCTACGTCAGC AGCAGTTTAATGTCCAGGCTCTTGTGGCGGTGGGAGAC CATGCAAGCAAGCAGATGGTTAAATTTGCTGCCAACAT CAACAAAGAGAGCATTGTGGATGTAGAAGGTGTTGTGA GAAAAGTGAATCAGAAAATTGGAAGCTGTACACAGCA AGACGTTGAGTTACATGTTCAGAAGATTTATGTGATCA GTTTGGCTGAACCCCGTCTG | 155 |
| DRS 23-154 | | GCGGCGGAAGATTATGCTAAAGAGAGATATGGAATATC TTCAATGATACAATCACAAGAAAAACCAGATCGAGTTT TGGTTCGGGTTAGAGACTTGACAATACAAAAAGCTGAT GAAGTTGTTTGGGTACGTGCAAGAGTTCATACAAGCAG AGCTAAAGGGAAACAGTGCTTCTTAGTCCTACGTCAGC AGCAGTTTAATGTCCAGGCTCTTGTGGCGGTGGGAGAC CATGCAAGCAAGCAGATGGTTAAATTTGCTGCCAACAT CAACAAAGAGAGCATTGTGGATGTAGAAGGTGTTGTGA GAAAAGTGAATCAGAAAATTGGAAGCTGTACACAGCA AGACGTTGAGTTACATGTTCAGAAGATTTATGTGATCA GTTTGGCTGAACCC | 156 |
| DRS 11-146 | | ATGCAGGAGAAGCCGCGGGAGATCATGGACGCGGCGG AAGATTATGCTAAAGAGAGATATGGAATATCTTCAATG ATACAATCACAAGAAAAACCAGATCGAGTTTTGGTTCG GGTTAGAGACTTGACAATACAAAAAGCTGATGAAGTTG TTTGGGTACGTGCAAGAGTTCATACAAGCAGAGCTAAA GGGAAACAGTGCTTCTTAGTCCTACGTCAGCAGCAGTT TAATGTCCAGGCTCTTGTGGCGGTGGGAGACCATGCAA GCAAGCAGATGGTTAAATTTGCTTGCAACATCAACAAA GAGAGCATTGTGGATGTAGAAGGTGTTGTGAGAAAAGT GAATCAGAAAATTGGAAGCTGTACACAGCAAGACGTTG AGTTACATGTTCAGAAGATTTATGTGATCAGT | 157 |
| DRS 13-146 | | ATGAAGCCGCGGGAGATCATGGACGCGGCGGAAGATT ATGCTAAAGAGAGATATGGAATATCTTCAATGATACAA TCACAAGAAAAACCAGATCGAGTTTTGGTTCGGGTTAG AGACTTGACAATACAAAAAGCTGATGAAGTTGTTTGGG TACGTGCAAGAGTTCATACAAGCAGAGCTAAAGGGAA ACAGTGCTTCTTAGTCCTACGTCAGCAGCAGTTTAATGT CCAGGCTCTTGTGGCGGTGGGAGACCATGCAAGCAAGC AGATGGTTAAATTTGCTTGCAACATCAACAAAGAGAGC ATTGTGGATGTAGAAGGTGTTGTGAGAAAAGTGAATCA GAAAATTGGAAGCTGTACACAGCAAGACGTTGAGTTAC ATGTTCAGAAGATTTATGTGATCAGT | 158 |
| DRS 13-146/A106C | | ATGAAGCCGCGGGAGATCATGGACGCGGCGGAAGATT ATGCTAAAGAGAGATATGGAATATCTTCAATGATACAA TCACAAGAAAAACCAGATCGAGTTTTGGTTCGGGTTAG AGACTTGACAATACAAAAAGCTGATGAAGTTGTTTGGG TACGTGCAAGAGTTCATACAAGCAGAGCTAAAGGGAA ACAGTGCTTCTTAGTCCTACGTCAGCAGCAGTTTAATGT CCAGGCTCTTGTGGCGGTGGGAGACCATGCAAGCAAGC AGATGGTTAAATTTGCTTGCAACATCAACAAAGAGAGC ATTGTGGATGTAGAAGGTGTTGTGAGAAAAGTGAATCA GAAAATTGGAAGCTGTACACAGCAAGACGTTGAGTTAC ATGTTCAGAAGATTTATGTGATCAGT | 159 |
| DRS 17-146 | | ATGATCATGGACGCGGCGGAAGATTATGCTAAAGAGA GATATGGAATATCTTCAATGATACAATCACAAGAAAAA CCAGATCGAGTTTTGGTTCGGGTTAGAGACTTGACAAT ACAAAAAGCTGATGAAGTTGTTTGGGTACGTGCAAGAG TTCATACAAGCAGAGCTAAAGGGAAACAGTGCTTCTTA GTCCTACGTCAGCAGCAGTTTAATGTCCAGGCTCTTGTG GCGGTGGGAGACCATGCAAGCAAGCAGATGGTTAAATT TGCTTGCAACATCAACAAAGAGAGCATTGTGGATGTAG | 160 |

TABLE D8-continued

DRS DNA Sequences

| Name | Amino Acid Residue Range of SEQ ID NO: 1 | Nucleic acid sequence | SEQ ID NO: |
|---|---|---|---|
| | | AAGGTGTTGTGAGAAAAGTGAATCAGAAAATTGGAAG CTGTACACAGCAAGACGTTGAGTTACATGTTCAGAAGA TTTATGTGATCAGT | |
| DRS 21-146 | | ATGGCGGAAGATTATGCTAAAGAGAGATATGGAATATC TTCAATGATACAATCACAAGAAAAACCAGATCGAGTTT TGGTTCGGGTTAGAGACTTGACAATACAAAAAGCTGAT GAAGTTGTTTGGGTACGTGCAAGAGTTCATACAAGCAG AGCTAAAGGGAAACAGTGCTTCTTAGTCCTACGTCAGC AGCAGTTTAATGTCCAGGCTCTTGTGGCGGTGGGAGAC CATGCAAGCAAGCAGATGGTTAAATTTGCTTGCAACAT CAACAAAGAGAGCATTGTGGATGTAGAAGGTGTTGTGA GAAAAGTGAATCAGAAAATTGGAAGCTGTACACAGCA AGACGTTGAGTTACATGTTCAGAAGATTTATGTGATCA GT | 161 |

Additional coding or non-coding sequences may, but need not, be present within a polynucleotide of the present invention, and a polynucleotide may, but need not, be linked to other molecules and/or support materials. Hence, the polynucleotides of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably.

It is therefore contemplated that a polynucleotide fragment of almost any length may be employed; with the total length preferably being limited by the ease of preparation and use in the intended recombinant DNA protocol. Included are polynucleotides of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 41, 43, 44, 45, 46, 47, 48, 49, 50, 60, 70, 80, 90, 100, 110, 120, 130, 140, 150, 160, 170, 180, 190, 200, 220, 240, 260, 270, 280, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000 or more (including all integers in between) bases in length, including any portion or fragment (e.g., greater than about 6, 7, 8, 9, or 10 nucleotides in length) of an AARS reference polynucleotide (e.g., base number X-Y, in which X is about 1-3000 or more and Y is about 10-3000 or more), or its complement.

Embodiments of the present invention also include "variants" of the AARS reference polynucleotide sequences. Polynucleotide "variants" may contain one or more substitutions, additions, deletions and/or insertions in relation to a reference polynucleotide. Generally, variants of an AARS reference polynucleotide sequence may have at least about 30%, 40% 50%, 55%, 60%, 65%, 70%, generally at least about 75%, 80%, 85%, desirably about 90% to 95% or more, and more suitably about 98% or more sequence identity to that particular nucleotide sequence (Such as for example, SEQ ID NO:2, 25-28, 30, 36-37, or 118-161) as determined by sequence alignment programs described elsewhere herein using default parameters. In certain embodiments, variants may differ from a reference sequence by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 41, 43, 44, 45, 46, 47, 48, 49, 50, 60, 70, 80, 90, 100 (including all integers in between) or more bases. In certain embodiments, such as when the polynucleotide variant encodes a DRS polypeptide having a non-canonical activity, the desired activity of the encoded DRS polypeptide is not substantially diminished relative to the unmodified polypeptide. The effect on the activity of the encoded polypeptide may generally be assessed as described herein.

Certain embodiments include polynucleotides that hybridize to a reference DRS polynucleotide sequence, (such as for example, SEQ ID NO: 2, 25-28, 30, 36-37, or 118-161) or to their complements, under stringency conditions described below. As used herein, the term "hybridizes under low stringency, medium stringency, high stringency, or very high stringency conditions" describes conditions for hybridization and washing. Guidance for performing hybridization reactions can be found in Ausubel et al., (1998, supra), Sections 6.3.1-6.3.6. Aqueous and non-aqueous methods are described in that reference and either can be used.

Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M $NaHPO_4$ (pH 7.2), 7% SDS for hybridization at 65° C., and (i) 2×SSC, 0.1% SDS; or (ii) 0.5% BSA, 1 mM EDTA, 40 mM $NaHPO_4$ (pH 7.2), 5% SDS for washing at room temperature. One embodiment of low stringency conditions includes hybridization in 6× sodium chloride/sodium citrate (SSC) at about 45° C., followed by two washes in 0.2×SSC, 0.1% SDS at least at 50° C. (the temperature of the washes can be increased to 55° C. for low stringency conditions).

Medium stringency conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 M $NaHPO_4$ (pH 7.2), 7% SDS for hybridization at 65° C., and (i) 2×SSC, 0.1% SDS; or (ii) 0.5% BSA, 1 mM EDTA, 40 mM $NaHPO_4$ (pH 7.2), 5% SDS for washing at 60-65° C. One embodiment of medium stringency conditions includes hybridizing in 6×SSC at about 45° C., followed by one or more washes in 0.2×SSC, 0.1% SDS at 60° C. High stringency conditions include and encompass from at least about 31% v/v to at least about 50% v/v formamide and from about 0.01 M to about 0.15 M salt for hybridization at 42° C., and about 0.01 M to about 0.02 M salt for washing at 55° C.

High stringency conditions also may include 1% BSA, 1 mM EDTA, 0.5 M NaHPO$_4$ (pH 7.2), 7% SDS for hybridization at 65° C., and (i) 0.2×SSC, 0.1% SDS; or (ii) 0.5% BSA, 1 mM EDTA, 40 mM NaHPO$_4$ (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C. One embodiment of very high stringency conditions includes hybridizing in 0.5 M sodium phosphate, 7% SDS at 65° C., followed by one or more washes in 0.2×SSC, 1% SDS at 65° C.

Other stringency conditions are well known in the art and a skilled artisan will recognize that various factors can be manipulated to optimize the specificity of the hybridization. Optimization of the stringency of the final washes can serve to ensure a high degree of hybridization. For detailed examples, see Ausubel et al., supra at pages 2.10.1 to 2.10.16 and Sambrook et al. (1989, supra) at sections 1.101 to 1.104. While stringent washes are typically carried out at temperatures from about 42° C. to 68° C., one skilled in the art will appreciate that other temperatures may be suitable for stringent conditions. Maximum hybridization rate typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel et al., supra at page 2.10.8).

In general, the $T_m$ of a perfectly matched duplex of DNA may be predicted as an approximation by the formula: $T_m=81.5+16.6 (\log_{10} M)+0.41 (\% G+C)-0.63 (\%$ formamide$)-(600/$length$)$ wherein: M is the concentration of Na$^+$, preferably in the range of 0.01 molar to 0.4 molar; % G+C is the sum of guanosine and cytosine bases as a percentage of the total number of bases, within the range between 30% and 75% G+C; % formamide is the percent formamide concentration by volume; length is the number of base pairs in the DNA duplex. The $T_m$ of a duplex DNA decreases by approximately 1° C. with every increase of 1% in the number of randomly mismatched base pairs. Washing is generally carried out at $T_m-15°$ C. for high stringency, or $T_m-30°$ C. for moderate stringency.

In one example of a hybridization procedure, a membrane (e.g., a nitrocellulose membrane or a nylon membrane) containing immobilized DNA is hybridized overnight at 42° C. in a hybridization buffer (50% deionized formamide, 5×SSC, 5×Denhardt's solution (0.1% ficoll, 0.1% polyvinylpyrollidone and 0.1% bovine serum albumin), 0.1% SDS and 200 mg/mL denatured salmon sperm DNA) containing a labeled probe. The membrane is then subjected to two sequential medium stringency washes (i.e., 2×SSC, 0.1% SDS for 15 min at 45° C., followed by 2×SSC, 0.1% SDS for 15 min at 50° C.), followed by two sequential higher stringency washes (i.e., 0.2×SSC, 0.1% SDS for 12 min at 55° C. followed by 0.2×SSC and 0.1% SDS solution for 12 min at 65-68° C.

Production of DRS Polypeptides and PEGylated DRS Polypeptides

DRS polypeptide may be prepared by any suitable procedure known to those of skill in the art for example, by using standard solid-phase peptide synthesis (Merrifield, J. Am. Chem. Soc. 85:2149-2154 (1963)), or by recombinant technology using a genetically modified host. Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the desired molecule.

DRS polypeptides can also be produced by expressing a DNA sequence encoding the DRS polypeptide in question) in a suitable host cell by well-known techniques. The polynucleotide sequence coding for the DRS polypeptide may be prepared synthetically by established standard methods, e.g., the phosphoamidite method described by Beaucage et al. (1981) Tetrahedron Letters 22:1859-1869, or the method described by Matthes et al. (1984) EMBO Journal 3:801-805. According to the phosphoramidite method, oligonucleotides are synthesized, e.g., in an automatic DNA synthesizer, purified, duplexed and ligated to form the synthetic DNA construct. Alternatively the DNA construct can be constructed using standard recombinant molecular biological techniques including restriction enzyme mediated cloning and PCR based gene amplification.

The polynucleotide sequences may also be of mixed genomic, cDNA, and synthetic origin. For example, a genomic or cDNA sequence encoding a leader peptide may be joined to a genomic or cDNA sequence encoding the DRS polypeptide, after which the DNA sequence may be modified at a site by inserting synthetic oligonucleotides encoding the desired amino acid sequence for homologous recombination in accordance with well-known procedures or preferably generating the desired sequence by PCR using suitable oligonucleotides. In some embodiments a signal sequence can be included before the coding sequence. This sequence encodes a signal peptide N-terminal to the coding sequence which communicates to the host cell to direct the polypeptide to the cell surface or secrete the polypeptide into the media. Typically the signal peptide is clipped off by the host cell before the protein leaves the cell. Signal peptides can be found in variety of proteins in prokaryotes and eukaryotes.

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems, including mammalian cell and more specifically human cell systems transformed with viral, plasmid, episomal or integrating expression vectors.

The "control elements" or "regulatory sequences" present in an expression vector are non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

Certain embodiments may employ E. coli-based expression systems (see, e.g., Structural Genomics Consortium et al., Nature Methods. 5:135-146, 2008). These and related embodiments may rely partially or totally on ligation-independent cloning (LIC) to produce a suitable expression vector. In specific embodiments, protein expression may be controlled by a T7 RNA polymerase (e.g., pET vector series). These and related embodiments may utilize the expression host strain BL21(DE3), a λDE3 lysogen of BL21 that supports T7-mediated expression and is deficient in lon and ompT proteases for improved target protein stability. Also included are expression host strains carrying plasmids encoding tRNAs rarely used in E. coli, such as ROSETTA™ (DE3) and Rosetta 2 (DE3) strains. Cell lysis and sample handling may also be improved using reagents sold under the trademarks BENZONASE® nuclease and BUG-BUSTER® Protein Extraction Reagent. For cell culture, auto-inducing media can improve the efficiency of many expression systems, including high-throughput expression systems. Media of this type (e.g., OVERNIGHT EXPRESS™ Autoinduction System) gradually elicit protein expression through metabolic shift without the addition of artificial inducing agents such as IPTG.

Particular embodiments employ hexahistidine tags (such as those sold under the trademark HIS•TAG® fusions), followed by immobilized metal affinity chromatography (IMAC) purification, or related techniques. In certain aspects, however, clinical grade proteins can be isolated from E. coli inclusion bodies, without or without the use of affinity tags (see, e.g., Shimp et al., Protein Expr Purif. 50:58-67, 2006). As a further example, certain embodiments may employ a cold-shock induced E. coli high-yield production system, because over-expression of proteins in Escherichia coli at low temperature improves their solubility and stability (see, e.g., Qing et al., Nature Biotechnology. 22:877-882, 2004).

Also included are high-density bacterial fermentation systems. For example, high cell density cultivation of Ralstonia eutropha allows protein production at cell densities of over 150 g/L, and the expression of recombinant proteins at titers exceeding 10 g/L. In the yeast Saccharomyces cerevisiae, a number of vectors containing constitutive or inducible promoters such as alpha factor, alcohol oxidase, and PGH may be used. For reviews, see Ausubel et al. (supra) and Grant et al., Methods Enzymol. 153:516-544 (1987). Also included are Pichia pandoris expression systems (see, e.g., Li et al., Nature Biotechnology. 24, 210-215, 2006; and Hamilton et al., Science, 301:1244, 2003). Certain embodiments include yeast systems that are engineered to selectively glycosylate proteins, including yeast that have humanized N-glycosylation pathways, among others (see, e.g., Hamilton et al., Science. 313:1441-1443, 2006; Wildt et al., Nature Reviews Microbiol. 3:119-28, 2005; and Gerngross et al., Nature-Biotechnology. 22:1409-1414, 2004; U.S. Pat. Nos. 7,629,163; 7,326,681; and 7,029,872). Merely by way of example, recombinant yeast cultures can be grown in Fernbach Flasks or 15 L, 50 L, 100 L, and 200 L fermentors, among others.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, EMBO J. 6:307-311 (1987)). Alternatively, plant promoters such as the small subunit of RUBISCO or heat shock promoters may be used (Coruzzi et al., EMBO J. 3:1671-1680 (1984); Broglie et al., Science 224:838-843 (1984); and Winter et al., Results Probl. Cell Differ. 17:85-105 (1991)). These constructs can be introduced into plant cells by direct DNA transformation or pathogen-mediated transfection. Such techniques are described in a number of generally available reviews (see, e.g., Hobbs in McGraw Hill, Yearbook of Science and Technology, pp. 191-196 (1992)).

An insect system may also be used to express a polypeptide of interest. For example, in one such system, Autographa californica nuclear polyhedrosis virus (AcNPV) is used as a vector to express foreign genes in Spodoptera frugiperda cells or in Trichoplusia cells. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, S. frugiperda cells or Trichoplusia cells in which the polypeptide of interest may be expressed (Engelhard et al., Proc. Natl. Acad. Sci. U.S.A. 91:3224-3227 (1994)). Also included are baculovirus expression systems, including those that utilize SF9, SF21, and T. ni cells (see, e.g., Murphy and Piwnica-Worms, Curr Protoc Protein Sci. Chapter 5:Unit5.4, 2001). Insect systems can provide post-translation modifications that are similar to mammalian systems.

In mammalian host cells, a number of expression systems are well known in the art and commercially available. Exemplary mammalian vector systems include for example, pCEP4, pREP4, and pREP7 from Invitrogen, the PerC6 system from Crucell, and Lentiviral based systems such as pLP1 from Invitrogen, and others. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, Proc. Natl. Acad. Sci. U.S.A. 81:3655-3659 (1984)). In addition, transcription enhancers, such as the Rous sarcoma virus (RSV) enhancer, may be used to increase expression in mammalian host cells.

Examples of useful mammalian host cell lines include monkey kidney CV1 line transformed by SV40 (COS-7, ATCC CRL 1651); human embryonic kidney line (293 or 293 cells sub-cloned for growth in suspension culture, Graham et al., J. Gen Virol. 36:59 (1977)); baby hamster kidney cells (BHK, ATCC CCL 10); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR-CHO cells (Urlaub et al., *PNAS USA* 77:4216 (1980)); and myeloma cell lines such as NSO and Sp2/0. For a review of certain mammalian host cell lines suitable for antibody production, see, e.g., Yazaki and Wu, *Methods in Molecular Biology*, Vol. 248 (B. K. C Lo, ed., Humana Press, Totowa, N.J., 2003), pp. 255-268. Certain preferred mammalian cell expression systems include CHO and HEK293-cell based expression systems. Mammalian expression systems can utilize attached cell lines, for example, in T-flasks, roller bottles, or cell factories, or suspension cultures, for example, in 1 L and 5 L spinners, 5 L, 14 L, 40 L, 100 L and 200 L stir tank bioreactors, or 20/50 L and 100/200 L WAVE bioreactors, among others known in the art.

Also included is cell-free expression of proteins. These and related embodiments typically utilize purified RNA polymerase, ribosomes, tRNA and ribonucleotides; these reagents may be produced by extraction from cells or from a cell-based expression system.

In addition, a host cell strain may be chosen for its ability to modulate the expression of the inserted sequences or to process the expressed protein in the desired fashion. Such modifications of the polypeptide include, but are not limited to, post-translational modifications such as acetylation, carboxylation, glycosylation, phosphorylation, lipidation, and acylation, or the insertion of non-naturally occurring amino acids (see generally U.S. Pat. Nos.; 7,939,496; 7,816,320; 7,947,473; 7,883,866; 7,838,265; 7,829,310; 7,820,766; 7,820,766; 7,7737,226; 7,736,872; 7,638,299; 7,632,924; and 7,230,068). In some embodiments, such non-naturally occurring amino acids may be inserted at position Cys130. Post-translational processing which cleaves a "prepro" form of the protein may also be used to facilitate correct insertion, folding and/or function. Different host cells such as yeast, CHO, HeLa, MDCK, HEK293, and W138, in addition to bacterial cells, which have or even lack specific cellular machinery and characteristic mechanisms for such post-translational activities, may be chosen to ensure the correct modification and processing of the foreign protein.

The DRS polypeptides produced by a recombinant cell can be purified and characterized according to a variety of techniques known in the art. Exemplary systems for performing protein purification and analyzing protein purity include fast protein liquid chromatography (FPLC) (e.g., AKTA and Bio-Rad FPLC systems), high-pressure liquid chromatography (HPLC) (e.g., Beckman and Waters HPLC). Exemplary chemistries for purification include ion exchange chromatography (e.g., Q, S), size exclusion chromatography, salt gradients, affinity purification (e.g., Ni, Co, FLAG, maltose, glutathione, protein A/G), gel filtration, reverse-phase, ceramic HYPERD® ion exchange chromatography, and hydrophobic interaction columns (HIC), among others known in the art. Several exemplary methods are also disclosed in the Examples sections.

PEGylated DRS Polypeptides

A wide variety of PEG polymers can be linked to DRS polypeptides of the present invention to modulate biological properties of the DRS polypeptide, and/or provide new biological properties to the DRS polypeptide. PEG polymers can be linked to the DRS polypeptide via a naturally encoded amino acid, via a non-naturally encoded amino acid, or any functional substituent of a natural or non-natural amino acid, or any substituent or functional group added to a natural or non-natural amino acid.

PEGylated polypeptides can also be designed so as to control the rate of release of the bioactive polypeptide into a patient's bloodstream, and thus, PEGylation of therapeutic polypeptides is a useful and attractive strategy for designing next generation polypeptide-based drugs. Moreover, site specific PEGylation also minimizes undesirable collateral effects on the therapeutic activities of the PEGylated polypeptide. PEGylation of polypeptide-based drugs can change their physical and chemical properties, such as conformation, electrostatic binding, hydrophobicity, and pharmacokinetic profile. PEGylation also improves drug solubility, stability, and the retention time of the conjugates in blood and decreases immunogenicity, proteolysis and renal excretion, thereby allowing a reduced dosing frequency.

In various embodiments, the present invention contemplates, in part, PEGylated DRS polypeptides, compositions comprising such PEGylated polypeptides, and methods of use thereof. In certain embodiments, the PEGylated DRS polypeptides described herein have improved pharmacokinetic properties compared to non-PEGylated DRS polypeptides.

PEG polymers suitable for conjugation to DRS polypeptides of the invention are not limited to a particular structure and can be linear (e.g., monofunctional PEG or bifunctional PEG), branched or multi-armed (e.g., PEG attached to a polyol core or forked PEG), dendritic. In one embodiment, the internal structure of a polyalkylene glycol polymer can be organized in any number of different patterns and can be selected from the group consisting of homopolymer, alternating copolymer, random copolymer, block copolymer, alternating tripolymer, random tripolymer, and block tripolymer.

In particular embodiments, the total average molecular weight of the PEG polymers polymer in the conjugate is typically from about 1,000 Daltons to about 150,000 Daltons. Exemplary ranges of total average molecular weights of PEG polymers conjugated to a DRS polypeptide of the invention include, but are not limited to: about 1,000 Daltons to about 120,000 Daltons, about 10,000 Daltons to about 100,000 Daltons, about 10,000 Daltons to about 80,000 Daltons, about 10,000 Daltons to about 60,000 Daltons, about 10,000 Daltons to about 40,000 Daltons, about 20,000 Daltons to about 100,000 Daltons, about 20,000 Daltons to about 80,000 Daltons, about 20,000 Daltons to about 60,000 Daltons, about 20,000 Daltons to about 40,000 Daltons, about 40,000 Daltons to about 120,000 Daltons, about 40,000 Daltons to about 100,000 Daltons, about 40,000 Daltons to about 80,000 Daltons, or about 40,000 Daltons to about 60,000 Daltons, or any intervening range.

In some embodiments, low molecular weight PEG polymers may be preferred, and these may range from about 200 Daltons to about 5,000 Daltons. Exemplary ranges of low molecular weight PEG polymers conjugated to a DRS polypeptide of the invention include, but are not limited to: about 200 Daltons to about 2,000 Daltons, about 500 Daltons to about 2,000 Daltons, about 800 Daltons to about 2000 Daltons, about 1000 Daltons to about 2000 Daltons.

Exemplary ranges of total average molecular weights of PEG polymers conjugated to a DRS polypeptide of the invention include, but are not limited to: about 500 Daltons, about 1,000 Daltons, about 5000 Daltons, about 10,000 Daltons, about 15,000 Daltons, about 20,000 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, about 75,000 Daltons, about 80,000 Daltons, about 85,000 Daltons, about 90,000 Daltons, about 100,000 Daltons, about 110,000 Daltons, about 120,000 Daltons, about 130,000 Daltons, about 140,000 Daltons, or about 150,000 Daltons any intervening molecular weight.

In particular embodiments comprising 1, 2, 3, 4, 5, 6, 7, 8, 9, or 10 or more PEG polymers conjugated to a DRS polypeptide of the present invention, the average molecular weight of each PEG polymer conjugated to the DRS polypeptide includes, but is not limited to: about 1000 Daltons, about 5000 Daltons, about 10,000 Daltons, about 15,000 Daltons, about 20,000 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, about 75,000 Daltons, about 80,000 Daltons, about 85,000 Daltons, about 90,000 Daltons, or about 100,000 Daltons, or any intervening molecular weight.

It will be appreciated that because virtually all PEG polymers exist as mixtures of diverse high molecular mass, the PEG polymer molecular weights (MW) above represent the average MWs of different sized chains within the polymer.

The PEG polymers of the invention will for a given molecular weight typically consist of a range of ethylene glycol (or ethyleneoxide; $OCH_2CH_2$) monomers. For example, a PEG polymer of molecular weight 2000 Da will typically consist of 43±10 monomers, the average being around 43-44 monomers.

The PEG polymers of the present invention will typically comprise a number of subunits, e.g., each "n", "$n_1$" or "$n_2$" in any of the claimed compounds may each independently be from about 1 to about 1000, from about 1 to about 800, from about 1 to about 600, from about 1 to about 400, from about 1 to about 300, from about 1 to about 200. Well-suited PEG groups are such wherein the number of subunits (i.e., n, $n_1$ or $n_2$) are independently selected from the group consisting of from about 800 to about 1000; from about 800 to about 950; from about 600 to about 850; from about 400 to about 650; from about 200 to about 450, from about 180 to about 350; from about 100 to about 150; from about 35 to about 55; from about 42 to about 62; from about 12 to about 25 subunits, from about 1 to 10 subunits. In certain embodiments the PEGylated DRS polypeptide will have a molecular weight of about 40 kDa, and thus n for each PEG chain in the branch chain PEGs will be within the range of about 440 to about 550, or about 450 to about 520.

Branched versions of the PEG polymer (e.g., a branched 40,000 Da PEG polymer comprised of two or more 10,000 Da to 20,000 Da PEG polymers or the like) having a total molecular weight of any of the foregoing can also be used.

Typically, PEG polymers are activated with a suitable activating group appropriate for coupling to a desired site on a DRS polypeptide. Thus, a polymeric reagent will possess a functional group for reaction with a corresponding functional group on a DRS polypeptide, e.g., lysine, cysteine, histidine, arginine, aspartic acid, glutamic acid, serine, threonine, tyrosine, and the N-terminal amino and C-terminal carboxylic acid group of amino acids. Representative polymeric reagents and methods for conjugating these polymers to an active moiety are known in the art and further described in Zalipsky, S., et al., "Use of Functionalized Poly (Ethylene Glycols) for Modification of Polypeptides" in *Polyethylene Glycol Chemistry Biotechnical and Biomedical Applications*, J. M. Harris, Plenus Press, New York (1992), Zalipsky (1995) *Advanced Drug Reviews* 16:157-182; and Roberts et al., *Advanced Drug Delivery Reviews* 54 (2002): 459-476.

In general, PEG functional groups suitable for conjugating PEG to a polypeptide of the invention include, but are not limited to a carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, or glyoxal.

In one embodiment, the active functional group of a PEG moiety selected from the group consisting of: a carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal forms a covalent linkage with a non-natural amino acid having the formula:

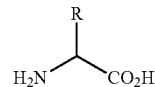

wherein the sidechain, R, of the non-naturally occurring amino acid comprises a functional group selected from the group consisting of: alkyl-, aryl-, aryl halide, vinyl halide, alkyl halide, acetyl, ketone, aziridine, nitrile, nitro, halide, acyl-, keto-, azido-, hydroxyl-, hydrazine, cyano-, halo-, hydrazide, alkenyl, alkynyl, ether, thio ether, epoxide, sulfone, boronic acid, boronate ester, borane, phenylboronic acid, thiol, seleno-, sulfonyl-, borate, boronate, phospho, phosphono, phosphine, heterocyclic-, pyridyl, naphthyl, benzophenone, a constrained ring such as a cyclooctyne, thio ester, enone, imine, aldehyde, ester, thioacid, hydroxylamine, amino, carboxylic acid, alpha-keto carboxylic acid, alpha or beta unsaturated acids and amides, glyoxylamide, or organosilane group, and the like and any combination thereof.

In another embodiment, the active functional group of a PEG moiety selected from the group consisting of: a carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal forms a covalent linkage with a non-natural amino acid selected from the group consisting of: p-acetyl-L-phenylalanine, O-methyl-L-tyrosine, L-3-(2-naphthyl)alanine, 3-methylphenylalanine, O-4-allyl-L-tyrosine, 4-propyl-L-tyrosine, tri-O-acetyl-GlcNAcβ-serine, β-O-GlcNAc-L-serine, tri-O-acetyl-GalNAc-α-threonine, α-GalNAc-L-threonine, L-Dopa, fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, and isopropyl-L-phenylalanine.

In particular embodiments, the active functional group of a PEG polymer is conjugated to an amino group of a DRS polypeptide. In this approach, the PEG bearing the active functional group is reacted with the DRS polypeptide in aqueous media under appropriate pH conditions, at room temperature or 4° C., for a few hours to overnight. Typically the polymeric reagent is coupled to the activated functional group via a linker as described herein.

Suitable active functional groups to conjugate PEG to an amino group of the polypeptide, such as those found in lysine, arginine, or histidine residues or an N-terminal residue of a DRS polypeptide, include, but are not limited to: succinimidyl esters (NHS), e.g., succinimidyl carbonate, succinimidyl carboxylmethyl, succinimidyl glutarate, succinimidyl valerate, succinimidyl succinate, and the like; p-nitrophenyl esters, e.g., p-nitrophenyl carbonate, p-nitrophenyl carboxymethyl, p-nitrophenyl glutarate, p-nitrophenyl valerate, p-nitrophenyl succinate, and the like; succinimidyl carbamate (NSC); dichlorotriazines; tresylates; benzotriazole carbonates; trichlorophenyl carbonates; isocyanates; isothiocyanates; acyl azides; sulfonyl chloride; aldehydes, e.g., proprionaldehyde, acetalaldehyde, butyraldehyde, and the like; carboxylic acid derivatives, e.g., propionic acid, butanoic acid, and the like; imidioesters, e.g., carbonylimidazole, oxycarbonylimidazoles, and the like; cyclic imide thiones; epoxides; acrylates; and anhydrides. Exemplary activated PEGs capable of reacting with amino groups of the DRS polypeptide include, e.g., those listed in Table D10.

PEGylation of a DRS polypeptide via amino group, with a PEG reagent bearing an N-hydroxysuccinimide ester (NHS group), is typically carried out at room temperature, or 4° C., in a polar aprotic solvent such as dimethylformamide (DMF) or acetonitrile, or a combination thereof (with small amounts of water to solubilize the peptide) under slightly basic pH conditions, e.g., from pHs ranging from about 7.5 to about 9. Reaction times are typically in the range of 1 to 24 hours, depending upon the pH and temperature of the reaction.

PEGylation of a DRS polypeptide via amino group, with a PEG reagent bearing an aldehyde group, is typically conducted under mild conditions, in the presence of sodium cyanoborohydride (10 equiv.), 4° C., at pHs from about 5 to 10, for about 20 to 36 hours. PEGylation may be conducted, for example, in 100 mM sodium acetate or 100 mM sodium biphosphate buffer at pH 5.06.0. The buffer may additionally contain 20 mM sodium cyanoborahydride. The molar ratio of compound to mPEG-aldehyde may be 1:5-1:10. The PEGylation reaction is then stirred overnight at ambient or refrigeration temperature.

PEGylation of a DRS polypeptide via amino group, with a PEG reagent bearing p-Nitrophenyloxycarbonyl group, is typically conducted with borate or phosphate buffer at pHs from about pH 8 to 8.3 pH, at room temperature overnight.

For all the coupling reactions, varying ratios of polymeric reagent to the DRS polypeptide may be employed, e.g., from an equimolar ratio up to a 10-fold molar excess of polymer reagent. Typically, up to a 2-fold molar excess of polymer reagent will suffice. In the following Table D10, selected PEGylation reagents are listed. Obviously other active groups and linkers may be employed, and are known to those skilled in the art.

TABLE D10

| Structure/Functionality | Abbreviation & Molecular Weight Range (in Da) |
|---|---|
| Exemplary Activated Linear PEGs Capable of Reacting With Amino Groups | |
| 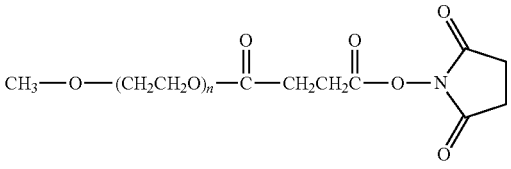<br>N-hydroxysuccinimide ester | SUNBRIGHT ME-020CS<br>MW = 2,000<br>SUNBRIGHT ME-050CS<br>MW = 5,000<br>SUNBRIGHT ME-100CS<br>MW = 10,000<br>SUNBRIGHT ME-200CS<br>MW = 20,000<br>SUNBRIGHT ME-300CS<br>MW = 30,000<br>SUNBRIGHT ME-400CS<br>MW = 40,000 |
| 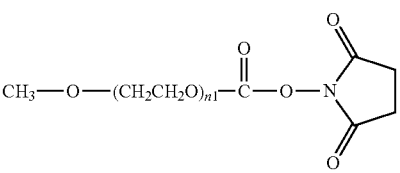<br>N-hydroxysuccinimide ester | SUNBRIGHT ME-050GS<br>MW = 5,000<br>SUNBRIGHT ME-200GS<br>MW = 20,000<br>SUNBRIGHT ME-300GS<br>MW = 30,000<br>SUNBRIGHT ME-400GS<br>MW = 40,000 |

TABLE D10-continued

| Structure/Functionality | Abbreviation & Molecular Weight Range (in Da) |
|---|---|
| CH$_3$—O—(CH$_2$CH$_2$O)$_{n1}$—C(=O)—O—N(succinimide)<br>N-hydroxysuccinimide ester | SUNBRIGHT ME-050TS<br>MW = 5,000<br>SUNBRIGHT ME-200TS<br>MW = 20,000<br>SUNBRIGHT ME-300TS<br>MW = 30,000<br>SUNBRIGHT ME-400TS<br>MW = 40,000 |
| CH$_3$—O—(CH$_2$CH$_2$O)$_{n1}$—CH$_2$—C(=O)—O—N(succinimide)<br>N-hydroxysuccinimide ester | SUNBRIGHT ME-020AS<br>MW = 2,000<br>SUNBRIGHT ME-050AS<br>MW = 5,000 |
| CH$_3$—O—(CH$_2$CH$_2$O)$_{n1}$—(CH$_2$)$_5$C(=O)—O—N(succinimide)<br>N-hydroxysuccinimide ester | SUNBRIGHT ME-050HS<br>MW = 5,000<br>SUNBRIGHT ME-200HS<br>MW = 20,000<br>SUNBRIGHT ME-300HS<br>MW = 30,000<br>SUNBRIGHT ME-400HS<br>MW = 40,000 |
| CH$_3$—O—(CH$_2$CH$_2$O)$_{n1}$—C(=O)—O—C$_6$H$_4$—NO$_2$<br>p-Nitrophenyl | SUNBRIGHT MENP-020H<br>MW = 2,000<br>SUNBRIGHT MENP-050H<br>MW = 5,000<br>SUNBRIGHT MENP-10T<br>MW = 10,000<br>SUNBRIGHT MENP-20T<br>MW = 20,000<br>SUNBRIGHT MENP-30T<br>MW = 30,000<br>SUNBRIGHT MENP-40T<br>MW = 40,000 |
| CH$_3$—O—(CH$_2$CH$_2$O)$_n$—N=C=O<br>Isocyanate | |
| CH$_3$—O—(CH$_2$CH$_2$O)$_n$—CH$_2$—C(=O)—O—CH$_2$CH$_2$CH(=O)<br>Aldehyde | SUNBRIGHT ME-050AL<br>MW = 5,000<br>SUNBRIGHT ME-100AL<br>MW = 10,000<br>SUNBRIGHT ME-200AL<br>MW = 20,000<br>SUNBRIGHT ME-300AL<br>MW = 30,000<br>SUNBRIGHT ME-400AL<br>MW = 40,000 |
| CH$_3$—O—(CH$_2$CH$_2$O)$_n$—CH$_2$CH$_2$CH(=O)<br>Aldehyde | SUNBIO P1PAL-5<br>MW = 5,000<br>SUNBIO P1PAL-10<br>MW = 10,000<br>SUNBIO P1PAL-20<br>MW = 20,000<br>SUNBIO P1PAL-30<br>MW = 30,000 |
| CH$_3$—O—(CH$_2$CH$_2$O)$_n$—CH$_2$C(=O)NHCH$_2$CH$_2$CH(=O)<br>Amide Aldehyde | SUNBIO P1APAL-5<br>MW = 5,000<br>SUNBIO P1APAL-10<br>MW = 10,000<br>SUNBIO P1APAL-20<br>MW = 20,000<br>SUNBIO P1APAL-30<br>MW = 30,000 |

TABLE D10-continued

| Structure/Functionality | Abbreviation & Molecular Weight Range (in Da) |
|---|---|
| 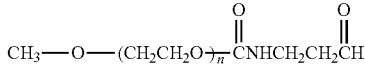<br>Urethane Aldehyde | SUNBIO P1TPAL-5<br>MW = 5,000 |
| 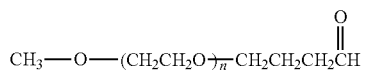<br>Aldehyde | SUNBIO P1BAL-5<br>MW = 5,000<br>SUNBIO P1BAL-10<br>MW = 10,000<br>SUNBIO P1BAL-20<br>MW = 20,000<br>SUNBIO P1BAL-30<br>MW = 30,000 |
| 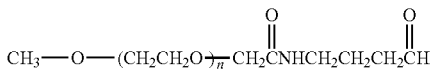<br>Amide Aldehyde | SUNBIO P1ABAL-5<br>MW = 5,000<br>SUNBIO P1ABAL-10<br>MW = 10,000<br>SUNBIO P1ABAL-20<br>MW = 20,000<br>SUNBIO P1ABAL-30<br>MW = 30,000 |
| $CH_3-O-(CH_2CH_2O)_n-\overset{O}{\overset{\|}{C}}NHCH_2CH_2CH_2\overset{O}{\overset{\|}{C}}H$<br>Urethane Aldehyde | SUNBIO P1TBAL-5<br>MW = 5,000 |
| 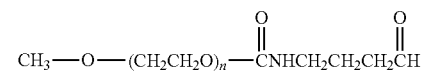<br>N-hydroxysuccinimide ester | X = 0, y = 1 SUNBRIGHT-AS<br>X = 0, y = 5 SUNBRIGHT-HS<br>X = 1, y = 2 SUNBRIGHT-CS<br>X = 1, y = 3 SUNBRIGHT-GS |
| 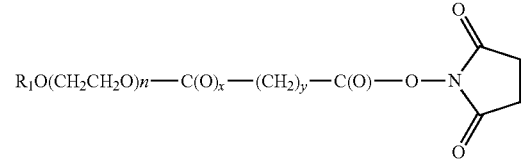<br>Maleimide | z = 2 SUNBRIGHT-MA<br>z = 5 SUNBRIGHT-MA3 |

Exemplary Activated Branched PEGs Capable of Reacting With Amino Groups

| | |
|---|---|
| 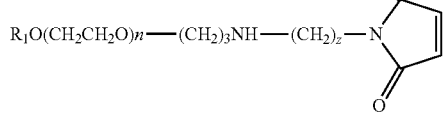<br>N-hydroxysuccinimide ester | JENKEM A0001-1 Y-NHS-40K |
| 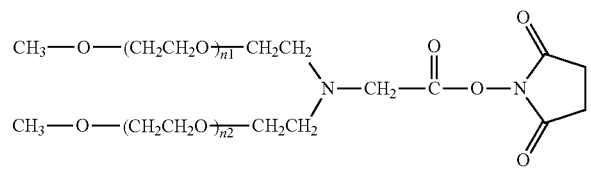<br>N-hydroxysuccinimide ester | SUNBRIGHT GL2-200GS2<br>MW = 20,000<br>SUNBRIGHT GL2-400GS2<br>MW = 40,000<br>SUNBRIGHT GL2-400GS2<br>MW = 60,000<br>SUNBRIGHT GL2-800GS2<br>MW = 80,000 |

TABLE D10-continued

| Structure/Functionality | Abbreviation & Molecular Weight Range (in Da) |
|---|---|
| 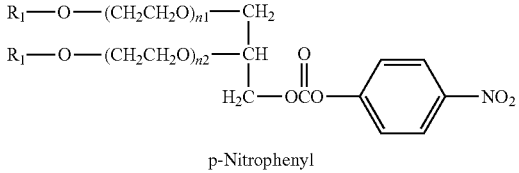<br>p-Nitrophenyl | SUNBRIGHT GL2-100NP<br>MW = 10,000<br>SUNBRIGHT GL2-200NP<br>MW = 20,000<br>SUNBRIGHT GL2-400NP<br>MW = 40,000<br>SUNBRIGHT GL2-600NP<br>MW = 60,000<br>SUNBRIGHT GL2-800NP<br>MW = 80,000 |
| 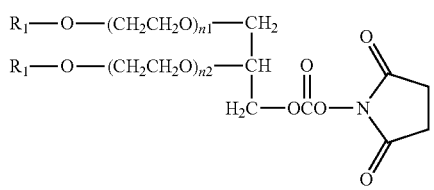<br>N-hydroxysuccinimide ester | SUNBRIGHT GL2-200TS<br>MW = 20,000<br>SUNBRIGHT GL2-400TS<br>MW = 40,000<br>SUNBRIGHT GL2-600TS<br>MW = 60,000<br>SUNBRIGHT GL2-800TS<br>MW = 80,000 |
| 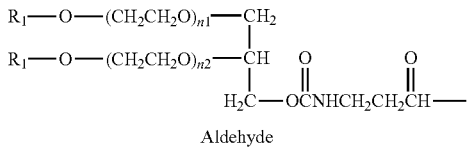<br>Aldehyde | SUNBRIGHT GL2-200AL3<br>MW = 20,000<br>SUNBRIGHT GL2-400AL3<br>MW = 40,000<br>SUNBRIGHT GL2-600AL3<br>MW = 60,000<br>SUNBRIGHT GL2-800AL3<br>MW = 80,000 |
| 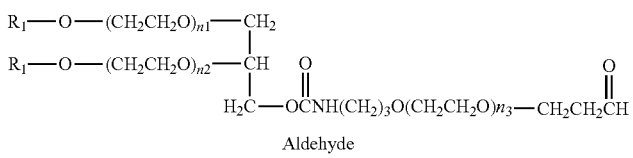<br>Aldehyde | SUNBRIGHT GL3-400AL100U<br>MW = 50,000 |
| 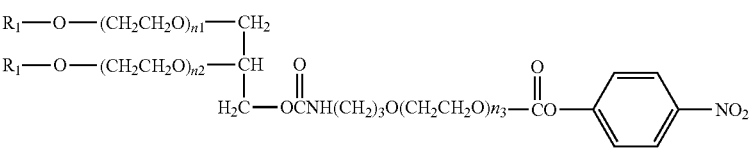<br>p-Nitrophenyl | SUNBRIGHT GL3-400NP100U<br>MW = 50,000 |
| 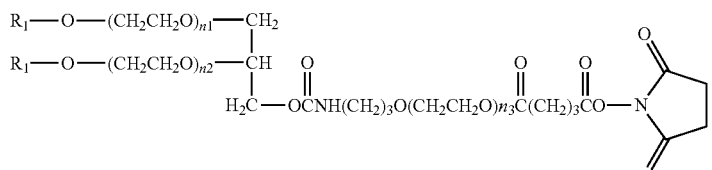<br>N-hydroxysuccinimide ester | SUNBRIGHT GL3-400GS100U<br>MW = 50,000 |
| 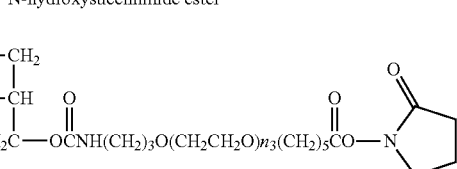<br>N-hydroxysuccinimide ester | SUNBRIGHT GL3-400HS100U<br>MW = 50,000 |

TABLE D10-continued

| Structure/Functionality | Abbreviation & Molecular Weight Range (in Da) |
|---|---|
| 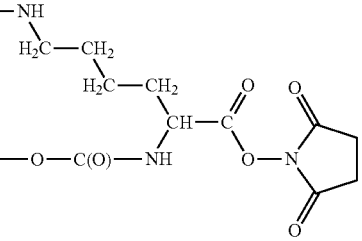 | SUNBRIGHT LY-400NS MW = 40,000 |
| 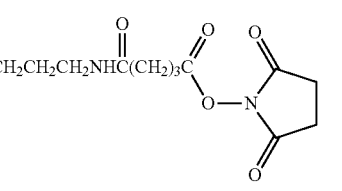 | MW = 40,000 |

In certain embodiments, the active functional group of a PEG polymer is conjugated to a thiol group of a DRS polypeptide. Suitable active functional groups to conjugate PEG to a thiol group of the polypeptide, such as those found in a cysteine residue of a DRS polypeptide, include, but are not limited to: thiols, maleimides, vinylsulfones, iodoacetamides, orthopyridyl disulfides, haloacetyls, alkyl halide derivatives, aziridines, acrylol derivatives arylating agents, and the like.

Exemplary activated PEGs capable of reacting with amino groups of the DRS polypeptide include, e.g., those listed in Table D11.

TABLE D11

| Structure/Functionality | Abbreviation & Molecular Weight Range (in Da) |
|---|---|
| Exemplary Activated Linear PEGs Capable of Reacting With Thiol Groups | |
| 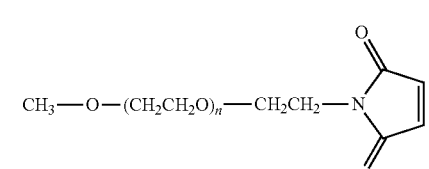  Maleimide | NOCS PEG2-0001 MW = 5000<br>NOCS PEG2-0002 MW = 2000<br>NANOCS PEG2-0003 MW = 1000<br>NANOCS PEG2-0004 MW = 10000<br>NANOCS PEG2-0005 MW = 20000<br>NANOCS PEG2-0006 MW = 30000<br>NANOCS PEG2-0006 MW = 40000 |
| 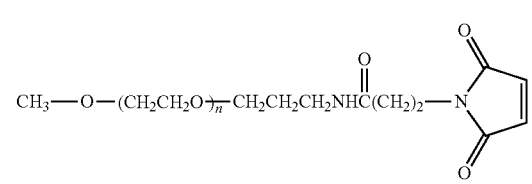  Maleimide | SUNBRIGHT ME-020MA MW = 2,000<br>SUNBRIGHT ME-050MA MW = 5,000<br>SUNBRIGHT ME-120MA MW = 12,000<br>SUNBRIGHT ME-200MA MW = 20,000<br>SUNBRIGHT ME-300MA MW = 30,000<br>SUNBRIGHT ME-400MA MW = 40,000 |
| 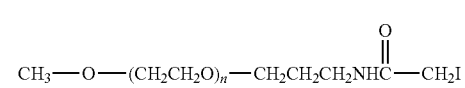  Iodoacetamide | SUNBRIGHT ME-200IA MW = 20,000<br>SUNBRIGHT ME-300IA MW = 30,000<br>SUNBRIGHT ME-400IA MW = 40,000 |
| 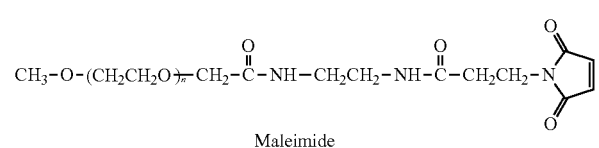  Maleimide | ENKEM A3073 M-MAL-2000<br>ENKEM A3014 M-MAL-5000<br>ENKEM A3045 M-MAL-10K<br>ENKEM A3002 M-MAL-20K<br>ENKEM A3046 M-MAL-30K<br>ENKEM A3042 M-MAL-40K |

TABLE D11-continued

| Structure/Functionality | Abbreviation & Molecular Weight Range (in Da) |
|---|---|
| CH$_3$—O—(CH$_2$CH$_2$O)$_n$—CH$_2$CH$_2$—S(=O)$_2$—CH=CH$_2$<br><br>Vinyl sulfone | JENKEM A3034 M-VS-5000<br>JENKEM A3006 M-VS-20K |
| CH$_3$—O—(CH$_2$CH$_2$O)$_n$—S—S—(2-pyridyl)<br><br>Orthopyridyl disufide | NANOCS PEG2-0011 MW = 5000<br>NANOCS PEG2-0012 MW = 2000<br>NANOCS PEG2-0014 MW = 10000 |
| *Exemplary Activated Branched PEGs Capable of Reacting With Thiol Groups* | |
| CH$_3$—O—(CH$_2$CH$_2$O)$_{n1}$—CH$_2$CH$_2$<br>                                    \<br>                                     N—CH$_2$—CH$_2$—N(maleimide)<br>                                    /<br>CH$_3$—O—(CH$_2$CH$_2$O)$_{n2}$—CH$_2$—CH$_2$<br><br>Maleimide | ENKEM A0002-1 Y-MAL-40K |
| CH$_3$—O—(CH$_2$CH$_2$O)$_{n1}$—CH$_2$<br>                                    \<br>CH$_3$—O—(CH$_2$CH$_2$O)$_{n2}$—CH<br>                                    /<br>H$_2$C—OCH$_2$CH$_2$CH$_2$NHC(=O)(CH$_2$)—N(maleimide)<br><br>Maleimide | SUNBRIGHT GL2-200GS MW = 20,000<br>SUNBRIGHT GL2-400GS MW = 40,000<br>SUNBRIGHT GL2-600GS MW = 60,000<br>SUNBRIGHT GL2-800GS MW = 80,000 |
| CH$_3$—O—(CH$_2$CH$_2$O)$_{n1}$—O—C(=O)—NH—CH$_2$CH$_2$CH$_2$CH$_2$—<br>CH$_3$—O—(CH$_2$CH$_2$O)$_{n1}$—O—C(=O)—HN—HC—CH$_2$—N(maleimide) | SUNBRIGHT LY-400MA MW = 40,000 |

PEGylation of a DRS polypeptide via amino group, with a PEG reagent bearing a maleimide group, iodoacetamide or vinyl sulfone is typically carried out in phosphate buffer 50-100 mM under mild conditions around pH 6.5-7.5 and at 4° C. for 4 to 24 hours.

In particular embodiments, PEG polymers may be attached to wild-type cysteine residues (i.e., cysteine residues present in the wild-type DRS sequence), or to "substituted" or "inserted" cysteine residues (e.g., cysteine residues introduced into the wild-type sequence by replacing a naturally-occurring residue with a cysteine, or by inserting a cysteine into the sequence without necessarily altering or removing the nearby residues, e.g., by appending an N- or C-terminal fusion protein;), so as to target the PEG to a desired location. In certain embodiments, certain of the wild-type DRS cysteines residues may be first substituted with another amino acid to prevent attachment of the PEG polymer to these wild-type cysteines (e.g., C76, C130), for example, to prevent the PEG molecule(s) from disrupting an otherwise desirable biological activity.

In other embodiments, the active functional group of a PEG polymer is conjugated to a carboxylic acid group of a DRS polypeptide, e.g., at the C-terminus. Suitable active functional groups to conjugate the PEG to the carboxylic acid group of the DRS polypeptide include, but are not limited to: primary amines, hydrazines, and hydrazides, e.g., carbazates, semicarbazates, thiocarbazates, and the like.

Exemplary activated PEGs capable of reacting with carboxylic acid groups of the DRS polypeptide include, e.g., those listed in Table D12.

TABLE D12

Exemplary Activated Linear PEGs Capable of Reacting With Carboxylate Groups

| Structure/Functionality | Abbreviation & Molecular Weight Range (in Da) |
|---|---|
| $CH_3\text{—}O\text{—}(CH_2CH_2)_n\text{—}CH_2CH_2CH_2NH_2$<br>Primary Amine | SUNBRIGHT MEPA-20H MW = 2,000<br>SUNBRIGHT MEPA-50H MW = 5,000<br>SUNBRIGHT MEPA-12T MW = 12,000<br>SUNBRIGHT MEPA-20T MW = 20,000<br>SUNBRIGHT MEPA-30T MW = 30,000<br>SUNBRIGHT MEPA-40T MW = 40,000 |
| $CH_3\text{—}O\text{—}(CH_2CH_2O)_n\text{—}CH_2CH_2NH_2$<br>Primary Amine | SUNBRIGHT MEPA-20H MW = 2,000<br>SUNBRIGHT ME-050EA MW = 5,000<br>SUNBRIGHT ME-100EA MW = 12,000<br>SUNBRIGHT ME-200EA MW = 20,000<br>SUNBRIGHT ME-300EA MW = 30,000<br>SUNBRIGHT ME-400EA MW = 40,000 |
| $CH_3\text{—}O\text{—}(CH_2CH_2O)_n\text{—}CH_2\overset{O}{\overset{\|}{C}}\text{—}NH\text{—}NH_2$ | JENKEM A3060 M-HZ MW = 5,000<br>JENKEM A3096 M-HZ MW = 10,000<br>JENKEM A3059 M-HZ MW = 20,000<br>JENKEM A3065 M-HZ MW = 30,000 |

PEGylation of a DRS polypeptide via carboxyl group, with a PEG reagent bearing a primary amine can be carried out in 50 mM Phosphate buffer (pH 7.2), in the presence of WSC(2 eq), 4C, for 10 to 24 hours. PEGylation of a DRS polypeptide via carboxyl group, with a PEG reagent bearing a hydrazide group can be carried out in the presence of N,N'-dicyclohexylcarbodiimide (DCC), or in presence of a water soluble coupling agent such as N-(-3-dimethylaminopropyl)-N'-ethylcarbodiimide hydrochloride (EDC) under mildly acid conditions (pH 6.0-6.5).

In further embodiments, the active functional group of a PEG polymer is conjugated to a hydroxyl group of a DRS polypeptide. Suitable active functional groups to conjugate the PEG to the hydroxyl group of the polypeptide, such as those found in a serine, threonine, or tyrosine residue of a polypeptide, include, but are not limited to: amines, hydrazides, epoxides, p-nitrophenylcarbonates, and isocyanates.

In various embodiments, the present invention provides PEGylated aspartyl-tRNA synthetase (DRS) polypeptides, comprising at least one PEG moiety covalently attached to an amino acid residue within about 5, about 10, about 15, about 20, or about 25 amino acid residues of the C-terminus, the N-terminus, or a solvent accessible surface amino acid of the DRS polypeptide or any combination thereof. In certain preferred embodiments, the PEG moieties comprise linear or branched PEG polymers.

In one embodiment, the present invention contemplates, in part, DRS polypeptides conjugated to a linear water soluble polymer, e.g., a PEG moiety. A wide variety of linear water soluble polymers, comprising functional groups suitable for conjugation to amino, thiol, hydroxyl, and carboxylic acid groups of a DRS polypeptide are commercially available in the art, e.g., from Nanocs Corporation, NOF Corporation, SunBio, Nektar, and Jenkem Technology. In particular embodiments, any commercially available water soluble polymer is suitable for conjugation to a DRS polypeptide. In various embodiments, a linear, water soluble polymer conjugated to a DRS polypeptide of the invention comprises a water soluble polymer moiety, optionally bound to a linker, and a covalent linkage that binds the DRS polypeptide to the remainder of the conjugate. A generalized structure (I) of a water soluble polymer conjugated to a DRS polypeptide of the invention has the following structure:

X-L-Y-DRS  (I)

wherein:
X is a water soluble polymer moiety;
L is an optional linker;
Y is a covalent linkage; and
DRS is a DRS polypeptide.

In another embodiment, the present invention, contemplates, in part, DRS polypeptides conjugated to branched chain water soluble polymers comprising two or more, e.g., two, three, four, five, six, seven, eight, nine, ten, or more water soluble moieties Illustrative multi-armed water soluble polymers having 2 arms, 3 arms, 4 arms, and 8 arms are known in the art, and are available commercially e.g., from Nanocs, NOF, Nektar, SunBio and Jenkem. In particular embodiments, any commercially available branched water soluble polymer, such as any branched chain PEG is suitable for PEGylation of a DRS polypeptide. Additional branched-water soluble polymers for use in forming a DRS polypeptide conjugate of the present invention can be prepared following techniques known to those skilled in the art. (See generally Pasut et al., (2004) Protein, peptide and non-peptide drug PEGylation for therapeutic application Expert Opinin. Ther. Patents 14(6) 859-894) and are also described in U.S. Patent Application Publication Nos. 20050009988, 20060194940, 20090234070, 20070031371, U.S. Pat. Nos. 6,664,331; 6,362,254; 6,437,025; 6,541,543; 6,664,331; 6,730,334; 6,774,180; 6,838,528; 7,030,278; 7,026,440; 7,053,150; 7,157,546; 7,223,803; 7,265,186; 7,419,600; 7,432,330; 7,432,331; 7,511,094; 7,528,202; 7,589,157; and PCT publication numbers WO2005000360, WO2005108463, WO2005107815, WO2005028539 and WO200605108463.

The branching moiety (i.e., central core molecule) can be an aliphatic hydrocarbon having a carbon chain length of at least three carbon atoms (i.e., propane, butane, pentane, hexane, heptane, octane, nonane, decane, and the like) or an appropriate amino acid backbone, e.g., lysine, arginine, histidine, glutamine, serine, threonine, asparagine, aspartic acid, glutamic acid, cysteine, and seleno cysteine.

Other suitable core molecules include polyols, which are then further functionalized. Such polyols include aliphatic polyols having from 1 to 10 carbon atoms and from 1 to 10 hydroxyl groups, including ethylene glycol, alkane diols, alkyl glycols, alkylidene alkyl diols, alkyl cycloalkane diols, 1,5-decalindiol, 4,8-bis(hydroxymethyl)tricyclodecane, cycloalkylidene diols, dihydroxyalkanes, trihydroxyalkanes, and the like. Cycloaliphatic polyols may also be employed, including straight chained or closed-ring sugars and sugar alcohols, such as mannitol, sorbitol, inositol, xylitol, quebrachitol, threitol, arabitol, erythritol, adonitol, ducitol, facose, ribose, arabinose, xylose, lyxose, rhamnose, galactose, glucose, fructose, sorbose, mannose, pyranose, altrose, talose, tagitose, pyranosides, sucrose, lactose, maltose, and the like. Additional aliphatic polyols include derivatives of glyceraldehyde, glucose, ribose, mannose, galactose, and related stereoisomers. Other core polyols that may be used include crown ether, cyclodextrins, dextrins and other carbohydrates such as starches and amylose. Typical polyols include glycerol, pentaerythritol, sorbitol, and trimethylolpropane. Other suitable cores include polyamines, and PEG moieties comprising multiple functional terminal end groups. In one embodiment, the branching moiety comprises a lysine residue.

Since the branched polymers of the invention combine at least two polymer arms in a single molecule, a polymer with sufficient molecular weight to impart beneficial properties to a DRS polypeptide can be formed using shorter, easier to prepare polymer chains. The branched polymers of the invention are preferably monofunctional, meaning the polymer molecule contains only a single reactive site for conjugation to a DRS polypeptide.

Although the carbon atoms of the branching moiety can have PEG polymers extending from any of the aforementioned carbons, in particular embodiments, the overall branched conjugate is symmetrical. For example, for a three carbon branching moiety, the PEG polymers extend from positions 1 and 3, with a site suitable for covalent attachment to a DRS polypeptide extending from the central carbon or the carbon at position 2. Similarly, for a five carbon branching moiety, the PEG polymers can extend from positions 1 and 5, with a site suitable for covalent attachment to a DRS polypeptide extending from position 3, or PEG polymers extending from positions 2 and 4, or, if a highly branched structure is desired, with PEG polymers extending from each of positions 1, 2, 4, and 5. In certain embodiments, the overall branched conjugate is asymmetrical, for example, in an embodiment comprising a four carbon branching moiety. For example, for a four carbon branching moiety, the PEG polymers extend from positions 1, 2, and 3, with a site suitable for covalent attachment to a DRS polypeptide extending from the central carbon or the carbon at position 4.

A DRS polypeptide comprising branched chain water soluble polymer conjugate of the invention will typically comprise at least two water soluble moieties, each optionally bound to a linker, covalently attached to a branching moiety, also optionally bound to a linker, covalently attached to a covalent linkage that binds the DRS polypeptide to the remainder of the conjugate. A generalized structure (II) of the branched DRS polypeptide polymer conjugates of the invention is shown below:

(X-L$_1$)$_m$-B-L$_2$-Y-DRS    (II)

wherein:
X is an independently selected water soluble polymer moiety, for each m;
L$_1$ and L$_2$ are independently selected optional linkers, wherein L$_1$ is also independently selected for each m;
m is 2, 3, 4, 5, 6, 7, 8, 9, or 10, preferably 2 to about 5 (e.g., 2, 3, 4, or 5);
B is a branching moiety;
Y is a covalent linkage between the DRS polypeptide and the remainder of the conjugate; and
DRS is a DRS polypeptide as disclosed elsewhere herein.

In certain embodiments the branched DRS polypeptide polymer conjugates of the invention may have a generalized formula (IIA)

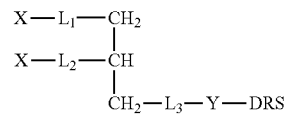

wherein:
X is an independently selected water soluble polymer moiety;
L$_1$, L$_2$ and L$_3$ are independently selected optional linkers;
Y is a covalent linkage between the DRS polypeptide and the remainder of the conjugate; and
DRS refers to a DRS polypeptide as disclosed herein.

In certain embodiments the branched DRS polypeptide polymer conjugates of the invention may have a generalized formula (IIB):

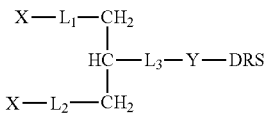

wherein:
X is an independently selected water soluble polymer moiety;
L$_1$, L$_2$ and L$_3$ are independently selected optional linkers;
Y is a covalent linkage between the DRS polypeptide and the remainder of the conjugate; and DRS refers to a DRS polypeptide as disclosed herein.

In certain embodiments the branched DRS polypeptide polymer conjugates of the invention may have a generalized formula (IIC):

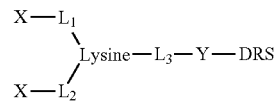

wherein:
X is an independently selected water soluble polymer moiety;
L$_1$, L$_2$ and L$_3$ are independently selected optional linkers, and wherein the linkers connecting the lysine residue to the water soluble polymer moiety are connected via the amino groups of the lysine molecule, and the linker connecting the lysine molecule to the DRS polypeptide is attached via the C-terminal carboxylate group of the lysine molecule;
Y is a covalent linkage between the DRS polypeptide and the remainder of the conjugate; and DRS refers to a DRS polypeptide as disclosed herein.

In certain embodiments the branched DRS polypeptide polymer conjugates of the invention may have a generalized formula (IID):

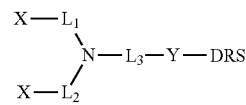

wherein:

X is an independently selected water soluble polymer moiety;

$L_1$, $L_2$ and $L_3$ are independently selected optional linkers;

Y is a covalent linkage between the DRS polypeptide and the remainder of the conjugate; and DRS refers to a DRS polypeptide as disclosed herein.

In different embodiments of any of the generalized structures (I), (II), (IIA), (IIB), (IIC) or (IID) each water soluble polymer moiety, X, is independently selected and is represented by the formula $R_1$—$(CH_2CH_2O)_n$ or $R_1$—$(OCH_2CH_2)_n$; wherein $R_1$ is selected from alkyl, alkoxy, and aryl groups.

In different embodiments n is from about 1 to about 1,200, from about 10 to about 1,000, from about 20 to about 800, from about 50 to about 600, or from about 100 to about 500. In one embodiment, n is about 5, about 10, about 20, about 50, about 100, about 200, about 300, about 400, about 500, about 600, about 700, about 800, about 900, about 1,000, about 1,100, about 1,200, about 1,300, about 1,400, or about 1,500 or any intervening integer. In some embodiments, n is from about 200 to about 800.

Typically, branched PEGylated DRS polypeptides of general formula (II) comprise two or more, three or more, four, or more, or five or more of the same PEG polymer. That is to say, the polymer arms are each PEG polymers composed of the same type of subunits, which have similar geometries and similar molecular weights. Typically in the PEGylated DRS polypeptides of general formula (I), (II), (IIA), (IIB), (IIC) or (IID), each PEG moiety, X, may be end-capped, having at least one terminus capped with a relatively inert group, $R_1$. Suitable inert groups for $R_1$ include, but are not limited to alkyl groups, alkoxy groups, aryl groups, and sugars, such as, for example glucose, galactose, fructose, or sucrose. In particular embodiments, $R_1$ is an alkoxy group including, but not limited to methoxy, ethoxy, propoxy, butoxy, pentoxy, hexoxy, or benzyloxy. In some embodiments, $R_1$ is methoxy, and the PEG moiety is a methoxy-PEG or mPEG.

Those of ordinary skill in the art will recognize that the foregoing discussion describing linear and branched chain PEGs for use in forming a DRS polypeptide conjugate is by no means exhaustive and is merely illustrative, and that all water soluble polymers, and PEG structures having the qualities described herein are contemplated. Moreover, based on the instant invention, one of ordinary skill in the art can readily determine the appropriate size and optimal structure of alternative PEGylated DRS polypeptides using routine experimentation, for example, by obtaining the clearance profile for each conjugate by administering the conjugate to a patient and taking periodic blood and/or urine samples, as described herein. Once a series of clearance profiles has been obtained for each tested conjugate, a conjugate or mixture of conjugates, having the desired clearance profile(s) can be determined Linkers In particular embodiments, the conjugates of the invention comprise one or more linkers, e.g., L, $L_1$, $L_2$. In a linear PEGylated DRS conjugate, linkers separate the PEG polymers from the covalent linkage to a DRS polypeptide. In a branched PEGylated DRS conjugate, linkers separate the PEG polymers from the branch moiety and/or the branch moiety from the covalent bond that links the conjugate to a DRS polypeptide of the invention. Each linker can be independently selected. Each linker in a branched conjugate can be the same linker or each linker can be different from each other linker. In certain embodiments any one or more of the linkers are optional.

The particular linkage between the DRS polypeptide and the water-soluble polymer or branch moiety depends on a number of factors, including the desired stability of the linkage, its hydrophobicity, the particular linkage chemistry employed, and impact on the aqueous solubility, and aggregation state of the PEGylated DRS polypeptide. Exemplary linkages are hydrolytically stable, and water soluble, representative suitable linker can comprise any combination of amide, a urethane (also known as carbamate), amine, thioether (also known as sulfide), or urea (also known as carbamide) groups.

There are many commercially available examples of suitable water-soluble linker moieties and/or these can be prepared following techniques known to those skilled in the art. Certain illustrative exemplary linker moieties are described below. The corresponding activated intermediates are provided in Tables D10-D12.

Suitable linkers can have an overall chain length of about 1-100 atoms, 1-80 atoms, 1-60 atoms, 1-40 atoms, 1-30 atoms, 1-20 atoms, or 1, 2, 3, 4, 5, 6, 7, 8, 9, 10, 11, 12, 13, 14, 15, 16, 17, 18, 19, or 20 atoms, wherein the atoms in the chain comprise C, S, N, P, and O. In certain embodiments, a linker is optional, e.g., a PEG conjugated polypeptide does not comprises a linker. In further embodiments a PEG comprising a functional group is directly conjugated to a polypeptide.

Illustrative examples of linkers or linkages useful in particular embodiments of the present invention include, but are not limited to one or more of the following: —O—, —NH—, —S—, —C(O)—, C(O)—NH, NH—C(O)—NH, O—C(O)—NH, —C(S)—, —$CH_2$—, —$CH_2$—$CH_2$—, —$CH_2$—$CH_2$—$CH_2$—, —$CH_2$—$CH_2$—$CH_2$—$CH_2$—, —O—$CH_2$—, —$CH_2$—O—, —O—$CH_2$—$CH_2$—, —$CH_2$—O—$CH_2$—, —$CH_2$—$CH_2$—O—, —O—$CH_2$—$CH_2$—$CH_2$—, —$CH_2$—O—$CH_2$—$CH_2$—, —$CH_2$—$CH_2$—O—$CH_2$—, —$CH_2$—$CH_2$—$CH_2$—O—, —O—$CH_2$—$CH_2$—$CH_2$—$CH_2$—, —$CH_2$—O—$CH_2$—$CH_2$—$CH_2$—, —$CH_2$—$CH_2$—O—$CH_2$—$CH_2$—, —$CH_2$—$CH_2$—$CH_2$—O—$CH_2$—, —$CH_2$—$CH_2$—$CH_2$—$CH_2$—O—, —C(O)—NH—$CH_2$—, —C(O)—NH—$CH_2$—$CH_2$—, —$CH_2$—C(O)—NH—$CH_2$—, —$CH_2$—$CH_2$—C(O)—NH—, —C(O)—NH—$CH_2$—$CH_2$—$CH_2$—, —$CH_2$—C(O)—NH—$CH_2$—$CH_2$—, —$CH_2$—$CH_2$—C(O)—NH—$CH_2$—, —$CH_2$—$CH_2$—$CH_2$—C(O)—NH—, —C(O)—NH—$CH_2$—$CH_2$—$CH_2$—$CH_2$—, —$CH_2$—C(O)—NH—$CH_2$—$CH_2$—$CH_2$—, —$CH_2$—$CH_2$—C(O)—NH—$CH_2$—$CH_2$—, —$CH_2$—$CH_2$—$CH_2$—C(O)—NH—$CH_2$—, —$CH_2$—$CH_2$—$CH_2$—$CH_2$—C(O)—NH—NH—C(O)—$CH_2$—, —$CH_2$—NH—C(O)—$CH_2$—, —$CH_2$—$CH_2$—NH—C(O)—$CH_2$—, —NH—C(O)—$CH_2$—$CH_2$—, —$CH_2$—NH—C(O)—$CH_2$—$CH_2$, —$CH_2$—$CH_2$—NH—C(O)—$CH_2$—$CH_2$, —C(O)—NH—$CH_2$—, —C(O)—NH—$CH_2$—$CH_2$—, —O—C(O)—NH—$CH_2$—, —O—C(O)—NH—$CH_2$—$CH_2$—, —NH—$CH_2$—, —NH—$CH_2$—$CH_2$—, —$CH_2$—NH—$CH_2$—, —$CH_2$—$CH_2$—NH—$CH_2$—, —C(O)—$CH_2$—, —C(O)—$CH_2$—$CH_2$—, —$CH_2$—C(O)—$CH_2$—, —$CH_2$—$CH_2$—C(O)—$CH_2$—, —$CH_2$—$CH_2$—C(O)—$CH_2$—$CH_2$—, —$CH_2$—$CH_2$—C(O)—, —$CH_2$—$CH_2$—$CH_2$—C(O)—NH—$CH_2$—$CH_2$—NH—, —$CH_2$—$CH_2$—$CH_2$—C(O)—NH—$CH_2$—$CH_2$—NH—C(O)—, —$CH_2$—$CH_2$—$CH_2$—C(O)—NH—$CH_2$—$CH_2$—NH—C(O)—$CH_2$—, bivalent cycloalkyl group, —N($R^6$)—, $R^6$ is H or an organic radical selected from the group consisting of alkyl, substituted alkyl, alkenyl, substituted alkenyl, alkynyl, substituted alkynyl, aryl and substituted aryl. Additionally, any of the above linker moieties may further include an ethylene oxide oligomer chain comprising 1 to 20 ethylene oxide monomer units [i.e., —(CH$_2$CH$_2$O)$_{1-20}$]— That is, the ethylene oxide oligomer chain can occur before or after the linker, and optionally in between any two atoms of a linker moiety comprised of two or more atoms. Also, the oligomer chain would not be considered part of the linker moiety if the oligomer is adjacent to a polymer segment and merely represent an extension of the polymer segment.

Each linker moiety may be hydrolytically stable or may include a releasable linkage such as a physiologically hydrolyzable or enzymatically degradable linkage.

Releasable Linkers

In particular embodiments, the PEG and related polymer derivatives of the invention are capable of imparting improved water solubility, increased size, a slower rate of kidney clearance, and reduced immunogenicity to a conjugate formed by covalent attachment thereto, while also providing for controllable hydrolytic release of a DRS polypeptide into an aqueous environment—by virtue of the design of the linkages provided herein. The invention can be used to enhance the solubility and blood circulation lifetime of DRS polypeptides in the bloodstream, while also delivering a DRS polypeptide into the bloodstream that, subsequent to hydrolysis, is substantially free of PEG. The invention is especially useful in those cases where DRS polypeptides, when permanently conjugated to PEG, demonstrate reduced activity. By using the linkages as provided herein, such DRS polypeptides can maintain their therapeutic activity when in conjugated form.

Representative, but non-limiting, examples of releasable linkages include physiologically cleavable bonds, hydrolyzable bonds, and enzymatically degradable linkages. In particular embodiments, a releasable linkage has a half life at pH 7.4, 25° C., e.g., a physiological pH, human body temperature, of about 30 min., about 1 hour, about 2 hour, about 3 hours, about 4 hours, about 5 hours, about 6 hours, about 12 hours, about 18 hours, about 24 hours, about 36 hours, about 48 hours, about 72 hours, or about 96 hours or more or any intervening half-life. One having skill in the art would appreciate that the half life of a PEGylated DRS polypeptide can be finely tailored by using a particular releasable linkage.

Appropriate hydrolytically unstable or weak linkages include, but are not limited to: carboxylate ester, phosphate ester, anhydride, acetal, ketal, acyloxyalkyl ether, imine, orthoester, thio ester, thiol ester, carbonate, and hydrazone, peptides and oligonucleotides.

Additional illustrative embodiments of hydrolytically unstable or weak linkages include, but are not limited to: —O$_2$C—(CH$_2$)$_b$—O—, where b is from 1 to 5, —O—(CH$_2$)$_b$—CO$_2$—(CH$_2$)$_c$—, where b is from 1 to 5 and c is from 2-5, —O—(CH$_2$)$_b$—CO$_2$—(CH$_2$)$_c$—O—, where b is from 1 to 5 and c is from 2-5, —(CH$_2$)$_b$—OPO$_3$—(CH$_2$)$_{b'}$—, where b is 1-5 and b' is 1-5, —C(O)—(NH—CHR—CO)$_a$—NH—CHR—, where a is 2 to 20 and R is a substituent found on an α-amino acid, —O—(CH$_2$)$_b$—CO$_2$—CHCH$_2$—CH$_2$—, where b is from 1-5, —O—C$_6$H$_4$—CH=N—(CH$_2$)$_b$—O—, where b is from 1-5, and —O—(CH$_2$)$_b$—CH$_2$—CH=N—(CH$_2$)$_b$—O—, where each b is independently from 1-5.

Other illustrative examples of releasable linkers can be benzyl elimination-based linkers, trialkyl lock-based linkers (or trialkyl lock lactonization based), bicine-based linkers, and acid labile linkers. Among the acid labile linkers can be disulfide bond, hydrazone-containing linkers and thiopropionate-containing linkers.

Enzymatically degradable linkages suitable for use in particular embodiments of the present invention include, but are not limited to: an amino acid sequence cleaved by a serine protease such as thrombin, chymotrypsin, trypsin, elastase, kallikrein, or substilisin. Illustrative examples of thrombin-cleavable amino acid sequences include, but are not limited to: -Gly-Arg-Gly-Asp- (SEQ ID NO:46), -Gly-Gly-Arg-, -Gly-Arg-Gly-Asp-Asn-Pro- (SEQ ID NO:47), -Gly-Arg-Gly-Asp-Ser- (SEQ ID NO:48), -Gly-Arg-Gly-Asp-Ser-Pro-Lys- (SEQ ID NO:49), -Gly-Pro-Arg-, -Val-Pro-Arg-, and -Phe-Val-Arg-. Illustrative examples of elastase-cleavable amino acid sequences include, but are not limited to: -Ala -Ala-Ala-, -Ala-Ala-Pro-Val- (SEQ ID NO:50), -Ala-Ala-Pro-Leu- (SEQ ID NO:51), -Ala-Ala-Pro-Phe - (SEQ ID NO:52), -Ala-Ala-Pro-Ala- (SEQ ID NO:53), and -Ala-Tyr-Leu-Val- (SEQ ID NO:54).

Enzymatically degradable linkages suitable for use in particular embodiments of the present invention also include amino acid sequences that can be cleaved by a matrix metalloproteinase such as collagenase, stromelysin, and gelatinase. Illustrative examples of matrix metalloproteinase-cleavable amino acid sequences include, but are not limited to: -Gly-Pro-Y-Gly-Pro-Z- (SEQ ID NO:55), -Gly-Pro -, Leu-Gly-Pro-Z- (SEQ ID NO:56), -Gly-Pro-Ile-Gly-Pro-Z- (SEQ ID NO:57), and -Ala-Pro-Gly-Leu-Z - (SEQ ID NO:58), where Y and Z are amino acids. Illustrative examples of collagenase-cleavable amino acid sequences include, but are not limited to: -Pro-Leu-Gly-Pro-D-Arg-Z- (SEQ ID NO:59), -Pro-Leu -Gly-Leu-Leu-Gly-Z-(SEQ ID NO:60), -Pro-Gln-Gly-Ile-Ala-Gly-Trp- (SEQ ID NO:61), -Pro-Leu-Gly -Cys(Me)-His- (SEQ ID NO:62), -Pro-Leu-Gly-Leu-Tyr-Ala- (SEQ ID NO:63), -Pro-Leu-Ala-Leu-Trp -Ala-Arg- (SEQ ID NO:64), and -Pro-Leu-Ala-Tyr-Trp-Ala-Arg- (SEQ ID NO:65), where Z is an amino acid. An illustrative example of a stromelysin-cleavable amino acid sequence is -Pro-Tyr-Ala-Tyr-Tyr -Met-Arg- (SEQ ID NO:66); and an example of a gelatinase-cleavable amino acid sequence is -Pro-Leu -Gly-Met-Tyr-Ser-Arg- (SEQ ID NO:67).

Enzymatically degradable linkages suitable for use in particular embodiments of the present invention also include amino acid sequences that can be cleaved by an angiotensin converting enzyme, such as, for example, -Asp-Lys-Pro-, -Gly-Asp-Lys-Pro- (SEQ ID NO:68), and -Gly-Ser-Asp-Lys-Pro - (SEQ ID NO:69).

Enzymatically degradable linkages suitable for use in particular embodiments of the present invention also include amino acid sequences that can be degraded by cathepsin B, such as, for example, Val-Cit, Ala-Leu-Ala-Leu (SEQ ID NO:70), Gly-Phe-Leu-Gly (SEQ ID NO:71) and Phe-Lys.

Examples of hydrolytically stable linkages include, but are not limited to, the following: succinimide, propionic acid, carboxymethylate linkages, ethers, carbamates, amides, amines, carbamides, imides, aliphatic C—C bonds, thio ethers, thiocarbamates, thiocarbamides, and the like. Generally, a hydrolytically stable linkage is one that exhibits a rate of hydrolysis of less than about 1-2% per day under physiological conditions.

In certain embodiments, the half-life of the PEGylated DRS polypeptide conjugate is regulated by incorporating one or more linkers of various stability into the conjugate. For example, if a relatively stable PEGylated DRS conjugate is desired, the conjugate can comprise one or more linkers that are hydrolytically stable or resistant to degradation.

Hydrolytically stable linkers are known in the art and are described elsewhere herein, and generally result in a rate of hydrolysis of about 0.5%, about 1%, about 2%, about 3%, about 4%, or about 5% per day. Illustrative examples of hydrolytically stable linkers that can be used in PEGylated DRS conjugates of the invention include, but are not limited to: succinimide, propionic acid, carboxymethylate linkages, ethers, carbamates, amides, amines, carbamides, imides, aliphatic C—C bonds, thio ethers, thiocarbamates, thiocarbamides, and the like.

In other embodiments, a PEGylated DRS conjugate comprises one or more releasable linkages that result in a shorter half-life and more rapid clearance of the conjugate. For example, PEG can be prepared with ester linkages in the polymer backbone that are subject to hydrolysis. This hydrolysis results in cleavage of the polymer into fragments of lower molecular weight. Other hydrolytically degradable linkages are known in the art and described elsewhere herein, and include carbonate linkages; imine linkages resulting, for example, from reaction of an amine and an aldehyde; phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; and ortho ester linkages that are, for example, formed by reaction between a formate and an alcohol. Other suitable releasable linkers for use in branched conjugates of the invention include enzymatically degradable linkages and discussed elsewhere herein.

Such optional features of the conjugate, i.e., the introduction of one or more degradable linkages into the polymer chain, may provide for additional control over the final desired pharmacological properties of the conjugate upon administration. For example, a large and relatively inert PEGylated DRS polypeptide conjugate (i.e., having one or more high molecular weight PEG chains attached thereto, for example, one or more PEG chains having a molecular weight greater than about 10,000) may be administered, which is then hydrolyzed in vivo to generate a bioactive DRS polypeptide conjugate possessing a portion of the original PEG chain or lacking PEG entirely. In this way, the properties of the PEGylated DRS polypeptide conjugate can be more effectively tailored to balance the bioactivity and circulating half-life of the conjugate over time.

Covalent Linkages ("Y")

In forming the PEGylated DRS polypeptide conjugates of the invention, the branching moiety or a linker comprises a functional group that forms a covalent bond or linkage, Y, with a functional group on a DRS polypeptide, thereby forming a conjugate. Exemplary functional groups of linkers and DRS polypeptides are disclosed elsewhere herein, supra. Illustrative examples of covalent linkages, Y, in any of the PEGylated DRS polypeptide conjugates of the invention include, but are not limited to: amide, secondary amine, carbonyl, carboxylate, carbamate, carbamide, ester, formyl, acyl, thiocarbonyl, thio ester, thioacetate, thioformate, thio ether, alkoxyl, phosphoryl, phosphonate, phosphinate, amino, amido, amidine, imine, cyano, nitro, azido, disulfide, sulthydryl, sulfate, sulfonate, sulfamoyl, sulfonamido, sulfonyl, heterocyclyl, aralkyl, aromatic moiety, hydrazone, heteroaromatic moiety, imino, sulfamoyl, sulfonate, silyl, ether, or alkylthio.

For example, a reaction between a PEG comprising a succinimidyl ester functional group and a DRS polypeptide comprising an amino group results in an amide linkage; a reaction between a PEG comprising a oxycarbonylimidizaole functional group and a DRS polypeptide comprising an amino group results in an carbamate linkage; a reaction between a PEG comprising a p-nitrophenyl carbonate functional group and a DRS polypeptide comprising an amino group results in an carbamate linkage; a reaction between a PEG comprising a trichlorophenyl carbonate functional group and a DRS polypeptide comprising an amino group results in an carbamate linkage; a reaction between a PEG comprising a thio ester functional group and a DRS polypeptide comprising an n-terminal amino group results in an amide linkage; a reaction between a PEG comprising a proprionaldehyde functional group and a DRS polypeptide comprising an amino group results in a secondary amine linkage; a reaction between a PEG comprising a butyraldehyde functional group and a DRS polypeptide comprising an amino group results in a secondary amine linkage; a reaction between a PEG comprising a acetal functional group and a DRS polypeptide comprising an amino group results in a secondary amine linkage; a reaction between a PEG comprising a piperidone functional group and a DRS polypeptide comprising an amino group results in a secondary amine linkage; a reaction between a PEG comprising a methylketone functional group and a DRS polypeptide comprising an amino group results in a secondary amine linkage; a reaction between a PEG comprising a tresylate functional group and a DRS polypeptide comprising an amino group results in a secondary amine linkage; a reaction between a PEG comprising a maleimide functional group and a DRS polypeptide comprising an amino group results in a secondary amine linkage; a reaction between a PEG comprising a aldehyde functional group and a DRS polypeptide comprising an amino group results in a secondary amine linkage; and a reaction between a PEG comprising a hydrazine functional group and a DRS polypeptide comprising an carboxylic acid group results in a secondary amine linkage.

In another non-limiting example, a reaction between a PEG comprising a maleimide functional group and a DRS polypeptide comprising a thiol group results in a thio ether linkage; a reaction between a PEG comprising a vinyl sulfone functional group and a DRS polypeptide comprising a thiol group results in a thio ether linkage; a reaction between a PEG comprising a thiol functional group and a DRS polypeptide comprising a thiol group results in a di-sulfide linkage; a reaction between a PEG comprising a orthopyridyl disulfide functional group and a DRS polypeptide comprising a thiol group results in a di-sulfide linkage; and a reaction between a PEG comprising an iodoacetamide functional group and a DRS polypeptide comprising a thiol group results in a thio ether linkage.

The particular coupling chemistry employed will depend upon the structure of the biologically active agent, the potential presence of multiple functional groups within the biologically active molecule, the need for protection/deprotection steps, chemical stability of the molecule, and the like, and will be readily determined by one skilled in the art. Illustrative linking chemistry useful for preparing the branched polymer conjugates of the invention can be found, for example, in Wong, S. H., (1991), "Chemistry of Protein Conjugation and Crosslinking", CRC Press, Boca Raton, Fla. and in Brinkley, M. (1992) "A Brief Survey of Methods for Preparing Protein Conjugates with Dyes, Haptens, and Crosslinking Reagents", in Bioconjug. Chem., 3, 2013.

More specific structural embodiments of the conjugates of the invention will now be described, all of which are intended to be encompassed by the structure above. The specific structures shown below are presented as exemplary structures only, and are not intended to limit the scope of the invention.

In one embodiment, a PEGylated DRS polypeptide comprises any of the structures 1-5:

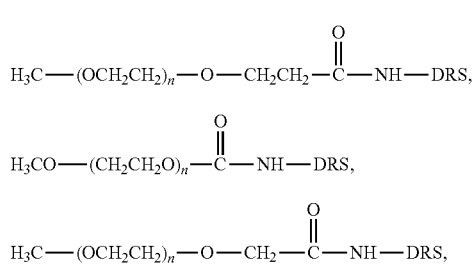

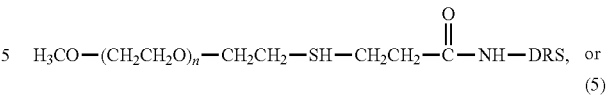

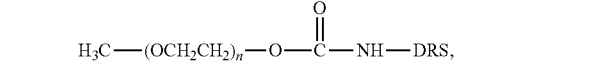

wherein "NH" of NH-DRS refers to an amino group of a DRS polypeptide and n is any integer from 1 to 800.

In another embodiment, a PEGylated DRS polypeptide comprises the structure:

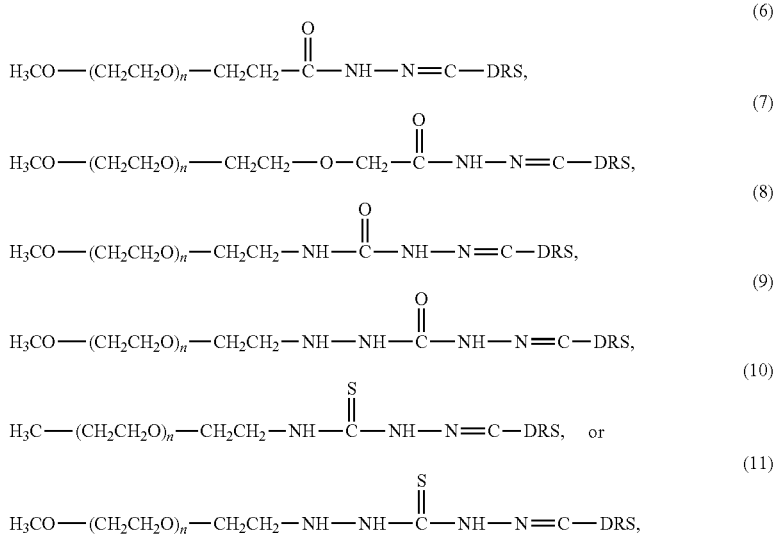

wherein "C" of C-DRS refers to carboxyl group of a DRS polypeptide and n is any integer from 1 to 800.

In another embodiment, a PEGylated DRS polypeptide comprises the structure:

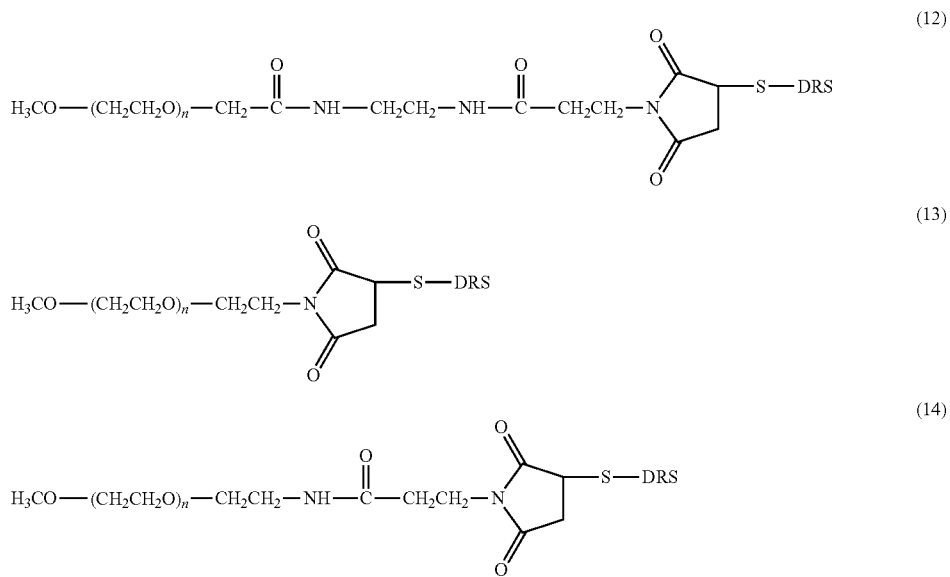

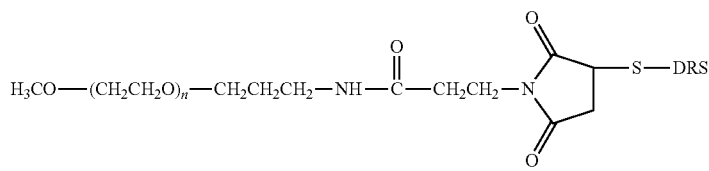
(15)
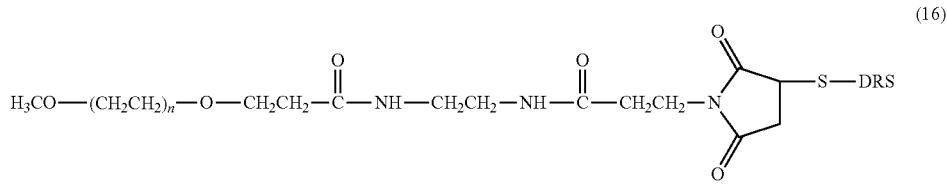
(16)
(17)
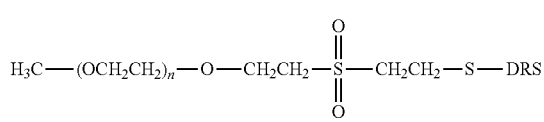
(17)
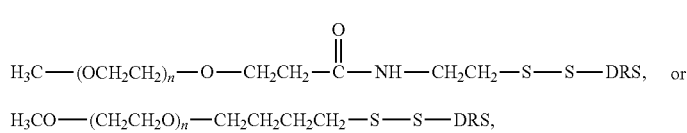
(18)
H₃CO—(CH₂CH₂O)$_n$—CH₂CH₂CH₂CH₂—S—S—DRS,
(19)
wherein "S" of S-DRS refers to thiol group of a DRS polypeptide and n is any integer from 1 to 800.
In one embodiment, a branched PEGylated DRS polypeptide of the invention comprises the structure:
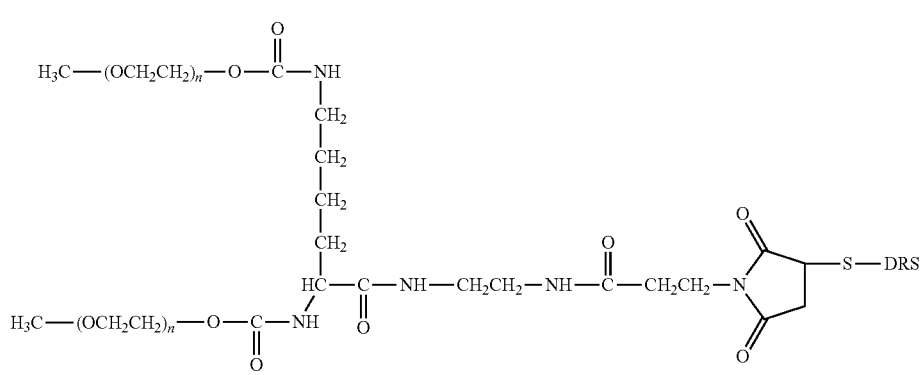
(20)
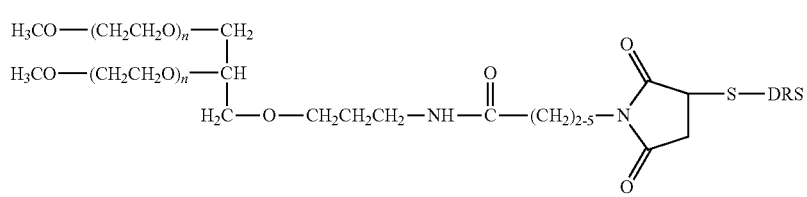
(21)
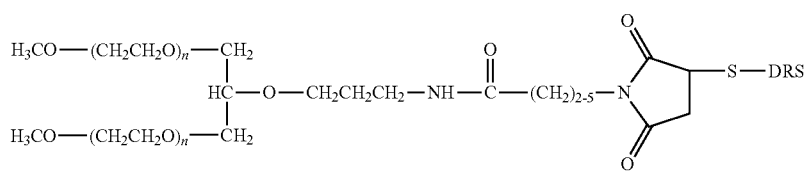
(22)

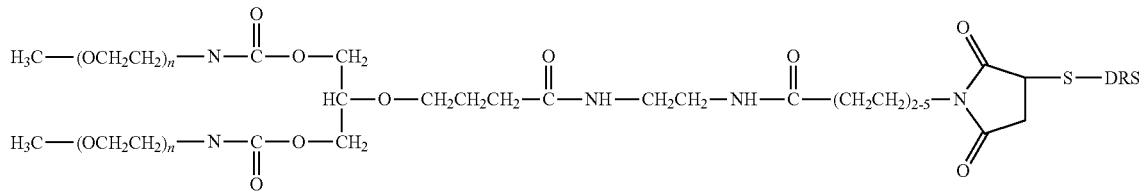

(23)

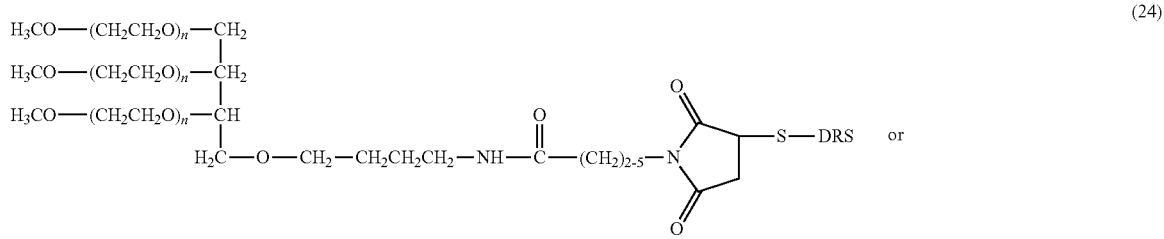

(24)

(25)

wherein "S" of S-DRS refers to thiol group of a DRS polypeptide and n is independently selected any integer from 1 to 800.

In different embodiments of any of the disclosed DRS conjugates, the DRS polypeptide is a full-length DRS polypeptide, or a truncated, or splice variant thereof, (see Sequence Listing or Tables) which comprises a linear or branched chain polyethylene glycol (mPEG) derivative of general formula (I), (II), (IIA), (IIB), (IIC) or (IID) of about 1,000 to 60,000 Daltons. In one aspect of any of these DRS conjugates, the conjugated polymer has a structure selected from any of compounds (1) to (25).

In some embodiments, the DRS polypeptide differs from any DRS polypeptides described herein (see Sequence Listing or Tables) by at least one amino acid selected from C76S and C130S. In some embodiments the conjugate comprises a linear or branched chain polyethylene glycol (mPEG) derivative of general formula (I), (II), (IIA), (IIB), (IIC) or (IID) of about 1,000 to 60,000 Daltons that is covalently attached to the DRS polypeptide via a thio ether linkage. In one aspect of any of these DRS conjugates, the conjugated polymer has a structure selected from any of compounds (12) to (25). In one aspect the conjugated DRS polypeptide is coupled via amino acid C130

In some embodiments, the present invention provides PEGylated aspartyl-tRNA synthetase (DRS) polypeptides, comprising the sequence set forth in SEQ ID NO: 3 (1-154), and which differs from SEQ ID NO:3 by at least the mutation C76S, and further comprises a maleimide monomethoxy polyethylene glycol (mPEG) derivative of general formula (I) having a molecular weight of about 1,000 to 60,000 Daltons that is covalently attached via a thio ether linkage to C130.

In some embodiments, the present invention provides PEGylated aspartyl-tRNA synthetase (DRS) polypeptides, comprising the sequence set forth in SEQ ID NO:4 (1-171), and which differs from SEQ ID NO:4 by at least the mutation C76S, and further comprises a maleimide monomethoxy polyethylene glycol (mPEG) derivative of general formula (I) having a molecular weight of about 1,000 to 60,000 Daltons that is covalently attached via a thio ether linkage to C130.

In some embodiments, the present invention provides PEGylated aspartyl-tRNA synthetase (DRS) polypeptides, comprising the sequence set forth in SEQ ID NO:5 (1-174), and which differs from SEQ ID NO:5 by at least the mutation C76S, and further comprises a maleimide monomethoxy polyethylene glycol (mPEG) derivative of general formula (I) having a molecular weight of about 1,000 to 60,000 Daltons that is covalently attached via a thio ether linkage to C130.

In some embodiments, the present invention provides PEGylated aspartyl-tRNA synthetase (DRS) polypeptides, comprising the sequence set forth in SEQ ID NO:6 (1-182), and which differs from SEQ ID NO:6 by at least the mutation C76S, and further comprises a maleimide monomethoxy polyethylene glycol (mPEG) derivative of general formula (I) having a molecular weight of about 1,000 to 60,000 Daltons that is covalently attached via a thio ether linkage to C130.

In some embodiments, the present invention provides PEGylated aspartyl-tRNA synthetase (DRS) polypeptides, comprising the sequence set forth in SEQ ID NO:7 (1-184), and which differs from SEQ ID NO:7 by at least the mutation C76S, and further comprises a maleimide monomethoxy polyethylene glycol (mPEG) derivative of general formula (I) having a molecular weight of about 1,000 to 60,000 Daltons that is covalently attached via a thio ether linkage to C130.

In some embodiments, the present invention provides PEGylated aspartyl-tRNA synthetase (DRS) polypeptides, comprising the sequence set forth in SEQ ID NO:11 (23-154), and which differs from SEQ ID NO:11 by at least the mutation C76S, and further comprises a maleimide monomethoxy polyethylene glycol (mPEG) derivative of general formula (I) having a molecular weight of about 1,000 to 60,000 Daltons that is covalently attached via a thio ether linkage to C130.

Methods for Use

Embodiments of the present invention relate to the discovery that aspartyl-tRNA synthetase (DRS) polypeptides, and fragments and variants thereof, with altered cysteine content offer improved methods of modulating Toll like receptors (TLRs) in a variety of useful ways, both in vitro and in vivo. The compositions of the invention may thus be useful as immunomodulators for treating anti- or pro-inflammatory indications by modulating the cells that mediate, either directly or indirectly, autoimmune and/or inflammatory disease, conditions and disorders. The utility of the compositions of the invention as immunomodulators can be monitored using any of a number of known and available techniques in the art including, for example, migration assays (e.g., using leukocytes or lymphocytes), cytokine production assays, or cell viability assays (e.g., using B-cells, T-cells, monocytes or NK cells).

"Inflammation" refers generally to the biological response of tissues to harmful stimuli, such as pathogens, damaged cells (e.g., wounds), and irritants. The term "inflammatory response" refers to the specific mechanisms by which inflammation is achieved and regulated, including, merely by way of illustration, immune cell activation or migration, cytokine production, vasodilation, including kinin release, fibrinolysis, and coagulation, among others described herein and known in the art. Ideally, inflammation is a protective attempt by the body to both remove the injurious stimuli and initiate the healing process for the affected tissue or tissues. In the absence of inflammation, wounds and infections would never heal, creating a situation in which progressive destruction of the tissue would threaten survival. On the other hand, excessive or chronic inflammation may associate with a variety of diseases, such as hay fever, atherosclerosis, and rheumatoid arthritis, among others described herein and known in the art.

Clinical signs of chronic inflammation are dependent upon duration of the illness, inflammatory lesions, cause and anatomical area affected, (see, e.g., Kumar et al., Robbins Basic Pathology-8 ft Ed., 2009 Elsevier, London; Miller, L M, Pathology Lecture Notes, Atlantic Veterinary College, Charlottetown, PEI, Canada). Chronic inflammation is associated with a variety of pathological conditions or diseases, including, for example, allergies, Alzheimer's disease, anemia, aortic valve stenosis, arthritis such as rheumatoid arthritis and osteoarthritis, cancer, congestive heart failure, fibromyalgia, fibrosis, heart attack, kidney failure, lupus, gout and gout flares, pancreatitis, hepatitis, stroke, surgical complications, acetaminophen-induced liver toxicity, inflammatory lung disease, inflammatory bowel diseases including Crohn's disease (CD), necrotizing enterocolitis, and ulcerative colitis (UC), atherosclerosis, neurological disorders, (neuro)inflammatory disorders, diabetes, metabolic disorders, obesity, graft versus host disease, myositis, emphysema/COPD and psoriasis, among others described herein and known in the art. Hence, DRS polypeptide compositions may be used to treat or manage chronic inflammation, modulate any of one or more of the individual chronic inflammatory responses, or treat any one or more diseases or conditions associated with chronic inflammation.

Certain specific inflammatory responses include cytokine production and activity, and related pathways. For instance, certain exemplary embodiments relate to modulating cell-signaling through nuclear factor-kB (NF-kB), such as by increasing the downstream activities of this transcription factor. In certain instances, increases in NF-kB activity can lead to increases in cytokine signaling or activity, such as pro-inflammatory cytokines (e.g., TNFalpha or beta), and anti-inflammatory cytokines (e.g., IL-10).

Criteria for assessing the signs and symptoms of inflammatory and other conditions, including for purposes of making differential diagnosis and also for monitoring treatments such as determining whether a therapeutically effective dose has been administered in the course of treatment, e.g., by determining improvement according to accepted clinical criteria, will be apparent to those skilled in the art and are exemplified by the teachings of e.g., Berkow et al., eds., The Merck Manual, 16th edition, Merck and Co., Rahway, N.J., 1992; Goodman et al., eds., Goodman and Gilman's The Pharmacological Basis of Therapeutics, 10th edition, Pergamon Press, Inc., Elmsford, N.Y., (2001); Avery's Drug Treatment: Principles and Practice of Clinical Pharmacology and Therapeutics, 3rd edition, ADIS Press, Ltd., Williams and Wilkins, Baltimore, Md. (1987); Ebadi, Pharmacology, Little, Brown and Co., Boston, (1985); Osolci al., eds., Remington's Pharmaceutical Sciences, 18th edition, Mack Publishing Co., Easton, Pa. (1990); Katzung, Basic and Clinical Pharmacology, Appleton and Lange, Norwalk, Conn. (1992).

Also included are methods of modulating an immune response, such as an innate immune response. As used herein, the term "immune response" includes a measurable or observable reaction to an antigen, vaccine composition, or immunomodulatory molecule mediated by one or more cells of the immune system. An immune response typically begins with an antigen or immunomodulatory molecule binding to an immune system cell. A reaction to an antigen or immunomodulatory molecule may be mediated by many cell types, including a cell that initially binds to an antigen or immunomodulatory molecule and cells that participate in mediating an innate, humoral, cell-mediated immune response.

An "innate immune response," as used herein, may involve binding of pathogen-associated molecular patterns (PAMPs) or damage-associated molecular pattern molecules, (DAMPS) or a DRS polypeptide to cell surface receptors, such as toll-like receptors. Activation of toll-like receptors and Ipaf-signaling pathways in response to PAMPs or other signals leads to the production of immunomodulatory molecules, such as cytokines and co-stimulatory molecules, which induce and/or enhance an immune response. Cells involved in the innate immune response include, for example, dendritic cells, macrophages, natural killer cells, and neutrophils, among others.

Certain embodiments relate to increasing an innate immune response. Other embodiments relate to decreasing an innate immune response. In certain aspects, an innate immune response is mediated by one or more toll-like receptors (TLRs), such as TLR2 and/or TLR4. Certain DRS polypeptides of the invention bind to TLRS such as TLR2 and/or TLR4. More generally, DRS polypeptides are capable of selectively modulating host immune responses via specific interactions with Toll like receptors, and may therefore be used to modulate host immune responses and thereby to manage diseases and conditions associated with the same, as described herein and known in the art. Exemplary uses for the DRS polypeptides of the invention therefore include both methods for the treatment and prevention of TLR associated diseases, as well as for use in the breakdown of immune tolerance, for example for the development of vaccines, and in the development of immune therapies.

Exemplary "TLR associated diseases" include for example, inflammatory conditions, and diseases and disorders associated with the dysfunction of the innate immune response, including for example, autoimmunity, cancer, allergy, autoimmunity, radiation induced toxicity, and the treatment and prevention of bacterial and viral infections. Accordingly in one embodiment the present invention includes a method for treating a TLR associated disease in a subject in need thereof, comprising administering to the subject a therapeutic dose of a DRS polypeptide (e.g., any of the proteins or nucleic acids listed in Tables D1 to D8 which i) retain detectable non canonical activity, and ii) which comprise, or have been modified to comprise at least one mutation at either Cys76 or Cys130 (using the numbering of SEQ ID NO:1) which replaces the native cysteine with another naturally, or non-naturally, occurring amino acid.

Exemplary uses associated with the breakdown of immune tolerance include for example the development of vaccines and adjutants comprising DRS polypeptides mixed with antigens, or comprising DRS fusion proteins with antigens, which exhibit enhanced immunogenicity. In some embodiments the antigen is a self-antigen. DRS polypeptide compositions that stimulate innate immunity (e.g., via TLR2 and/r TLR4) can be useful in the treatment of a wide variety of conditions, either alone or in combination with other therapies. Specific examples of such conditions include infectious diseases, such as bacterial, viral, and parasitic infectious diseases. DRS polypeptide compositions that stimulate innate immunity can also be useful as vaccine adjuvants, to enhance a subject's immune response to the primary antigen, whether in a live, attenuated, or other type of vaccine.

Examples of viral infectious diseases or agents (and their corresponding vaccines) include, but are not limited to, Hepatitis A, Hepatitis B, Hepatitis C, Hepatitis E, Caliciviruses associated diarrhoea, Rotavirus diarrhoea, *Haemophilus influenzae* B pneumonia and invasive disease, influenza, measles, mumps, rubella, Parainfluenza associated pneumonia, Respiratory syncytial virus (RSV) pneumonia, Severe Acute Respiratory Syndrome (SARS), Human papillomavirus, Herpes simplex type 2 genital ulcers, HIV/AIDS, Dengue Fever, Japanese encephalitis, Tick-borne encephalitis, West-Nile virus associated disease, Yellow Fever, Epstein-Barr virus, Lassa fever, Crimean-Congo haemorrhagic fever, Ebola haemorrhagic fever, Marburg haemorrhagic fever, Rabies, Rift Valley fever, Smallpox, leprosy, upper and lower respiratory infections, poliomyelitis, among others described elsewhere herein.

Examples of bacterial infections disease or agents include, but are not limited to, *Bacillus antracis, Borellia burgdorferi, Brucella abortus, Brucella canus, Brucella melitensis, Brucella suis, Campylobacter jejuni, Chlamydia pneumoniae, Chlamydia psitacci, Chlamydia trachomatis, Clostridium botulinum, C. difficile, C. perfringens, C. tetani, Corynebacterium diphtheriae* (i.e., diphtheria), *Enterococcus, Escherichia coli, Haemophilus influenza, Helicobacter pylori, Legionella pneumophila, Leptospira, Listeria monocytogenes, Mycobacterium leprae, M. tuberculosis, Mycoplasma pneumoniae, Neisseria gonorrhea, N. meningitidis, Pseudomonas aeruginosa, Rickettsia recketisii, Salmonella typhi, S. typhimurium, Shigella sonnei, Staphylococcus aureus, S. epidermidis, S. saprophytics, Streptococcus agalactiae, S. pneumoniae, S. pyogenes, Treponema pallidum, Vibrio cholera, Yersinia pestis, Bordatella pertussis*, and otitis media (e.g., often caused by *Streptococcus pneumoniae, Haemophilus influenzae,* or *Moraxella catarrhalis*), among others described elsewhere herein.

Examples of parasitic infectious diseases include, but are not limited to, Amoebiasis (e.g., *Entemoeba histolytica*), Hookworm Disease (e.g., nematode parasites such as *Necator americanus* and *Ancylostoma duodenale*), Leishmaniasis, Malaria (four species of the protozoan parasite *Plasmodium; P. falciparum, P. vivax, P. ovale,* and *P. malariae*), Schistosomiasis (parasitic *Schistosoma; S. mansoni, S. haematobium,* and *S. japonicum*), *Onchocerca volvulus* (River blindness), *Trypanosoma cruzi* (Chagas disease/American sleeping sickness), and *Dracunculus medinensis*, lymphatic filariasis. Certain DRS polypeptide compositions may be useful in the treatment or reduction of endotoxic shock, which often results from exposure to foreign antigens, such as lipopolysacchande (LPS). Because endotoxic shock can be mediated by TLR signaling, and naturally-occurring endogenous DRS polypeptide fragments may stimulate TLRs, certain of the binding agents, antisense agents, or RNAi agents provided herein may render a subject more resistant to endotoxic shock by antagonizing or otherwise reducing the endogenous DRS polypeptide fragment-mediated stimulation of TLR2 and/or TLR4.

Also included are methods of treating immune diseases. Illustrative immune system diseases, disorders or conditions that may be treated according to the present invention include, but are not limited to, primary immunodeficiencies, immune-mediated thrombocytopenia, Kawasaki syndrome, bone marrow transplant (for example, recent bone marrow transplant in adults or children), chronic B cell lymphocytic leukemia, HIV infection (for example, adult or pediatric HIV infection), chronic inflammatory demyelinating polyneuropathy, post-transfusion purpura, and the like.

Additionally, further diseases, disorders and conditions include Guillain-Barre syndrome, anemia (for example, anemia associated with parvovirus B19, patients with stable multiple myeloma who are at high risk for infection (for example, recurrent infection), autoimmune hemolytic anemia (for example, warm-type autoimmune hemolytic anemia), thrombocytopenia (for example, neonatal thrombocytopenia), and immune-mediated neutropenia), transplantation (for example, cytomegalovirus (CMV)-negative recipients of CMV-positive organs), hypogammaglobulinemia (for example, hypogammaglobulinemic neonates with risk factor for infection or morbidity), epilepsy (for example, intractable epilepsy), systemic vasculitic syndromes, myasthenia gravis (for example, decompensation in myasthenia gravis), dermatomyositis, and polymyositis.

Further autoimmune diseases, disorders and conditions include but are not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (for example, IgA nephropathy), multiple sclerosis, neuritis, uveitis ophthalmia, polyendochnopathies, purpura (for example, Henloch-Scoenlein purpura), Reiter's disease, stiff-man syndrome, autoimmune pulmonary inflammation, Guillain-Barre Syndrome, insulin dependent diabetes mellitus, and autoimmune inflammatory eye disease.

Additional autoimmune diseases, disorders or conditions include, but are not limited to, autoimmune thyroiditis;

hypothyroidism, including Hashimoto's thyroiditis and thyroiditis characterized, for example, by cell-mediated and humoral thyroid cytotoxicity; SLE (which is often characterized, for example, by circulating and locally generated immune complexes); Goodpasture's syndrome (which is often characterized, for example, by anti-basement membrane antibodies); pemphigus (which is often characterized, for example, by epidermal acantholytic antibodies); receptor autoimmunities such as, for example, Graves' disease (which is often characterized, for example, by antibodies to a thyroid stimulating hormone receptor; myasthenia gravis, which is often characterized, for example, by acetylcholine receptor antibodies); insulin resistance (which is often characterized, for example, by insulin receptor antibodies); autoimmune hemolytic anemia (which is often characterized, for example, by phagocytosis of antibody-sensitized red blood cells); and autoimmune thrombocytopenic purpura (which is often characterized, for example, by phagocytosis of antibody-sensitized platelets).

Further autoimmune diseases, disorders or conditions include, but are not limited to, rheumatoid arthritis (which is often characterized, for example, by immune complexes in joints); scleroderma with anti-collagen antibodies (which is often characterized, for example, by nucleolar and other nuclear antibodies); mixed connective tissue disease, (which is often characterized, for example, by antibodies to extractable nuclear antigens, for example, ribonucleoprotein); polymyositis/dermatomyositis (which is often characterized, for example, by nonhistone anti-nuclear antibodies); pernicious anemia (which is often characterized, for example, by antiparietal cell, antimicrosome, and anti-intrinsic factor antibodies); idiopathic Addison's disease (which is often characterized, for example, by humoral and cell-mediated adrenal cytotoxicity); infertility (which is often characterized, for example, by antispennatozoal antibodies); glomerulonephritis (which is often characterized, for example, by glomerular basement membrane antibodies or immune complexes); by primary glomerulonephritis, by IgA nephropathy; bullous pemphigoid (which is often characterized, for example, by IgG and complement in the basement membrane); Sjogren's syndrome (which is often characterized, for example, by multiple tissue antibodies and/or the specific nonhistone antinuclear antibody (SS-B)); diabetes mellitus (which is often characterized, for example, by cell-mediated and humoral islet cell antibodies); and adrenergic drug resistance, including adrenergic drug resistance with asthma or cystic fibrosis (which is often characterized, for example, by beta-adrenergic receptor antibodies).

Still further autoimmune diseases, disorders or conditions include, but are not limited to chronic active hepatitis (which is often characterized, for example by smooth muscle antibodies); primary biliary cirrhosis (which is often characterized, for example, by anti-mitochondrial antibodies); other endocrine gland failure (which is characterized, for example, by specific tissue antibodies in some cases); vitiligo (which is often characterized, for example, by anti-melanocyte antibodies); vasculitis (which is often characterized, for example, by immunoglobulin and complement in vessel walls and/or low serum complement); post-myocardial infarction conditions (which are often characterized, for example, by anti-myocardial antibodies); cardiotomy syndrome (which is often characterized, for example, by anti-myocardial antibodies); urticaria (which is often characterized, for example, by IgG and IgM antibodies to IgE); atopic dermatitis (which is often characterized, for example, by IgG and IgM antibodies to IgE); asthma (which is often characterized, for example, by IgG and IgM antibodies to IgE); inflammatory myopathies; and other inflammatory, granulomatous, degenerative, and atrophic disorders.

Further embodiments the present invention include methods for killing cancer cells, comprising administering a vaccine or immunogenic composition comprising a DRS polypeptide of the invention fused to, or associated with an antigen, or vector comprising a nucleic acid encoding a DRS polypeptide fused to an antigen, to a subject in need thereof. Such DRS polypeptides may comprise any of the proteins or nucleic acids listed in Tables D1 to D8 which i) retain detectable non canonical activity, and ii) which comprise, or have been modified to comprise at least one mutation at either Cys76 or Cys130 (using the numbering of SEQ ID NO:1) which replaces the native cysteine with another naturally, or non-naturally, occurring amino acid). In some embodiments the antigen is a self-antigen, in some embodiments the antigen is a tumor derived antigen. In some embodiments, the antigen is a pathogen derived antigen. In some embodiments the pathogen derived antigen is derived from a virus, bacteria or prion. In some embodiments, the antigen is fused to the DRS polypeptide through conjugation at Cys130. In some embodiments the antigen and DRS polypeptide are mixed together.

In some embodiments the present invention includes a method for treating a subject with cancer, or preventing the development of cancer in a subject, comprising administering a vaccine or immunogenic composition comprising a DRS polypeptide of the invention fused to an antigen, or vector comprising a nucleic acid encoding a DRS polypeptide fused to an antigen, wherein the vaccine elicits an immune response to the cancer. Such DRS polypeptides may comprise any of the proteins or nucleic acids listed in Tables D1 to D8 which i) retain detectable non canonical activity, and ii) which comprise, or have been modified to comprise at least one mutation at either Cys76 or Cys130 (using the numbering of SEQ ID NO:1) which replaces the native cysteine with another naturally, or non-naturally, occurring amino acid). In some embodiments the antigen is a self-antigen, in some embodiments the antigen is a tumor derived antigen. In some embodiments, the antigen is a pathogen derived antigen. In some embodiments the pathogen derived antigen is derived from a virus, bacteria or prion. In some embodiments, the antigen is fused to the DRS polypeptide through conjugation at Cys130.

In some embodiments the present invention includes a method for overcoming tolerance of a subject to an antigen, comprising administering a vaccine or immunogenic composition comprising a DRS polypeptide of the invention fused to the antigen, or vector comprising a nucleic acid encoding a DRS polypeptide fused to the antigen. In different embodiments, the antigen may be selected self-antigens, tumor derived antigens, pathogen derived antigens. In some embodiments the pathogen derived antigen is derived from a virus, bacteria or prion. In some embodiments, the antigen is fused to the DRS polypeptide through conjugation at Cys130.

Pharmaceutical Formulations, Administration, and Kits

Embodiments of the present invention include compositions comprising PEGylated DRS polypeptides formulated in pharmaceutically-acceptable or physiologically-acceptable solutions for administration to a cell, subject, or an animal, either alone, or in combination with one or more other modalities of therapy. It will also be understood that, if desired, the compositions of the invention may be administered in combination with other agents as well, such as, e.g., other proteins or polypeptides or various pharmaceutically-active agents. There is virtually no limit to other components that may also be included in the compositions, provided that the additional agents do not adversely affect the modulatory or other effects desired to be achieved.

For pharmaceutical production, DRS polypeptide therapeutic compositions will typically be substantially endotoxin free. Endotoxins are toxins associated with certain bacteria, typically gram-negative bacteria, although endotoxins may be found in gram-positive bacteria, such as *Listeria monocytogenes*. The most prevalent endotoxins are lipopolysaccharides (LPS) or lipo-oligo-saccharides (LOS) found in the outer membrane of various Gram-negative bacteria, and which represent a central pathogenic feature in the ability of these bacteria to cause disease. Small amounts of endotoxin in humans may produce fever, a lowering of the blood pressure, and activation of inflammation and coagulation, among other adverse physiological effects.

Endotoxins can be detected using routine techniques known in the art. For example, the *Limulus* Ameobocyte Lysate assay, which utilizes blood from the horseshoe crab, is a very sensitive assay for detecting presence of endotoxin. In this test, very low levels of LPS can cause detectable coagulation of the *limulus* lysate due a powerful enzymatic cascade that amplifies this reaction. Endotoxins can also be quantitated by enzyme-linked immunosorbent assay (ELISA).

To be substantially endotoxin free, endotoxin levels may be less than about 0.001, 0.005, 0.01, 0.02, 0.03, 0.04, 0.05, 0.06, 0.08, 0.09, 0.1, 0.5, 1.0, 1.5, 2, 2.5, 3, 4, 5, 6, 7, 8, 9, or 10 EU/mg of protein. Typically, 1 ng lipopolysaccharide (LPS) corresponds to about 1-10 EU.

In certain embodiments, as noted herein, the DRS polypeptide compositions have an endotoxin content of less than about 10 EU/mg of DRS polypeptide, or less than about 5 EU/mg of DRS polypeptide, less than about 3 EU/mg of DRS polypeptide, or less than about 1 EU/mg of DRS polypeptide, or less than about 0.1 EU/mg of DRS polypeptide, or less than about 0.01EU/mg of DRS polypeptide. In certain embodiments, as noted above, the DRS polypeptide pharmaceutical compositions are about 95% endotoxin free, preferably about 99% endotoxin free, and more preferably about 99.99% endotoxin free on wt/wt protein basis.

Pharmaceutical compositions comprising a therapeutic dose of a PEGylated DRS polypeptide include all homologues, orthologs, and naturally-occurring isoforms of aspartyl-tRNA synthetase (e.g., any of the proteins or nucleic acids listed in Tables D1 to D8 which i) retain detectable non canonical activity, and ii) which comprise, or have been modified to comprise, at least one mutation at either Cys76 or Cys130 (using the numbering of SEQ ID NO:1) which replaces the native cysteine with another amino acid.

In some embodiments such pharmaceutical compositions may comprise an arginine buffer, which may be present in any of the pharmaceutical compositions within the range of about 1 mM to about 100 mM. In different embodiments, the arginine buffer may be present at a concentration of about 1 mM, about 10 mM, about 20 mM, about 40 mM, about 50 mM, about 60 mM, about 70 mM, about 80 mM, about 90 mM, or about 100 mM.

In one aspect such compositions may comprises PEGylated DRS polypeptides that are substantially monodisperse, meaning that the DRS polypeptide compositions exist primarily (i.e., at least about 90%, or greater) in one apparent molecular weight form when assessed for example, by size exclusion chromatography, dynamic light scattering, or analytical ultracentrifugation.

In another aspect, such compositions have a purity (on a protein basis) of at least about 90%, or in some aspects at least about 95% purity, or in some embodiments, at least 98% purity. Purity may be determined via any routine analytical method as known in the art.

In another aspect, such compositions have a high molecular weight aggregate content of less than about 10%, compared to the total amount of protein present, or in some embodiments such compositions have a high molecular weight aggregate content of less than about 5%, or in some aspects such compositions have a high molecular weight aggregate content of less than about 3%, or in some embodiments a high molecular weight aggregate content of less than about 1%. High molecular weight aggregate content may be determined via a variety of analytical techniques including for example, by size exclusion chromatography, dynamic light scattering, or analytical ultracentrifugation.

Pharmaceutical compositions may include pharmaceutically acceptable salts of a DRS polypeptide. For a review on suitable salts, see *Handbook of Pharmaceutical Salts: Properties, Selection, and Use* by Stahl and Wermuth (Wiley-VCH, 2002). Suitable base salts are formed from bases which form non-toxic salts. Representative examples include the aluminum, arginine, benzathine, calcium, choline, diethylamine, diolamine, glycine, lysine, magnesium, meglumine, olamine, potassium, sodium, tromethamine, and zinc salts. Hemisalts of acids and bases may also be formed, e.g., hemisulphate and hemicalcium salts. Compositions to be used in the invention suitable for parenteral administration may comprise sterile aqueous solutions and/or suspensions of the pharmaceutically active ingredients preferably made isotonic with the blood of the recipient, generally using sodium chloride, glycerin, glucose, mannitol, sorbitol, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl)benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), 4-methylbicyclo(2.2.2)-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

In particular embodiments, the carrier may include water. In some embodiments, the carrier may be an aqueous solution of saline, for example, water containing physiological concentrations of sodium, potassium, calcium, magnesium, and chloride at a physiological pH. In some embodiments, the carrier may be water and the formulation may further include NaCl. In some embodiments, the formulation may be isotonic. In some embodiments, the formulation may be hypotonic. In other embodiments, the formulation may be hypertonic. In some embodiments, the formulation may be isomostic. In some embodiments, the formulation is substantially free of polymers (e.g., gel-forming polymers, polymeric viscosity-enhancing agents, etc.). In some embodiments, the formulation is substantially free of viscosity-increasing agents (e.g., carboxymethylcellulose, polyanionic polymers, etc.). In some embodiments, the formulation is substantially free of gel-forming polymers. In some embodiments, the viscosity of the formulation is about the same as the viscosity of a saline solution containing the same concentration of a DRS polypeptide (or a pharmaceutically acceptable salt thereof).

In the pharmaceutical compositions of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

In certain embodiments, the PEGylated DRS polypeptide have a solubility that is desirable for the particular mode of administration, such intravenous administration. Examples of desirable solubility's include at least about 1 mg/ml, at least about 10 mg/ml, at least about 25 mg/ml, and at least about 50 mg/ml.

In certain applications, the pharmaceutical compositions disclosed herein may be delivered via oral administration to a subject. As such, these compositions may be formulated with an inert diluent or with an edible carrier, or they may be enclosed in hard- or soft-shell gelatin capsule, or they may be compressed into tablets, or they may be incorporated directly with the food of the diet.

Pharmaceutical compositions suitable for the delivery of DRS polypeptides and methods for their preparation will be readily apparent to those skilled in the art. Such compositions and methods for their preparation may be found, e.g., in *Remington's Pharmaceutical Sciences,* 19th Edition (Mack Publishing Company, 1995).

Administration of a therapeutic dose of a DRS polypeptide may be by any suitable method known in the medicinal arts, including for example, oral, intranasal, parenteral administration include intravitreal, subconjuctival, subtenon, retrobulbar, suprachoroidal intravenous, intra-arterial, intraperitoneal, intrathecal, intraventricular, intraurethral, intrasternal, intracranial, intramuscular, intrasynovial, intraocular, topical and subcutaneous. Suitable devices for parenteral administration include needle (including microneedle) injectors, needle-free injectors, and infusion techniques.

Parenteral formulations are typically aqueous solutions which may contain excipients such as salts, carbohydrates, and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, e.g., by lyophilization, may readily be accomplished using standard pharmaceutical techniques well-known to those skilled in the art.

Formulations for parenteral administration may be formulated to be immediate and/or sustained release. Sustained release compositions include delayed, modified, pulsed, controlled, targeted and programmed release. Thus a DRS polypeptide may be formulated as a suspension or as a solid, semi-solid, or thixotropic liquid for administration as an implanted depot providing sustained release of DRS polypeptides. Examples of such formulations include without limitation, drug-coated stents and semi-solids and suspensions comprising drug-loaded poly(DL-lactic-co-glycolic) acid (PGLA), poly(DL-lactide-co-glycolide) (PLG) or poly (lactide) (PLA) lamellar vesicles or microparticles, hydrogels (Hoffman A S: *Ann. N.Y. Acad. Sci.* 944: 62-73 (2001)), poly-amino acid nanoparticles systems, such as the Medusa system developed by Flamel Technologies Inc., non aequous gel systems such as Atrigel developed by Atrix, Inc., and SABER (Sucrose Acetate Isobutyrate Extended Release) developed by Durect Corporation, and lipid-based systems such as DepoFoam developed by SkyePharma.

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., *Remington's Pharmaceutical Sciences,* 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions can be prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

PEGylated DRS polypeptides for use in the present invention may also be administered topically, (intra)dermally, or transdermally to the skin, mucosa, or surface of the eye, either alone or in combination with one or more antihistamines, one or more antibiotics, one or more antifungal agents, one or more beta blockers, one or more anti-inflammatory Agents, one or more antineoplastic agents, one or more immunosuppressive agents, one or more antiviral agents, one or more antioxidant agents, or other active agents. Formulations for topical and ocular administration may be formulated to be immediate and/or modified release. Modified release formulations include delayed, sustained, pulsed, controlled, targeted and programmed release.

Typical formulations for this purpose include gels, hydrogels, lotions, solutions, eye drops, creams, ointments, dusting powders, dressings, foams, films, skin patches, wafers, implants, sponges, fibers, bandages, and microemulsions. Liposomes may also be used. Typical carriers include alcohol, water, mineral oil, liquid petrolatum, white petrolatum, glycerin, polyethylene glycol, and propylene glycol. Penetration enhancers may be incorporated—see, e.g., Finnin and Morgan: *J. Pharm. Sci.* 88(10): 955-958, (1999). Other means of topical administration include delivery by electroporation, iontophoresis, phonophoresis, sonophoresis, and microneedle or needle-free injection (e.g., the systems sold under the trademarks POWDERJECT™, BIOJECT™).

Examples of antihistamines include, but are not limited to, loradatine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, and trimprazine doxylamine, pheniramine, pyrilamine, chiorcyclizine, thonzylamine, and derivatives thereof.

Examples of antibiotics include, but are not limited to: Aminoglycosides (e.g., amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, trospectomycin), amphenicols (e.g., azidamfenicol, chloramphenicol, florfenicol, thiamphenicol), ansamycins (e.g., rifamide, rifampin, rifamycin sv, rifapentine, rifaximin), lactams (e.g., carbacephems (e.g., loracarbef), carbapenems (e.g., biapenem, imipenem, meropenem, panipenem), cephalosporins (e.g., cefaclor, cefadroxil, cefamandole, cefatrizine, cefazedone, cefazolin, cefcapene pivoxil, cefclidin, cefdinir, cefditoren, cefepime, cefetamet, cefixime, cefinenoxime, cefodizime, cefonicid, cefoperazone, ceforanide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin), cephamycins (e.g., cefbuperazone, cefinetazole, cefminox, cefotetan, cefoxitin), monobactams (e.g., aztreonam, carumonam, tigemonam), oxacephems, flomoxef, moxalactam), penicillins (e.g., amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin g benethamine, penicillin g benzathine, penicillin g benzhydrylamine, penicillin g calcium, penicillin g hydrabamine, penicillin g potassium, penicillin g procaine, penicillin n, penicillin o, penicillin v, penicillin v benzathine, penicillin v hydrabamine, penimepicycline, phenethicillin potassium, piperacillin, pivampicillin, propicillin, quinacillin, sulbenicillin, sultamicillin, talampicillin, temocillin, ticarcillin), other (e.g., ritipenem), lincosamides (e.g., clindamycin, lincomycin), macrolides (e.g., azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin), polypeptides (e.g., amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin, zinc bacitracin), tetracyclines (e.g., apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, tetracycline), and others (e.g., cycloserine, mupirocin, tuberin). 2.4-Diaminopyrimidines (e.g., brodimoprim, tetroxoprim, trimethoprim), nitrofurans (e.g., furaltadone, furazolium chloride, nifuradene, nifuratel, nifurfoline, nifurpirinol, nifurprazine, nifurtoinol, nitrofurantoin), quinolones and analogs (e.g., cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin), sulfonamides (e.g., acetyl sulfamethoxypyrazine, benzylsulfamide, chloramine-b, chloramine-t, dichloramine t, $n^2$-formylsulfisomidine, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, 4-sulfanilamidosalicylic acid, $n^4$-sulfanilylsulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole) sulfones (e.g., acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone), and others (e.g., clofoctol, hexedine, methenamine, methenamine anhydromethylene-citrate, methenamine hippurate, methenamine mandelate, methenamine sulfosalicylate, nitroxoline, taurolidine, xibornol).

Examples of antifungal agents include, but are not limited to Polyenes (e.g., amphotericin b, candicidin, dermostatin, filipin, fungichromin, hachimycin, hamycin, lucensomycin, mepartricin, natamycin, nystatin, pecilocin, perimycin), others (e.g., azaserine, griseofulvin, oligomycins, neomycin undecylenate, pyrrolnitrin, siccanin, tubercidin, viridin), Allylamines (e.g., butenafine, naftifine, terbinafine), imidazoles (e.g., bifonazole, butoconazole, chlordantoin, chlormidazole, cloconazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole), thiocarbamates (e.g., tolciclate, tolindate, tolnaftate), triazoles (e.g., fluconazole, itraconazole, saperconazole, terconazole) others (e.g., acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, zinc propionate).

Examples of beta blockers include but are not limited to acebutolol, atenolol, labetalol, metoprolol, propranolol, timolol, and derivatives thereof.

Examples of antineoplastic agents include, but are not limited to Antibiotics and analogs (e.g., aclacinomycins, actinomycin $f_1$, anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycines, peplomycin, pirarubicin, plicamycin, porfiromycin, puromycin, streptonigrin, streptozocin, tubercidin, zinostatin, zorubicin), antimetabolites (e.g., folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thioguanine), pyrimidine analogs (e.g., ancitabine, azacitidine, 6-azauridine, carmofur, cytarabine, doxifluridine, emitefur, enocitabine, floxuridine, fluorouracil, gemcitabine, tagafur).

Examples of Antiinflammatory Agents Include but are not Limited to Steroidal Antiinflammatory Agents and Non-Steroidal Antiinflammatory Agents. Exemplary Steroidal Antiinflammatory include acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, predincarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide.

Exemplary Non-Steroidal Antiinflammatory Agents include Aminoarylcarboxylic acid derivatives (e.g., enfenamic acid, etofenamate, flufenamic acid, isonixin, meclofenamic acid, mefenamic acid, niflumic acid, talniflumate, terofenamate, tolfenamic acid), arylacetic acid derivatives (e.g., aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac), arylbutyric acid derivatives (e.g., bumadizon, butibufen, fenbufen, xenbucin), arylcarboxylic acids (e.g., clidanac, ketorolac, tinoridine), arylpropionic acid derivatives (e.g., alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (e.g., difenamizole, epirizole), pyrazolones (e.g., apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (e.g., acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicylsulfuric acid, salsalate, sulfasalazine), thiazinecarboxamides (e.g., ampiroxicam, droxicam, isoxicam, lornoxicam, piroxicam, tenoxicam), g-acetamidocaproic acid, s-adenosylmethionine, 3-amino-4-hydroxybutyric acid, amixetrine, bendazac, benzydamine, bucolome, difenpiramide, ditazol, emorfazone, fepradinol, guaiazulene, nabumetone, nimesulide, oxaceprol, paranyline, perisoxal, proquazone, superoxide dismutase, tenidap, and zileuton.

Examples of antiviral agents include interferon gamma, zidovudine, amantadine hydrochloride, ribavirin, acyclovir, valciclovir, dideoxycytidine, phosphonoformic acid, ganciclovir, and derivatives thereof.

Examples of antioxidant agents include ascorbate, alpha-tocopherol, mannitol, reduced glutathione, various carotenoids, cysteine, uric acid, taurine, tyrosine, superoxide dismutase, lutein, zeaxanthin, cryotpxanthin, astazanthin, lycopene, N-acetyl-cysteine, carnosine, gamma-glutamyl-cysteine, quercitin, lactoferrin, dihydrolipoic acid, citrate, *Ginkgo Biloba* extract, tea catechins, bilberry extract, vitamins E or esters of vitamin E, retinyl palmitate, and derivatives thereof. Other therapeutic agents include squalamine, carbonic anhydrase inhibitors, alpha-2 adrenergic receptor agonists, antiparasitics, antifungals, and derivatives thereof.

The exact dose of each component administered will, of course, differ depending on the specific components prescribed, on the subject being treated, on the severity of the disease, e.g., severity of the inflammatory reaction, on the manner of administration and on the judgment of the prescribing physician. Thus, because of patient-to-patient variability, the dosages given above are a guideline and the physician may adjust doses of the compounds to achieve the treatment that the physician considers appropriate.

As will be understood by the skilled artisan, for DRS polypeptide ocular formulations where the carrier includes a gel-forming polymer, in certain formulations the inclusion of salt(s), in particular saline solution, is contraindicated as inclusion of salt may either cause the solution to gel prior to topical administration, as with certain in situ gel-forming polymers (e.g., gellan gel), or the inclusion of salts may inhibit the gelling properties of the gel-forming polymer. The skilled artisan will be able to select appropriate combinations based on the desired properties of the formulation and characteristics of gel-forming polymers known in the art.

Suitable aqueous saline solutions will be understood by those of skill in the art and may include, for example, solutions at a pH of from about pH 4.5 to about pH 8.0. In further variations of aqueous solutions (where water is included in the carrier), the pH of the formulation is between any of about 6 and about 8.0; between about 6 and about 7.5; between about 6 and about 7.0; between about 6.2 and about 8; between about 6.2 and about 7.5; between about 7 and about 8; between about 6.2 and about 7.2; between about 5.0 and about 8.0; between about 5 and about 7.5; between about 5.5 and about 8.0; between about 6.1 and about 7.7; between about 6.2 and about 7.6; between about 7.3 and about 7.4; about 6.0; about 7.1; about 6.2; about 7.3; about 6.4; about 6.5; about 6.6; about 6.7; about 6.8; about 6.9; about 7.0; about 7.1; about 7.2; about 7.3; about 7.4; about 7.5; about 7.6; or about 8.0. In some variations, the DRS polypeptide formulation has a pH of about 6.0 to about 7.0. In some variations, the formulation has a pH of about 7.4. In particular variations, the formulation has a pH of about 6.2 to about 7.5.

In certain embodiments the concentration of the salt (e.g., NaCl) will be, for example, from about 0% to about 0.9% (w/v). For example, the concentration of salt may be from about 0.01 to about 0.9%, from about 0.02% to about 0.9%, from about 0.03% to about 9%, from about 0.05% to about 0.9% from about 0.07% to about 0.9%, from about 0.09% to about 0.9%, from about 0.1% to about 0.9% from about 0.2% to about 0.9%, from about 0.3% to about 0.9%, from about 0.4% to about 0.9% from about 0.5% to about 0.9%, from about 0.6% to about 0.9%, from about 0.7% to about 0.9%, from about 0.8% to about 0.9%, about 0.9%, about 0%, about 0.05%, about 0.01%, about 0.09%, about 0.1%, about 0.2%, about 0.3%, about 0.4%, about 0.5%, about 0.6%, about 0.7%, or about 0.8%. In certain embodiments, the aqueous saline solution will be isotonic (e.g., NaCl concentration of about 0.9% NaCl (w/v)). In certain embodiments, the aqueous solution will contain a NaCl concentration of about 0.5%, about 0.7%, about 0.8%, about 0.85, or about 0.75%. As will be appreciated the skilled artisan, depending on the concentrations of other components, for example where the DRS polypeptides are present as salts of, the concentration of NaCl or other salt needed to achieve an formulation suitable for administration may vary.

In some embodiments, where the ocular formulation is substantially free of viscosity-increasing agents, the formulation may be substantially free of viscosity-increasing agents such as, but not limited to polyanionic polymers, water soluble cellulose derivatives (e.g., hypromellose (also known as HPMC, hydroxypropylmethyl cellulose, and hydroxypropylcellulose), hydroxyethylcellulose, carboxmethylcellulose, etc.), polyvinyl alcohol, polyvinyl pyrrolidone, chondroitin sulfate, hyaluronic acid, soluble starches, etc. In some variations, the formulation does not incorporate a hydrogel or other retention agent (e.g., such as those disclosed in U.S. Pat. Pub. No. 2005/0255144 (incorporated by reference herein in its entirety)), e.g., where they hydrogel may include, hydrogels incorporating homopolymers; copolymers (e.g., tetrapolymers of hydroxymethylmethacrylate, ethylene glycol, dimethylmethacrylate, and methacrylic acid), copolymers of trimethylene carbonate and polyglycolicacid, polyglactin 910, glyconate, poly-p-dioxanone, polyglycolic acid, polyglycolic acid felt, poly-4-hydroxybutyrate, a combination of poly(L-lactide) and poly(L-lactide-co-glycolide), glycol methacrylate, poly-DL-lactide, or Primacryl); composites of oxidized regenerated cellulose, polypropylene, and polydioxanone or a composite of polypropylene and poligelcaprone; etc. In some variations, the formulations do not include one or more of polyvinyl alcohol, hydroxypropyl methylcellulose, polyethylene glycol 400 castor oil emulsion, carboxymethylcellulose sodium, propylene glycol, hydroxypropyl guar, carboxymethylcelluose sodium, white petrolatum, mineral oil, dextran 70, glycerin, hypromellose, flaxseed oil, fish oils, omega 3 and omega 6 fatty acids, lutein, or primrose oil. In some variations, the formulations do not include one or more of the carriers described in U.S. Pat. No. 4,888,354 (incorporated by reference herein in its entirety), e.g., such as one or more of oleic acid, ethanol, isopropanol, glycerol monooleate, glycerol diooleate, methyl laurate, propylene glycol, propanol or dimethyl sulfoxide. In some variations, the formulations are substantially free of glycerol diooleate and isopropanol.

In particular embodiments, the gel-forming polymer may be, for example, a polysaccharide. In certain embodiments, the polysaccharide is gellan gum. Gellan gum refers to a heteropolysaccharide elaborated by the bacterium *Pseudomonas elodea*, though the name "gellan gum" is more commonly used in the field. Gellan gum, in particular the formulation GELRITE® is described in detail in U.S. Pat. No. 4,861,760 (hereby incorporated by reference in its entirety), in particular in its use in formulation of timolol. GELRITE®, a low acetyl clarified grade of gellan gum, is commercially available from Merck & Co (Rahway, N.J.) and gellan gum can be commercially obtained from, among others CPKelco (Atlanta, Ga.). The preparation of polysaccharides such as gellan gum is described in, for example, U.S. Pat. Nos. 4,326,053 and 4,326,052, which are hereby incorporated by reference in their entirety.

In certain embodiments, the gel-forming polymer is present at a concentration of from about 0.03% to about 2% (w/v). In some embodiments, the gel-forming polymer is present at a concentration from about 0.03% to about 1.75%; from about 0.03% to about 1.5%, from about 0.03% to about 1.25%, from about 0.03% to about 1%, from about 0.03% to about 0.9%, from about 0.03% to about 0.8%, from about 0.03% to about 0.7%, from about 0.03% to about 0.6%, from about 0.03% to about 0.5%, from about 0.05% to about 2%, from about 0.05% to about 1.75%; from about 0.05% to about 1.5%, from about 0.05% to about 1.25%, from about 0.05% to about 1%, from about 0.05% to about 0.9%, from about 0.05% to about 0.8%, from about 0.05% to about 0.7%, from about 0.05% to about 0.6%, from about 0.05% to about 0.5%, from about 0.1% to about 2%, from about 0.1% to about 1.75%; from about 0.1% to about 1.5%, from about 0.1% to about 1.25%, from about 0.1% to about 1%, from about 0.1% to about 0.9%, from about 0.1% to about 0.8%, from about 0.1% to about 0.7%, from about 0.1% to about 0.6%, from about 0.1% to about 0.5%, from about 0.2% to about 2%, from about 0.2% to about 1.75%; from about 0.2% to about 1.5%, from about 0.2% to about 1.25%, from about 0.2% to about 1%, from about 0.2% to about 0.9%, from about 0.2% to about 0.8%, from about 0.2% to about 0.7%, from about 0.2% to, about 0.6%, from about 0.2% to about 0.5%, or from about 0.5% to about 1.5%. In some embodiments, the concentration of gel-forming polymer is about 0.1%, about 0.2%, about 0.4%, about 0.6%, about 0.8%, about 1%.

In particular embodiments, the gel-forming polymer is gellan gum at a concentration of from about 0.05% to about 2% (w/v), from about 0.1% to about 2% (w/v), from about 0.1% to about 1% (w/v), from about 0.05% to about 1% (w/v) or from about 0.1% to about 0.6% (w/v). In some embodiments, the concentration of gellan gum is about 0.1%, about 0.2%, about 0.4%, about 0.6%, about 0.8%, about 1%.

In some embodiments of the ocular formulations, the formulation may include additional components such as one or more preservatives, one or more surfactants, or one or more pharmaceutical agents. In particular embodiments, the formulation may include additional components such as one or more preservatives, one or more surfactants, one or more tonicity agents, one or more buffering agents, one or more chelating agents, one or more viscosity-increasing agents, one or more salts, or one or more pharmaceutical agents. In certain of these embodiments, the formulation may include (in addition to a DRS polypeptide (or a pharmaceutically acceptable salt thereof) and carrier): one or more preservatives, one or more buffering agents (e.g., one, two, three, etc.), one or more chelating agents, and one or more salts. In some embodiments, the formulation may include (in addition to a DRS polypeptide (or a pharmaceutically acceptable salt thereof) and carrier): one or more preservatives, one or more tonicity agents, one or more buffering agents, one or more chelating agents, and one or more viscosity-increasing agents.

In some embodiments, the viscosity of the formulation is about the same as the viscosity of a saline solution containing the same concentration of a DRS polypeptide (or a pharmaceutically acceptable salt thereof). In some embodiments, the formulation is substantially free of gel-forming polymers. In certain embodiments, where the carrier is water, the formulation may additionally include one or more chelating agents (e.g., EDTA disodium (EDTA), one or more preservatives (e.g., benzalkonium chloride, benzethonium chloride, chlorhexidine, chlorobutanol, methylparaben, phenylethyl alcohol, propylparaben, thimerosal, phenylmercuric nitrate, phenylmercuric borate, phenylmercuric acetate, or combinations of two or more of the foregoing), salt (e.g., NaCl) and one or more buffering agents (e.g., one or more phosphate buffers (e.g., dibasic sodium phosphate, monobasic sodium phosphate, combinations thereof, etc.), citrate buffers, maleate buffers, borate buffers, and combination of two or more of the foregoing.).

In particular embodiments, the chelating agent is EDTA disodium, the preservative is benzalkonium chloride, the salt is NaCl, and the buffering agents are dibasic sodium phosphate and monobasic sodium phosphate. In certain of these embodiments, the formulation is substantially free of polymer. In some embodiments, the formulation is substantially free of substantially viscosity-increasing agent(s) (e.g., carboxymethylcellulose, polyanionic polymers, etc.). In some embodiments, the viscosity of the formulation is about the same as the viscosity of a saline solution containing the same concentration of a DRS polypeptide (or a pharmaceutically acceptable salt thereof). In some of these embodiments, the concentration of a DRS polypeptide (or a pharmaceutically acceptable salt thereof) if from about 0.02% to about 3%, from about 0.02% to about 2%, from about 0.02% to about 1% (w/v). In certain embodiments, the concentration of a DRS polypeptide (or a pharmaceutically acceptable salt thereof), is about 0.01%, about 0.02%, about 0.03%, about 0.05%, about 0.07%, about 0.1%, about 0.3%, about 0.4%, about 0.5%, about 0.6%, about 0.8% or about 1% (w/v).

In certain embodiments, where the carrier includes water, a viscosity-increasing agent may also be included in the formulation. The skilled artisan will be familiar with viscosity-increasing agents that are suitable (e.g., water-soluble cellulose derivatives (e.g., hypromellose (also known as HPMC, hydroxypropylmethyl cellulose, and hydroxypropylcellulose), hydroxyethylcellulose, carboxymethylcellulose, etc.), polyvinyl alcohol, polyvinyl pyrrolidone, chondroitin sulfate, hyaluronic acid, and soluble starches. It is intended that when viscosity-increasing agents are used, they are not included in high enough concentrations such that the formulation would form a gel prior to or after administration (e.g., wherein the concentration of the viscosity-increasing agent is not sufficient to induce gel formation).

While exact concentrations of viscosity-increasing agents will depend upon the selection and concentration of other components in the formulation as well as the particular viscosity-increasing agent(s) selected, in general, viscosity-increasing agents may be present in a concentration such that the viscosity of the resulting solution is less than about 1000 centipoise. In certain embodiments, the viscosity of the formulation is less than about 900, less than about 800, less than about 700, less than about 600, less than about 500, less than about 400, less than about 300, less than about 200, less than about 150, less than about 100, less than about 50 centipoise. In some embodiments, the viscosity of the formulation is about 200, about 150, about 100, about 50 centipoise. In particular embodiments, the viscosity is less than about 200 centipoise. In others, less than about 120 centipoise or less than about 100 centipoise. In some embodiments, the viscosity is about 100 centipoise. In others about 50 centipoise. In still other embodiments the viscosity is about 200 centipoise. Methods for measuring viscosity are well known to the skilled artisan. For example, as described in United States Pharmacopoeia 29 (Chapter 911) Viscosity, page 2785 (which is herein incorporated by reference in its entirety). As is well known to the skilled artisan, formulations commonly considered "gels" will have viscosity significantly greater than 1000 centipoise, for example, greater than about 2000 centipoise, greater than about 5000 centipoise.

In some embodiments, including (but not limited to) where the use of salts is contraindicated as described above, the ocular formulation may further include one or more tonicity agents. As used herein, the term "tonicity agent" and its cognates refers to agents that adjust the tonicity of the formulation, but are not salts (e.g., not NaCl), which, as will be appreciated by the skill artisan in view of the teaching provided herein, are contraindicated for some formulations due to the presence of certain of the gel-forming polymers or viscosity-increasing agents. These agents may be used to prepare formulations that are isotonic or near isotonic (e.g., somewhat hyper- or hypo-isotonic; e.g., within about ±20%, about ±15%, about ±10%, about ±5% of being isotonic). Tonicity agent(s) may also be used in formulations where the use of salts is not contraindicated.

Tonicity agents that may be used to adjust the tonicity of formulation the formulations described herein and are known to the skilled artisan and can be selected based on the teaching provided herein. For example, tonicity agents include polyols (e.g., sugar alcohols (e.g., mannitol, etc.), trihydroxy alcohols (e.g., glycerin, etc.), propylene glycol or polyethylene glycol, etc.), or combinations of two or more polyols. Likewise, the concentration of the tonicity agent(s) will depend upon the identity and concentrations of the other components in the formulation and can be readily determined by the skilled artisan in view of the teaching provided herein.

In certain embodiments, the tonicity agent is glycerin or mannitol. In some embodiments, the tonicity agent is glycerin. In other embodiments it is, mannitol. In still others a combination of mannitol and glycerin may be used. Exemplary concentrations of tonicity agents include, for example from about 0.001 to about 3%. In some embodiments, the concentration of the tonicity agent (e.g., mannitol or glycerin) is, for example, about 0.001% to about 2.7%, about 0.001% to about 2.5%, about 0.001% to about 2%, about 0.001% to about 1.5%, about 0.001% to about 1%, about 0.01% to about 3%, about 0.01% to about 2.7%, about 0.01% to about 2.5%, about 0.01% to about 2%, about 0.01% to about 1.5%, about 0.01% to about 1%, about 0.1% to about 3%, about 0.1% to about 2.7%, about 0.1% to about 2.5%, about 0.1% to about 2%, about 0.1% to about 1.5%, about 0.1% to about 1%, about 0.01% about 1% to about 3%; about 1% to about 2.5%; about 1% to about 2%; about 1% to about 1.8%; about 1% to about 1.5%; or about 0.001%, about 0.01%, about 0.05%, about 0.08%, about 0.1%, about 0.2%, about 0.5%, about 0.8%, about 1%, about 1.5%, about 1.8%, about 2%, about 2.2%, about 2.5%, about 2.8%, or about 3% (w/v). In certain embodiments, the tonicity agent is mannitol. In some of these embodiments, the carrier includes a gel-forming agent (e.g., gellan gum).

In some embodiments, the tonicity agent is mannitol. In certain of these embodiments, the carrier includes a viscosity-increasing agent (e.g., water soluble cellulose derivatives (e.g., hypromellose), polyvinyl alcohol, polyvinyl pyrrolidone, chondroitin sulfate, hyaluronic acid, or soluble starches).

In some embodiments, the ocular formulation may additionally include a preservative (e.g., benzalkonium chloride, benzethonium chloride, chlorhexidine, chlorobutanol, methylparaben, Phenylethyl alcohol, propylparaben, thimerosal, phenylmercuric nitrate, phenylmercuric borate, or phenylmercuric acetate, peroxides), or a combination of two or more of the foregoing preservatives. In certain embodiments, the preservative is benzalkonium chloride.

As will be appreciated by the skilled artisan, preservatives may be present in concentrations of from about 0.001% to about 0.7% (w/v). In particular embodiments, the preservative(s) may be present in a concentration of from about 0.001% to about 0.5% (w/v); from about 0.001% to about 0.05% (w/v), from about 0.001% to about 0.02% (w/v), from about 0.001% to about 0.015% (w/v), from about 0.001% to about 0.005% (w/v), from about 0.01% to about 0.02%, from about 0.002% to about 0.01%, from about 0.015% to about 0.05%, less than about <0.5%, from about 0.005% to about 0.01%, from about 0.001% to about 0.15%, from about 0.002% to about 0.004%, from about 0.001% to about 0.002%. In some embodiments the concentration of the preservative may be, for example, about 0.001%, about 0.005%, about 0.01%, about 0.02%, about 0.03%, about 0.05%, about 0.1%, about 0.2%, about 0.5%, or about 0.7% (w/v). Typical concentrations (w/v) for various commonly used preservatives are listed in Table C below.

TABLE C

| Preservative | Approximate Concentration Range (w/v) |
| --- | --- |
| Benzalkonium chloride | 0.01-0.02% |
| Benzethonium chloride | 0.01-0.02% |
| Chlorhexidine | 0.002-0.01% |
| Chlorobutanol | <0.5% |
| Methylparaben | 0.015-0.05% |
| Phenylethyl alcohol | <0.5% |
| Propylparaben | 0.005-0.01% |
| Thimerosal | 0.001-0.15% |
| Phenylmercuric nitrate | 0.002-0.004% |
| Phenylmercuric borate | 0.002-0.004 |
| Phenylmercuric acetate | 0.001-0.002 |

In certain embodiments, the formulation may additionally include a surfactant, or combinations of two or more surfactants. In particular embodiments, the formulation is substantially free of surfactant. As used herein, the term "substantially free" is intended to refer to levels of a particular component that are undetectable using routine detection methods and protocols known to the skilled artisan. For example, HPLC (including chiral HPLC, chiral HPLC/MS, LC/MS/MS etc.), thin layer chromatography, mass spectrometry, polarimetry measurements, Gas-chromatography-mass spectrometry, or others.

In particular embodiments, the ocular formulation may further include a chelating agent (e.g., EDTA disodium (EDTA) (e.g., EDTA disodium (dihydrate), etc.) citrates, etc.). In some embodiments, a combination of chelating agents may be present. As will be appreciated by those of skill in the field, chelating agents can be used to hinder degradation of the formulation components and thereby increase the shelf life of ocular formulations. As will be appreciated by the skilled artisan, use of EDTA in combination with gellan gum formulation may be contraindicated as the EDTA can cause gel formation prior to administration of the gellan gum formulation.

Typical concentrations for chelating agents are from about 0.005% to 0.1% (w/v). For example, from about 0.005% to about 0.09%, from about 0.005% to about 0.08%, from about 0.005% to about 07%, from about 0.005%, to about 0.06%, from about 0.005% to about 0.05%, from about 0.005 to about 0.04%, from about 0.005% to about 0.03%, from about 0.01% to about 0.1%, from about 0.01% to about 0.09%, from about 0.01% to about 0.08%, from about 0.01% to about 0.07%, from about 0.01% to about 0.06%, from about 0.01% to about 0.05%, from about 0.01% to about 0.04%, etc. In certain embodiments, the concentration of chelating agent(s) is about 0.005%, about 0.01%, about 0.02%, about 0.03%, about 0.05%, about 0.06%, about 0.07%, about 0.08%, about 0.09%, or about 0.1%.

In particular embodiments, the chelating agent is EDTA disodium. In certain embodiments, the chelating agent is EDTA disodium (dihydrate). In some of these embodiments, the EDTA disodium dihydrate is present at a concentration of about 0.01% (w/v).

In some embodiments, the ocular formulation may additionally include one or more buffering agents (e.g., phosphate buffer(s) (e.g., sodium phosphate buffers (e.g., dibasic sodium phosphate, monobasic sodium phosphate, etc.), citrate buffers, maleate buffers, borate buffers, etc.). As will be appreciated by the skilled artisan, the one or more buffering agent(s) should be selected in combination with the other components of a given formulation to achieve a pH suitable for use (e.g., pH of about 4.5 to about 8).

In certain embodiments, the buffering agent is a phosphate buffer or combination of two or more phosphate buffers. In certain embodiments, the buffering agents are dibasic sodium phosphate and monobasic sodium phosphate.

Typical concentrations for buffering agent(s) for example, phosphate buffering agent(s) may be from about 0.005 molar to 0.1 molar. In some embodiments, the buffering agent(s) may be at a concentration of about 0.01 to about 0.1, from about 0.01 to about 0.08, from about 0.01 to about 0.05, from about 0.01 to about 0.04, from about 0.02 to about 0.1, from about 0.02 to about 0.08, from about 0.02 to about 0.06, from about 0.02 to about 0.05, from about 0.02 to about 0.04 molar, etc. In particular embodiments, there are two buffering agents. Exemplary buffering agents include a combination of dibasic sodium phosphate (e.g., dibasic sodium phosphate.7H$_2$O) and monobasic sodium phosphate (e.g., monobasic sodium phosphate anhydrous). In some embodiments, the concentration of the buffering agent(s) is about 0.005 molar, about 0.01 molar, about 0.02 molar, about 0.03 molar, about 0.04 molar, about 0.05 molar, about 0.06 molar, about 0.07 molar, or about 0.1 molar.

An additional aspect of the invention includes use of the formulations as described herein in the manufacture of a medicament. Particularly, the manufacture of a medicament for use in the treatment and/or prevention of conditions as described herein. Further, the formulations, variously described herein, are also intended for use in the manufacture of a medicament for use in treatment and/or prevention of the conditions and, in accordance with the methods, described herein, unless otherwise noted.

Methods of formulation are well known in the art and are disclosed, for example, in Remington: The Science and Practice of Pharmacy, Mack Publishing Company, Easton, Pa., 19th Edition (1995). The compositions and agents provided herein may be administered according to the methods of the present invention in any therapeutically effective dosing regime. The dosage amount and frequency are selected to create an effective level of the agent without harmful effects. The effective amount of a compound of the present invention will depend on the route of administration, the type of warm-blooded animal being treated, and the physical characteristics of the specific warm-blooded animal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

In certain embodiments, the pharmaceutical compositions may be delivered by intranasal sprays, inhalation, and/or other aerosol delivery vehicles. Methods for delivering genes, polynucleotides, and peptide compositions directly to the lungs via nasal aerosol sprays have been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

In certain embodiments, the delivery may occur by use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

In certain embodiments, the agents provided herein may be attached to a pharmaceutically acceptable solid substrate, including biocompatible and biodegradable substrates such as polymers and matrices. Examples of such solid substrates include, without limitation, polyesters, hydrogels (for example, poly(2-hydroxyethyl-methacrylate), or poly(vinyl-alcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as poly(lactic-co-glycolic acid) (PLGA) and the LUPRON DEPOT™ (injectable microspheres composed of lactic acid-glycolic acid copolymer and leuprolide acetate), poly-D-(−)-3-hydroxybutyric acid, collagen, metal, hydroxyapatite, bioglass, aluminate, bioceramic materials, and purified proteins.

In one particular embodiment, the solid substrate comprises Atrigel™ (QLT, Inc., Vancouver, B.C.). The Atrigel® drug delivery system consists of biodegradable polymers dissolved in biocompatible carriers. Pharmaceuticals may be blended into this liquid delivery system at the time of manufacturing or, depending upon the product, may be added later by the physician at the time of use. When the liquid product is injected into the subcutaneous space through a small gauge needle or placed into accessible tissue sites through a cannula, water in the tissue fluids causes the polymer to precipitate and trap the drug in a solid implant. The drug encapsulated within the implant is then released in a controlled manner as the polymer matrix biodegrades with time.

In particular embodiments, the amount of a PEGylated DRS composition the agent administered will generally range from a dosage of from about 0.1 to about 100 mg/kg/day, and typically from about 0.1 to 10 mg/kg where administered orally or intravenously. In particular embodiments, a dosage is 5 mg/kg or 7.5 mg/kg. For humans, the daily dosage used may range from, about 0.1 mg/kg to 0.5 mg/kg, about 1 mg/kg to 5 mg/kg, about 5 mg/kg to 10 mg/kg, about 10 mg/kg to 20 mg/kg, about 20 mg/kg to 30 mg/kg, about 30 mg/kg to 50 mg/kg, and about 50 mg/kg to 100 mg/kg/24 hours.

In certain embodiments, a composition or agent is administered in a single dosage of 0.1 to 10 mg/kg or 0.5 to 5 mg/kg. In other embodiments, a composition or agent is administered in a dosage of 0.1 to 50 mg/kg/day, 0.5 to 20 mg/kg/day, or 5 to 20 mg/kg/day.

In various embodiments, the dosage is about 50-2500 mg per day, 100-2500 mg/day, 300-1800 mg/day, or 500-1800 mg/day. In one embodiment, the dosage is between about 100 to 600 mg/day. In another embodiment, the dosage is between about 300 and 1200 mg/day. In particular embodiments, the composition or agent is administered at a dosage of 100 mg/day, 240 mg/day 300 mg/day, 600 mg/day, 1000 mg/day, 1200 mg/day, or 1800 mg/day, in one or more doses per day (i.e., where the combined doses achieve the desired daily dosage). In related embodiments, a dosage is 100 mg bid, 150 mg bid, 240 mg bid, 300 mg bid, 500 mg bid, or 600 mg bid. In various embodiments, the composition or agent is administered in single or repeat dosing. The initial dosage and subsequent dosages may be the same or different.

In some embodiments, total daily dose may be about 0.001 mg, about 0.005 mg, about 0.01 mg, about 0.05 mg, about 0.1 mg, 0.5 mg, 1 mg, about 2 mg, about 3 mg, about 4 mg, about 5 mg, about 6 mg, about 7 mg, about 8 mg, about 9 mg, about 10 mg, about 20 mg, about 30 mg, about 40 mg, about 50 mg, about 60 mg, about 70 mg, about 80 mg, about 90 mg or about 100 mg/24 hours. For repeated administrations over several days or longer, depending on the condition, the treatment is sustained until a desired suppression of disease symptoms occurs. The progress of these and other therapies (e.g., ex vivo therapies) can be readily monitored by conventional methods and assays and based on criteria known to the physician or other persons of skill in the art.

It will be further appreciated that for sustained delivery devices and compositions the total dose of DRS contained in such delivery system will be correspondingly larger depending upon the release profile of the sustained release system. Thus, a sustained release composition or device that is intended to deliver DRS polypeptide over a period of 5 days will typically comprise at least about 5 to 10 times the daily dose of DRS polypeptide; a sustained release composition or device that is intended to deliver a DRS peptide over a period of 365 days will typically comprise at least about 400 to 800 times the daily dose of the DRS polypeptide (depending upon the stability and bioavailability of the DRS polypeptide when administered using the sustained release system).

In certain embodiments, a composition or agent is administered orally or intravenously, e.g., by infusion over a period of time of about, e.g., 10 minutes to 90 minutes. In other related embodiments, a composition or agent is administered by continuous infusion, e.g., at a dosage of between about 0.1 to about 10 mg/kg/hr over a time period. While the time period can vary, in certain embodiments the time period may be between about 10 minutes to about 24 hours or between about 10 minutes to about three days.

In particular embodiments, an effective amount or therapeutically effective amount is an amount sufficient to achieve a total concentration of the composition or agent in the blood plasma of a subject with a $C_{max}$ of between about 0.1 µg/ml and about 20 µg/ml or between about 0.3 µg/ml and about 20 µg/ml. In certain embodiments, an oral dosage is an amount sufficient to achieve a blood plasma concentration ($C_{max}$) of between about 0.1 µg/ml to about 5 µg/ml or between about 0.3 µg/ml to about 3 µg/ml. In certain embodiments, an intravenous dosage is an amount sufficient to achieve a blood plasma concentration ($C_{max}$) of between about 1 µg/ml to about 10 µg/ml or between about 2 µg/ml and about 6 µg/ml. In a related embodiment, the total concentration of an agent in the blood plasma of the subject has a mean trough concentration of less than about 20 µg/ml and/or a steady state concentration of less than about 20 µg/ml. In a further embodiment, the total concentration of an agent in the blood plasma of the subject has a mean trough concentration of less than about 10 µg/ml and/or a steady state concentration of less than about 10 µg/ml.

In yet another embodiment, the total concentration of an agent in the blood plasma of the subject has a mean trough concentration of between about 1 ng/ml and about 10 µg/ml and/or a steady state concentration of between about 1 ng/ml and about 10 µg/ml. In one embodiment, the total concentration of an agent in the blood plasma of the subject has a mean trough concentration of between about 0.3 µg/ml and about 3 µg/ml and/or a steady state concentration of between about 0.3 µg/ml and about 3 µg/ml.

In particular embodiments, a composition or agent is administered in an amount sufficient to achieve in the mammal a blood plasma concentration having a mean trough concentration of between about 1 ng/ml and about 10 µg/ml and/or a steady state concentration of between about 1 ng/ml and about 10 µg/ml. In related embodiments, the total concentration of the agent in the blood plasma of the mammal has a mean trough concentration of between about 0.3 µg/ml and about 3 µg/ml and/or a steady state concentration of between about 0.3 µg/ml and about 3 µg/ml.

In particular embodiments of the present invention, the effective amount of a composition or agent, or the blood plasma concentration of composition or agent is achieved or maintained, e.g., for at least 15 minutes, at least 30 minutes, at least 45 minutes, at least 60 minutes, at least 90 minutes, at least 2 hours, at least 3 hours, at least 4 hours, at least 8 hours, at least 12 hours, at least 24 hours, at least 48 hours, at least 3 days, at least 4 days, at least 5 days, at least 6 days, at least one week, at least 2 weeks, at least one month, at least 2 months, at least 4 months, at least 6 months, at least one year, at least 2 years, or greater than 2 years.

In certain DRS polypeptide-based embodiments, the amount of polypeptide administered will typically be in the range of about 0.1 µg/kg to about 0.1 mg/kg to about 50 mg/kg of patient body weight. Depending on the type and severity of the disease, about 0.1 µg/kg to about 0.1 mg/kg to about 50 mg/kg body weight (e.g., about 0.1-15 mg/kg/dose) of polypeptide can be an initial candidate dosage for administration to the patient, whether, for example, by one or more separate administrations, or by continuous infusion. For example, a dosing regimen may comprise administering an initial loading dose of about 4 mg/kg, followed by a weekly maintenance dose of about 2 mg/kg of the polypeptide, or about half of the loading dose. However, other dosage regimens may be useful. A typical daily dosage might range from about 0.1 µg/kg to about 1 µg/kg to 100 mg/kg or more, depending on the factors mentioned above.

For repeated administrations over several days or longer, depending on the condition, the treatment is sustained until a desired suppression of disease symptoms occurs.

In particular embodiments, the effective dosage achieves the blood plasma levels or mean trough concentration of a composition or agent described herein. These may be readily determined using routine procedures.

Embodiments of the present invention, in other aspects, provide kits comprising one or more containers filled with one or more of the polypeptides, polynucleotides, antibodies, multiunit complexes, compositions thereof, etc., of the invention, as described herein. The kits can include written instructions on how to use such compositions (e.g., to modulate cellular signaling, angiogenesis, cancer, inflammatory conditions, diagnosis etc.).

The kits herein may also include a one or more additional therapeutic agents or other components suitable or desired for the indication being treated, or for the desired diagnostic application. An additional therapeutic agent may be contained in a second container, if desired. Examples of additional therapeutic agents include, but are not limited to anti-neoplastic agents, anti-inflammatory agents, antibacterial agents, antiviral agents, angiogenic agents, etc.

The kits herein can also include one or more syringes or other components necessary or desired to facilitate an intended mode of delivery (e.g., stents, implantable depots, etc.).

The present invention now will be described more fully by the following examples. This invention may, however, be embodied in many different forms and should not be construed as limited to the embodiments set forth herein; rather, these embodiments are provided so that this disclosure will be thorough and complete, and will fully convey the scope of the invention to those skilled in the art.

EXAMPLES

Example 1

Production of DRS Polypeptides

Codon Optimization and Gene Synthesis: An *E. coli* codon optimized nucleic acid sequence encoding the DRS polypeptide AspRS1$^{N1}$ (C76S) (comprising amino acids 1-154, and a cysteine→serine mutation at position 76) was designed for optimal *E. coli* expression using the algorithm developed by DNA2.0 (Menlo Park, Calif.). The gene was synthesized with a C-terminal V5H is tag and subcloned into pJExpress411 vector where the T7 promoter was used to drive the transcription and the kanamycin resistance was used for antibiotic selection. The codon-optimized DNA sequence is as follows:

```
                                         (SEQ ID NO: 28)
ATGCCGAGCGCGAGCGCCAGCCGTAAGAGCCAGGAAAAACCACGTGAGAT

TATGGATGCCGCAGAGGACTATGCGAAAGAACGTTACGGTATTTCCAGCA

TGATCCAATCTCAGGAGAAACCGGACCGCGTTCTGGTTCGTGTTCGCGAT

CTGACCATTCAGAAGGCGGACGAGGTGGTTTGGGTGCGTGCGCGCGTGCA

CACCAGCCGTGCAAAAGGCAAACAGAGCTTTCTGGTCCTGCGTCAGCAGC

AATTCAACGTCCAGGCGCTGGTGGCAGTGGGTGACCACGCCAGCAAACAA

ATGGTGAAGTTCGCTGCTAACATCAATAAAGAATCCATTGTTGATGTTGA

AGGCGTCGTTCGCAAGGTCAATCAAAAGATCGGCTCGTGTACGCAACAAG

ATGTCGAGCTGCATGTGCAGAAGATTTACGTCATCAGCCTGGCGGAGCCG

CGTTTGCCGCTGGGTAAGCCGATCCCTAACCCGCTGTTGGGTCTGGACAG

CACGCATCACCATCACCACCACTAA
```

The corresponding translated protein sequence is:

```
                                         (SEQ ID NO: 29)
MPSASASRKSQEKPREIMDAAEDYAKERYGISSMIQSQEKPDRVLVRVRD

LTIQKADEVVWVRARVHTSRAKGKQSFLVLRQQQFNVQALVAVGDHASKQ

MVKFAANINKESIVDVEGVVRKVNQKIGSCTQQDVELHVQKIYVISLAEP

RLPLGKPIPNPLLGLDSTHHHHHH
```

As a control, the non-mutated AspRS1$^{N1}$ protein was also prepared, using wild type (human codon usage), and cloned into the identical expression cassette. The nucleic acid sequence of the native AspRS1$^{N1}$ is as follows:

```
                                         (SEQ ID NO: 30)
ATGCCCAGCGCCAGCGCCAGCCGCAAGAGTCAGGAGAAGCCGCGGGAGAT

CATGGACGCGGCGGAAGATTATGCTAAAGAGAGATATGGAATATCTTCAA

TGATACAATCACAAGAAAAACCAGATCGAGTTTTGGTTCGGGTTAGAGAC

TTGACAATACAAAAAGCTGATGAAGTTGTTTGGGTACGTGCAAGAGTTCA

TACAAGCAGAGCTAAAGGGAAACAGTGCTTCTTAGTCCTACGTCAGCAGC

AGTTTAATGTCCAGGCTCTTGTGGCGGTGGGAGACCATGCAAGCAAGCAG

ATGGTTAAATTTGCTGCCAACATCAACAAAGAGAGCATTGTGGATGTAGA

AGGTGTTGTGAGAAAAGTGAATCAGAAAATTGGAAGCTGTACACAGCAAG

ACGTTGAGTTACATGTTCAGAAGATTTATGTGATCAGTTTGGCTGAACCC

CGTCTGCCCCTGGGTAAGCCTATCCCTAACCCTCTCCTCGGTCTCGATTC

TACGCACCACCACCACCACCACTGA
```

The encoding protein, containing the identical C-terminal tag, but the wild type Cys76 is shown below:

```
                                         (SEQ ID NO: 31)
MPSASASRKSQEKPREIMDAAEDYAKERYGISSMIQSQEKPDRVLVRVRD

LTIQKADEVVWVRARVHTSRAKGKQCFLVLRQQQFNVQALVAVGDHASKQ

MVKFAANINKESIVDVEGVVRKVNQKIGSCTQQDVELHVQKIYVISLAEP

RLPLGKPIPNPLLGLDSTHHHHHH
```

Expression Strains: BL21-CodonPlus (DE3)-RIPL competent cells (Agilent cat. no. 230280) were transformed with the non-mutated AspRS1$^{N1}$ expression construct. BL21 (DE3) competent cells (Novagen, cat. no. 69450) were transformed with the AspRS1$^{N1}$ (C76S) expression construct. Briefly, the plasmid (1 μL) was added into 50 μL of the competent cells. The reaction was mixed and incubated on ice for 30 minutes. The reaction was heat-shocked for at 42° C. for 30 sec followed by a cold-shock on ice for 2 minutes. Then the SOC medium (500 μL) was added and the tube was incubated at 37° C., 250 rpm for 1 hour. Finally, an aliquot of the culture (50 μL) was spread on the Kanamycin plate (Teknova S9641) and incubated at 37° C. overnight. Single colony was picked and used for expression scale-up.

Fed-Batch Fermentation Production of Proteins: M9YE medium was prepared by mixing 200 mL sterile M9 minimal salt 5× (BD248510), 778 mL 30 g/L yeast extract in sterile purified water (BD212750), 20 mL sterilized 20% glucose (Sigma G7021) and 2 mL sterile 1.0 M MgSO$_4$ (Sigma M7506). The feeding solution contains 5% yeast extract, 50% glucose, trace elements and 2 g/L magnesium sulfate.

Kanamycin sulfate (Invitrogen 15160) was added to a final concentration of 100 μg/mL in both M9YE and feeding solution.

A 4 L fermentor (Sartorius Biostat B plus) with MFCS/DA software was used for the fed-batch fermentation of both proteins. The agitation was set at 1000 rpm. The pH value was controlled at 7.0 automatically by the addition of 30% ammonium hydroxide (Sigma 221228) and 30% phosphoric acid (Sigma P5811). The air was provided at a flow rate of 4 L/min with an oil-free diaphragm air compressor (Cole-Parmer). The air was passed through a 0.2 μm Midisart 2000 filter (Sartorius 17805). The pure oxygen (West Air) was supplied automatically to control the dissolved oxygen level at 70%. The temperature was controlled at 30° C. with a Neslab RTE7 circulator (Thermo Scientific). The foaming was controlled by addition of the antifoam 204 (Sigma A8311). The initial volume of M9YE medium in the fermentor was 3 L. The fermentor was inoculated with 150 mL of the seed culture grown overnight at 30° C. and 250 rpm. When the glucose was depleted in the vessel, the concentrated feeding solution was introduced into the vessel by a peristaltic pump set at 0.9 ml/min. When the optical density of the cells at 600 nm reached about 30, the culture was induced with 0.5 mM IPTG (Fisher Scientific BP1755). The culture was run overnight (about 18-hour fed-batch phase) and harvested by centrifugation at 6,000 g for 1 hour. The cell pellet was stored at −20° C. until purification. The expression of each protein was confirmed by SDS-PAGE analysis (data not shown).

Purification of Proteins: Frozen cell pellets from each production run were resuspended in 4 volumes (i.e., 4 mL/g cell pellet) of Lysis Buffer (50 mM Tris, 300 mM NaCl, 25 mM Imidazole, 14 mM 13-ME, pH 8.0). Complete EDTA-FREE protease inhibitor cocktail tablets (Roche Cat. #05 056 489 001) were added to the suspension at a ratio of 1 tablet/50 mL. The suspension was passed through a microfluidizer (Microfluidics) twice at 14,000 psi with cooling by ice. The lysate was centrifuged at 35,000×g for 45 min at 4° C. The supernatant was filtered through 0.45+0.22 μm Sartobran capsule filters (Sartorius).

The clarified lysate was bound to the Ni-NTA resin (Qiagen), pre-equilibrated with Ni-NTA Binding Buffer (50 mM Tris, 300 mM NaCl, 25 mM Imidazole, pH 8.0). The column was washed with 300 column volumes of Ni-NTA Binding Buffer+0.1% Triton X-114 followed by 33 column volumes of the Ni-NTA Binding Buffer. The bound protein, D1-C76S, was eluted with 5 column volumes of Ni-NTA Elution Buffer (50 mM Tris, 300 mM NaCl, 300 mM Imidazole, pH 8.0).

The purified proteins were dialyzed into a buffer containing 20 mM sodium phosphate, 200 mM Arginine, at pH 7.3. The dialyzed protein was passed through a Q membrane filter (Sartobind-Q from Sartorius or Mustang-Q from Pall) or a Q-Sepharose column (GE Healthcare) for further endotoxin removal, and then filtered through a 0.22 μm sterile filter.

Comparison of Production Yield, Purity and Endotoxin Content of AspRS1$^{N1}$ (C76S) with AspRS1$^{N1}$.

A direct comparison of the yields of soluble proteins from the AspRS1$^{N1}$ (C76S) and non-mutated AspRS1$^{N1}$ constructs, over several independent production runs, (Table E1) reveals that the AspRS1$^{N1}$ (C76S) variant has a consistently higher yield compared to the non-mutated parent protein. Table E1 lists the average purification yield of AspRS1$^{N1}$ (C76S) and non-mutated AspRS1$^{N1}$.

TABLE E1

Production yields for different AspRS1$^{N1}$ variants

| DRS polypeptide form | Purified protein yield (mg/g cell pellet) |
| --- | --- |
| AspRS1$^{N1}$ (C76S) | 1.72 ± 0.25 (n = 8) |
| AspRS1$^{N1}$ | 1.38 ± 0.57 (n = 7) |

Figure 1:
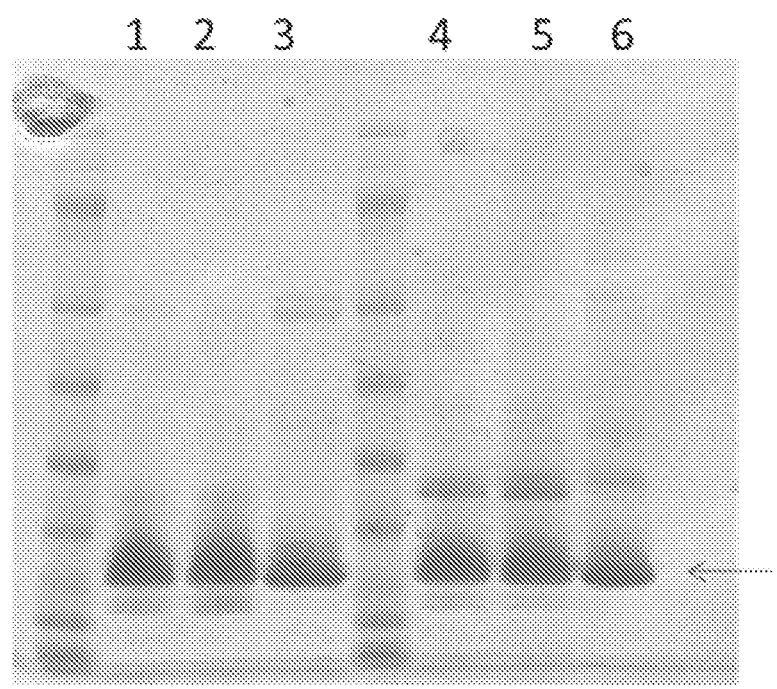
FIG. 1 shows an SDS-PAGE analysis of the purified proteins AspRS1$^{N1}$ (C76S) (DRS(1-154)(C76S) and the corresponding non mutated protein AspRS1$^{N1}$ (DRS(1-154)). Lanes 1-3 were run under reduced conditions, and lanes 4-6 were run under non-reduced conditions. Lanes 1 and 4: AspRS1$^{N1}$ DRS(1-154) lot # D-N1-V5H-046, lanes 2 and 5

An analysis of representative proteins by SDS-gel is shown in FIG. 1. The gel demonstrates that the purified AspRS1$^{N1}$ (C76S) has less low molecular weight impurities, and contains less disulfide cross-linked dimer species, compared to comparable batches of AspRS1$^{N1}$ prepared under identical conditions.

Moreover an analysis of the proteins endotoxin content reveals that the AspRS1$^{N1}$ (C76S) proteins exhibited a significantly reduced endotoxin content compared to the non-mutated AspRS1$^{N1}$. (Table E2).

TABLE E2

Endotoxin Content

| DRS polypeptide form | Average Endotoxin level in purified protein (EU/mg) |
| --- | --- |
| AspRS1$^{N1}$ (C76S) | 7.3 (n = 8) |
| AspRS1$^{N1}$ | 43.5 (n = 7) |

Accordingly it is concluded that the DRS polypeptides comprising a reduced a cysteine content, specifically AspRS1$^{N1}$ (C76S) exhibits improved manufacturability, improved production yields and significantly less endotoxin contamination compared to the corresponding non mutated protein.

Example 2

Production of DRS Polypeptides in Mammalian Cells

As an alternative production system, exemplary DRS polypeptides were prepared using a mammalian expression system. This approach has the potential advantage of eliminating any potential contamination of the DRS polypeptides with E. coli derived endotoxins.

Cloning: The AspRS1$^{N1}$ fragment (amino acid 1-154 of human cytoplasmic Aspartyl-tRNA synthetase) was amplified by polymerase chain reaction (PCR) using the following primer pairs synthesized at Integrated DNA Technologies to create either cytoplasmic, or secreted versions of the AspRS1$^{N1}$.

Primer Pair 1

(SEQ ID NO: 32)
AGTCTTGCACTTGTCACGAATTCGATGCCCAGCGCCAGCGCCAGC (SEQ ID NO: 33)
CGGTGGGCATGTGTGAGTTTTGTCTCACTTGTCGTCATCGTCTTTGTAGT

CCGTAGAATCGAGACCGAGGAGAGG

-continued

Primer Pair 2

(SEQ ID NO: 34)
GATCACCGGCGAAGGAGGGCCACCATGCCCAGCGCCAGCGCCAGC (SEQ ID NO: 35)
CGGTGGGCATGTGTGAGTTTTGTCTCACTTGTCGTCATCGTCTTTGTAGT

CCGTAGAATCGAGACCGAGGAGAGG

The primers were mixed with the template (AspRS1$^{N1}$ nucleic acid fragment in the pET28 vector)(see above), Accuprime pfx supermix (Invitrogen cat. no. 12344-040) and denatured for 5 minutes at 95° C. The amplification was done in the Eppendorf thermal cycler for 35 cycles of 95° C. for 30 seconds, 52° C. for 30 seconds and 68° C. for 40 seconds. The amplified fragments were purified with QIAquick PCR Purification Kit (Qiagen cat. no. 28104). The fragment size, quantity and purity were confirmed on the 1% agarose gel in the TAE buffer (Invitrogen cat. no. 15558). The fragment was inserted into the pFUSE-hIgG1-Fc2 (Invivogen cat. no. pfuse-hg1fc2) by mutagenesis using the QuikChange Lightning Site-Directed Mutagenesis Kit (Agilent, cat. no. 210518). Eighteen thermal cycles were performed at 95° C. for 30 seconds, 52° C. for 30 seconds and 68° C. for 4 minutes. After mutagenesis, the sample was treated with Dpn I enzyme at 37° C. and transformed into XL10 gold competent cells. The heat shock was done at 42° C. for 30 seconds followed by 2 minutes on ice. The XL10 gold transformants were resuspended in SOC medium and incubated at 37° C. for 1 hour and then were spread onto zeocin agar and incubated at 37° C. overnight. Multiple colonies were grown in terrific broth overnight at 37° C. and the plasmids were purified with QIAprep Spin Miniprep Kit (Qiagen cat. no. 27106). The plasmids were sequenced to confirm the DNA identity. The correct clones were transformed into NovaBlue competent cells (Novagen cat. no. 70181) and grown in 250 ml M9YE medium at 37° C. overnight. The maxiprep was performed using the HiSpeed Plasmid Maxi Kit (Qiagen cat. no. 12663). The concentration and purity were determined by measuring A260, A280 and A230. The purified plasmids were stored at −20° C. before transfection.

The secretory AspRS1$^{N1}$ sequence is as follows:

(SEQ ID NO: 36)
ATGTACAGGATGCAACTCCTGTCTTGCATTGCACTAAGTCTTGCACTTGT

CACGAATTCGATGCCCAGCGCCAGCGCCAGCCGCAAGAGTCAGGAGAAGC

CGCGGGAGATCATGGACGCGGCGGAAGATTATGCTAAAGAGAGATATGGA

ATATCTTCAATGATACAATCACAAGAAAAACCAGATCGAGTTTTGGTTCG

GGTTAGAGACTTGACAATACAAAAAGCTGATGAAGTTGTTTGGGTACGTG

CAAGAGTTCATACAAGCAGAGCTAAAGGGAAACAGTGCTTCTTAGTCCTA

CGTCAGCAGCAGTTTAATGTCCAGGCTCTTGTGGCGGTGGGAGACCATGC

AAGCAAGCAGATGGTTAAATTTGCTGCCAACATCAACAAAGAGAGCATTG

TGGATGTAGAAGGTGTTGTGAGAAAAGTGAATCAGAAAATTGGAAGCTGT

ACACAGCAAGACGTTGAGTTACATGTTCAGAAGATTTATGTGATCAGTTT

GGCTGAACCCCGTCTGCCCCTGGGTAAGCCTATCCCTAACCCTCTCCTCG

GTCTCGATTCTACGGACTACAAAGACGATGACGACAAGTGA

The intracellular AspRS1$^{N1}$ sequence is as follows:

(SEQ ID NO: 37)
ATGCCCAGCGCCAGCGCCAGCCGCAAGAGTCAGGAGAAGCCGCGGGAGAT

CATGGACGCGGCGGAAGATTATGCTAAAGAGAGATATGGAATATCTTCAA

TGATACAATCACAAGAAAAACCAGATCGAGTTTTGGTTCGGGTTAGAGAC

TTGACAATACAAAAAGCTGATGAAGTTGTTTGGGTACGTGCAAGAGTTCA

TACAAGCAGAGCTAAAGGGAAACAGTGCTTCTTAGTCCTACGTCAGCAGC

AGTTTAATGTCCAGGCTCTTGTGGCGGTGGGAGACCATGCAAGCAAGCAG

ATGGTTAAATTTGCTGCCAACATCAACAAAGAGAGCATTGTGGATGTAGA

AGGTGTTGTGAGAAAAGTGAATCAGAAAATTGGAAGCTGTACACAGCAAG

ACGTTGAGTTACATGTTCAGAAGATTTATGTGATCAGTTTGGCTGAACCC

CGTCTGCCCCTGGGTAAGCCTATCCCTAACCCTCTCCTCGGTCTCGATTC

TACGGACTACAAAGACGATGACGACAAGTGA

The hEF1-HTLV promoter comprising the Elongation Factor-1α (EF-1α) core promoter and the R segment and part of the U5 sequence of the Human T-Cell Leukemia Virus (HTLV) Type 1 Long Terminal Repeat was used to drive the transcription. The V5 (GKPIPNPLLGLDST) (SEQ ID NO:72) and Flag (DYKDDDDK) (SEQ ID NO:73) tags were added to the C-terminus of the D1 fragments for detection and purification purpose. The Sh ble gene from Streptoalloteichus hindustanus was used for antibiotic resistance. The Simian Virus 40 late polyadenylation signal enables the cleavage and polyadenylation resulting in stable mRNA.

Expression. The FREESTYLE™ MAX CHO Expression System (Invitrogen cat. no. K9000-20) was used for expression of the secretory form of AspRS1$^{N1}$. The CHO-S cells were thawed from liquid nitrogen and grown in the serum-free medium (FREESTYLE™ CHO Expression Medium) supplemented with 8 mM L-Glutamine in a 37° C. incubator containing a humidified atmosphere of 8% $CO_2$ in air on an orbital shaker platform rotating at 125 rpm. The cells were diluted to 2-3×10$^5$ cells/ml when the density reached about 10$^6$ cells/ml and were repeated a few passages. The DNA was mixed 1:1 with the Freestyle Max reagent in the Optipro SFM and incubated 10 minutes at room temperature. The complex was added slowly into the cells at the density about 10$^6$ cells/ml. The cell density and viability were monitored daily until harvest.

The FREESTYLE™ 293 Expression (Invitrogen cat. no. K9000-01) was used for expression of the intracellular form of AspRS1$^{N1}$. The 293-F cells were thawed from liquid nitrogen and grown in the serum-free medium (FREESTYLE™ 293 Expression Medium) supplemented with Glutamax-I in a 37° C. incubator containing a humidified atmosphere of 8% $CO_2$ in air on an orbital shaker platform rotating at 125 rpm. The cells were diluted to 2-3×10$^5$ cells/ml when the density reached about 10$^6$ cells/ml and were repeated for a few passages. The DNA was mixed 1:2 with the 293transfectin reagent in the Opti-MEM I and incubated 20-30 minutes at room temperature. The complex was added slowly into the cells at the density about 10$^6$ cells/ml. The cell density and viability were monitored daily until harvest.

Purification. In the case of secretory form of AspRS1$^{N1}$, the supernatant of the cell culture was separated from the cells by centrifugation. The clarified sample was loaded onto M2 agarose (Sigma cat. no. A2220) in a gravity column. The resin was then washed with TBS (50 mM Tris HCl, with 150 mM NaCl, pH 7.4). The bound protein was eluted with 0.1 M glycine HCl, pH 3.0 and neutralized immediately with 1M Tris buffer at pH8.0.

In the case of intracellular form of AspRS1$^{N1}$, the cells were recovered by centrifugation. The cells were lysed using M-PER Mammalian Protein Extraction Reagent (Pierce cat. no. 78501) and then centrifuged to remove the insoluble debris. The clarified lysate was loaded onto M2 agarose (Sigma cat. no. A2220) in a gravity column. The resin was then washed with TBS (50 mM Tris HCl, with 150 mM NaCl, pH 7.4). The bound protein was eluted with 0.1 M glycine HCl, pH 3.0 and neutralized immediately with 1M Tris buffer at pH8.0. The purified protein was analyzed by SDS-PAGE and Western blot. Purified proteins may be evaluated for binding to TLRs as described in Example 3 below.

Example 3

Evaluation of Biological Activity

To evaluate the binding of the DRS polypeptides to human toll like receptors a series of studies were conducted with commercially available reporter HEK 293 and THP-1 cell lines over expressing the TLR 2 and TLR 4 receptors.

Genetically modified Human HEK293 cells sold under the trademark HEK-Blue™ TLR cells (Invivogen) selectively express the TLR2 or TLR4 receptors and include a secreted embryonic alkaline phosphatase (SEAP)reporter gene under the control of an IFN-beta minimal promoter which is fused to five NF-kB and AP-1 transcription factors binding sites. With the use of specific TLR 2 or 4 agonists (respectively), HEK-BLUE™ TLR2 and HEK-BLUE™ TLR4 cells activate NF-kB and/or AP-1 leading to the secretion of SEAP which is measurable when using SEAP detection reagent. The HEK-BLUE™ TLR2 cells are co-transfected with the LPS co-receptor protein CD14 to enhance TLR2 responsiveness and improve signal quality. The parent cell expresses endogenous levels of TLR1, 3, 5, 6 and also NOD1. The THP-1 monocyte reporter cells (Invivogen THP1-XBlue™ cells). Stably express CD14, MD-2, & and also include a secreted embryonic alkaline phosphatase (SEAP) reporter gene under the control of NF-kB and AP-1 promoter elements as described above.

Methods. HEK-BLUE™-TLR2 or HEK-BLUE™-TLR4 cells were washed twice with PBS, trypsinized and resuspended in fresh Growth Medium (Growth Medium: DMEM, 4.5 g/L glucose, 10% heat-inactivated fetal bovine serum (30 minutes at 56° C.), 100 mg/mL ZEOCIN™, 2 mM L-glutamine). Cells were plated at a concentration of 50,000 cells/well in a 96 well plate in a total volume of 100 μL, and DRS polypeptides, (AspRS1$^{N1}$ or AspRS1$^{N1}$(C76S)), were added to each well at the concentrations shown for 16 hours. On the next day, SEAP detection medium (QUANTI-BLUE™) (Invivogen Catalog code: rep-qb1) was prepared following the manufacturer's instructions and 120 μL was added per well to a clear flat-bottom 96-well plate, followed by (20 μL) of cell supernatant. Samples were incubated at 37° C. for 24 hours. SEAP levels were determined using a spectrophotometer and reading absorbance at 650 nM.

Results. The results shown in FIGS. 2 and 3, demonstrate that the DRS polypeptide AspRS1$^{N1}$ (C76S) exhibited significantly more activity, and displayed an apparent EC$_{50}$ which was significantly higher compared to the non-mutated AspRS1$^{N1}$ parent molecule with respect to both TLR2 and TLR4 receptor binding (Table E3).

TABLE E3

Activity of AspRS1$^{N1}$ variant C76S on TLR2 and TLR4 receptors

| DRS polypeptide form | Fold increase in activity over AspRS1$^{N1}$ |
|---|---|
| TLR2 Activity | |
| AspRS1$^{N1}$ (C76S) | 3.2 ± 0.14 (n = 2) |
| TLR4 Activity | |
| AspRS1$^{N1}$ (C76S) | 3.6 ± 0.17 (n = 2) |

These results demonstrate the DRS polypeptides with altered cysteine content, and in particular DRS mutants comprising the mutation of cysteine 76 to another amino acid, result in the creation of new product forms which surprisingly exhibit enhanced activities, improved production yields and further surprisingly demonstrate reduced endotoxin content.

Example 4

Mutation of C76 and 0130 to Other Amino Acids

To determine whether other favorable mutations in addition to Cys76→Ser could be identified, both cysteine residues (i.e., those at either Cys76 or Cys130) were mutated to all 19 alternative naturally occurring amino acid residues. To accomplish this in either the native human codon usage DRS polypeptides, or the E. coli optimized DRS polypeptides, the following primers were used:

TABLE E4

Mutagenesis Primer Sequences

| Name | Amino Acid Residue Range of SEQ ID NO: 1 | Nucleic acid sequence | SEQ ID NO: |
|---|---|---|---|
| Human C76X Primer | 211-247 | GCTAAAGGGAAACAGNNNTTCTTAGTCCTACGTCAG C (NNN = AGC) | 38 |
| Human C130X Primer | 367-403 | GTGAATCAGAAAATTGGAAGCNNNACACAGCAAGA CG (NNN = AGC) | 39 |
| E. coli codon optimized C76X Primer | 208-247 | CGTGCAAAAGGCAAACAGNNNTTTCTGGTCCTGCGT CAGC (NNN = AGC) | 40 |

TABLE E4-continued

Mutagenesis Primer Sequences

| Name | Amino Acid Residue Range of SEQ ID NO: 1 | Nucleic acid sequence | SEQ ID NO: |
|---|---|---|---|
| E. coli codon optimized C130X Primer | 369-409 | CAATCAAAAGATCGGCTCGNNNACGCAACAAGATGT CGAGC (NNN = AGC) | 41 |

Mutations at either position were introduced by mutagenesis using the QuikChange Lightning Site-Directed Mutagenesis Kit (Agilent, cat. no. 210518) as described above. After mutagenesis, the sample was treated with Dpn I enzyme at 37° C. and transformed into XL10 gold competent cells as described in Example 2. Multiple colonies were grown in terrific broth overnight at 37° C. and the resulting plasmids were purified with QIAprep Spin Miniprep Kit (Qiagen cat. no. 27106). The plasmids were sequenced to confirm the identity of the amino acid substitution of each clone. The representative clones were transformed into NovaBlue competent cells (Novagen cat. no. 70181) and grown in 250 ml M9YE medium at 37° C. overnight. A maxiprep was performed using the HiSpeed Plasmid Maxi Kit (Qiagen cat. no. 12663) to create a plasmid stock of mutant for further analysis. The concentration and purity were determined by measuring A260, A280 and A230. The purified plasmids were stored at −20° C. before transfection into E. coli or mammalian cells using the methods described above in Examples 1 and 2.

To assess the impact of the mutation of Cys76 or Cys130, representative clones were transformed into E. coli, or mammalian cells, and the production yields, endotoxin contents were compared. Also, the relative activity of the purified proteins are compared in the HEK293-TLR2 and HEK293-TLR4 expressing cell lines as described above. The optimal substitutions are identified based on the results obtained. Representative results are shown in Table E5.

TABLE E5

| Variant | Yield + <1.2 mg, ++ >1.2 mg, +++ >1.4 mg, ++++ >2.0 mg | EU/mg + <1 EU/mg, ++ <5 EU/mg, +++ <10 EU/mg, ++++ <20 EU/mg, +++++ >20 EU/mg |
|---|---|---|
| C76A | ++++ | +++++ |
| C76I | +++ | +++ |
| C76L | + | +++ |
| C76T | ++ | +++ |
| C76V | + | + |
| C130F | ++ | + |
| C130L | +++ | ++++ |
| C130T | + | +++ |
| C130V | + | +++++ |

The results show that C76V, C76L, and C76T show enhanced yields and reduced endotoxin content. Additionally the results show that C130T and C130V demonstrate enhanced yields and reduced endotoxin content.

Example 5

Production of DRS Cysteine Mutants

Creation of DRS Cysteine Mutants: To improve the stability of full length DRS and reduce the impact of non-specific disulfide bond mediated aggregation formation, potential problematic cysteines were identified based on the crystal structure (see, e.g., commonly owned U.S. application Ser. No. 12/751,358), and mutated into Ser or Ala or Val. In particular cysteines C334, C349, C203 and C259 in wild type DRS were initially targeted for mutagenesis. To systematically assess the impact of each cysteine in mediating protein aggregation, mini libraries were created in which each DRS cysteine mutant could contain either a mutation on one cysteine position or multiple positions. To make DRS mutants C334S, C349S, C334S/C349S, C334S/C349S/C259A/C203A, C334S/C349S/C259A/C203V, C334S/C349S/C203A, C334S/C349S/C203V, C203A and C203V, the following primers were used as listed in Table E6:

TABLE E6

| Mutation | Oligo sequence | SEQ ID NO: |
|---|---|---|
| C334S | CAGTTCCCATCTGAGCCATTC | 162 |
| C349S | GACTAGAATATTCTGAAGCATTGGC | 163 |
| C203A | CCAGTCTGGCATCGCCCATCTCTTCC | 164 |
| C203V | CCAGTCTGGCATCGTCCATCTCTTCC | 165 |
| C259A | CCACAGCTATATAAGCAAATGTGCAT TGCGGCTGATTTTGAG | 166 |

Mutations at cysteine positions were introduced by mutagenesis using the QuickChange Lightning Site-Directed Mutagenesis Kit (Agilent, cat. no. 210518) following the manufacturer's instructions. After mutagenesis, the sample was treated with Dpn I enzyme at 37° C. and transformed into XL10 gold competent cells using routine procedures. Multiple colonies were grown in LB media overnight at 37° C. and the resulting plasmids are purified with QIAprep Spin Miniprep Kit (Qiagen cat. no. 27106). The plasmids were sequenced to confirm the identity of the amino acid substitution of each clone.

The DRS cysteine mutant DNA sequences are as follows:

1. DRS-C334S:
(SEQ ID NO: 118)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

-continued

```
CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGAAGAGCTACTGTTAACCAGGATACAAGATTAGACAACAGAGT

CATTGATCTTAGGACATCAACTAGTCAGGCAGTCTTCCGTCTCCAGTCTGGCATCTGCCATCT

CTTCCGAGAAACTTTAATTAACAAAGGTTTTGTGGAAATCCAAACTCCTAAAATTATTTCAG

CTGCCAGTGAAGGAGGAGCCAATGTTTTTACTGTGTCATATTTTAAAAATAATGCATACCTG

GCTCAGTCCCCACAGCTATATAAGCAAATGTGCATTTGTGCTGATTTTGAGAAGGTTTTCTCT

ATTGGACCAGTATTCAGAGCGGAAGACTCTAATACCCATAGACATCTAACTGAGTTTGTTGG

TTTGGACATTGAAATGGCTTTTAATTACCATTACCACGAAGTTATGGAAGAAATTGCTGACA

CCATGGTACAAATATTCAAAGGACTTCAAGAAAGGTTTCAGACTGAAATTCAAACAGTGAA

TAAACAGTTCCCATCTGAGCCATTCAAATTTTTGGAGCCAACTCTAAGACTAGAATATTGTG

AAGCATTGGCTATGCTTAGGGAAGCTGGAGTCGAAATGGGAGATGAAGACGATCTGAGCAC

ACCAAATGAAAAGCTGTTGGGTCATTTGGTAAAGGAAAAGTATGATACAGATTTTTATATTC

TTGATAAATATCCATTGGCTGTAAGACCTTTCTATACCATGCCTGACCCAAGAAATCCCAAA

CAGTCCAACTCTTACGATATGTTCATGAGAGGAGAAGAAATATTGTCAGGAGCTCAAAGAA

TACATGATCCTCAACTGCTAACAGAGAGAGCTTTACATCATGGAATTGATTTGGAGAAAATT

AAGGCTTACATTGATTCCTTCCGCTTTGGAGCCCCTCCTCATGCTGGTGGAGGCATTGGATTG

GAACGAGTTACTATGCTGTTTCTGGGATTGCATAATGTTCGTCAGACCTCCATGTTCCCTCGT

GATCCCAAACGACTCACTCCT
```

2. DRS-C349S:

(SEQ ID NO: 119)

```
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGAAGAGCTACTGTTAACCAGGATACAAGATTAGACAACAGAGT

CATTGATCTTAGGACATCAACTAGTCAGGCAGTCTTCCGTCTCCAGTCTGGCATCTGCCATCT

CTTCCGAGAAACTTTAATTAACAAAGGTTTTGTGGAAATCCAAACTCCTAAAATTATTTCAG

CTGCCAGTGAAGGAGGAGCCAATGTTTTTACTGTGTCATATTTTAAAAATAATGCATACCTG

GCTCAGTCCCCACAGCTATATAAGCAAATGTGCATTTGTGCTGATTTTGAGAAGGTTTTCTCT

ATTGGACCAGTATTCAGAGCGGAAGACTCTAATACCCATAGACATCTAACTGAGTTTGTTGG

TTTGGACATTGAAATGGCTTTTAATTACCATTACCACGAAGTTATGGAAGAAATTGCTGACA

CCATGGTACAAATATTCAAAGGACTTCAAGAAAGGTTTCAGACTGAAATTCAAACAGTGAA
```

-continued

TAAACAGTTCCCATGTGAGCCATTCAAATTTTTGGAGCCAACTCTAAGACTAGAATATTCTG

AAGCATTGGCTATGCTTAGGGAAGCTGGAGTCGAAATGGGAGATGAAGACGATCTGAGCAC

ACCAAATGAAAAGCTGTTGGGTCATTTGGTAAAGGAAAAGTATGATACAGATTTTTATATTC

TTGATAAATATCCATTGGCTGTAAGACCTTTCTATACCATGCCTGACCCAAGAAATCCCAAA

CAGTCCAACTCTTACGATATGTTCATGAGAGGAGAAGAAATATTGTCAGGAGCTCAAAGAA

TACATGATCCTCAACTGCTAACAGAGAGCTTTACATCATGGAATTGATTTGGAGAAAATT

AAGGCTTACATTGATTCCTTCCGCTTTGGAGCCCCTCCTCATGCTGGTGGAGGCATTGGATTG

GAACGAGTTACTATGCTGTTTCTGGGATTGCATAATGTTCGTCAGACCTCCATGTTCCCTCGT

GATCCCAAACGACTCACTCCT

3. DRS C334S/C349S:
(SEQ ID NO: 120)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTAT

GTGATCAGTTTGGCTGAACCCCGTCTGCCCCTGCAGCTGGATGATGCTGTTCGGCCTGAGGC

AGAAGGAGAAGAGGAAGGAAGAGCTACTGTTAACCAGGATACAAGATTAGACAACAGAGT

CATTGATCTTAGGACATCAACTAGTCAGGCAGTCTTCCGTCTCCAGTCTGGCATCTGCCATCT

CTTCCGAGAAACTTTAATTAACAAAGGTTTTGTGGAAATCCAAACTCCTAAAATTATTTCAG

CTGCCAGTGAAGGAGGAGCCAATGTTTTTACTGTGTCATATTTTAAAAATAATGCATACCTG

GCTCAGTCCCCACAGCTATATAAGCAAATGTGCATTTGTGCTGATTTTGAGAAGGTTTTCTCT

ATTGGACCAGTATTCAGAGCGGAAGACTCTAATACCCATAGACATCTAACTGAGTTTGTTGG

TTTGGACATTGAAATGGCTTTTAATTACCATTACCACGAAGTTATGGAAGAAATTGCTGACA

CCATGGTACAAATATTCAAAGGACTTCAAGAAAGGTTTCAGACTGAAATTCAAACAGTGAA

TAAACAGTTCCCATCTGAGCCATTCAAATTTTTGGAGCCAACTCTAAGACTAGAATATTCTG

AAGCATTGGCTATGCTTAGGGAAGCTGGAGTCGAAATGGGAGATGAAGACGATCTGAGCAC

ACCAAATGAAAAGCTGTTGGGTCATTTGGTAAAGGAAAAGTATGATACAGATTTTTATATTC

TTGATAAATATCCATTGGCTGTAAGACCTTTCTATACCATGCCTGACCCAAGAAATCCCAAA

CAGTCCAACTCTTACGATATGTTCATGAGAGGAGAAGAAATATTGTCAGGAGCTCAAAGAA

TACATGATCCTCAACTGCTAACAGAGAGCTTTACATCATGGAATTGATTTGGAGAAAATT

AAGGCTTACATTGATTCCTTCCGCTTTGGAGCCCCTCCTCATGCTGGTGGAGGCATTGGATTG

GAACGAGTTACTATGCTGTTTCTGGGATTGCATAATGTTCGTCAGACCTCCATGTTCCCTCGT

GATCCCAAACGACTCACTCCT

4. DRS C203A:
(SEQ ID NO: 121)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

-continued

```
AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGAAGAGCTACTGTTAACCAGGATACAAGATTAGACAACAGAGT

CATTGATCTTAGGACATCAACTAGTCAGGCAGTCTTCCGTCTCCAGTCTGGCATCGCCCATCT

CTTCCGAGAAACTTTAATTAACAAAGGTTTTGTGGAAATCCAAACTCCTAAAATTATTTCAG

CTGCCAGTGAAGGAGGAGCCAATGTTTTTACTGTGTCATATTTTAAAAATAATGCATACCTG

GCTCAGTCCCCACAGCTATATAAGCAAATGTGCATTTGTGCTGATTTTGAGAAGGTTTTCTCT

ATTGGACCAGTATTCAGAGCGGAAGACTCTAATACCCATAGACATCTAACTGAGTTTGTTGG

TTTGGACATTGAAATGGCTTTTAATTACCATTACCACGAAGTTATGGAAGAAATTGCTGACA

CCATGGTACAAATATTCAAAGGACTTCAAGAAAGGTTTCAGACTGAAATTCAAACAGTGAA

TAAACAGTTCCCATGTGAGCCATTCAAATTTTTGGAGCCAACTCTAAGACTAGAATATTGTG

AAGCATTGGCTATGCTTAGGGAAGCTGGAGTCGAAATGGGAGATGAAGACGATCTGAGCAC

ACCAAATGAAAAGCTGTTGGGTCATTTGGTAAAGGAAAAGTATGATACAGATTTTTATATTC

TTGATAAATATCCATTGGCTGTAAGACCTTTCTATACCATGCCTGACCCAAGAAATCCCAAA

CAGTCCAACTCTTACGATATGTTCATGAGAGGAGAAGAAATATTGTCAGGAGCTCAAAGAA

TACATGATCCTCAACTGCTAACAGAGAGAGCTTTACATCATGGAATTGATTTGGAGAAAATT

AAGGCTTACATTGATTCCTTCCGCTTTGGAGCCCCTCCTCATGCTGGTGGAGGCATTGGATTG

GAACGAGTTACTATGCTGTTTCTGGGATTGCATAATGTTCGTCAGACCTCCATGTTCCCTCGT

GATCCCAAACGACTCACTCCT
```

5. DRS C203V:
(SEQ ID NO: 122)
```
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGAAGAGCTACTGTTAACCAGGATACAAGATTAGACAACAGAGT

CATTGATCTTAGGACATCAACTAGTCAGGCAGTCTTCCGTCTCCAGTCTGGCATCGTCCATCT

CTTCCGAGAAACTTTAATTAACAAAGGTTTTGTGGAAATCCAAACTCCTAAAATTATTTCAG

CTGCCAGTGAAGGAGGAGCCAATGTTTTTACTGTGTCATATTTTAAAAATAATGCATACCTG

GCTCAGTCCCCACAGCTATATAAGCAAATGTGCATTTGTGCTGATTTTGAGAAGGTTTTCTCT

ATTGGACCAGTATTCAGAGCGGAAGACTCTAATACCCATAGACATCTAACTGAGTTTGTTGG

TTTGGACATTGAAATGGCTTTTAATTACCATTACCACGAAGTTATGGAAGAAATTGCTGACA

CCATGGTACAAATATTCAAAGGACTTCAAGAAAGGTTTCAGACTGAAATTCAAACAGTGAA

TAAACAGTTCCCATGTGAGCCATTCAAATTTTTGGAGCCAACTCTAAGACTAGAATATTGTG

AAGCATTGGCTATGCTTAGGGAAGCTGGAGTCGAAATGGGAGATGAAGACGATCTGAGCAC

ACCAAATGAAAAGCTGTTGGGTCATTTGGTAAAGGAAAAGTATGATACAGATTTTTATATTC
```

```
TTGATAAATATCCATTGGCTGTAAGACCTTTCTATACCATGCCTGACCCAAGAAATCCCAAA

CAGTCCAACTCTTACGATATGTTCATGAGAGGAGAAGAAATATTGTCAGGAGCTCAAAGAA

TACATGATCCTCAACTGCTAACAGAGAGAGCTTTACATCATGGAATTGATTTGGAGAAAATT

AAGGCTTACATTGATTCCTTCCGCTTTGGAGCCCCTCCTCATGCTGGTGGAGGCATTGGATTG

GAACGAGTTACTATGCTGTTTCTGGGATTGCATAATGTTCGTCAGACCTCCATGTTCCCTCGT

GATCCCAAACGACTCACTCCT

6. DRS C334S/C349S/C203A:
                                                    (SEQ ID NO: 123)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGAAGAGCTACTGTTAACCAGGATACAAGATTAGACAACAGAGT

CATTGATCTTAGGACATCAACTAGTCAGGCAGTCTTCCGTCTCCAGTCTGGCATCGCCCATCT

CTTCCGAGAAACTTTAATTAACAAAGGTTTTGTGGAAATCCAAACTCCTAAAATTATTTCAG

CTGCCAGTGAAGGAGGAGCCAATGTTTTTACTGTGTCATATTTTAAAAATAATGCATACCTG

GCTCAGTCCCCACAGCTATATAAGCAAATGTGCATTTGTGCTGATTTTGAGAAGGTTTTCTCT

ATTGGACCAGTATTCAGAGCGGAAGACTCTAATACCCATAGACATCTAACTGAGTTTGTTGG

TTTGGACATTGAAATGGCTTTTAATTACCATTACCACGAAGTTATGGAAGAAATTGCTGACA

CCATGGTACAAATATTCAAAGGACTTCAAGAAAGGTTTCAGACTGAAATTCAAACAGTGAA

TAAACAGTTCCCATCTGAGCCATTCAAATTTTTGGAGCCAACTCTAAGACTAGAATATTCTG

AAGCATTGGCTATGCTTAGGGAAGCTGGAGTCGAAATGGGAGATGAAGACGATCTGAGCAC

ACCAAATGAAAAGCTGTTGGGTCATTTGGTAAAGGAAAAGTATGATACAGATTTTTATATTC

TTGATAAATATCCATTGGCTGTAAGACCTTTCTATACCATGCCTGACCCAAGAAATCCCAAA

CAGTCCAACTCTTACGATATGTTCATGAGAGGAGAAGAAATATTGTCAGGAGCTCAAAGAA

TACATGATCCTCAACTGCTAACAGAGAGAGCTTTACATCATGGAATTGATTTGGAGAAAATT

AAGGCTTACATTGATTCCTTCCGCTTTGGAGCCCCTCCTCATGCTGGTGGAGGCATTGGATTG

GAACGAGTTACTATGCTGTTTCTGGGATTGCATAATGTTCGTCAGACCTCCATGTTCCCTCGT

GATCCCAAACGACTCACTCCT

7. DRS C334S/C349S/C203V:
                                                    (SEQ ID NO: 124)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC
```

AGAAGGAGAAGAGGAAGGAAGAGCTACTGTTAACCAGGATACAAGATTAGACAACAGAGT

CATTGATCTTAGGACATCAACTAGTCAGGCAGTCTTCCGTCTCCAGTCTGGCATCGTCCATCT

CTTCCGAGAAACTTTAATTAACAAAGGTTTTGTGGAAATCCAAACTCCTAAAATTATTTCAG

CTGCCAGTGAAGGAGGAGCCAATGTTTTTACTGTGTCATATTTTAAAAATAATGCATACCTG

GCTCAGTCCCCACAGCTATATAAGCAAATGTGCATTTGTGCTGATTTTGAGAAGGTTTTCTCT

ATTGGACCAGTATTCAGAGCGGAAGACTCTAATACCCATAGACATCTAACTGAGTTTGTTGG

TTTGGACATTGAAATGGCTTTTAATTACCATTACCACGAAGTTATGGAAGAAATTGCTGACA

CCATGGTACAAATATTCAAAGGACTTCAAGAAAGGTTTCAGACTGAAATTCAAACAGTGAA

TAAACAGTTCCCATCTGAGCCATTCAAATTTTTGGAGCCAACTCTAAGACTAGAATATTCTG

AAGCATTGGCTATGCTTAGGGAAGCTGGAGTCGAAATGGGAGATGAAGACGATCTGAGCAC

ACCAAATGAAAAGCTGTTGGGTCATTTGGTAAAGGAAAAGTATGATACAGATTTTTATATTC

TTGATAAATATCCATTGGCTGTAAGACCTTTCTATACCATGCCTGACCCAAGAAATCCCAAA

CAGTCCAACTCTTACGATATGTTCATGAGAGGAGAAGAAATATTGTCAGGAGCTCAAAGAA

TACATGATCCTCAACTGCTAACAGAGAGAGCTTTACATCATGGAATTGATTTGGAGAAAATT

AAGGCTTACATTGATTCCTTCCGCTTTGGAGCCCCTCCTCATGCTGGTGGAGGCATTGGATTG

GAACGAGTTACTATGCTGTTTCTGGGATTGCATAATGTTCGTCAGACCTCCATGTTCCCTCGT

GATCCCAAACGACTCACTCCT

8. DRS C334S/C349S/C259A/C203A:

(SEQ ID NO: 125)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGAAGAGCTACTGTTAACCAGGATACAAGATTAGACAACAGAGT

CATTGATCTTAGGACATCAACTAGTCAGGCAGTCTTCCGTCTCCAGTCTGGCATCGCCCATCT

CTTCCGAGAAACTTTAATTAACAAAGGTTTTGTGGAAATCCAAACTCCTAAAATTATTTCAG

CTGCCAGTGAAGGAGGAGCCAATGTTTTTACTGTGTCATATTTTAAAAATAATGCATACCTG

GCTCAGTCCCCACAGCTATATAAGCAAATGTGCATTGCGGCTGATTTTGAGAAGGTTTTCTCT

ATTGGACCAGTATTCAGAGCGGAAGACTCTAATACCCATAGACATCTAACTGAGTTTGTTGG

TTTGGACATTGAAATGGCTTTTAATTACCATTACCACGAAGTTATGGAAGAAATTGCTGACA

CCATGGTACAAATATTCAAAGGACTTCAAGAAAGGTTTCAGACTGAAATTCAAACAGTGAA

TAAACAGTTCCCATCTGAGCCATTCAAATTTTTGGAGCCAACTCTAAGACTAGAATATTCTG

AAGCATTGGCTATGCTTAGGGAAGCTGGAGTCGAAATGGGAGATGAAGACGATCTGAGCAC

ACCAAATGAAAAGCTGTTGGGTCATTTGGTAAAGGAAAAGTATGATACAGATTTTTATATTC

TTGATAAATATCCATTGGCTGTAAGACCTTTCTATACCATGCCTGACCCAAGAAATCCCAAA

CAGTCCAACTCTTACGATATGTTCATGAGAGGAGAAGAAATATTGTCAGGAGCTCAAAGAA

TACATGATCCTCAACTGCTAACAGAGAGAGCTTTACATCATGGAATTGATTTGGAGAAAATT

-continued

```
AAGGCTTACATTGATTCCTTCCGCTTTGGAGCCCCTCCTCATGCTGGTGGAGGCATTGGATTG

GAACGAGTTACTATGCTGTTTCTGGGATTGCATAATGTTCGTCAGACCTCCATGTTCCCTCGT

GATCCCAAACGACTCACTCCT
```

9. DRS C334S/C349S/C259A/C203V:

(SEQ ID NO: 126)

```
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGAAGAGCTACTGTTAACCAGGATACAAGATTAGACAACAGAGT

CATTGATCTTAGGACATCAACTAGTCAGGCAGTCTTCCGTCTCCAGTCTGGCATCGTCCATCT

CTTCCGAGAAACTTTAATTAACAAAGGTTTTGTGGAAATCCAAACTCCTAAAATTATTTCAG

CTGCCAGTGAAGGAGGAGCCAATGTTTTTACTGTGTCATATTTTAAAAATAATGCATACCTG

GCTCAGTCCCCACAGCTATATAAGCAAATGTGCATTGCGGCTGATTTTGAGAAGGTTTTCTCT

ATTGGACCAGTATTCAGAGCGGAAGACTCTAATACCCATAGACATCTAACTGAGTTTGTTGG

TTTGGACATTGAAATGGCTTTTAATTACCATTACCACGAAGTTATGGAAGAAATTGCTGACA

CCATGGTACAAATATTCAAAGGACTTCAAGAAAGGTTTCAGACTGAAATTCAAACAGTGAA

TAAACAGTTCCCATCTGAGCCATTCAAATTTTTGGAGCCAACTCTAAGACTAGAATATTCTG

AAGCATTGGCTATGCTTAGGGAAGCTGGAGTCGAAATGGGAGATGAAGACGATCTGAGCAC

ACCAAATGAAAAGCTGTTGGGTCATTTGGTAAAGGAAAAGTATGATACAGATTTTTATATTC

TTGATAAATATCCATTGGCTGTAAGACCTTTCTATACCATGCCTGACCCAAGAAATCCCAAA

CAGTCCAACTCTTACGATATGTTCATGAGAGGAGAAGAAATATTGTCAGGAGCTCAAAGAA

TACATGATCCTCAACTGCTAACAGAGAGAGCTTTACATCATGGAATTGATTTGGAGAAAATT

AAGGCTTACATTGATTCCTTCCGCTTTGGAGCCCCTCCTCATGCTGGTGGAGGCATTGGATTG

GAACGAGTTACTATGCTGTTTCTGGGATTGCATAATGTTCGTCAGACCTCCATGTTCCCTCGT

GATCCCAAACGACTCACTCCT
```

The corresponding translated protein sequences are:

1. DRS C334S:

(SEQ ID NO: 109)

```
MPSASASRKSQEKPREIMDAAEDYAKERYGISSMIQSQEKPDRVLVRVRDLTIQKADEVVWRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATVNQDTRLDNRVIDLRTSTS

QAVFRLQSGICHLFRETLINKGFVEIQTPKIISAASEGGANVFTVSYFKNNAYLAQSPQLYKQMCI

CADFEKVFSIGPVFRAEDSNTHRHLTEFVGLDIEMAFNYHYHEVMEEIADTMVQIFKGLQERFQT

EIQTVNKQFPSEPFKFLEPTLRLEYCEALAMLREAGVEMGDEDDLSTPNEKLLGHLVKEKYDTDF

YILDKYPLAVRPFYTMPDPRNPKQSNSYDMFMRGEEILSGAQRIHDPQLLTERALHHGIDLEKIK

AYIDSFRFGAPPHAGGGIGLERVTMLFLGLHNVRQTSMFPRDPKRLTP
```

-continued

2. DRS C349S:
(SEQ ID NO: 110)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATVNQDTRLDNRVIDLRTSTS

QAVFRLQSGICHLFRETLINKGFVEIQTPKIISAASEGGANVFTVSYFKNNAYLAQSPQLYKQMCI

CADFEKVFSIGPVFRAEDSNTHRHLTEFVGLDIEMAFNYHYHEVMEEIADTMVQIFKGLQERFQT

EIQTVNKQFPCEPFKFLEPTLRLEYSEALAMLREAGVEMGDEDDLSTPNEKLLGHLVKEKYDTDF

YILDKYPLAVRPFYTMPDPRNPKQSNSYDMFMRGEEILSGAQRIHDPQLLTERALHHGIDLEKIK

AYIDSFRFGAPPHAGGGIGLERVTMLFLGLHNVRQTSMFPRDPKRLTP

3. DRS C334S/C349S:
(SEQ ID NO: 111)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATVNQDTRLDNRVIDLRTSTS

QAVFRLQSGICHLFRETLINKGFVEIQTPKIISAASEGGANVFTVSYFKNNAYLAQSPQLYKQMCI

CADFEKVFSIGPVFRAEDSNTHRHLTEFVGLDIEMAFNYHYHEVMEEIADTMVQIFKGLQERFQT

EIQTVNKQFPSEPFKFLEPTLRLEYSEALAMLREAGVEMGDEDDLSTPNEKLLGHLVKEKYDTDF

YILDKYPLAVRPFYTMPDPRNPKQSNSYDMFMRGEEILSGAQRIHDPQLLTERALHHGIDLEKIK

AYIDSFRFGAPPHAGGGIGLERVTMLFLGLHNVRQTSMFPRDPKRLTP

4. DRS C203A:
(SEQ ID NO: 112)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATVNQDTRLDNRVIDLRTSTS

QAVFRLQSGIAHLFRETLINKGFVEIQTPKIISAASEGGANVFTVSYFKNNAYLAQSPQLYKQMCI

CADFEKVFSIGPVFRAEDSNTHRHLTEFVGLDIEMAFNYHYHEVMEEIADTMVQIFKGLQERFQT

EIQTVNKQFPCEPFKFLEPTLRLEYCEALAMLREAGVEMGDEDDLSTPNEKLLGHLVKEKYDTD

FYILDKYPLAVRPFYTMPDPRNPKQSNSYDMFMRGEEILSGAQRIHDPQLLTERALHHGIDLEKIK

AYIDSFRFGAPPHAGGGIGLERVTMLFLGLHNVRQTSMFPRDPKRLTP

5. DRS C203V:
(SEQ ID NO: 113)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATVNQDTRLDNRVIDLRTSTS

QAVFRLQSGIVHLFRETLINKGFVEIQTPKIISAASEGGANVFTVSYFKNNAYLAQSPQLYKQMCI

CADFEKVFSIGPVFRAEDSNTHRHLTEFVGLDIEMAFNYHYHEVMEEIADTMVQIFKGLQERFQT

EIQTVNKQFPCEPFKFLEPTLRLEYCEALAMLREAGVEMGDEDDLSTPNEKLLGHLVKEKYDTD

FYILDKYPLAVRPFYTMPDPRNPKQSNSYDMFMRGEEILSGAQRIHDPQLLTERALHHGIDLEKIK

AYIDSFRFGAPPHAGGGIGLERVTMLFLGLHNVRQTSMFPRDPKRLTP

6. DRS C334S/C349S/C203A:
(SEQ ID NO: 114)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATVNQDTRLDNRVIDLRTSTS

-continued

```
QAVFRLQSGIAHLFRETLINKGFVEIQTPKIISAASEGGANVFTVSYFKNNAYLAQSPQLYKQMCI

CADFEKVFSIGPVFRAEDSNTHRHLTEFVGLDIEMAFNYHYHEVMEEIADTMVQIFKGLQERFQT

EIQTVNKQFPSEPPFKFLEPTLRLEYSEALAMLREAGVEMGDEDDLSTPNEKLLGHLVKEKYDTDF

YILDKYPLAVRPFYTMPDPRNPKQSNSYDMFMRGEEILSGAQRIHDPQLLTERALHHGIDLEKIK

AYIDSFRFGAPPHAGGGIGLERVTMLFLGLHNVRQTSMFPRDPKRLTP

7. DRS C334S/C349S/C203V
                                                      (SEQ ID NO: 115)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATVNQDTRLDNRVIDLRTSTS

QAVFRLQSGIVHLFRETLINKGFVEIQTPKIISAASEGGANVFTVSYFKNNAYLAQSPQLYKQMCI

AADFEKVFSIGPVFRAEDSNTHRHLTEFVGLDIEMAFNYHYHEVMEEIADTMVQIFKGLQERFQT

EIQTVNKQFPSEPPFKFLEPTLRLEYSEALAMLREAGVEMGDEDDLSTPNEKLLGHLVKEKYDTDF

YILDKYPLAVRPFYTMPDPRNPKQSNSYDMFMRGEEILSGAQRIHDPQLLTERALHHGIDLEKIK

AYIDSFRFGAPPHAGGGIGLERVTMLFLGLHNVRQTSMFPRDPKRLTP

8. DRS C334S/C349S/C259A/C203A:
                                                      (SEQ ID NO: 116)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATVNQDTRLDNRVIDLRTSTS

QAVFRLQSGIAHLFRETLINKGFVEIQTPKIISAASEGGANVFTVSYFKNNAYLAQSPQLYKQMCI

AADFEKVFSIGPVFRAEDSNTHRHLTEFVGLDIEMAFNYHYHEVMEEIADTMVQIFKGLQERFQT

EIQTVNKQFPSEPPFKFLEPTLRLEYSEALAMLREAGVEMGDEDDLSTPNEKLLGHLVKEKYDTDF

YILDKYPLAVRPFYTMPDPRNPKQSNSYDMFMRGEEILSGAQRIHDPQLLTERALHHGIDLEKIK

AYIDSFRFGAPPHAGGGIGLERVTMLFLGLHNVRQTSMFPRDPKRLTP

9. DRS C334S/C349S/C259A/C203V:
                                                      (SEQ ID NO: 117)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATVNQDTRLDNRVIDLRTSTS

QAVFRLQSGIVHLFRETLINKGFVEIQTPKIISAASEGGANVFTVSYFKNNAYLAQSPQLYKQMCI

AADFEKVFSIGPVFRAEDSNTHRHLTEFVGLDIEMAFNYHYHEVMEEIADTMVQIFKGLQERFQT

EIQTVNKQFPSEPPFKFLEPTLRLEYSEALAMLREAGVEMGDEDDLSTPNEKLLGHLVKEKYDTDF

YILDKYPLAVRPFYTMPDPRNPKQSNSYDMFMRGEEILSGAQRIHDPQLLTERALHHGIDLEKIK

AYIDSFRFGAPPHAGGGIGLERVTMLFLGLHNVRQTSMFPRDPKRLTP
```

Expression of DRS Cysteine Mutants: DRS cysteine mutant constructs were transformed into BL21 (DE3) competent cells (Novagen, cat. N. 69450-4) and expressed in LB media in flask at 30° C. for 16 hrs.

Purification of DRS Cysteine Mutants: Frozen cell pellets were resuspended in lysis buffer (50 mM Tris, 300 mM NaCl, 25 mM Imidazole, 5 mM DTT, pH 8.0 with complete EDTA-FREE protease inhibitor cocktail tablets (Roche cat. no: 05 056 489 001) and the then rotated for 30 mins at 4° C. with 300 mg chicken egg lysozyme. The suspension was sonicated for two cycles 50% and 75% for 60 seconds each with 10 second on and 5 second off. The lysate was centrifuged at 35,000×g for 45 min at 4° C. The supernatant was filtered through 0.22 μm Sartobran capsule filters (Sartorius). The clarified lysate was bound to the Ni-NTA resin (Qiagen), pre-equilibrated with Ni-NTA Binding Buffer (50 mM Tris, 300 mM NaCl, 25 mM Imidazole, 5 mM DTT, pH 8.0). The column was washed with 1000 column volumes of Ni-NTA Binding Buffer plus 0.1% Triton X-114 and 5 mM DTT followed by 50 column volumes of the Ni-NTA Binding Buffer. The bound protein was eluted with 5 column volumes of Ni-NTA Elution Buffer (50 mM Tris, 300 mM NaCl, 300 mM Imidazole, 1 mM DTT pH 8.0).

The purified proteins were dialyzed into a PBS. The dialyzed protein was passed through a Q membrane filter (Sartobind-Q from Sartorius or Mustang-Q from Pall) or a Q-Sepharose column (GE Healthcare) for further endotoxin removal when endotoxin level is detectable using Charles River endotoxin detection kit (product code: PTS20), and then filtered through a 0.22 μm sterile filter.

Testing of the relative activity of the purified proteins compared in the HEK293-TLR2 and HEK293-TLR4 expressing cell lines as described above confirmed that the proteins were active (data not shown).

Comparison of Production Yield and Stability of Purified DRS Cysteine Mutants: Purification yield of each DRS cysteine mutant is summarized in Table E7. Tm of these mutants is measured by DSF (differential scanning fluorimetry) using Protein Thermo Shift Dye Kit from Life Technologies (cat. no. 4461146) following the manufacturer's instructions. Stability was assessed by incubating 50 μl of each of thr DRS cysteine mutants in PBS at 1 mg/ml at 37° C. for 1 hrs, and then by running an analytical SEC column (YMC America, Inc, cat. no. YMC-Pack Diol-300) using 200 mM phosphate, 100 mM NaCl pH7.0 as running buffer to compare monomer loss with samples before incubation.

TABLE E7

| Variant | Yield (mg/L) | Tm (° C., in PBS) | % monomer loss* |
|---|---|---|---|
| wild type | 6.8 | 47.7 | + |
| C334S | 6.5 | 53.2 | +++++ |
| C349S | 16.9 | 53.8 | ++ |
| C334S/C349S | 11.9 | 53.8 | +++ |
| C203A | 9.3 | 53.1 | NA |
| C203V | 10.2 | 53.5 | NA |
| C334S/C349S/C203A | 12.7 | 53.8 | + |
| C3334S/C349S/C203V | 13.9 | 53.4 | + |
| C334S/C3349S/C259A/C203A | 16.8 | 50.8 | + |
| C334S/C349S/C259A/C203V | 11.1 | 51 | + |

*monomer loss after 1 hr incubation at 37° C.
+: >5%;
++: >50%;
+++: 75%;
+++++: >90%;
NA: no loss The results demonstrate that the cysteine mutants at position 203 display enhanced stability, and reduced tendency for aggregation formation. Surprisingly the C203 mutants also enhanced stability in the context of mutations at position C334, C349 and C259, even if these mutations alone did not themselves confer significantly enhanced stability alone. The results thus demonstrate that C203 represents a key residue in the non specific cysteine dependent aggregation of DRS.

Example 6

Construction and Production of Truncated Homeokine (DRS) Mutants

To systematically evaluate the minimal active, and most stable N-terminal DRS polypeptide fragment, a series of N-terminal, C-terminal and double truncated Homeokine (DRS 1-154) variants were made using the primers listed in Table E8. The corresponding DNA and protein sequences for the constructs are listed below. Briefly, the N-terminal truncated form variants of Homeokine (DRS) were designed by truncating two amino acids at a time from the N- or C terminus of the Homeokine (DRS 1-154) sequence. Additionally a series of C-terminal extension variants was created to extend the C-terminal of the Homeokine sequence from amino acid 154 to 182 by 2 amino acid additions. Double truncated Homeokine variants were designed based on the DRS structure in order to define a minimally active core domain of Homeokine.

TABLE E8

| HK variants | Primers | SEQ ID NO: |
|---|---|---|
| C-terminal truncation variant | Reverse primers | |
| 1-148 | 5'- GGG TTA GGG ATA GGC TTA CCA GCC AAA CTG ATC ACA TAA ATC -3' | 167 |
| 1-150 | 5'- GGG TTA GGG ATA GGC TTA CCG GGT TCA GCC AAA CTG ATC AC -3' | 168 |
| 1-152 | 5'- GGG TTA GGG ATA GGC TTA CCC AGA CGG GGT TCA GCC AAA C -3' | 169 |
| 1-156 | 5'- GGG TTA GGG ATA GGC TTA CCC AGC TGC AGG GGC AGA CGG GG -3' | 170 |
| 1-158 | 5'- GGG TTA GGG ATA GGC TTA CCA TCA TCC AGC TGC AGG GGC AG -3' | 171 |
| 1-160 | 5'- GGG TTA GGG ATA GGC TTA CCA ACA GCA TCA TCC AGC TGC AGG -3' | 172 |
| 1-162 | 5'- GGG TTA GGG ATA GGC TTA CCA GGC CGA ACA GCA TCA TCC AG -3' | 173 |
| 1-164 | 5'- GGG TTA GGG ATA GGC TTA CCT GCC TCA GGC CGA ACA GCA TC -3' | 174 |
| 1-166 | 5'- GGG TTA GGG ATA GGC TTA CCT CCT TCT GCC TCA GGC CGA AC -3' | 175 |
| 1-168 | 5'- GGG TTA GGG ATA GGC TTA CCC TCT TCT CCT TCT GCC TCA GG -3' | 176 |
| 1-170 | 5'- GGG TTA GGG ATA GGC TTA CCT CCT TCC TCT TCT CCT TCT GC -3' | 177 |
| 1-172 | 5'- GGG TTA GGG ATA GGC TTA CCA GCT CTT CCT TCC TCT TCT CC -3' | 178 |
| 1-176 | 5'- GGG TTA GGG ATA GGC TTA CCC TGG TTA ACA GTA GCT CTT CC -3' | 179 |
| 1-178 | 5'- GGG TTA GGG ATA GGC TTA CCT GTA TCC TGG TTA ACA GTA GC -3' | 180 |
| 1-180 | 5'- GGG TTA GGG ATA GGC TTA CCT AAT CTT GTA TCC TGG TTA AC -3' | 181 |
| 1-182 | 5'-GGG TTA GGG ATA GGC TTA CCG TTG TCT AAT CTT GTA TCC TGG-3' | 182 |
| N-terminal truncation variant | Forward primers | |
| 3-154 | 5'- GAA GGA GAT ATA CCATGA GCG CCA GCG CCA GCC G -3' | 183 |
| 5-154 | 5'- GAA GGA GAT ATA CCATGA GCG CCA GCC GCA AGA G -3' | 184 |
| 7-154 | 5'- GAA GGA GAT ATA CCATGA GCC GCA AGA GTC AGG AG-3' | 185 |
| 9-154 | 5'- GAA GGA GAT ATA CCATGA AGA GTC AGG AGA AGC C -3' | 186 |
| 11-154 | 5'-GAAGGAGATATCATATGCAGGAGAAGCCGCGGGAG-3' | 187 |

TABLE E8-continued

| HK variants | Primers | SEQ ID NO: |
|---|---|---|
| 13-154 | 5'-GAAGGAGATATCATATGAAGCCGCGGGAGATCATG-3' | 188 |
| 15-154 | 5'-GAAGGAGATATCATATGCGGGAGATCATGGACGCGG-3' | 189 |
| 17-154 | 5'-GAAGGAGATATCATATGATCATGGACGCGGCGG-3' | 190 |
| 21-154 | 5'-GAAGGAGATATCATATGGCGGAAGATTATGCTAAAG-3' | 191 |
| 23-154 | 5'-GAAGGAGATATCATATGGATTATGCTAAAG-3' | 192 |

| double truncated HK variant | Forward primers | |
|---|---|---|
| 11-146-F | 5'-ACC GAT CAC ATA TGC AGG AGA AGC CGC GGG AGA TCA TGG A-3' | 193 |
| 13-146-F | 5'-AAG CTT ACG CAT ATG AAG CCG CGG GAG ATC ATG GAC GCG-3' | 194 |
| 17-146-F | 5'-AAC TGT TAC CAT ATG ATC ATG GAC GCG GCG GAA GAT TAT G-3' | 195 |
| 21-146-F | 5'-AAC TGT CAT CAT ATG GCG GAA GAT TAT GCT AAA GAG AGA TAT-3' | 196 |

| | Reverse primer | |
|---|---|---|
| X-146-R | 5'-TGA CGG CTC GAG ACT GAT CAC ATA AAT CTT CTG-3' | 197 |

| | Forward primers | |
|---|---|---|
| A106C-F | 5'-GCA GAT GGT TAA ATT TGC TTG CAA CAT CAA CAA AGA GAG CAT TGT GG-3' | 198 |

The truncated Homeokine (DRS) DNA sequences are as follows

DRS 1-182
(SEQ ID NO: 127)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGAAGAGCTACTGTTAACCAGGATACAAGATTAGACAAC

DRS 1-180
(SEQ ID NO: 128)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGAAGAGCTACTGTTAACCAGGATACAAGATTA

DRS 1-178
(SEQ ID NO: 129)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

-continued

```
CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGAAGAGCTACTGTTAACCAGGATACA
```

DRS 1-176
(SEQ ID NO: 130)
```
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGAAGAGCTACTGTTAACCAG
```

DRS 1-174
(SEQ ID NO: 131)
```
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGAAGAGCTACTGTT
```

DRS 1-172
(SEQ ID NO: 132)
```
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGAAGAGCT
```

DRS 1-170
(SEQ ID NO: 133)
```
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG
```

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGA

DRS 1-168
(SEQ ID NO: 134)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAG

DRS 1-166
(SEQ ID NO: 135)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGA

DRS 1-164
(SEQ ID NO: 136)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

A

DRS 1-162
(SEQ ID NO: 137)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

-continued

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCT

DRS 1-160

(SEQ ID NO: 138)

ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTT

DRS 1-158

(SEQ ID NO: 139)

ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGAT

DRS 1-156

(SEQ ID NO: 140)

ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTG

DRS 1-154

(SEQ ID NO: 141)

ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTG

-continued

DRS 1-152 (SEQ ID NO142)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTG

DRS 1-150 (SEQ ID NO: 143)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCC

DRS 1-148 (SEQ ID NO: 144)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCT

DRS 1-146 (SEQ ID NO: 145)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGT

DRS 3-154 (SEQ ID NO: 146)
GCCAGCGCCAGCCGCAAGAGTCAGGAGAAGCCGCGGGAGATCATGGACGCGGCGGAAGAT

TATGCTAAAGAGAGATATGGAATATCTTCAATGATACAATCACAAGAAAAACCAGATCGAG

TTTTGGTTCGGGTTAGAGACTTGACAATACAAAAAGCTGATGAAGTTGTTTGGGTACGTGCA

-continued

AGAGTTCATACAAGCAGAGCTAAAGGGAAACAGTGCTTCTTAGTCCTACGTCAGCAGCAGTT

TAATGTCCAGGCTCTTGTGGCGGTGGGAGACCATGCAAGCAAGCAGATGGTTAAATTTGCTG

CCAACATCAACAAAGAGAGCATTGTGGATGTAGAAGGTGTTGTGAGAAAAGTGAATCAGAA

AATTGGAAGCTGTACACAGCAAGACGTTGAGTTACATGTTCAGAAGATTTATGTGATCAGTT

TGGCTGAACCCCGTCTGCCCCTG

DRS 5-154
(SEQ ID NO: 147)
GCCAGCCGCAAGAGTCAGGAGAAGCCGCGGGAGATCATGGACGCGGCGGAAGATTATGCTA

AAGAGAGATATGGAATATCTTCAATGATACAATCACAAGAAAAACCAGATCGAGTTTTGGT

TCGGGTTAGAGACTTGACAATACAAAAAGCTGATGAAGTTGTTTGGGTACGTGCAAGAGTTC

ATACAAGCAGAGCTAAAGGGAAACAGTGCTTCTTAGTCCTACGTCAGCAGCAGTTTAATGTC

CAGGCTCTTGTGGCGGTGGGAGACCATGCAAGCAAGCAGATGGTTAAATTTGCTGCCAACAT

CAACAAAGAGAGCATTGTGGATGTAGAAGGTGTTGTGAGAAAAGTGAATCAGAAAATTGGA

AGCTGTACACAGCAAGACGTTGAGTTACATGTTCAGAAGATTTATGTGATCAGTTTGGCTGA

ACCCCGTCTGCCCCTG

DRS 7-154
(SEQ ID NO: 148)
CGCAAGAGTCAGGAGAAGCCGCGGGAGATCATGGACGCGGCGGAAGATTATGCTAAAGAG

AGATATGGAATATCTTCAATGATACAATCACAAGAAAAACCAGATCGAGTTTTGGTTCGGGT

TAGAGACTTGACAATACAAAAAGCTGATGAAGTTGTTTGGGTACGTGCAAGAGTTCATACA

AGCAGAGCTAAAGGGAAACAGTGCTTCTTAGTCCTACGTCAGCAGCAGTTTAATGTCCAGGC

TCTTGTGGCGGTGGGAGACCATGCAAGCAAGCAGATGGTTAAATTTGCTGCCAACATCAACA

AAGAGAGCATTGTGGATGTAGAAGGTGTTGTGAGAAAAGTGAATCAGAAAATTGGAAGCTG

TACACAGCAAGACGTTGAGTTACATGTTCAGAAGATTTATGTGATCAGTTTGGCTGAACCCC

GTCTGCCCCTG

DRS 9-154
(SEQ ID NO: 149)
AGTCAGGAGAAGCCGCGGGAGATCATGGACGCGGCGGAAGATTATGCTAAAGAGAGATAT

GGAATATCTTCAATGATACAATCACAAGAAAAACCAGATCGAGTTTTGGTTCGGGTTAGAGA

CTTGACAATACAAAAAGCTGATGAAGTTGTTTGGGTACGTGCAAGAGTTCATACAAGCAGA

GCTAAAGGGAAACAGTGCTTCTTAGTCCTACGTCAGCAGCAGTTTAATGTCCAGGCTCTTGT

GGCGGTGGGAGACCATGCAAGCAAGCAGATGGTTAAATTTGCTGCCAACATCAACAAAGAG

AGCATTGTGGATGTAGAAGGTGTTGTGAGAAAAGTGAATCAGAAAATTGGAAGCTGTACAC

AGCAAGACGTTGAGTTACATGTTCAGAAGATTTATGTGATCAGTTTGGCTGAACCCCGTCTG

CCCCTG

DRS 11-154
(SEQ ID NO: 150)
GAGAAGCCGCGGGAGATCATGGACGCGGCGGAAGATTATGCTAAAGAGAGATATGGAATAT

CTTCAATGATACAATCACAAGAAAAACCAGATCGAGTTTTGGTTCGGGTTAGAGACTTGACA

ATACAAAAAGCTGATGAAGTTGTTTGGGTACGTGCAAGAGTTCATACAAGCAGAGCTAAAG

GGAAACAGTGCTTCTTAGTCCTACGTCAGCAGCAGTTTAATGTCCAGGCTCTTGTGGCGGTG

GGAGACCATGCAAGCAAGCAGATGGTTAAATTTGCTGCCAACATCAACAAAGAGAGCATTG

TGGATGTAGAAGGTGTTGTGAGAAAAGTGAATCAGAAAATTGGAAGCTGTACACAGCAAGA

CGTTGAGTTACATGTTCAGAAGATTTATGTGATCAGTTTGGCTGAACCCCGTCTGCCCCTG

-continued

DRS 13-154
(SEQ ID NO: 151)
CCGCGGGAGATCATGGACGCGGCGGAAGATTATGCTAAAGAGAGATATGGAATATCTTCAA

TGATACAATCACAAGAAAAACCAGATCGAGTTTTGGTTCGGGTTAGAGACTTGACAATACA

AAAAGCTGATGAAGTTGTTTGGGTACGTGCAAGAGTTCATACAAGCAGAGCTAAAGGGAAA

CAGTGCTTCTTAGTCCTACGTCAGCAGCAGTTTAATGTCCAGGCTCTTGTGGCGGTGGGAGA

CCATGCAAGCAAGCAGATGGTTAAATTTGCTGCCAACATCAACAAAGAGAGCATTGTGGAT

GTAGAAGGTGTTGTGAGAAAAGTGAATCAGAAAATTGGAAGCTGTACACAGCAAGACGTTG

AGTTACATGTTCAGAAGATTTATGTGATCAGTTTGGCTGAACCCCGTCTGCCCCTG

DRS 15-154
(SEQ ID NO: 152)
GAGATCATGGACGCGGCGGAAGATTATGCTAAAGAGAGATATGGAATATCTTCAATGATAC

AATCACAAGAAAAACCAGATCGAGTTTTGGTTCGGGTTAGAGACTTGACAATACAAAAAGC

TGATGAAGTTGTTTGGGTACGTGCAAGAGTTCATACAAGCAGAGCTAAAGGGAAACAGTGC

TTCTTAGTCCTACGTCAGCAGCAGTTTAATGTCCAGGCTCTTGTGGCGGTGGGAGACCATGC

AAGCAAGCAGATGGTTAAATTTGCTGCCAACATCAACAAAGAGAGCATTGTGGATGTAGAA

GGTGTTGTGAGAAAAGTGAATCAGAAAATTGGAAGCTGTACACAGCAAGACGTTGAGTTAC

ATGTTCAGAAGATTTATGTGATCAGTTTGGCTGAACCCCGTCTGCCCCTG

DRS 17-154
(SEQ ID NO: 153)
ATGGACGCGGCGGAAGATTATGCTAAAGAGAGATATGGAATATCTTCAATGATACAATCAC

AAGAAAAACCAGATCGAGTTTTGGTTCGGGTTAGAGACTTGACAATACAAAAAGCTGATGA

AGTTGTTTGGGTACGTGCAAGAGTTCATACAAGCAGAGCTAAAGGGAAACAGTGCTTCTTAG

TCCTACGTCAGCAGCAGTTTAATGTCCAGGCTCTTGTGGCGGTGGGAGACCATGCAAGCAAG

CAGATGGTTAAATTTGCTGCCAACATCAACAAAGAGAGCATTGTGGATGTAGAAGGTGTTGT

GAGAAAAGTGAATCAGAAAATTGGAAGCTGTACACAGCAAGACGTTGAGTTACATGTTCAG

AAGATTTATGTGATCAGTTTGGCTGAACCCCGTCTGCCCCTG

DRS 19-154
(SEQ ID NO: 154)
GCGGCGGAAGATTATGCTAAAGAGAGATATGGAATATCTTCAATGATACAATCACAAGAAA

AACCAGATCGAGTTTTGGTTCGGGTTAGAGACTTGACAATACAAAAAGCTGATGAAGTTGTT

TGGGTACGTGCAAGAGTTCATACAAGCAGAGCTAAAGGGAAACAGTGCTTCTTAGTCCTAC

GTCAGCAGCAGTTTAATGTCCAGGCTCTTGTGGCGGTGGGAGACCATGCAAGCAAGCAGAT

GGTTAAATTTGCTGCCAACATCAACAAAGAGAGCATTGTGGATGTAGAAGGTGTTGTGAGA

AAAGTGAATCAGAAAATTGGAAGCTGTACACAGCAAGACGTTGAGTTACATGTTCAGAAGA

TTTATGTGATCAGTTTGGCTGAACCCCGTCTGCCCCTG

DRS 21-154
(SEQ ID NO: 155)
GCGGCGGAAGATTATGCTAAAGAGAGATATGGAATATCTTCAATGATACAATCACAAGAAA

AACCAGATCGAGTTTTGGTTCGGGTTAGAGACTTGACAATACAAAAAGCTGATGAAGTTGTT

TGGGTACGTGCAAGAGTTCATACAAGCAGAGCTAAAGGGAAACAGTGCTTCTTAGTCCTAC

GTCAGCAGCAGTTTAATGTCCAGGCTCTTGTGGCGGTGGGAGACCATGCAAGCAAGCAGAT

GGTTAAATTTGCTGCCAACATCAACAAAGAGAGCATTGTGGATGTAGAAGGTGTTGTGAGA

AAAGTGAATCAGAAAATTGGAAGCTGTACACAGCAAGACGTTGAGTTACATGTTCAGAAGA

TTTATGTGATCAGTTTGGCTGAACCCCGTCTG

-continued

DRS 23-154
(SEQ ID NO: 156)
GCGGCGGAAGATTATGCTAAAGAGAGATATGGAATATCTTCAATGATACAATCACAAGAAA

AACCAGATCGAGTTTTGGTTCGGGTTAGAGACTTGACAATACAAAAAGCTGATGAAGTTGTT

TGGGTACGTGCAAGAGTTCATACAAGCAGAGCTAAAGGGAAACAGTGCTTCTTAGTCCTAC

GTCAGCAGCAGTTTAATGTCCAGGCTCTTGTGGCGGTGGGAGACCATGCAAGCAAGCAGAT

GGTTAAATTTGCTGCCAACATCAACAAAGAGAGCATTGTGGATGTAGAAGGTGTTGTGAGA

AAAGTGAATCAGAAAATTGGAAGCTGTACACAGCAAGACGTTGAGTTACATGTTCAGAAGA

TTTATGTGATCAGTTTGGCTGAACCC

Double truncated coding sequences are as follows:

DRS 11-146:
(SEQ ID NO: 157)
ATGCAGGAGAAGCCGCGGGAGATCATGGACGCGGCGGAAGATTATGCTAAAGAGAGATAT

GGAATATCTTCAATGATACAATCACAAGAAAAACCAGATCGAGTTTTGGTTCGGGTTAGAGA

CTTGACAATACAAAAAGCTGATGAAGTTGTTTGGGTACGTGCAAGAGTTCATACAAGCAGA

GCTAAAGGGAAACAGTGCTTCTTAGTCCTACGTCAGCAGCAGTTTAATGTCCAGGCTCTTGT

GGCGGTGGGAGACCATGCAAGCAAGCAGATGGTTAAATTTGCTTGCAACATCAACAAAGAG

AGCATTGTGGATGTAGAAGGTGTTGTGAGAAAAGTGAATCAGAAAATTGGAAGCTGTACAC

AGCAAGACGTTGAGTTACATGTTCAGAAGATTTATGTGATCAGT

DRS 13-146:
(SEQ ID NO: 158)
ATGAAGCCGCGGGAGATCATGGACGCGGCGGAAGATTATGCTAAAGAGAGATATGGAATAT

CTTCAATGATACAATCACAAGAAAAACCAGATCGAGTTTTGGTTCGGGTTAGAGACTTGACA

ATACAAAAAGCTGATGAAGTTGTTTGGGTACGTGCAAGAGTTCATACAAGCAGAGCTAAAG

GGAAACAGTGCTTCTTAGTCCTACGTCAGCAGCAGTTTAATGTCCAGGCTCTTGTGGCGGTG

GGAGACCATGCAAGCAAGCAGATGGTTAAATTTGCTTGCAACATCAACAAAGAGAGCATTG

TGGATGTAGAAGGTGTTGTGAGAAAAGTGAATCAGAAAATTGGAAGCTGTACACAGCAAGA

CGTTGAGTTACATGTTCAGAAGATTTATGTGATCAGT

DRS 13-146/A106C:
(SEQ ID NO: 159)
ATGAAGCCGCGGGAGATCATGGACGCGGCGGAAGATTATGCTAAAGAGAGATATGGAATAT

CTTCAATGATACAATCACAAGAAAAACCAGATCGAGTTTTGGTTCGGGTTAGAGACTTGACA

ATACAAAAAGCTGATGAAGTTGTTTGGGTACGTGCAAGAGTTCATACAAGCAGAGCTAAAG

GGAAACAGTGCTTCTTAGTCCTACGTCAGCAGCAGTTTAATGTCCAGGCTCTTGTGGCGGTG

GGAGACCATGCAAGCAAGCAGATGGTTAAATTTGCTTGCAACATCAACAAAGAGAGCATTG

TGGATGTAGAAGGTGTTGTGAGAAAAGTGAATCAGAAAATTGGAAGCTGTACACAGCAAGA

CGTTGAGTTACATGTTCAGAAGATTTATGTGATCAGT

DRS 17-146:
(SEQ ID NO: 160)
ATGATCATGGACGCGGCGGAAGATTATGCTAAAGAGAGATATGGAATATCTTCAATGATAC

AATCACAAGAAAAACCAGATCGAGTTTTGGTTCGGGTTAGAGACTTGACAATACAAAAAGC

TGATGAAGTTGTTTGGGTACGTGCAAGAGTTCATACAAGCAGAGCTAAAGGGAAACAGTGC

TTCTTAGTCCTACGTCAGCAGCAGTTTAATGTCCAGGCTCTTGTGGCGGTGGGAGACCATGC

AAGCAAGCAGATGGTTAAATTTGCTTGCAACATCAACAAAGAGAGCATTGTGGATGTAGAA

-continued

```
GGTGTTGTGAGAAAAGTGAATCAGAAAATTGGAAGCTGTACACAGCAAGACGTTGAGTTAC

ATGTTCAGAAGATTTATGTGATCAGT

DRS 21-146:
                                                       (SEQ ID NO: 161)
ATGGCGGAAGATTATGCTAAAGAGAGATATGGAATATCTTCAATGATACAATCACAAGAAA

AACCAGATCGAGTTTTGGTTCGGGTTAGAGACTTGACAATACAAAAAGCTGATGAAGTTGTT

TGGGTACGTGCAAGAGTTCATACAAGCAGAGCTAAAGGGAAACAGTGCTTCTTAGTCCTAC

GTCAGCAGCAGTTTAATGTCCAGGCTCTTGTGGCGGTGGGAGACCATGCAAGCAAGCAGAT

GGTTAAATTTGCTTGCAACATCAACAAAGAGAGCATTGTGGATGTAGAAGGTGTTGTGAGA

AAAGTGAATCAGAAAATTGGAAGCTGTACACAGCAAGACGTTGAGTTACATGTTCAGAAGA

TTTATGTGATCAGT
```

The corresponding protein sequences of the DRS truncations are as follows:

```
DRS 1-182
                                                       (SEQ ID NO: 74)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATVNQDTRLDN

DRS 1-180
                                                       (SEQ ID NO: 75)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATVNQDTRL

DRS 1-178
                                                       (SEQ ID NO: 76)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATVNQDT

DRS 1-176
                                                       (SEQ ID NO: 77)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATVNQ

DRS 1-174
                                                       (SEQ ID NO: 78)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATV

DRS 1-172
                                                       (SEQ ID NO: 79)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRA
```

DRS 1-170
(SEQ ID NO: 80)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEG

DRS 1-168
(SEQ ID NO: 81)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEE

DRS 1-166
(SEQ ID NO: 82)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEG

DRS 1-164
(SEQ ID NO: 83)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEA

DRS 1-162
(SEQ ID NO: 84)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRP

DRS 1-160
(SEQ ID NO: 85)
MPSASASRKSQEKPREIMDAAEDYAKERYGISSM1QSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAV

DRS 1-158
(SEQ ID NO86)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDD

DRS 1-156
(SEQ ID NO: 87)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQL

DRS 1-154
(SEQ ID NO88)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAAMNKESIVDVEGVVRKVNQK

IGSCTQQDVELHVQKIYVISLAEPRLPL

DRS 1-152
(SEQ ID NO: 89)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRL

-continued

DRS 1-150

(SEQ ID NO: 90)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEP

DRS 1-148

(SEQ ID NO: 91)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLA

DRS 1-146

(SEQ ID NO: 92)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVIS

DRS 3-154

(SEQ ID NO: 93)
ASASRKSQEKPREIMDAAEDYAKERYGISSMIQSQEKPDRVLVRVRDLTIQKADEVVWVRARVH

TSRAKGKQCFLVLRQQQFNVQALVAVGDHASKQMVKFAANINKESIVDVEGVVRKVNQKIGSC

TQQDVELHVQKIYVISLAEPRLPL

DRS 5-154

(SEQ ID NO: 94)
ASRKSQEKPREIMDAAEDYAKERYGISSMIQSQEKPDRVLVRVRDLTIQKADEVVWVRARVHTS

RAKGKQCFLVLRQQQFNVQALVAVGDHASKQMVKFAANINKESIVDVEGVVRKVNQKIGSCT

QQDVELHVQKIYVISLAEPRLPL

DRS 7-154

(SEQ ID NO: 95)
RKSQEKPREIMDAAEDYAKERYGISSMIQSQEKPDRVLVRVRDLTIQKADEVVWVRARVHTSRA

KGKQCFLVLRQQQFNVQALVAVGDHASKQMVKFAANINKESIVDVEGVVRKVNQKIGSCTQQ

DVELHVQKIYVISLAEPRLPL

DRS 9-154

(SEQ ID NO: 96)
SQEKPREIMDAAEDYAKERYGISSMIQSQEKPDRVLVRVRDLTIQKADEVVWVRARVHTSRAKG

KQCFLVLRQQQFNVQALVAVGDHASKQMVKFAANINKESIVDVEGVVRKVNQKIGSCTQQDVE

LHVQKIYVISLAEPRLPL

DRS 11-154

(SEQ ID NO: 97)
EKPREIMDAAEDYAKERYGISSMIQSQEKPDRVLVRVRDLTIQKADEVVWVRARVHTSRAKGK

QCFLVLRQQQFNVQALVAVGDHASKQMVKFAANINKESIVDVEGVVRKVNQKIGSCTQQDVEL

HVQKIYVISLAEPRLPL

DRS 13-154

(SEQ ID NO: 98)
PREIMDAAEDYAKERYGISSMIQSQEKPDRVLVRVRDLTIQKADEVVWVRARVHTSRAKGKQC

FLVLRQQQFNVQALVAVGDHASKQMVKFAANINKESIVDVEGVVRKVNQKIGSCTQQDVELHV

QKIYVISLAEPRLPL

DRS 15-154

(SEQ ID NO: 99)
EIMDAAEDYAKERYGISSMIQSQEKPDRVLVRVRDLTIQKADEVVWVRARVHTSRAKGKQCFL

VLRQQQFNVQALVAVGDHASKQMVKFAANINKESIVDVEGVVRKVNQKIGSCTQQDVELHVQ

KIYVISLAEPRLPL

DRS 17-154
(SEQ ID NO: 100)
MDAAEDYAKERYGISSMIQSQEKPDRVLVRVRDLTIQKADEVVWVRARVHTSRAKGKQCFLVL
RQQQFNVQALVAVGDHASKQMVKFAANINKESIVDVEGVVRKVNQKIGSCTQQDVELHVQKIY
VISLAEPRLPL

DRS 19-154
(SEQ ID NO: 101)
MDAAEDYAKERYGISSMIQSQEKPDRVLVRVRDLTIQKADEVVWVRARVHTSRAKGKQCFLVL
RQQQFNVQALVAVGDHASKQMVKFAANINKESIVDVEGVVRKVNQKIGSCTQQDVELHVQKIY
VISLAEPRL

DRS 21-154
(SEQ ID NO: 102)
MDAAEDYAKERYGISSMIQSQEKPDRVLVRVRDLTIQKADEVVWVRARVHTSRAKGKQCFLVL
RQQQFNVQALVAVGDHASKQMVKFAANINKESIVDVEGVVRKVNQKIGSCTQQDVELHVQKIY
VISLAEPRL

DRS 23-154
(SEQ ID NO: 103)
AAEDYAKERYGISSMIQSQEKPDRVLVRVRDLTIQKADEVVWVRARVHTSRAKGKQCFLVLRQ
QQFNVQALVAVGDHASKQMVKFAANINKESIVDVEGVVRKVNQKIGSCTQQDVELHVQKIYVI
SLAEPRL

DRS 11-146:
(SEQ ID NO: 104)
MQEKPREIMDAAEDYAKERYGISSMIQSQEKPDRVLVRVRDLTIQKADEVVWVRARVHTSRAK
GKQCFLVLRQQQFNVQALVAVGDHASKQMVKFACNINKESIVDVEGVVRKVNQKIGSCTQQD
VELHVQKIYVIS

DRS 13-146:
(SEQ ID NO: 105)
MKPREIMDAAEDYAKERYGISSMIQSQEKPDRVLVRVRDLTIQKADEVVWVRARVHTSRAKGK
QCFLVLRQQQFNVQALVAVGDHASKQMVKFACNINKESIVDVEGVVRKVNQKIGSCTQQDVEL
HVQKIYVIS

DRS 13-146/A106C:
(SEQ ID NO: 106)
MKPREIMDAAEDYAKERYGISSMIQSQEKPDRVLVRVRDLTIQKADEVVWVRARVHTSRAKGK
QCFLVLRQQQFNVQALVAVGDHASKQMVKFACNINKESIVDVEGVVRKVNQKIGSCTQQDVEL
HVQKIYVIS

DRS 17-146:
(SEQ ID NO: 107)
MIMDAAEDYAKERYGISSMIQSQEKPDRVLVRVRDLTIQKADEVVWVRARVHTSRAKGKQCFL
VLRQQQFNVQALVAVGDHASKQMVKFACNINKESIVDVEGVVRKVNQKIGSCTQQDVELHVQ
KIYVIS

DRS 21-146:
(SEQ ID NO: 108)
MAEDYAKERYGISSMIQSQEKPDRVLVRVRDLTIQKADEVVWVRARVHTSRAKGKQCFLVLRQ
QQFNVQALVAVGDHASKQMVKFACNINKESIVDVEGVVRKVNQKIGSCTQQDVELHVQKIYVI
S

N-terminal truncated Homeokine variants 3-154, 5-154, 7-154 and 9-154 were made by QuickChange Lightning Site-Directed Mutagenesis Kit (Agilent, cat. no. 210518) following the manufacturer's instructions using construct plasmid pET28a-C-V5/His-DRS aa1-154 as template. Homeokine variants 13-146/A106C were also made by direct mutagenesis approach using the truncated form DRS 13-146 as template.

C-terminal Homeokine variants 1-148, 1-150, 1-152, 1-156, 1-158, 1-160, 1-162, 1-164, 1-166, 1-168, 1-170, 1-172, 1-174, 1-176, 1-178 and 1-180 were made by via Kunkle mutagenesis approach using pET28a C-V5/H is DRS as template. The whole process can be divided into two steps, ssDNA preparation and Kunkle mutagenesis. To prepare ssDNA, the dsDNA vector was transformed into CJ236 bacterial cells (NEB, cat no E4141S) and plated on ampicillin (100 ug/mL) and chloramphenicol (30 ug/mL) containing LB-Agar plates. Plates were incubated overnight at 37° C. A colony was used to inoculate LB medium containing ampicillin and chloramphenicol and incubated overnight at 225 rpm and 37° C. 20 mL of LB containing ampicillin and chloramphenicol was inoculated with 200 uL of the overnight culture and grown for 2 hr at 225 rpm and 37° C. The culture was infected with 5e9 pfu of M13KO7 Helper Phage (NEB, cat no N0315S). After 1 hr, kanamycin was added to the culture at a final concentration of 50 ug/mL and incubated overnight at 225 rpm and 37° C. Bacteria were separated and discarded from culture by two centrifugations at 1900×g. ssDNA was precipitated by incubation at 4° C. with final concentrations of 4% PEG-8000 and 500 mM Sodium Acetate for 2 hr. ssDNA was centrifuged at 12000×g and resuspended in 1.4 mL LB medium. Cell debris was eliminated by subsequent centrifugation at 14500×g. ssDNA was purified from the supernatant using Qiagen QIAprep M13 kit (Qiagen, cat no 27704). Kunkel mutagenesis was performed by first diluting primers to 100 ng/uL. 100 ng of the oligo was then incubated with 5U PNK kinase (Roche, cat no 10633542001) in the presence of 1×PNK kinase buffer and 0.5 mM ATP. This reaction was incubated at 37° C. for 1 hr. 100 ng of ssDNA vector was incubated with 6.9 ng of kinased oligo in annealing buffer (20 mM Tris, pH7.4, 2 mM MgCl$_2$, 50 mM NaCl, final concentrations) for 5 min in a heat block at 75° C. Reactions were allowed to cool to room temperature while contained in the heat block. For elongation of the plasmid, 1U of T4 DNA Polymerase (Roche, cat no 11004786001) and 1U T4 DNA Ligase (Roche, cat no 10481220001) was added to the reaction. Additionally, synthesis buffer was added to a final concentration of 0.45 mM dNTPs, 0.91 mM ATP, 9.1 mM Tris, pH7.4, 4.5 mM MgCl2, and 1.8 mM DTT. This reaction was incubated on ice for 5 min and then at 37° C. for 90 min. 5 uL of the elongation reaction was transformed into 200 uL DH5a cells. Transformations were plated on Ampicillin plates and incubated overnight at 37° C. Individual colonies were used to inoculate 6 mL LB medium containing ampicillin. Cultures were grown overnight at 37° C. DNA plasmids were prepared using Qiagen Spin Miniprep kit (Qiagen, cat no 27106) and sequence verified.

Double truncated Homeokine variants 11-146, 13-146, 17-146 and 21-146 were made by traditional cloning method using construct pet28a+_CtermV5His_DRS_NdeI-XhoI_revcomp as template. Briefly, the desired fragment was amplified by PCR (Invitrogen, cat no 12344-040) and double digested by NdeI (NEB, cat. no R0111S) and XhoI (NEB, cat no. RO146S) restriction enzymes. Purified double digested fragment was ligated with NdeI/XhoI double vector pet28a+_CtermV5His_DRS_NdeI-XhoI_revcomp by T4 DNA Ligase (Roche, cat no 10481220001) and transformed into DH5α competent cells (Invitrogen, cat. no 18263-012) and plated on LB-agar plates containing ampicillin (100 ug/mL). Colonies were grown individually in LB/Amp media and sequenced to confirm sequence.

Expression of Truncated Homeokine Variant: Homeokine truncated variant constructs with correct sequences are transformed into BL21 (DE3) competent cells (Novagen, cat. no. 69450-4) and expressed at 30° C. for 16 hrs in LB media with 100 ug/ml ampicillin as described above.

Purification of truncated Homeokine variants were prepared as described in Example 5, except for the final lysis step. In which for these constructs frozen cell pellets were resuspended in lysis buffer (50 mM Tris, 300 mM NaCl, 25 mM Imidazole, 5 mM DTT, pH 8.0 with complete EDTA-FREE protease inhibitor cocktail tablets (Roche cat. no: 05 056 489 001) and the then rotated for 30 mins at 4° C. with 300 mg chicken egg lysozyme. The suspension was then sonicated for two cycles 50% and 75% for 60 seconds each with 10 second on and 5 second off. The lysate was centrifuged at 35,000×g for 45 min at 4° C., and the supernatant then filtered through 0.22 μm Sartobran capsule filters (Sartorius). The clarified lysate was bound to the Ni-NTA resin (Qiagen), pre-equilibrated with Ni-NTA Binding Buffer (50 mM Tris, 300 mM NaCl, 25 mM Imidazole, 5 mM DTT, pH 8.0). The column was washed with 1000 column volumes of Ni-NTA Binding Buffer plus 0.1% Triton X-114 and 5 mM DTT followed by 50 column volumes of the Ni-NTA Binding Buffer. The bound protein was eluted with 5 column volumes of Ni-NTA Elution Buffer (50 mM Tris, 300 mM NaCl, 300 mM Imidazole, 1 mM DTT pH 8.0).

The purified proteins were dialyzed into 20 mM sodium phosphate, 200 mM Arginine, at pH7.3. The dialyzed protein was passed through a Q membrane filter (Sartobind-Q from Sartorius or Mustang-Q from Pall) or a Q-Sepharose column (GE Healthcare) for further endotoxin removal when endotoxin level is detectable using Charles River endotoxin detection kit (product code: PTS20), and then filtered through a 0.22 μm sterile filter.

Testing of the relative activity of the purified proteins compared in the HEK293-TLR2 and HEK293-TLR4 expressing cell lines as described above confirmed that the majority of proteins were active (data not shown).

Example 7

Comparison of Stability of Purified Truncated Homeokine (DRS) Mutants

Stability was assessed by incubating 50 μl of each of the deletion mutants in PBS at 1 mg/ml at 37° C. for 1 hrs, and then by running an analytical SEC column (YMC America, Inc, cat. no. YMC-Pack Diol-300) using 200 mM phosphate, 100 mM NaCl pH7.0 as running buffer to compare the % High molecular weight (HMW) component after incubation at 37 C, and via determining turbidity as assessed via absorption at A340 nM. Results are summarized in Table E9.

TABLE E9

| Variant | % Change A340 nm after incubation after 5 hr at 37 C. +: <50%; ++: >50%; +++: >100%; ++++: >500%; | % HMW determined via SEC (Time zero) +: <7%; ++: >7%; +++: >10%; ++++: >15%; | % HMW determined via SEC after incubation after 5 hr at 37 C. +: <7%; ++: >7%; +++: >10%; ++++: >15%; |
|---|---|---|---|
| 1-148 | + | + | + |
| 1-150 | ++ | + | + |
| 1-152 | +++ | + | + |
| 1-154 | ++ | + | + |
| 1-156 | ++ | + | + |
| 1-158 | ++ | + | + |
| 1-160 | +++ | ++ | ++ |

TABLE E9-continued

| | | | |
|---|---|---|---|
| 1-162 | + | + | ++ |
| 1-164 | + | + | ++ |
| 1-166 | ++++ | ++++ | + |
| 1-168 | + | ++ | ++++ |
| 1-170 | + | + | +++ |
| 1-172 | + | + | ++++ |
| 1-174 | + | + | ++++ |
| 1-176 | +++ | ++++ | ++ |
| 1-178 | + | ++ | ++++ |
| 1-180 | + | + | +++ |
| 1-182 | + | ++ | ++++ |
| N-terminal mutations | | | |
| 3-154 | ++++ | ++++ | ++ |
| 5-154 | ++++ | ++++ | ++ |
| 7-154 | ++++ | ++++ | ++ |
| 9-154 | ++++ | ++++ | ++ |
| 11-154 | + | + | + |
| 13-154 | + | + | + |
| 17-154 | + | + | + |
| 21-154 | ++ | + | + |
| 23-154 | ++ | + | + |

| Double truncations | | | % HMW determined via SEC after incubation after 24 hr at 37 C. |
|---|---|---|---|
| 11-146 | Not determined | + | Not determined |
| 13-146 | Not determined | + | +++ |
| 17-146 | Not determined | + | Not determined |
| 21-146 | Not determined | + | Not determined |
| 13-146/A106C | Not determined | + | ++ |

These results demonstrate that C-terminal deletions from about 1-158 to about 1-146 of DRS display enhanced stability and reduced tendency for aggregation. With respect to N-terminal deletions, deletions in the range of 11-154 to 17-154 of DRS results in constructs with improved stability profiles. Additionally all of the doubly deleted constructs, including 11-146, 13-146, 17-146 and 21-146 of DRS all exhibited extremely low tendency for aggregation and enhanced stability.

Example 8

Preparation of Linear PEGylated DRS Polypeptides

Pre-activated linear 30 kDa, and 40 kDa PEG-maleimide reagents were purchased from NOF Corporation (Tokyo Japan), (SUNBRIGHT® ME-300MA, ME-400MA), and used to create 30 kDa, and 40 kDa, PEGylated versions of AspRS1$^{N1}$(C76S) (DRS(1-154)C76S).

Purified DRS polypeptide DRS(1-154)C76S (1.0-2 mg/ml) (Example 1) was incubated with 1 mM dithiothreitol (Fluka 43819) overnight at 4° C. or with >8 mM effective concentration of immobilized TCEP (tris(2-carboxyethyl) phosphine) agarose (Pierce, 77712) at room temperature for 2 hours to reduce any disulfide bond formation. The samples were buffer exchanged to 20 mM sodium phosphate, containing 200 mM Arginine, pH7.3) The samples were then passed through an HiTrap Q HP column (General Electric 17-1153-01) as a polishing step and to remove endotoxins.

The Methoxy PEG Maleimide PEGylation reagents from the manufacturer were resuspended to make a final concentration of 50-100 mg/ml. The DRS polypeptide DRS(1-154) C76S was mixed with the activated PEG reagent at molar ratio of either 1:1 or 1:5. The reactions were run for either 2 hours at room temperature or overnight at 4° C. on a

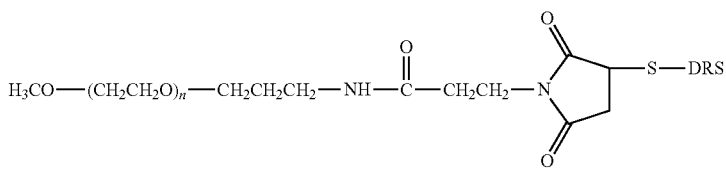

wherein n=about 200 to 800;
DRS is DRS(1-154)C76S
wherein the PEG moiety is attached via C130 shaker. Completion of the reaction was checked using SDS-PAGE (Example 8) to confirm the molecular weight shift due to PEGylation (FIG. 4).

Example 9

Preparation of Additional Linear PEGylated DRS Polypeptides

Using similar reaction conditions as described in Example 8, and using the following reagents in place of the NOF reagents, the following PEGylated DRS polypeptides of MW 10 KDa to 60 KDa may be readily prepared.

Use of Jenkem 40 K linear PEG (Cat # A3042-1), yields:

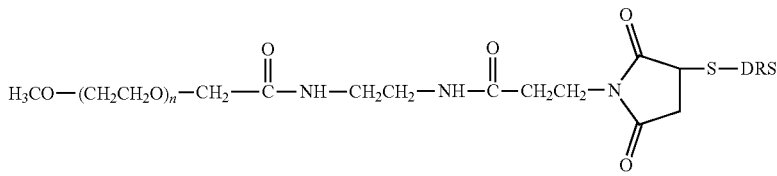

wherein n=about 400 to 600;
DRS is DRS(1-154)C76S, and
wherein the PEG moiety is attached via Cys130.

The resulting PEGylated DRS polypeptides were analyzed by SDS-PAGE as described in Example 8.

Use of PEG2-0007 from Nanocs, yields:

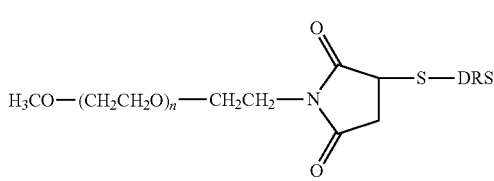

wherein n=about 400 to 600;
DRS is DRS(1-154)C76S, and
wherein the PEG moiety is attached via Cys130.

Use of JENKEM M-VS-20K yields:

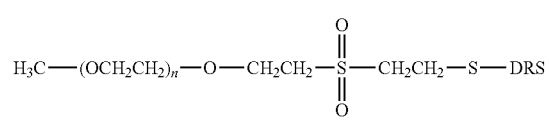

wherein n=about 100 to 600;
DRS is DRS(1-154)C76S, and
wherein the PEG moiety is attached via Cys130.

Use of NANOCS PEG2-0014 yields:

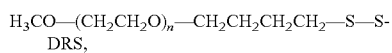

wherein n=about 100 to 600;
DRS is DRS(1-154)C76S, and
wherein the PEG moiety is attached via Cys130.

Example 10

Preparation of Exemplary Branched PEGylated DRS Polypeptides

Using similar reaction conditions as described in Example 8, and using the following reagents in place of the Jenkem reagents, the following PEGylated DRS polypeptides with branched chain PEG moieties of MW 10 KDa to 60 KDa may be readily prepared.

Use of SUNBRIGHT LY-400MA from NOF yields:

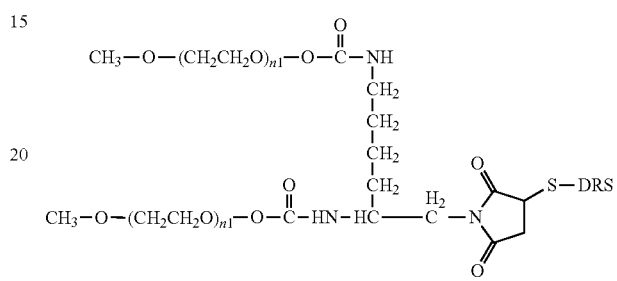

wherein $n_1$=about 100 to 600;
DRS is DRS(1-154)C76S, and
wherein the PEG moiety is attached via Cys130.

Use of A0002-1 Y-MAL-40K from JENKEM yields:

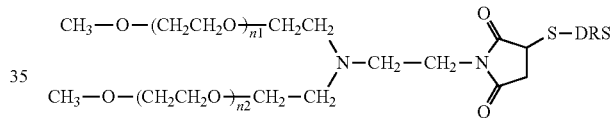

wherein $n_1$ and $n_2$=about 100 to 600;
DRS is DRS(1-154)C76S, and
wherein the PEG moiety is attached via Cys130.

Use of SUNBRIGHT GL2-200GS, GL2-400GS or GL2-600GS from NOF yields:

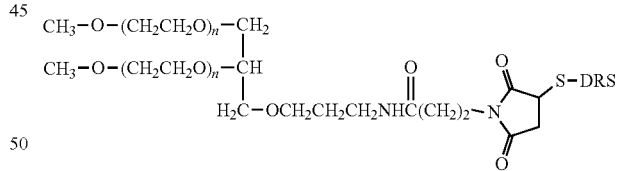

wherein n=about 100 to 600;
DRS is DRS(1-154)C76S, and
wherein the PEG moiety is attached via Cys130.

Example 11

SDS-PAGE Analysis of PEGylated DRS Polypeptides

Protein samples (15 µl) mixed with 4×LDS sample buffer (5 µl) (Invitrogen, NP0007) plus β-mercaptoethanol (Fisher Scientific, 034461-100) of selected 40K PEGylated DRS proteins from Examples 5 and 6 (Jenkem-DRS(1-154)C76S-40K, SUNBRIGHT-NOF-DRS(1-154)C76S-40K, SUNBRIGHT-NOF-DRS(1-154)C76S)-30K were analyzed by sodium dodecyl sulfate polyacrylamide gel electrophoresis using 4-12% NuPAGE Bis-Tris gel (Invitrogen, NP0335) and MOPS running buffer (Invitrogen, NP000102). Electrophoresis was carried out at 150 volts until the dye front reached the bottom of the gel. The gel was stained with Coomassie-based reagent, Instant Blue (Novexin) and destained with water. (FIG. 4) The bands for unPEGylated DRS(1-154)C76S migrated with an apparent molecular weight of approximately 19 kDa. The bands for PEGylated DRS(1-154)C76S which were PEGylated with any of the 40 kDa PEGs migrated with an apparent molecular weight of approximately >80 kDa.

Example 12

Characterization of In Vitro Activity

Samples of the PEGylated DRS polypeptide DRS(1-154) C76S (SUNBRIGHT-NOF-DRS(1-154)C76S-40K) were compared to unPEGylated protein samples in the TLR2 assay, as described in Example 3. The results shown in FIG. 5, demonstrate that the PEGylated forms of this protein demonstrate similar activity compared to the non-PEGylated proteins.

Example 13

Pharmacokinetics of PEGylated DRS Polypeptides In Vivo

Samples of the PEGylated DRS polypeptide DRS(1-154) C76S (SUNBRIGHT-NOF-DRS(1-154)C76S-40K) were compared to unPEGylated protein samples by IV invention in rats (n=3) at an initial concentration of 5 mg/kg. The data, presented in FIGS. 6, 7 and 8 and Table E10 demonstrates that the PEGylated protein had a significantly longer terminal half life, and moderately decreased ability to stimulate TNFalpha and IL-10 (see FIGS. 9 and 10).

TABLE E10

Pharmacokinetic characterization of PEGylated and unPEGylated DRS polypeptides

| Parameter | UnPEGylated Protein | PEGylated protein |
|---|---|---|
| Rsq | 0.94 | 0.97 |
| Lower time point | 30' | 30' |
| Upper time point | 480' | 480' |
| Terminal Half-life (min) | 66.1 | 137.8 |
| C0 (ng/ml) | 11082 | 53981.8 |
| AUCinf (min*ng/ml) | 349273 | 2705770 |
| AUCinf % extrapolated | 0.44 | 7.8 |
| CL (ml/min/kg) | 14.3 | 0.0018 |
| Vss (ml/kg) | 807 | 0.30 |

Example 14

Stability of PEGylated DRS Polypeptides During Storage

Samples of the PEGylated DRS polypeptide DRS(1-154) C76S (SUNBRIGHT-NOF-DRS(1-154)C76S-40K) were compared to unPEGylated protein samples during storage at room temperature for one week. Samples were dialyzed in PBS pH 7.4, and concentrated to 1.5 to 1.8 mg/ml, soluble protein levels were determined after one week storage. The results shown in Table E11 demonstrate that the PEGylated proteins exhibit significantly enhanced stability compared to the non-PEGylated proteins.

TABLE E11

Stability of PEGylated and Non-PEGylated DRS proteins

| Protein | 24 h Timepoint (% of starting concentration) | 7 day timepoint (% of starting concentration) |
|---|---|---|
| DRS(1-154) | 85.4 | 66.5 |
| DRS(1-154)C76S-NOF-40K PEG | 90.8 | 91.8 |

Example 15

Testing of Reduced Cysteine Variants In Vivo in a Partial Body Irradiation Survival Model Methods. Adult (10-12 week) C57BL/6 male mice were divided into 10 groups of 26. Mice were irradiated at 15:00 hours +/−1 hour with 14Gy (five groups) or 14.5Gy (five groups) irradiation. Irradiation was performed using a Pantak HF320 X-ray operated at 300 kV, 10 mA. The X-ray tube had additional filtration to give a radiation quality of 2.3 mm Cu half-value layer (HVL). Mice were anaesthetized and restrained in a jig and irradiation was delivered at a dose rate of 70.0cGy/min. (Epistem, UK). Animals received partial body irradiation to the abdomen only—the head, thorax and forelimbs were lead shielded. This equates to approximately 40% bone marrow shielding. 24 hours post irradiation each group of mice was dosed i.v. (5 ml/kg) with a test item via the tail vein. The test item groups tested at each radiation dose using a PBS diluent. Mice were then dosed every 24 hours for a total of 7 days with DRS(1-154) C76S or with PBS as a control.

Mice were weighed daily and signs of diarrhea noted twice daily from day 4-10 post irradiation. Moribund mice from day 10 onwards were anaesthetized and subjected to terminal cardiac puncture to obtain a cardiac bleed. An aliquot of blood was used to perform a complete blood count, with the remainder used to isolate serum, which was then snap frozen. The small and large intestine were removed and fixed. The spleen, femur, Iliac bones and vertebrae, heart, lung and kidneys were also collected from selected mice on day 15 following 14Gy and fixed in formalin.

Results. The survival data obtained with 14Gy is shown in FIG. 11, and demonstrates that the cysteine variant DRS1-154 C76S displays improved survival in a radiation survival model.

Example 16

Testing of Reduced Cysteine Variants In Vivo in a MSU Induced Gout Model

Methods. Gout like inflammation was induced in groups of 5 female C57BL/6 mice by single administration of MSU crystals into the left tarsal joint (Performed by Comparative Biosciences Inc., Sunnyvale, Calif.). One hour before the injection of the MSU crystals, mice were dosed prophylactically once by single injection of vehicle, DRS1-154(C76S) (5 mg/kg, IV) or dexamethasone. Clinical measurements of joint inflammation severity (joint thickness, erythema and lameness) were assessed three times during the study. Mice were sacrificed one day after dosing; blood for serum was collected and the hind limbs were collected for histopathological evaluation. Throughout the study, general clinical observations were recorded daily; body weights were recorded prior to dosing and at necropsy.

Results. Administration of MSU induced an appropriate brisk inflammatory response characterized by joint swelling and erythema which corresponded clinically to the acute inflammation as seen by histopathology examination. Clinically, dexamethasone administration was associated with reduced swelling (attenuated severity score and mean joint diameter) compared to those treated with saline. Histopathologic examination (FIGS. 12A and 12B) of the MSU injected left tarsal joint showed that dexamethasone and DRS1-154 (C76S) induced a significant reduction in inflammation.

These results demonstrate that DRS1-154 comprising the C76S mutation exhibits enhanced anti-inflammatory activity in the MSU induced model of gout and gout flares.

Example 17

Activity of DRS(1-154) C76S in the TNBS Mouse Model

The DRS(1-154) C76S polypeptide was tested in the TNBS mouse model of colitis. In this model, colonic irritation is induced by intracolonic administration of TNBS in ethanol. This provokes an acute colitis that has a TH1-type cytokine profile, which is characterised by the expression of genes coding for TNF-α, IFN-γ and IL-12 amongst others (see Fichtner-Feigl et al., *J. Clin. Invest.* 115:3057-3071, 2005). The colitis can be severe and localised to the area of the colon into which the TNBS is introduced. The inflammatory response results in localised swelling, inflammatory cell infiltration, and epithelial loss.

Methods. A total of 62 male BDF-1 mice were used in this study. The mice were randomised into four treatment groups of 12 mice each, one treatment group of eight mice and one group of six mice each. All mice in the five largest treatment groups received 3 mg TNBS in 50% ethanol/saline by colonic instillation on study day 0, in order to induce colitis. Test items (DRS(1-154) C76S)) were first administered three hours prior to the instillation of TNBS, by i.v. injection, at a dose of 5 mg/Kg, and subsequently on study days 1-3 inclusive. Budesonide was employed as a reference test item and was dosed daily, by oral gavage, at 5 mg/kg, with the first dose being given 3 hours prior to the instillation of TNBS. Weight, faecal consistency and presence of overt blood, in faeces and around the anus, were assessed daily. All mice were euthanised on study day 4, and the large bowel taken for assessment of intestinal morphology, a small sample was also snap-frozen.

Harvesting and Preparation of Tissue for Histological Examination. Mice were sacrificed at 09:00 by cervical dislocation on study day 4, 24 hours after receiving the last dose of test item. Blood was collected, post-sacrifice, by cardiac puncture, into EDTA-treated tubes, and immediately placed on ice. Plasma was prepared by centrifugation of blood samples at 3000 g for 10 minutes, and stored at −80° C. The large intestine was removed and flushed with PBS and its length and wet weight were recorded, prior to cutting into caecum, mid-colon and rectum and fixation in Carnoy's solution. A small sample of mid-colon was also snap-frozen in liquid nitrogen. Fixed tissue was dehydrated through a series of alcohols and xylene and embedded in paraffin, using a Leica TP1020 tissue processor and an EG1140H work station. Sections (3 μm thick) were cut using a Leica RM2125RTF microtome, and air-dried on to microscope slides, overnight at 37° C. Subsequently, slides were dewaxed in xylene and rehydrated through graded alcohols to PBS. All sections were then stained with haematoxylin and eosin (H&E), and mounted. The results are shown in Table E12 below.

TABLE E12

| | % of surviving animals | | | |
|---|---|---|---|---|
| Study Day | untreated | TNBS alone | TNBS + budesonide | TNBS + DRS(1-154)C76S |
| 0 | 100 | 100 | 100 | 100 |
| 1 | 100 | 90 | 100 | 100 |
| 2 | 100 | 90 | 100 | 100 |
| 3 | 100 | 75 | 75 | 100 |
| 4 | 100 | 45 | 75 | 75 |
| 5 | 100 | 45 | 70 | 75 |

These results demonstrate that the DRS polypeptide DRS (1-154) C76S exhibits anti-inflammatory activity in the TNBS model of inflammatory bowel disease.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A PEGylated aspartyl-tRNA synthetase (DRS) polypeptide selected from,
(a) a DRS polypeptide consisting of a sequence that is at least 95% identical to the sequence set forth in SEQ ID NO:3 DRS(1-154), which is modified by C76S substitution, where a maleimide monomethoxy polyethylene glycol (mPEG) derivative of about 40,000 Daltons is covalently attached via a thio ether linkage to C130; and
(b) a DRS polypeptide of up to 200 amino acids in length comprising a sequence that is at least 95% identical to the sequence set forth in SEQ ID NO:3 DRS(1-154), which is modified by C76S substitution, where a maleimide monomethoxy polyethylene glycol (mPEG) derivative of about 40,000 Daltons is covalently attached via a thio ether linkage to C130.

2. The PEGylated DRS polypeptide of claim 1, wherein the PEGylated polypeptide exhibits a higher stability compared to a corresponding non-PEGylated polypeptide.

3. The PEGylated DRS polypeptide of claim 1, comprising the structure

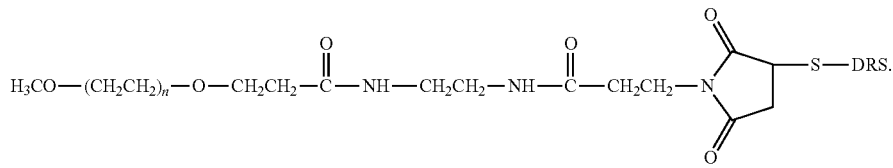

4. The PEGylated DRS polypeptide of claim 1, comprising the structure:

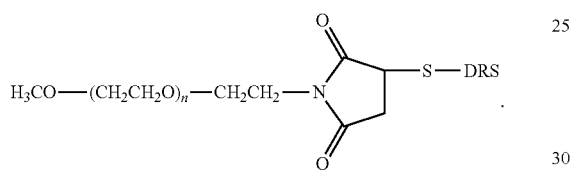

5. The PEGylated DRS polypeptide of claim 1, comprising the structure:

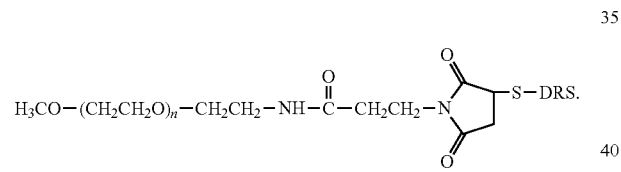

6. The PEGylated DRS polypeptide of claim 1, comprising the structure:

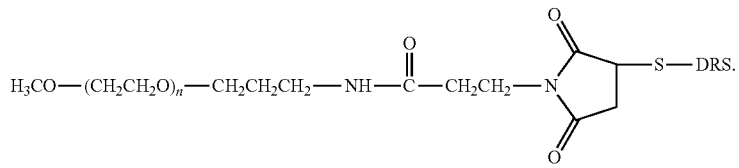

7. The PEGylated DRS polypeptide of claim 1, wherein the DRS polypeptide has substantially the same secondary structure as unmodified DRS polypeptide, as determined via UV circular dichroism analysis.

8. The PEGylated DRS polypeptide of claim 1, wherein the PEGylated DRS polypeptide has a plasma or sera pharmacokinetic AUC profile at least 5-fold greater than unmodified DRS polypeptide when administered to rats.

9. A pharmaceutical composition comprising a PEGylated aspartyl-tRNA synthetase (DRS) polypeptide of claim 1, and a pharmaceutically acceptable carrier or excipient.

* * * * *